US011786591B2

(12) United States Patent
Kwong et al.

(10) Patent No.: US 11,786,591 B2
(45) Date of Patent: Oct. 17, 2023

(54) RECOMBINANT METAPNEUMOVIRUS F PROTEINS AND THEIR USE

(71) Applicants: The United States of America, as represented by the Secretary, Department of Health and Human Services, Bethesda, MD (US); Institute for Research in Biomedicine, Bellinzona (CH)

(72) Inventors: Peter Kwong, Washington, DC (US); Michael Gordon Joyce, Washington, DC (US); Baoshan Zhang, Bethesda, MD (US); Yongping Yang, Potomac, MD (US); Peter Collins, Kensington, MD (US); Ursula Buchholz, Silver Spring, MD (US); Davide Corti, Bellinzona (CH); Antonio Lanzavecchia, Bellinzona (CH); Guillaume Stewart-Jones, Cambridge, MA (US)

(73) Assignees: The United States of America, as represented by the Secretary, Department of Health and Human Services, Bethesda, MD (US); Institute for Research in Biomedicine, Bellinzona (CH)

( * ) Notice: Subject to any disclaimer, the term of this patent is extended or adjusted under 35 U.S.C. 154(b) by 314 days.

(21) Appl. No.: 17/334,505

(22) Filed: May 28, 2021

(65) Prior Publication Data

US 2021/0283240 A1 Sep. 16, 2021

Related U.S. Application Data

(62) Division of application No. 16/578,748, filed on Sep. 23, 2019, now Pat. No. 11,027,007, which is a division of application No. 15/539,640, filed as application No. PCT/IB2015/059991 on Dec. 24, 2015, now Pat. No. 10,420,834.

(60) Provisional application No. 62/096,744, filed on Dec. 24, 2014.

(51) Int. Cl.

| | |
|---|---|
| ***C07K 14/005*** | (2006.01) |
| ***A61K 39/155*** | (2006.01) |
| ***A61K 39/39*** | (2006.01) |
| ***A61K 48/00*** | (2006.01) |
| ***C07K 14/135*** | (2006.01) |

(52) U.S. Cl.

CPC ........... *A61K 39/155* (2013.01); *A61K 39/39* (2013.01); *A61K 48/00* (2013.01); *C07K 14/005* (2013.01); *C07K 14/135* (2013.01); *C07K 2319/70* (2013.01); *C07K 2319/73* (2013.01); *C12N 2760/18322* (2013.01); *C12N 2760/18334* (2013.01); *C12N 2760/18522* (2013.01); *C12N 2760/18534* (2013.01)

(58) Field of Classification Search

None

See application file for complete search history.

(56) References Cited

U.S. PATENT DOCUMENTS

2014/0072958 A1 3/2014 Nabel et al.

FOREIGN PATENT DOCUMENTS

WO WO 2010/149743 12/2010
WO WO 2012/158613 11/2012

OTHER PUBLICATIONS

Bastien et al., "Sequence analysis of the N, P, M and F genes of Canadian human metapneumovirus strains," *Virus Research 93.1*: 51-62, 2003.

Corti et al., "Cross-neutralization of four paramyxoviruses by a human monoclonal antibody," *Nature 501.7467*: 439-443, 2013.

Edwards et al., "Burden of human metapneumovirus infection in young children," *New England Journal of Medicine 368.7*: 633-643, 2013.

Lee et al., "Reversible inhibition of the fusion activity of measles virus F protein by an engineered intersubunit disulfide bridge," *Journal of Virology 81.16*: 8821-8826, 2007.

Liu et al., "A live attenuated human metapneumovirus vaccine strain provides complete protection against homologous viral infection and cross-protection against heterologous viral infection in BALB/c mice," *Clinical and Vaccine Immunology 20.8*: 1246-1254, 2013.

McLellan et al., "Structure-based design of a fusion glycoprotein vaccine for respiratory syncytial virus," *Science 342.6158*: 592-598, 2013.

Wen et al., "Structure of the human metapneumovirus fusion protein with neutralizing antibody identifies a pneumovirus antigenic site," *Nature Structural & Molecular Biology 19.4*: 461-463, 2012.

International Search Report and Written Opinion dated Apr. 12, 2016 for International Application No. PCT/IB2015/059991 (11 pages).

*Primary Examiner* — Stacy B Chen

(74) *Attorney, Agent, or Firm* — Klarquist Sparkman, LLP

(57) ABSTRACT

Metapneumovirus (MPV) F proteins stabilized in a prefusion conformation, nucleic acid molecules and vectors encoding these proteins, and methods of their use and production are disclosed. In several embodiments, the MPV F proteins and/or nucleic acid molecules can be used to generate an immune response to MPV in a subject. In additional embodiments, the therapeutically effective amount of the MPV F ectodomain trimers and/or nucleic acid molecules can be administered to a subject in a method of treating or preventing MPV infection.

36 Claims, 15 Drawing Sheets

Specification includes a Sequence Listing.

Membrane

Assessing deposited hMPV F structure

Comparison of antigenic site Ø

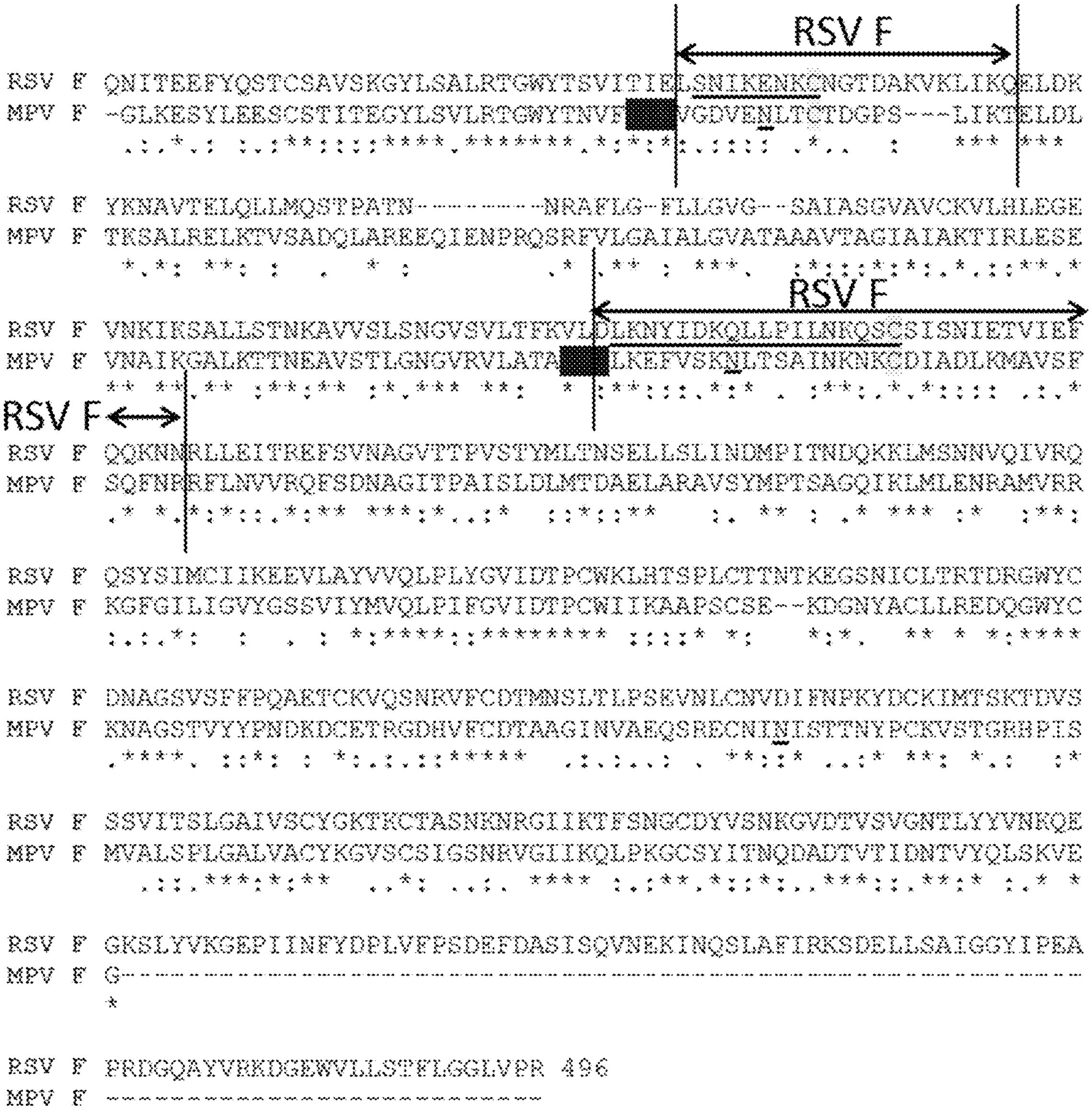

FIG. 5

```
RSV F  QNITEEFYQSTCSAVSKGYLSALRTGWYTSVITIELSNIKENKCNGTDAKVKLIKQELDK
MPV F  -GLKESYLEESCSTITEGYLSVLRTGWYTNVF   VGDVENLTCTDGPS---LIKTELDL
       .:.*.: :.:.:**.:::****.*******.*:*:*:.::.: .*.. :    *** ***
                                        |──────────── RSV F ────────────→
RSV F  YKNAVTELQLLMQSTPATN---------NRAFLG-FLLGVG--SAIASGVAVCKVLHLEGE
MPV F  TKSALRELKTVSADQLAREEQIENPRQSRFVLGAIALGVATAAAVTAGIAIAKTIRLESE
       *.*: **: :   :    .    *  :   .* :** :***. :.*:.:*:*.*.:::**.*
                                           |←──────── RSV F ────────────
RSV F  VNKIKSALLSTNKAVVSLSNGVSVLTFKVLDLKNYIDKQLLPILNKQSCSISNIETVIEF
MPV F  VNAIKGALKTTNEAVSTLGNGVRVLATA   LKEFVSKNLTSAINKNKCDIADLKMAVSF
       **.**:**  :**:**.*.**:*** :*     * :..*:*.*.:**:**.*.:.: .:*
RSV F ←→
RSV F  QQKNN|RLLEITREFSVNAGVTTPVSTYMLTNSELLSLINDMPITNDQKKLMSNNVQIVRQ
MPV F  SQFNP RFLNVVRQFSDNAGITPAISLDLMTDAELARAVSYMPTSAGQIKLMLENRAMVRR
       .* *.*.:*::.:*** ***:**:* :*:*..** * ..:.****:..**:*:.*.*:**:

RSV F  QSYSIMCIIKEEVLAYVVQLPLYGVIDTPCWKLHTSPLCTTNTKEGSNICLTRTDRGWYC
MPV F  KGFGILIGVYGSSVIYMVQLPIFGVIDTPCWIIKAAPSCSE--KDGNYACLLREDQGWYC
       :.:.*:  :  . * .::****::*******::: :* *.*  *:**: **  **:****

RSV F  DNAGSVSFFPQAETCKVQSNRVFCDTMNSLTLPSEVNLCNVDIFNPKYDCKIMTSKTDVS
MPV F  KNAGSTVYYPNDKDCETRGDHVFCDTAAGINVAEQSRECNINISTTNYPCKVSTGRHPIS
       .****: ::*: :.*::::::****  .:*. .:....***::*:.:*.**::*.::.:*

RSV F  SSVITSLGAIVSCYGKTKCTASNKNRGIIKTFSNGCDYVSNKGVDTVSVGNTLYYVNKQE
MPV F  MVALSPLGALVACYKGVSCSIGSNRVGIIKQLPKGCSYITNQDADTVTIDNTVYQLSKVE
        .: :.:***:*:**  ..*:..:*.****.  .**.*::*:..***::.**:*::.* *

RSV F  GKSLYVKGEPIINFYDPLVFPSDEFDASISQVNEKINQSLAFIRKSDELLSAIGGYIPEA
MPV F  G-----------------------------------------------------------
       *

RSV F  PRDGQAYVRKDGEWVLLSTFLGGLVPR  496
MPV F  --------------------------
```

FIG. 10
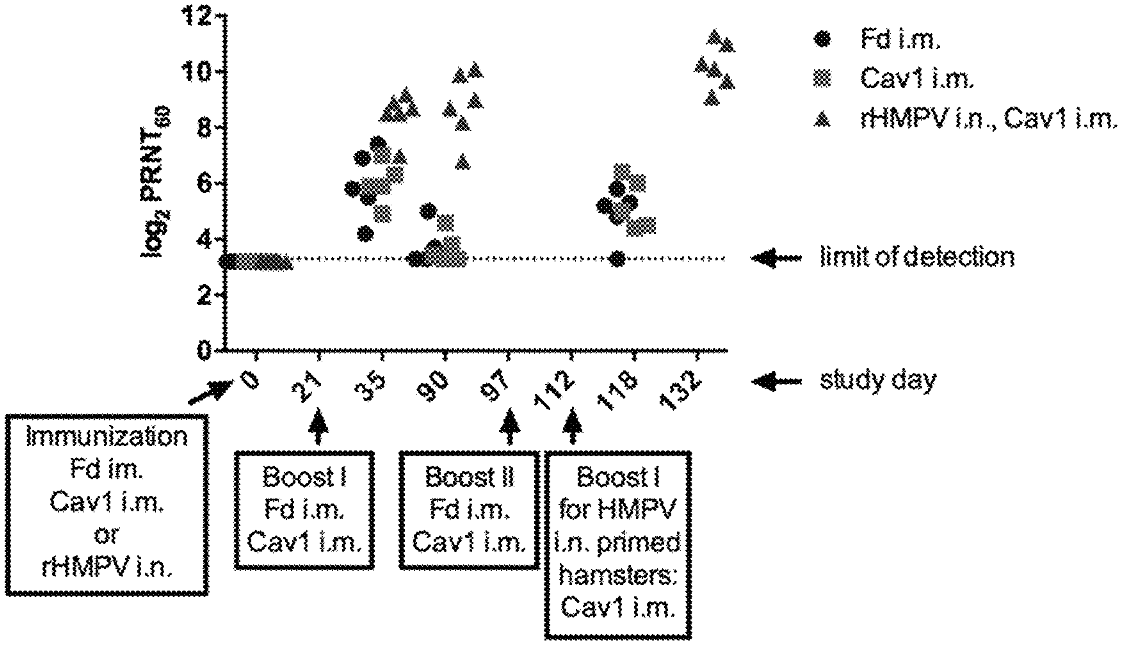
FIG. 11
Introduction of a novel disulfide bond by Ala113Cys and Ala339Cys
| Mutation | | | | | 1.5 W at 4 °C | 50 C treatment | | 60 C treatment | | 70 C treatment | |
|---|---|---|---|---|---|---|---|---|---|---|---|
| | MPE8 | DS7 | 234 | 338 | MPE8 | MPE8 | DS7 | MPE8 | DS7 | MPE8 | DS7 |
| Fd | 2.9 | 3.2 | 3.2 | 3.2 | 3.1 | 2.7 | 3.0 | 0.6 | 2.7 | 0.1 | 0.2 |
| 113C339C | 2.8 | 2.2 | 2.1 | 2.0 | 3.0 | 3.0 | 2.6 | 2.4 | 2.5 | 0.1 | 0.4 |
ELISA binding after initial expression, 1.5 weeks and following physical extremes
FIG. 12
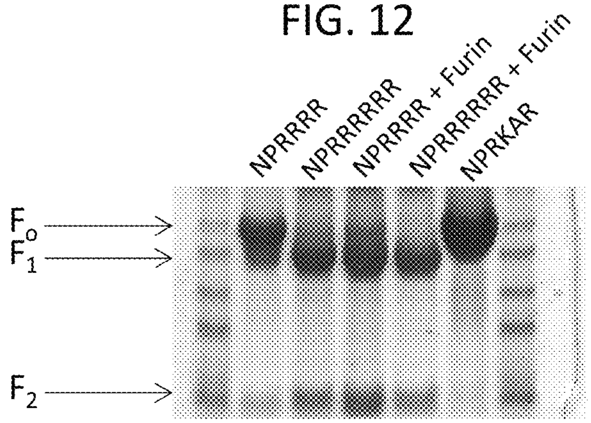

T160 cavity

I177 cavity

Cleavage site differences

HMPV glycan sites

FIG. 18
Structural alignment of 4DAG and rebuilt structure
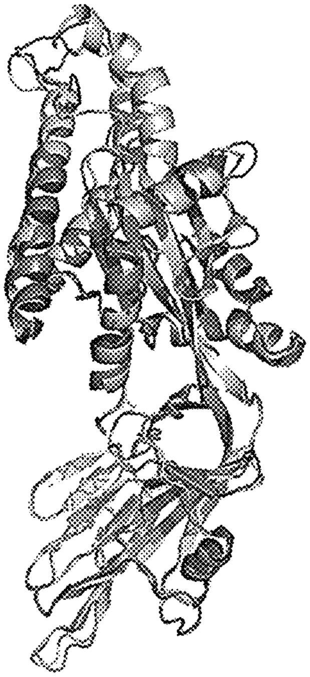
Membrane distal region of 4DAG and rebuilt structure
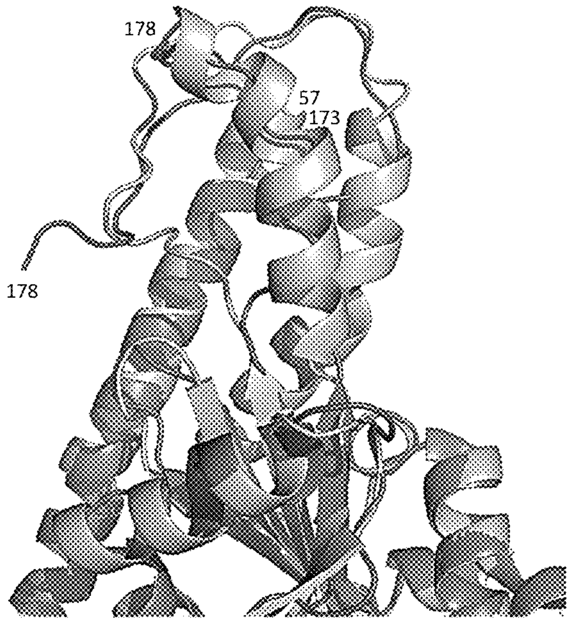

FIG. 19

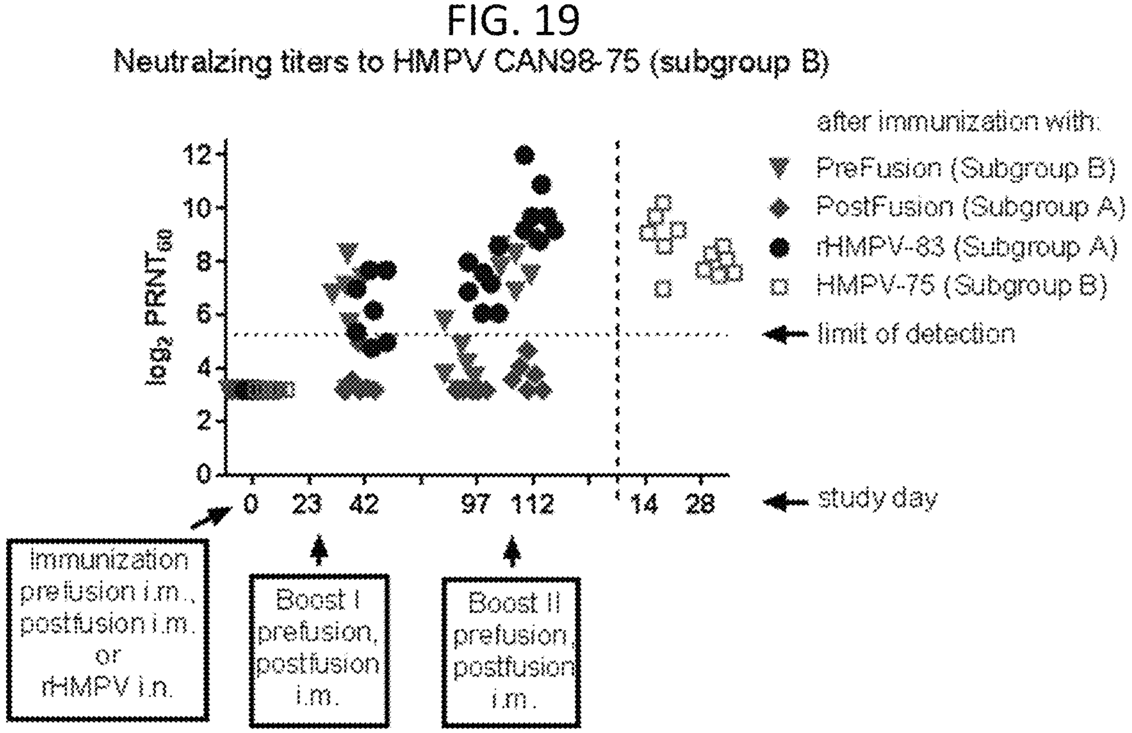

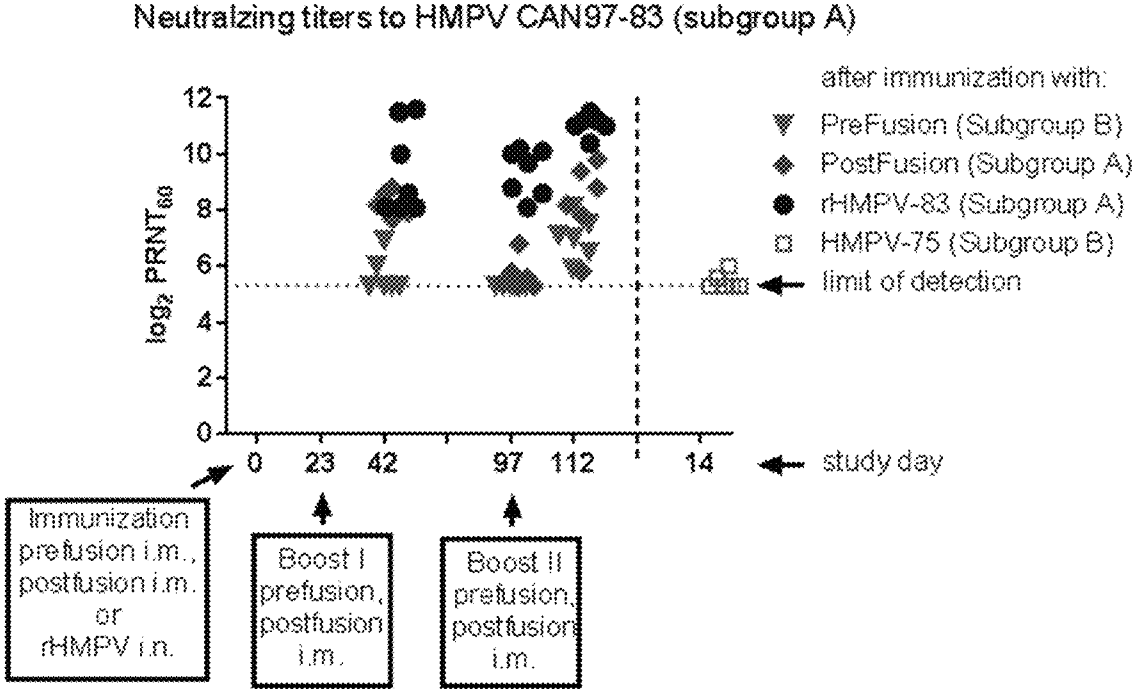

Neutralizing titers to HMPV CAN98-75 (subgroup B)

after immunization with:
- ▼ PreFusion (Subgroup B)
- ◆ PostFusion (Subgroup A)
- ● rHMPV-83 (Subgroup A)
- ◻ HMPV-75 (Subgroup B)

← limit of detection y-axis: $\log_2 PRNT_{60}$
x-axis: study day (0, 23, 42, 97, 112, 14, 28)

- Immunization prefusion i.m., postfusion i.m. or rHMPV i.n. (day 0)
- Boost I prefusion, postfusion i.m. (day 23)
- Boost II prefusion, postfusion i.m. (day 97)

Neutralizing titers to HMPV CAN97-83 (subgroup A)

after immunization with:
- ▼ PreFusion (Subgroup B)
- ◆ PostFusion (Subgroup A)
- ● rHMPV-83 (Subgroup A)
- ◻ HMPV-75 (Subgroup B)

← limit of detection y-axis: $\log_2 PRNT_{60}$
x-axis: study day (0, 23, 42, 97, 112, 14)

- Immunization prefusion i.m., postfusion i.m. or rHMPV i.n. (day 0)
- Boost I prefusion, postfusion i.m. (day 23)
- Boost II prefusion, postfusion i.m. (day 97)

RECOMBINANT METAPNEUMOVIRUS F PROTEINS AND THEIR USE

CROSS REFERENCE TO RELATED APPLICATIONS

This is a divisional of U.S. application Ser. No. 16/578,748, filed Sep. 23, 2019, which is a divisional of U.S. application Ser. No. 15/539,640, filed Jun. 23, 2017, now U.S. Pat. No. 10,420,834, issued Sep. 24, 2019, which is the U.S. National Stage of International Application No. PCT/IB2015/059991, filed Dec. 24, 2015, which was published in English under PCT Article 21(2), which in turn claims the benefit of U.S. Provisional Application No. 62/096,744, filed Dec. 24, 2014. The prior applications are incorporated by reference in their entirety.

FIELD

This disclosure relates to recombinant metapneumovirus (MPV) F proteins and immunogenic fragments thereof for treatment and prevention of MPV infection and disease.

BACKGROUND

Metapneumovirus (MPV) is an enveloped non-segmented negative-strand RNA virus in the family Paramyxoviridae, genus Pneumovirus. It is a common cause of bronchiolitis and pneumonia among children and the elderly. MPV also causes repeated infections including severe lower respiratory tract disease, which may occur at any age, especially among the elderly or those with compromised cardiac, pulmonary, or immune systems. Current treatment includes administration of the anti-viral agent Ribaviran.

In nature, the MPV F protein is initially expressed as a single polypeptide precursor, designated $F_0$. $F_0$ trimerizes in the endoplasmic reticulum and is proteolytically processed at a conserved cleavage site, generating $F_1$ and $F_2$ polypeptides. Three protomers of the $F_2$-$F_1$ heterodimer assemble to form a mature trimeric F protein, which adopts a metastable prefusion conformation that can be triggered to undergo a conformational change that fuses the viral and target-cell membranes. Due to its obligatory role in MPV entry, the MPV F protein is the target of neutralizing antibodies and the subject of vaccine development; however, like other MPV antigens, prior efforts to develop an MPV F protein-based vaccine have proven unsuccessful.

SUMMARY

Surprisingly, a detailed analysis of published structures of the MPV F protein revealed that the structural model of the membrane-distal aspect of the MPV F protein (a potential immunodominant site of vaccine interest) was incorrect. Correction of the published structural model through re-refinement of the deposited structure (PDB No. 4DAG) was used to obtain a corrected structural model of the prefusion form of the MPV F ectodomain trimer (including $F_2$ and the extracellular portion of $F_1$) in its prefusion conformation, which is disclosed herein. The disclosed structure has been substantially refined compared to prior MPV F protein structures. The refinement allows, for the first time, the design and generation of recombinant MPV F proteins that are stabilized in the prefusion conformation. These proteins can be used, for example, as immunogens to generate an immune response to MPV F in a subject.

In several embodiments, an immunogen is provided that comprises a recombinant MPV F protein or immunogenic fragment thereof stabilized in a prefusion conformation by one or more amino acid substitutions compared to a native MPV F protein sequence. The recombinant MPV F protein comprises a $F_2$ polypeptide and an $F_1$ ectodomain and can trimerize to form a trimeric MPV F protein. The recombinant MPV F protein or immunogenic fragment can specifically bind to a MPE8 monoclonal antibody.

In some embodiments, the recombinant MPV F protein comprises a non-natural disulfide bond between cysteine residues at positions 113 and 339 that stabilizes the recombinant MPV F protein in the prefusion conformation. The cysteine residues can be provided by amino acid substitutions, such as A113C and A339C amino acid substitutions. In additional embodiments, the recombinant MPV F protein comprises a cavity filling amino acid substitution at position 160 or a cavity filling amino acid substitution at position 177, or cavity filling amino acid substitutions at positions 160 and 177, that stabilizes the recombinant MPV F protein in the prefusion conformation. The cavity filling amino acid substitutions can comprise a T160F substitution, an I177L substitution, or T160F and I177L substitutions. In one non-limiting embodiment, the recombinant MPV F protein can be stabilized in the prefusion conformation by A113C, A339C, T160F, and I177L substitutions. The amino acid positions correspond to a reference MPV F protein sequence set forth as SEQ ID NO: 7.

In more embodiments, the recombinant MPV F protein not glycosylated at N57 or N172 N-linked glycosylation sites, which are present on the native form of the F protein. For example, in some embodiments, the recombinant MPV F protein comprises a N57Q substitution, a N172Q substitution, or a N57Q and a N172Q substitution, to remove N-linked glycosylation sequons at N57 and N172.

The MPV F protein can be linked to a trimerization domain to promote formation of an MPV F protein trimer. For example, the trimerization domain can be linked to the C-terminus of the $F_1$ ectodomain included in the recombinant MPV F protein.

In some embodiments, the recombinant MPV F protein can be a single chain MPV F ectodomain protein, wherein the C-terminus of the $F_2$ polypeptide is linked to the N-terminus of the $F_1$ ectodomain.

In additional embodiments, the recombinant MPV F protein can be included on a protein nanoparticle, such as a ferritin or lumazine synthase protein nanoparticle. In additional embodiments, the recombinant MPV F protein can be linked to an oligomerization peptide (such as a peptide comprising the amino acid sequence set forth as SEQ ID NO: 150. Nucleic acid molecules encoding the recombinant MPV F proteins and vectors (such as an inactivated or attenuated paramyxovirus vector) including the nucleic acid molecules are also provided.

Compositions including the recombinant MPV F proteins or immunogenic fragments thereof, protein nanoparticles, nucleic acid molecules or vectors are also provided. The composition may be a pharmaceutical composition suitable for administration to a subject, and may also be contained in a unit dosage form. The compositions can further include an adjuvant. The recombinant MPV F proteins may also be conjugated to a carrier (such as a monomeric subunit of a protein nanoparticle) to facilitate presentation to the immune system.

Methods of generating an immune response in a subject are disclosed, as are methods of treating, inhibiting or preventing a MPV infection in a subject. In such methods a subject, such as a human subject, is administered an effective amount of a disclosed recombinant MPV F protein or fragment thereof, protein nanoparticle, nucleic acid molecule or viral vector.

Methods for detecting or isolating an MPV binding antibody in a subject infected with MPV are disclosed. In such methods, a disclosed immunogen is contacted with an amount of bodily fluid from a subject and the binding of the MPV binding antibody to the immunogen is detected, thereby detecting or isolating the MPV binding antibody in a subject.

The foregoing and other features and advantages of this disclosure will become more apparent from the following detailed description of several embodiments which proceeds with reference to the accompanying figures.

BRIEF DESCRIPTION OF THE FIGURES

FIG. 5 is a sequence alignment illustrating the amino acid sequences of the MPV F ectodomain (residues 18-432 of SEQ ID NO: 7, "Meta") and the RSV F ectodomain (SEQ ID NO: 75, "RSV"). The sequences shown are those deposited in PDB as Nos. 4MMU (RSV) and 4DAG (MPV). The antigenic site Ø from RSV as described in McLellan et al., *Science,* 340, 1113-1117, 2013 is underlined. The asparagine residue of N-linked glycan sequons at MPV F positions N75, N172 and N353 are also underlined. The residues marked with double arrows were re-refined compared to the PDB: 4DAG structure to generate the new MPV F prefusion structure provided herein.

FIG. 10 shows a graph illustrating the immune response to MPV F protein in animals immunized with a native soluble trimeric MPV F protein linked to a foldon domain (Fd), a soluble trimeric MPV F protein linked to a foldon domain and including T160F and I177L substitutions (Cav1), or infected with 5.7 log 10 plaque forming units (PFU) native virus (rHMPV CAN97-83, Genbank No. NC_004148.2). Boost immunizations were administered as indicated in the graph. The immune response was assayed using a plaque reduction (60%) neutralization ($PRNT_{60}$) assay.

FIG. 11 is a table illustrating the antigenicity and stability of a soluble trimeric MPV F protein trimer linked to a foldon domain and including A113C and A339C substitutions to introduce a non-natural disulfide bond that stabilized the F protein in the prefusion conformation. To examine antigenicity, purified MPV F ectodomain with native sequence (Fd), or with the A113C/A339C substitutions (DS), each linked to a foldon trimerization domain, were assayed binding to the MPE8, DS7, 234, and 338 monoclonal antibodies. Specific binding activity was assayed following initial purification, and also after incubation at 4° C., 50° C., 60° C., or 70° C. for 1.5 weeks.

FIG. 12 shows a coommassie blue stained SDS-PAGE gel illustrating furin cleavage of recombinant MPV F proteins. As indicated in the figure, the MPV F proteins were expressed with or without furin. The MPV F proteins included A113C, A339C, T160F, and I177L substitutions, as well as substitution of the native cleavage site (RQSR, residues 99-102 of SEQ ID NO: 8) for RRRR (SEQ ID NO: 10) or RRRRRR (SEQ ID NO: 9) residues. After expression, the MPV F proteins were partially purified, separated by SDS-PAGE, and stained with coommassie blue.

FIGS. 13-18 show ribbon diagrams illustrating the three-dimensional structure of the MPV F protein in a prefusion conformation. FIG. 13 illustrates the T160 and I177 cavities in the MPV F prefusion structure. FIG. 14 shows a comparison of the MPV F and RSV F proteins in their prefusion conformations. FIG. 15 shows N-linked glycan moieties linked to the MPV F protein, including glycans linked to N57, N172, and N353. FIG. 16 illustrates the A125-A260 distance in the refined MPV F structure provided herein compared to the corresponding distance between these residues in the PDB No. 4DAG structure. FIG. 17 illustrates the A113-A339 distance in the refined MPV F structure provided herein compared to the corresponding distance between residues T114 and A339 in the PDB No. 4DAG structure. FIG. 18 illustrates the differences between the refined MPV F structure provided herein compared to the structure of the MPV F protein defined by the coordinates deposited as PDB No. 4DAG.

FIG. 19 is a set of graphs showing immunization with pre-fusion HMPV F (subgroup B strain) or post-fusion HMPV F (subgroup A strain) or infection by HMPV CAN97-83 (a subgroup A virus) or HPMV CAN98-75 (a subgroup B virus). The elicited neutralizing activity was tested on HMPV, subgroup B strain CAN98-75 (top panel), and on HMPV, subgroup A strain CAN97-83 (bottom panel). The elicited neutralization titers indicate that the prefusion MPV protein is immunogenic and can elicit neutralization activity against subgroup A and subgroup B HMPV strains, and is particularly effective when used to boost immunity following natural MPV infection.

SEQUENCES

Figure 1A:
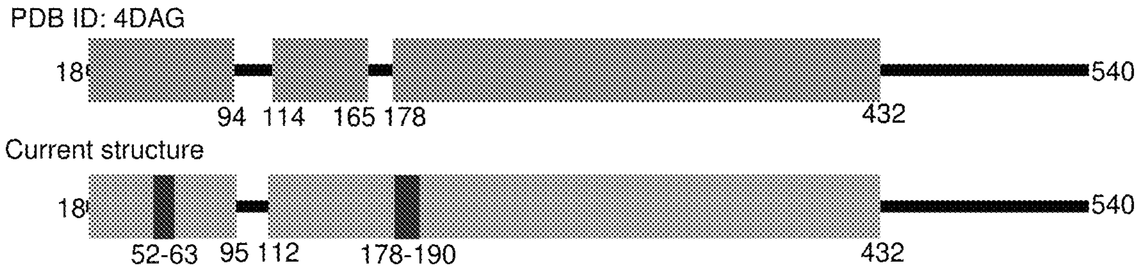
FIGS. 1A-1D show a set of diagrams illustrating the structure of HMPV F protein and a comparison of the previously published HMPV F protein structure with the corrected structure provided herein. A detailed analysis of a previously published structure of the MPV F protein (PDB ID 4DAG) revealed that the conformation of the membrane-distal aspect of the MPV F protein (a potential immunodominant site of vaccine interest) was incorrect. Correction of these errors through re-refinement of the deposited structure was used to obtain a corrected structural model of the prefusion form of the hMPV F glycoprotein. (A) Sequence mapping of HMPV F structural model. The corrected and re-refined HMPV F structure maps from residues 18-95 and 112-432 and has significant differences (>5 Å r.m.s.d.) at residues 52-63 and 178-190 (dark grey) allowing modeling of the membrane distal DIII domain and associated glycans N57 and N172. Glycan moieties linked to these sites were built into the electron density of the MPV F structure provided herein. Thicker bar represents modelled region of MPV F, thin bar represents unmodelled region, dark grey shows areas of >5 Å r.m.s.d. between the PDB 4DAG structure and the structure provided herein. (B) Corrected HMPV F protein ectodomain trimer structure in ribbon and molecular surface representations. Glycans are shown in sphere representation. (C) Surface diagram illustrating the corrected and re-refined MPV F protein ectodomain structure in its prefusion conformation. Using the PDB deposited structure in Buster-TNT, the original deposited structure R factor: 20.4% and Rfree: 23.2%, whereas R factor with new model: 18.8% and Rfree: 21.3%. (D) A single protomer is shown with terminal residues, domains and glycan sites highlighted.
Figure 1B:
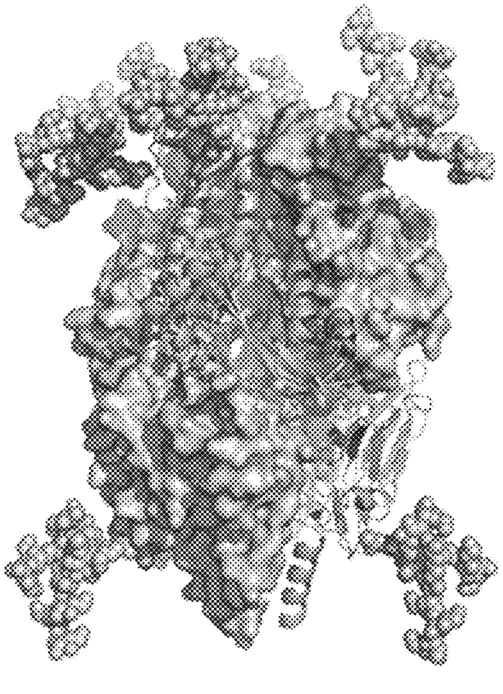
Figure 1C:
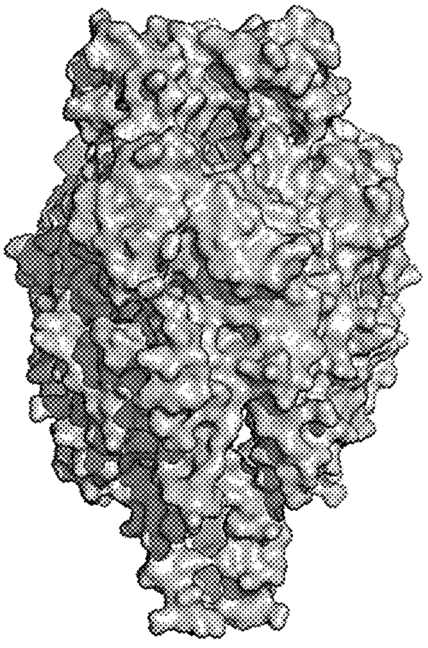
Figure 1D:
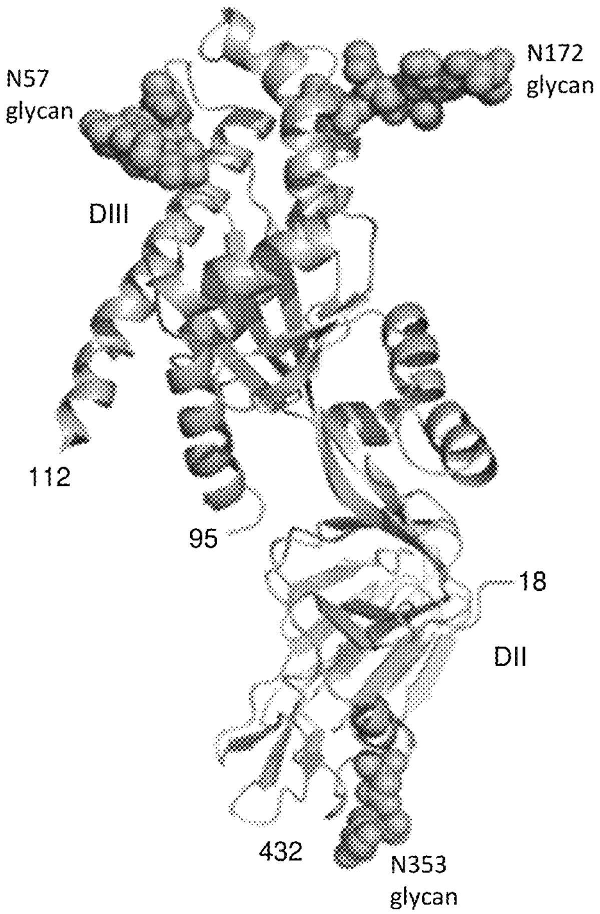

The nucleic and amino acid sequences are shown using standard letter abbreviations for nucleotide bases, and amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~460 kb), which was created on May 12, 2021, which is incorporated by reference herein. In the accompanying sequence listing:

SEQ ID NOs: 1-7 are the amino acid sequence of native MPV F proteins.

SEQ ID NOs: 8-11 and 82 are the amino acid sequences of protease cleavage sites.

SEQ ID NOs: 12-15 are the amino acid sequences of recombinant MPV F proteins.

SEQ ID NOs: 16-23 and 38 are the amino acid sequences of peptide linkers.

SEQ ID NOs: 24-32 and 83 are the amino acid sequences of residues 95-106 or residues 95-110 of recombinant MPV F proteins including modification of the native F protein sequence to generate a single chain F protein.

SEQ ID NOs: 33-37 are the amino acid sequences of trimerization domains.

SEQ ID NO: 39 is the amino acid sequence of a cleavable trimerization domain.

SEQ ID NOs: 40-50 and 84-100 are amino acid sequences including cysteine residues that can be used to introduce a cysteine ring to stabilize a trimeric protein.

SEQ ID NOs: 51-64 are the amino acid sequence of residues 468-478 of exemplary recombinant MPV F proteins including one or more non-native N-linked glycosylation sites.

SEQ ID NOs: 65-67 are exemplary nucleic acid sequences encoding recombinant MPV F proteins including A113C/A339C, T160F/I177L, or A113C/A339C/T160F/I177L amino acid substitutions, respectively.

SEQ ID NOs: 68-70 are the amino acid sequences of transmembrane domains.

SEQ ID NO: 71-74 are the amino acid sequences of protein nanoparticle subunits.

SEQ ID NO: 75 is the amino acid sequence of the RSV F protein ectodomain.

SEQ ID NOs: 76 and 77 are the amino acid sequences of the heavy and light chain variable regions of the DS7 antibody.

SEQ ID NOs: 78 and 79 are the amino acid sequences of the heavy and light chain variable regions of the MPE8 antibody.

SEQ ID NOs: 80-81 are the amino acid sequence of recombinant MPV F proteins linked to a trimerization domain.

SEQ ID NOs: 101-149 and 178-192 are exemplary amino acid sequences of recombinant MPV F ectodomains stabilized in a prefusion conformation by one or more amino acid substitutions.

SEQ ID NOs: 150-156 are exemplary amino acid sequences of oligomerization peptides.

SEQ ID NOs: 157-177 are exemplary amino acid sequences of recombinant MPV F ectodomains stabilized in a prefusion conformation by one or more amino acid substitutions and linked to a foldon trimerization domain and an oligomerization peptide.

Structural Coordinates

The atomic coordinates of the three-dimensional structure of an asymmetric unit of the structure of an MPV F ectodomain bound to DS7 Fab in the prefusion conformation described in Example 1 are recited in Table 1 of U.S. Provisional Patent Application No. 62/096,744, filed Dec. 24, 2014, which was submitted as an ASCII text file in the form of the file named "Table_1.txt" (~1 MB), was created on Dec. 23, 2014, and which is incorporated by reference herein in its entirety.

DETAILED DESCRIPTION

I. Summary of Terms

Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

234 Antibody: A neutralizing monoclonal antibody that specifically binds to an epitope on MPV F protein that is present on the pre- and post-fusion forms of the protein. The 234 antibody and methods for its production are described, for example, in Ulbrandt et al. (*J. Virology,* 80; p 7799, 2006), which is incorporated by reference herein in its entirety. The amino acid sequences of the heavy and light variable regions of the 234 antibody are provided as SEQ ID NOs: 2 and 18 of PCT App. No. WO2006110214, and have been deposited as ATCC deposit no. PTA6713, each of which is incorporated by reference herein as present in the database on Dec. 7, 2014.

338 Antibody: A neutralizing monoclonal antibody that specifically binds to an epitope on MPV F protein that is present on the pre- and post-fusion forms of the protein. The 338 antibody and methods for its production are described, for example, in Ulbrandt et al. (*J. Virology,* 80; p 7799, 2006), which is incorporated by reference herein in its entirety. The amino acid sequences of the heavy and light variable regions of the 338 antibody are provided as SEQ ID NOs: 10 and 26 of PCT App. No. WO2006110214, and have been deposited as ATCC deposit no. PTA6713, each of which is incorporated by reference herein as present in the database on Dec. 7, 2014).

Adjuvant: A vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL, immune stimulating complex (ISCOM) matrix, and toll-like receptor (TLR) agonists, such as TLR-9 agonists, Poly I:C, or PolyICLC. The person of ordinary skill in the art is familiar with adjuvants (see, e.g., Singh (ed.) Vaccine Adjuvants and Delivery Systems. Wiley-Interscience, 2007). Adjuvants can be used in combination with the disclosed MPV F immunogens.

Administration: The introduction of a composition into a subject by a chosen route. Administration can be local or systemic. For example, if the chosen route is intravenous, the composition (such as a composition including a disclosed immunogen) is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Agent: Any substance or any combination of substances that is useful for achieving an end or result; for example, a substance or combination of substances useful for inhibiting MPV infection in a subject. Agents include proteins, nucleic acid molecules, compounds, small molecules, organic compounds, inorganic compounds, or other molecules of interest. An agent can include a therapeutic agent (such as an anti-retroviral agent), a diagnostic agent or a pharmaceutical agent. In some embodiments, the agent is a protein agent (such as a recombinant MPV F polypeptide or immunogenic fragment thereof), or an anti-viral agent. The skilled artisan will understand that particular agents may be useful to achieve more than one result.

Amino acid substitutions: The replacement of one amino acid in a polypeptide with a different amino acid or with no amino acid (i.e., a deletion). In some examples, an amino acid in a polypeptide is substituted with an amino acid from a homologous polypeptide, for example, and amino acid in a recombinant group A MPV F polypeptide can be substituted with the corresponding amino acid from a group B MPV F polypeptide.

Antibody: A polypeptide that specifically binds and recognizes an analyte (antigen) such as MPV F or an antigenic fragment of MPV F. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space. The CDRs are primarily responsible for binding to an epitope of an antigen.

A "monoclonal antibody" is an antibody produced by a single clone of B-lymphocytes or by a cell into which nucleic acid encoding the light and heavy chains of a single antibody have been transfected, or a progeny thereof. Monoclonal antibodies are produced by methods known to those of skill in the art, for instance by making hybrid antibody-forming cells from a fusion of myeloma cells with immune spleen cells. These fused cells and their progeny are termed "hybridomas." In some examples monoclonal antibodies are isolated from a subject. Monoclonal antibodies can have conservative amino acid substitutions which have substantially no effect on antigen binding or other immunoglobulin functions. (See, for example, Harlow & Lane, *Antibodies, A Laboratory Manual,* $2^{nd}$ ed. Cold Spring Harbor Publications, New York (2013).)

Atomic Coordinates or Structure coordinates: Mathematical coordinates derived from mathematical equations related to the patterns obtained on diffraction of a monochromatic beam of X-rays by the atoms (scattering centers) such as an antigen, or an antigen in complex with an antibody. In some examples that antigen can be MPV F polypeptide (for example stabilized in a prefusion conformation by binding to a prefusion-specific antibody, or by introduction of stabilizing modifications) in a crystal. The diffraction data are used to calculate an electron density map of the repeating unit of the crystal. The electron density maps are used to establish the positions of the individual atoms within the unit cell of the crystal. In one example, the term "structure coordinates" refers to Cartesian coordinates derived from mathematical equations related to the patterns obtained on diffraction of a monochromatic beam of X-rays, such as by the atoms of a MPV F polypeptide in crystal form.

Those of ordinary skill in the art understand that a set of structure coordinates determined by X-ray crystallography is not without standard error. For the purpose of this disclosure, any set of structure coordinates that have a root mean square deviation of protein backbone atoms (N, Cα, C and O) of less than about 1.0 Angstroms when superimposed, such as about 0.75, or about 0.5, or about 0.25 Angstroms, using backbone atoms, shall (in the absence of an explicit statement to the contrary) be considered identical.

Cavity-filling amino acid substitution: An amino acid substitution that fills a cavity within the protein core of the MPV F protein. Cavities are essentially voids within a folded protein where amino acids or amino acid side chains are not present. In several embodiments, a cavity filling amino acid substitution is introduced to fill a cavity in the MPV F ectodomain core present in the prefusion conformation of MPV F ectodomain.

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, *Antibodies, A Laboratory Manual,* $2^{nd}$ ed. Cold Spring Harbor Publications, New York (2013) for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Conservative variants: "Conservative" amino acid substitutions are those substitutions that do not substantially affect or decrease a function of a protein, such as the ability of the protein to induce an immune response when administered to a subject. For example, a recombinant MPV F protein can include up to 1, 2, 3, 4, 5, 6, 7, 8, 9, 10, 15, 20, 25, or up to 30 conservative substitutions compared to a corresponding native MPV F protein sequence and induce an immune response to MPV F protein in a subject. The term conservative variation also includes the use of a substituted amino acid in place of an unsubstituted parent amino acid.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or function of the recombinant MPV F protein, such as the ability to induce an immune response when administered to a subject. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as a peptide, that contacts another polypeptide. Contacting can also include contacting a cell for example by placing a polypeptide in direct physical association with a cell.

Control: A reference standard. In some embodiments, the control is a negative control sample obtained from a healthy patient. In other embodiments, the control is a positive control sample obtained from a patient diagnosed with MPV infection. In still other embodiments, the control is a historical control or standard reference value or range of values (such as a previously tested control sample, such as a group of MPV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

DS7 Antibody: A neutralizing monoclonal antibody that specifically binds to an epitope on MPV F protein that is present on the pre- and post-fusion conformations of the MPV F protein. The DS7 antibody does not specifically bind to MPV F in its postfusion conformation. The DS7 antibody and methods for its production are described, for example, in Wen et al., *Nat. Struct. Mol. Biol.,* 19, 461-463, 2012, which is incorporated by reference herein in its entirety. The amino acid sequences of the heavy and light variable regions of the DS7 antibody are provided as SEQ ID NOs: 76 and 77, and have been deposited in PDB as Nos. 4DAG_H (DS7 $V_H$) and 4DAG_L (DS7 $V_L$), each of which is incorporated by reference herein as present in the database on Nov. 10, 2014).

(SEQ ID NO: 76)
DS7 $V_H$ - EVQLLESGGGLVQPGGSRRLSCAASGFTVSSSYMSWVRQTPG

KGLEWISVFYSGGTTYYADAVKGRFSISMDTSKNTLHLQMNSLRVEDTAI

YYCARVLSRASGMPDAFDIWGPGTMVTVSS (SEQ ID NO: 77)
DS7 $V_L$ - ELALIQPASVSVSPGQTASITCSGDKLGDKYASWYQQKPG

QSPVLVIYQDSERPSGIPERFSGSNSGNTATLTISGTQAMDEADYY

CQAWDSSTAVFGGGTTLTVLGQ

Degenerate variant: In the context of the present disclosure, a "degenerate variant" refers to a polynucleotide encoding a polypeptide (such as a recombinant MPV F protein or immunogenic fragment thereof) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detecting: To identify the existence, presence, or fact of something. General methods of detecting are known to the skilled artisan and may be supplemented with the protocols and reagents disclosed herein. For example, included herein are methods of detecting the level of a protein in a sample or a subject.

Epitope: An antigenic determinant. These are particular chemical groups or peptide sequences on a molecule that are antigenic, such that they elicit a specific immune response, for example, an epitope is the region of an antigen to which B and/or T cells respond. An antibody can bind to a particular antigenic epitope, such as an epitope on MPV F.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Heterologous: Originating from a different genetic source. A nucleic acid molecule that is heterologous to a cell originated from a genetic source other than the cell in which it is expressed. In one specific, non-limiting example, a heterologous nucleic acid molecule encoding a recombinant MPV F polypeptide is expressed in a cell, such as a mammalian cell. Methods for introducing a heterologous nucleic acid molecule in a cell or organism are well known in the art, for example transformation with a nucleic acid, including electroporation, lipofection, particle gun acceleration, and homologous recombination.

Ferritin: A protein that stores iron and releases it in a controlled fashion. The protein is produced by almost all living organisms. Ferritin polypeptides assemble into a globular protein complex of 24 protein subunits, each of the 24 subunits includes a single ferritin polypeptide. In some examples, ferritin is used to form a nanoparticle presenting antigens on its surface, for example, an MPV antigen.

Foldon domain: An amino acid sequence that naturally forms a trimeric structure. In some examples, a foldon domain can be included in the amino acid sequence of a disclosed recombinant protein so that the antigen will form a trimer. In one example, a foldon domain is the T4 foldon domain including the amino acid sequence set forth as (GYIPEAPRDGQAYVRKDGEWVLLSTF, SEQ ID NO: 33). Several embodiments include a foldon domain that can be cleaved from a purified protein, for example by incorporation of a thrombin cleave site adjacent to the foldon domain that can be used for cleavage purposes.

Glycosylation site: An amino acid sequence on the surface of a polypeptide, such as a protein, which accommodates the attachment of a glycan. An N-linked glycosylation site is triplet sequence of NX(S/T) in which N is asparagine, X is any residues except proline, and (S/T) is a serine or threonine residue. A glycan is a polysaccharide or oligosaccharide. Glycan may also be used to refer to the carbohydrate portion of a glycoconjugate, such as a glycoprotein, glycolipid, or a proteoglycan.

Homologous proteins: Proteins that have a similar structure and function, for example, proteins from two or more species or viral strains that have similar structure and function in the two or more species or viral strains. For example a MPV F protein from a group A virus is a homologous protein to a MPV F protein from a group B virus. Homologous proteins share similar protein folding characteristics and can be considered structural homologs.

Homologous proteins typically share a high degree of sequence conservation, such as at least 80%, at least 90%, at least 91%, at least 92%, at least 93%, at least 94%, or at least 95%, at least 96%, at least 97%, at least 98%, or at least 99% sequence conservation, and a high degree of sequence identity, such as at least 80%, at least 90%, at least 91%, at least 92%, at least 93%, at least 94%, or at least 95%, at least 96%, at least 97%, at least 98%, or at least 99% sequence identity.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to pre-treatment of a subject with an adjuvant to increase the desired immune response to a later administered immunogenic agent. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immunogen: A compound, composition, or substance that can stimulate the production of antibodies or a T cell response in an animal, including compositions that are injected or absorbed into an animal. An immunogen reacts with the products of specific humoral or cellular immunity, including those induced by heterologous antigens, such as the disclosed recombinant MPV F proteins. An immunogen can include one or more epitopes.

In some embodiments, an immunogen can be a recombinant MPV F protein or immunogenic fragment thereof, a protein nanoparticle or virus-like particle including the recombinant MPV F protein or immunogenic fragment thereof, or nucleic acid or vector encoding the recombinant MPV F protein or immunogenic fragment thereof, that is capable of inducing an immune response in a mammal, such as a mammal infected or at risk of infection with a pathogen. Administration of an immunogen to a subject can lead to protective immunity and/or proactive immunity against a pathogen of interest.

Immunogenic composition: A composition comprising an immunogen that induces a measurable CTL response against an antigen, or induces a measurable B cell response (such as production of antibodies) against an antigen, included on the immunogen or encoded by a nucleic acid molecule included in the immunogen. In one example, an immunogenic composition is a composition that includes a disclosed recombinant MPV F polypeptide or immunogenic fragment thereof, that induces a measurable CTL response against an MPV virus, or induces a measurable B cell response (such as production of antibodies) against a MPV F polypeptide when administered to a subject. An immunogenic composition can include isolated nucleic acids encoding an antigen, such as a nucleic acid that can be used to express the antigen (and thus be used to elicit an immune response against this peptide). Thus, in another example, an immunogenic composition is a composition that includes a nucleic acid molecule encoding a disclosed recombinant MPV F polypeptide or immunogenic fragment thereof, that induces a measurable CTL response against an MPV virus, or induces a measurable B cell response (such as production of antibodies) against a MPV F polypeptide when administered to a subject.

For in vivo use, the immunogenic composition will typically include an immunogenic polypeptide or nucleic acid molecule encoding an immunogenic polypeptide in a pharmaceutically acceptable carrier and may also include other agents, such as an adjuvant. Any particular polypeptide, such as a disclosed recombinant MPV F protein or a nucleic acid encoding the protein, can be readily tested for its ability to induce a CTL or B cell response by art-recognized assays.

Immunogenic polypeptide: A polypeptide which comprises an allele-specific motif, an epitope, or other sequence such that the polypeptide will bind an MHC molecule and induce an immune response, such as a cytotoxic T lymphocyte ("CTL") response, and/or a B cell response (for example, antibody production), and/or a T-helper lymphocyte response against the antigen from which the immunogenic polypeptide is derived.

Isolated: An "isolated" biological component has been substantially separated or purified away from other biological components, such as other biological components in which the component naturally occurs, such as other chromosomal and extrachromosomal DNA, RNA, and proteins. Proteins, peptides and nucleic acids that have been "isolated" include proteins purified by standard purification methods. The term also embraces proteins or peptides prepared by recombinant expression in a host cell as well as chemically synthesized proteins, peptides and nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated. The MPV F proteins disclosed herein that are stabilized in a prefusion conformation are isolated from MPV F proteins in a postfusion conformation, for example, are at least 80% isolated, at least 90%, 95%, 98%, 99%, or even 99.9% isolated from MPV F proteins in a postfusion conformation.

Linker: A bi-functional molecule that can be used to link two molecules into one contiguous molecule, for example, to link a carrier molecule to a immunogenic polypeptide. Non-limiting examples of peptide linkers include glycine-serine linkers, such as a gly-ser linker.

The terms "conjugating," "joining," "bonding," or "linking" can refer to making two molecules into one contiguous molecule; for example, linking two polypeptides into one contiguous polypeptide, or covalently attaching a carrier molecule or other molecule to an immunogenic polypeptide, such as an recombinant MPV F protein as disclosed herein. The linkage can be either by chemical or recombinant means. "Chemical means" refers to a reaction, for example, between the immunogenic polypeptide moiety and the carrier molecule such that there is a covalent bond formed between the two molecules to form one molecule.

Metapneumovirus (MPV): An enveloped non-segmented negative-sense single-stranded RNA virus of the family Paramyxoviridae. It is a common cause of lower respiratory tract infections, including bronchiolitis and pneumonia, among children and adults and infects nearly all humans by five years of age. MPV causes repeated infections including severe lower respiratory tract disease, which may occur at any age, especially among the elderly or those with compromised cardiac, pulmonary, or immune systems.

The MPV genome includes eight genes encoding nine proteins, including the glycoproteins SH, G and F. The F protein mediates fusion, allowing entry of the virus into the cell cytoplasm. Two groups of human MPV strains have been described, the A and B groups, which are further divided into subgroups A1, A2, B1, and B2. Exemplary MPV strain sequences are known to the person of ordinary skill in the art. Further, several models of human MPV infection are available, including model organisms infected with hMPV (see, e.g., Herfst et al., J General Virol., 88, 2702-2709, 2007; Bayon et al., Rev. Med. Virol., 2, 15-34, 2013; and Liu et al., Clinical Vaccine Immunol., 20, 1246-1254, 2013).

Methods of diagnosing MPV infection are known, including use of Direct Fluorescent Antibody detection (DFA), Chromatographic rapid antigen detection, and detection of viral RNA using RT PCR. Quantification of viral load can be determined, for example, by Plaque Assay, antigen capture enzyme immunoassay (EIA), or PCR. Quantification of antibody levels can be performed by subgroup-specific neutralization assay or ELISA. Current MPV treatment includes use of the anti-viral Ribaviran and passive administration of experimental monoclonal antibodies such as MPE8 (see, e.g., Corti et al., *Nature,* 501, 439-443, 2013) and mAb338 (Medimmune, Inc., see Hamelin et al., *Antiviral Res.,* 88, 31-37, 2010), which recognize the MPV F protein and reduces incidence of MPV infection and disease in animal models.

There are several subgroups of MPV, including groups A and B, and subgroups A1, A2, B1, and B2 in human MPV. Within the subgroups of MPV, there are individual strains of each subgroup. Sequences of F proteins from particular MPV strains are known and provided herein (see, e.g., Table 1).

MPV Fusion (F) protein: An MPV envelope glycoprotein that facilitates fusion of viral and cellular membranes. In nature, the MPV F protein is initially synthesized as a single polypeptide precursor approximately 540 amino acids in length, designated $F_0$. $F_0$ includes an N-terminal signal peptide that directs localization to the endoplasmic reticulum, where the signal peptide (approximately the first 18 residues of $F_0$) is proteolytically cleaved. The remaining $F_0$ residues oligomerize to form a trimer which is again processed at a protease site (between approximately Fopositions 102 and 103; for example, $RQSR_{102}$ (SEQ ID NO: 7, residues 99-102) to generate two disulfide-linked fragments, $F_1$ and $F_2$. The smaller of these fragments, $F_2$, originates from the N-terminal portion of the $F_0$ precursor and includes approximately residues 20-102 of $F_0$. The larger of these fragments, $F_1$, includes the C-terminal portion of the $F_0$ precursor (approximately residues 103-540) including an extracellular/lumenal region (~residues 103-490), a transmembrane domain (~residues 491-513), and a cytoplasmic domain (~residues 514-540) at the C-terminus.

Three $F_2$-$F_1$ protomers oligomerize in the mature F protein, which adopts a metastable "prefusion" conformation that is triggered to undergo a conformational change (to a "postfusion" conformation) upon contact with a target cell membrane. This conformational change exposes a hydrophobic sequence, known as the fusion peptide, which is located at the N-terminus of the $F_1$ polypeptide, and which associates with the host cell membrane and promotes fusion of the membrane of the virus, or an infected cell, with the target cell membrane.

The extracellular portion of the MPV F protein is the MPV F ectodomain, which includes the $F_2$ protein (approximately MPV F positions 20-102) and the $F_1$ ectodomain (approximately MPV F positions 103-490). An MPV F ectodomain trimer includes a protein complex of three MPV F ectodomains.

MPV $F_0$ polypeptide ($F_0$): The precursor of the MPV F protein, including the amino acids of a N-terminal signal peptide, a $F_2$ polypeptide, and a $F_1$ polypeptide including the $F_1$ extracellular domain, transmembrane domain and cytosolic tail. The native $F_0$ polypeptide is processed at a signal sequence cleavage site, and a protease site separating $F_1$ and $F_2$ (approximately Fopositions 102 and 103; for example, $RQSR_{102}$ (SEQ ID NO: 7, residues 99-102), resulting in the $F_1$ and $F_2$ fragments. Examples of $F_0$ polypeptides from different MPV subgroups are known, including from the A and B groups and A1, A2, B1, and B2 subgroups, examples of which are set forth herein as SEQ ID NOs: 1-7.

MPV $F_1$ polypeptide ($F_1$): A peptide chain of the MPV F protein. As used herein, "$F_1$ polypeptide" refers to both native $F_1$ polypeptides and $F_1$ polypeptides including modifications (e.g., amino acid substitutions, insertions, or deletion) from the native sequence. Native $F_1$ includes approximately residues 103-540 of the MPV $F_0$ precursor, and includes (from N- to C-terminus) an extracellular/lumenal region (~ residues 103-490), a transmembrane domain (~residues 491-513), and a cytoplasmic domain (~residues 514-540) at the C-terminus. Several embodiments include an $F_1$ polypeptide modified from a native $F_1$ sequence, for example an $F_1$ polypeptide that lacks the transmembrane and cytosolic domain, and/or includes one or more amino acid substitutions that stabilize a recombinant F protein (containing the $F_1$ polypeptide) in a prefusion conformation. In one example, a disclosed MPV F protein includes a $F_1$ polypeptide with deletion of the transmembrane and cytosolic domains, and a non-natural disulfide bond between A113C and A339C and/or T160F and I177L cavity filling substitutions that stabilize the F protein in a prefusion conformation.

MPV $F_2$ polypeptide ($F_2$): A polypeptide chain of the MPV F protein. As used herein, "$F_2$ polypeptide" refers to both native $F_2$ polypeptides and $F_2$ polypeptides including modifications (e.g., amino acid substitutions) from the native sequence, for example, modifications designed to stabilize a recombinant F protein (including the modified $F_2$ polypeptide) in a MPV F protein prefusion conformation. Native $F_2$ includes approximately residues 20-102 of the MPV $F_0$ precursor. In native MPV F protein, the $F_2$ polypeptide is linked to the $F_1$ polypeptide by two disulfide bonds.

Figure 2:
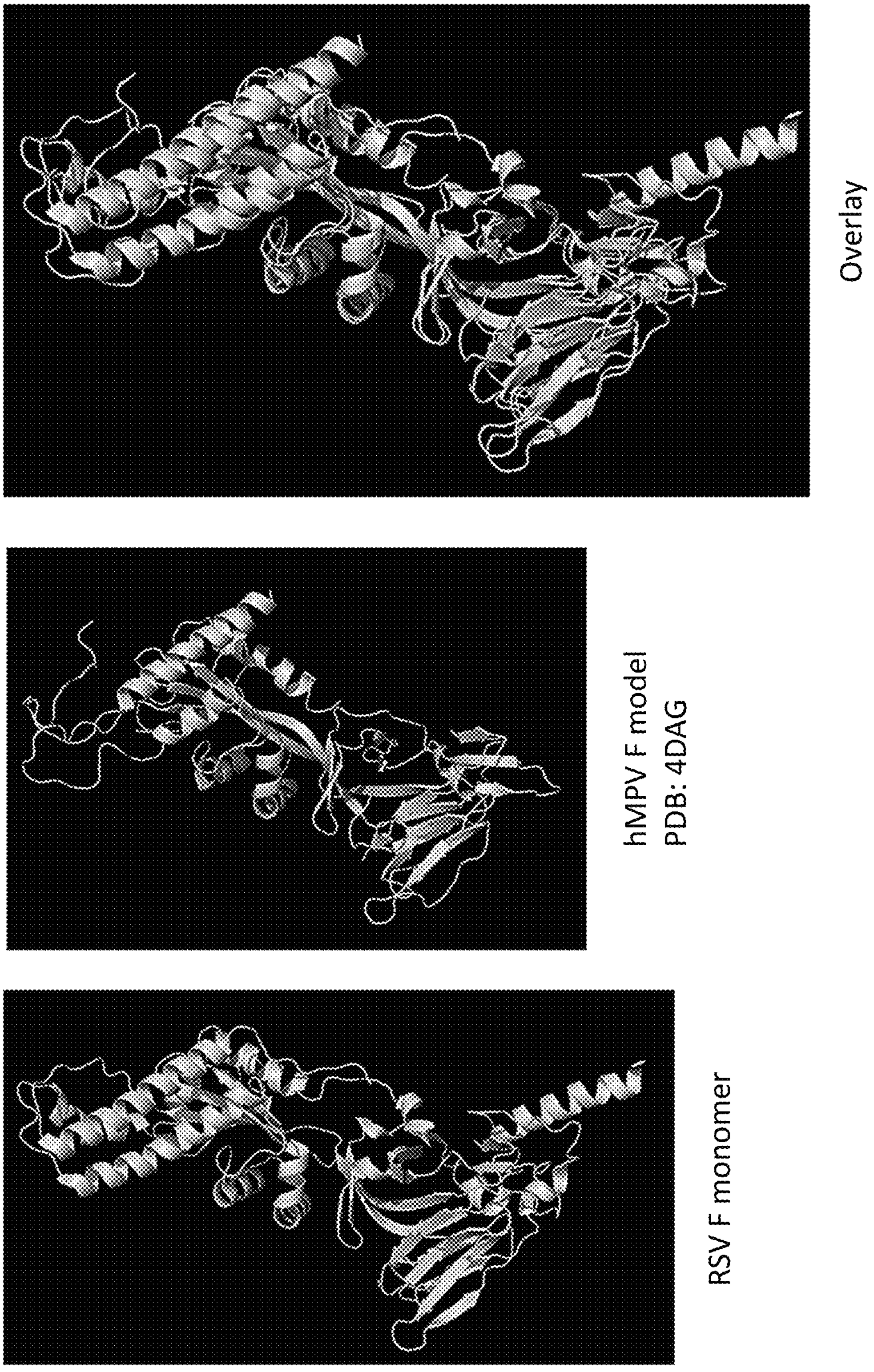
FIGS. 2 and 3 show a set of ribbon diagrams illustrating the three-dimensional structure of single RSV F ectodomain and MPV F ectodomain protomers in their prefusion conformations. The overlay image illustrates differences in the structures, particularly at the membrane distal apex.
Figure 3:
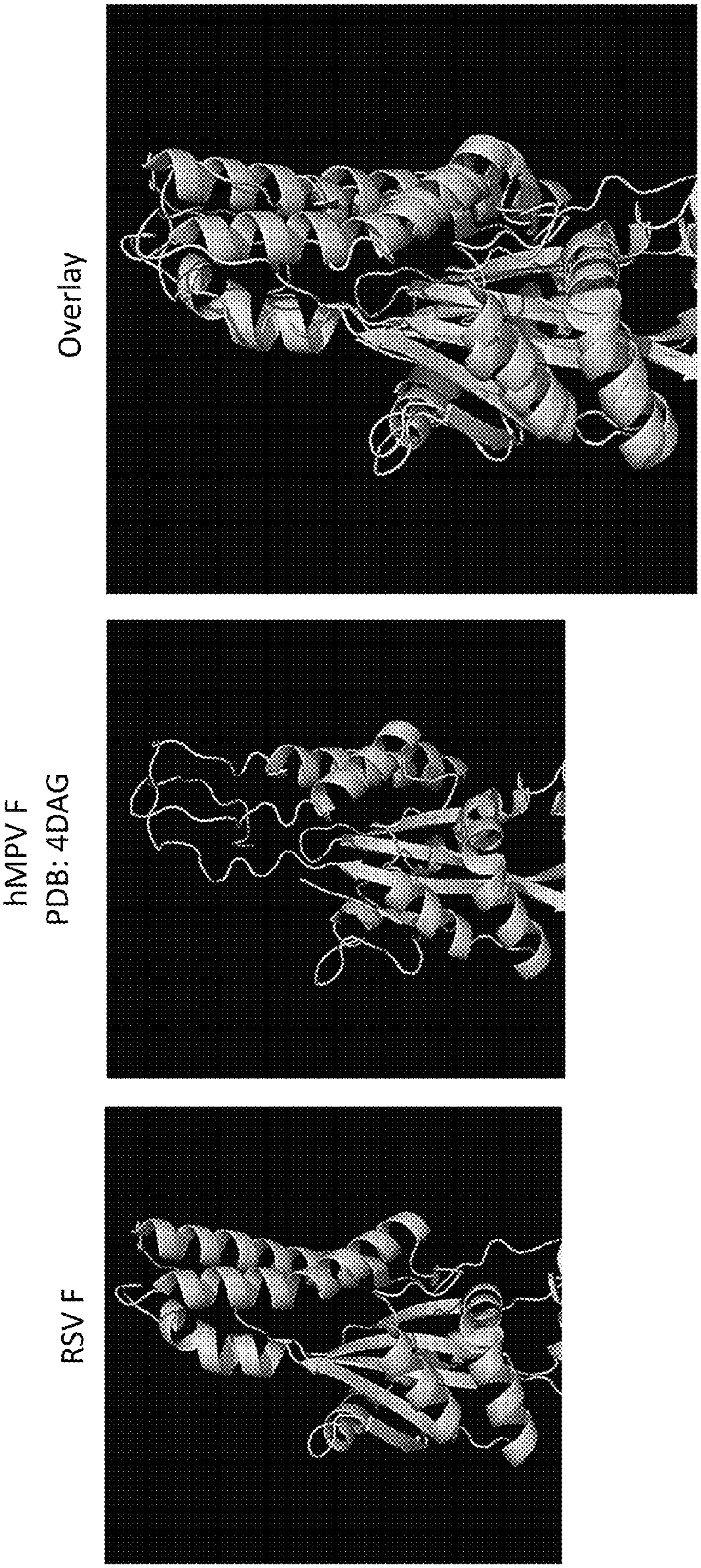
Figure 4:
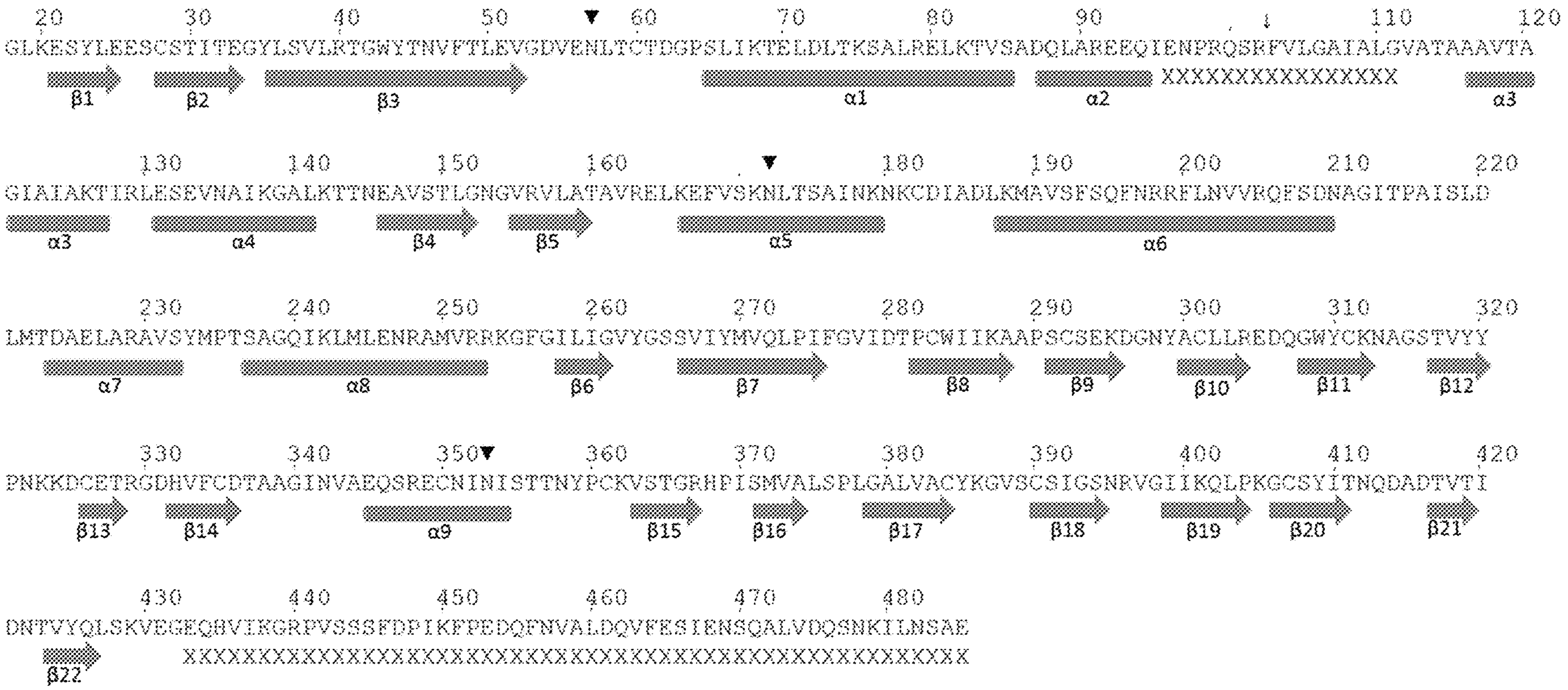
FIG. 4 shows the MPV F sequence (residues 18-485 of SEQ ID NO: 7) with the secondary structure elements identified in the new re-refined structure.

MPV F prefusion conformation: A structural conformation adopted by the MPV F protein prior to triggering of the fusogenic event that leads to transition of MPV F to the postfusion conformation and following processing into a mature MPV F protein in the secretory system. The three-dimensional structure of an exemplary MPV F protein in a prefusion conformation is disclosed herein (see Example 1). As shown herein, the prefusion conformation of MPV F is similar in overall structure to the prefusion conformation of the F protein of other paramyxoviruses (such as RSV, see FIGS. 1-3), though with some significant differences. In several embodiments, a recombinant MPV F protein stabilized in the prefusion conformation specifically binds to an antibody (such as MPE8 antibody) specific for the trimeric form of the MPV F ectodomain in the prefusion, but not postfusion, conformation.

MPE8 Antibody: A neutralizing monoclonal antibody that specifically binds to an epitope on MPV F protein that is present on the prefusion, but not the postfusion conformation, of the MPV F protein. Thus, the MPE8 antibody does not specifically bind to MPV F in its postfusion conformation. The MPE8 antibody and methods for its production are described, for example, in Corti et al. (Nature, 501, 439-443, 2013), which is incorporated by reference herein. The amino acid sequences of the heavy and light variable regions of the MPE8 antibody used herein are provided as SEQ ID NOs: 78 and 79. MPE8 heavy and light chain sequences have been deposited in GenBank as Nos. AGU13651.1 (MPE8 $V_H$) and AGU13652.1 (MPE8 $V_L$), each of which is incorporated by reference herein as present in the database on Nov. 10, 2014).

(SEQ ID NO: 78)
MPE8 $V_H$ - EVQLVESGGGLVKPGGSLRLSCAASGFTFSSYSMNWVRQA

PGKGLEWVSSISASSSYSDYADSAKGRFTISRDNAKTSLFLQMNSLRAE

DTAIYFCARARATGYSSITPYFDIWGQGTLVTVSS (SEQ ID NO: 79)
MPE8 $V_L$ - QSVVTQPPSVSGAPGQRVTISCTGSSSNIGAGYDVHWYQQ

LPGTAPKLLIYDNNNRPSGVPDRFSASKSGTSASLAITGLQAEDEADYY

CQSYDRSLSGVFGTGTKVTVL

Neutralizing antibody: An antibody which reduces the infectious titer of an infectious agent by binding to a specific antigen on the infectious agent. In some examples the infectious agent is a virus. In some examples, an antibody that is specific for MPV F neutralizes the infectious titer of MPV. A "broadly neutralizing antibody" is an antibody that binds to and inhibits the function of related antigens, such as antigens that share at least 85%, 90%, 95%, 96%, 97%, 98% or 99% identity antigenic surface of antigen. With regard to an antigen from a pathogen, such as a virus, the antibody can bind to and inhibit the function of an antigen from more than one class and/or subclass of the pathogen. For example, with regard to MPV, the antibody can bind to and inhibit the function of an antigen, such as MPV F from more than one group. In one embodiment, broadly neutralizing antibodies to MPV are distinct from other antibodies to MPV in that they neutralize a high percentage of the many types of MPV in circulation.

MPV broadly neutralizing antibody: An antibody that reduces the infectious titer of MPV by binding to and inhibiting the function of related MPV antigens, such as antigens that share at least 85%, 90%, 95%, 96%, 97%, 98% or 99% sequence identity with antigenic surface of the antigen. In some embodiments, broadly neutralizing antibodies to MPV are distinct from other antibodies to MPV in that they neutralize a high percentage (such as at least 50% or at least 80%) of the strains of MPV in circulation. A non-limiting example of an MPV broadly neutralizing antibody is the MPE8 antibody.

Native protein, sequence, or di-sulfide bond: A polypeptide, sequence or di-sulfide bond that has not been modified, for example by selective mutation. For example, selective mutation to focus the antigenicity of the antigen to a target epitope, or to introduce a di-sulfide bond into a protein that does not occur in the native protein. Native protein or native sequence are also referred to as wild-type protein or wild-type sequence. A non-native di-sulfide bond is a disulfide bond that is not present in a native protein, for example a di-sulfide bond that forms in a protein due to introduction of one or more cysteine residues into the protein by genetic engineering.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A first sequence is an "antisense" with respect to a second sequence if a polynucleotide whose sequence is the first sequence specifically hybridizes with a polynucleotide whose sequence is the second sequence.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed immunogens.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired anti-MPV immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide: Any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues.

In many instances, one or more polypeptides can fold into a specific three-dimensional structure including surface-exposed amino acid residues and non-surface-exposed amino acid residues. In some instances a protein can include multiple polypeptides that fold together into a functional unit. For example, the mature MPV F protein on the cell surface includes three $F_2/F_1$ heterodimers that trimerize in to a multimeric protein. "Surface-exposed amino acid residues" are those amino acids that have some degree of exposure on the surface of the protein, for example such that they can contact the solvent when the protein is in solution. In contrast, non-surface-exposed amino acids are those amino acid residues that are not exposed on the surface of the protein, such that they do not contact solution when the protein is in solution. In some examples, the non-surface-exposed amino acid residues are part of the protein core.

A "protein core" is the interior of a folded protein, which is substantially free of solvent exposure, such as solvent in the form of water molecules in solution. Typically, the protein core is predominately composed of hydrophobic or apolar amino acids. In some examples, a protein core may contain charged amino acids, for example aspartic acid, glutamic acid, arginine, and/or lysine. The inclusion of uncompensated charged amino acids (a compensated charged amino can be in the form of a salt bridge) in the protein core can lead to a destabilized protein. That is, a protein with a lower Tm then a similar protein without an uncompensated charged amino acid in the protein core. In other examples, a protein core may have a cavity within the protein core. Cavities are essentially voids within a folded protein where amino acids or amino acid side chains are not present. Such cavities can also destabilize a protein relative to a similar protein without a cavity. Thus, when creating a stabilized form of a protein, it may be advantageous to substitute amino acid residues within the core in order to fill cavities present in the wild-type protein.

Amino acids in a peptide, polypeptide or protein generally are chemically bound together via amide linkages (CONH). Additionally, amino acids may be bound together by other chemical bonds. For example, linkages for amino acids or amino acid analogs can include $CH_2NH$—, —$CH_2S$—, —$CH_2$—$CH_2$—, —CH═CH— (cis and trans), —$COCH_2$—, —$CH(OH)CH_2$—, and —$CHH_2SO$—(These and others can be found in Spatola, in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci pp. 463-468, 1980; Hudson, et al., *Int J Pept Prot Res* 14:177-185, 1979; Spatola et al. *Life Sci* 38:1243-1249, 1986; Harm *J. Chem. Soc Perkin Trans.*

1307-314, 1982; Almquist et al. *J. Med. Chem.* 23:1392-1398, 1980; Jennings-White et al. *Tetrahedron Lett* 23:2533, 1982; Holladay et al. *Tetrahedron. Lett* 24:4401-4404, 1983; and Hruby Life Sci 31:189-199, 1982.

Polypeptide modifications: Polypeptides and peptides, such as the recombinant MPV F proteins disclosed herein can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Prime-boost vaccination: An immunotherapy including administration of a first immunogenic composition (the primer vaccine) followed by administration of a second immunogenic composition (the booster vaccine) to a subject to induce an immune response. The booster vaccine is administered to the subject after the primer vaccine; the skilled artisan will understand a suitable time interval between administration of the primer vaccine and the booster vaccine, and examples of such timeframes are disclosed herein. Additional administrations can be included in the prime-boost protocol, for example a second boost. In some embodiments, the primer vaccine, the booster vaccine, or both primer vaccine and the booster vaccine additionally include an adjuvant. In one non-limiting example, the primer vaccine is a DNA-based vaccine (or other vaccine based on gene delivery), and the booster vaccine is a protein-based vaccine (such as a protein subunit or protein nanoparticle).

Protein nanoparticle: A multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. *Int. J. Mol. Sci.,* 12:5406-5421, 2011, incorporated by reference herein), encapsulin nanoparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., *J. Mol. Biol.,* 306: 1099-1114, 2001) or pyruvate dehydrogenase nanoparticles (see, e.g., Izard et al., PNAS 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. In some examples, ferritin, encapsulin, SOR, lumazine synthase, or pyruvate dehydrogenase monomers are linked to a recombinant MPV F protein and self-assemble into a protein nanoparticle presenting the recombinant MPV F protein on its surface, which can be administered to a subject to stimulate an immune response to the antigen.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Root mean square deviation (RMSD): The square root of the arithmetic mean of the squares of the deviations from the mean. In several embodiments, RMSD is used as a way of expressing deviation or variation from the structural coordinates of a reference three dimensional structure. This number is typically calculated after optimal superposition of two structures, as the square root of the mean square distances between equivalent $C_\alpha$ atoms.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Com-*

*puter Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 amino acids is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

As used herein, reference to "at least 80% identity" refers to "at least 80%, at least 85%, at least 90%, at least 91%, at least 92%, at least 93%, at least 94%, at least 95%, at least 96%, at least 97%, at least 98%, at least 99%, or even 100% identity" to a specified reference sequence. As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence.

Single chain MPV F protein: A recombinant MPV F protein that is expressed as a single polypeptide chain including the MPV $F_1$ ectodomain and the MPV $F_2$ polypeptide. The single chain MPV F protein can trimerize to form a trimeric MPV F protein. A single chain MPV F protein does not include a protease cleave site between the $F_1$ and $F_2$ polypeptides and is not cleaved into separate $F_1$ and $F_2$ polypeptides when produced in cells. In one embodiment, MPV F positions 98 and 103 are linked with a heterologous peptide linker to generate the single chain construction.

Signal Peptide: A short amino acid sequence (e.g., approximately 18-25 amino acids in length) that directs newly synthesized secretory or membrane proteins to and through membranes (for example, the endoplasmic reticulum membrane). Signal peptides are typically located at the N-terminus of a polypeptide and are removed by signal peptidases after the polypeptide has crossed the membrane. Signal peptide sequences typically contain three common structural features: an N-terminal polar basic region (n-region), a hydrophobic core, and a hydrophilic c-region). An exemplary signal peptide sequence is set forth as residues 1-18 of SEQ ID NO: 7 (MPV F protein signal peptide).

Specifically bind: When referring to the formation of an antibody:antigen protein complex, or a protein:protein complex, refers to a binding reaction which determines the presence of a target protein, peptide, or polysaccharide (for example a glycoprotein), in the presence of a heterogeneous population of proteins and other biologics. Thus, under designated conditions, a particular antibody or protein binds preferentially to a particular target protein, peptide or polysaccharide (such as an antigen present on the surface of a pathogen, for example MPV F protein) and does not bind in a significant amount to other proteins or polysaccharides present in the sample or subject. Specific binding can be determined by methods known in the art. A first protein or antibody "specifically binds" to a target protein when the interaction has a $K_D$ of less than about $10^{-6}$ Molar, such as less than about $10^{-7}$ Molar, $10^{-8}$ Molar, $10^{-9}$, or even less than about $10^{-10}$ Molar. In some embodiments, an antibody does not specifically bind to a disclosed recombinant MPV F protein if the binding interaction of the antibody to trimer has a $K_D$ of more than $10^{-6}$ when assayed at stoichiometry of at least one antibody Fab per protomer in the trimer.

Subject: Living multi-cellular vertebrate organisms, a category that includes human and non-human mammals. In an example, a subject is a human. In a particular example, the subject is a newborn infant. In an additional example, a subject is selected that is in need of inhibiting of an MPV infection. For example, the subject is either uninfected and at risk of MPV infection or is infected in need of treatment.

Therapeutically effective amount: The amount of agent, such as a disclosed immunogen or immunogenic composition that is sufficient to prevent, treat (including prophylaxis), reduce and/or ameliorate the symptoms and/or underlying causes of a disorder or disease, for example to prevent, inhibit, and/or treat MPV infection. In some embodiments, a therapeutically effective amount is sufficient to reduce or eliminate a symptom of a disease, such as MPV infection. For instance, this can be the amount necessary to inhibit or prevent viral replication or to measurably alter outward symptoms of the viral infection. In general, this amount will be sufficient to measurably inhibit virus replication or infectivity.

In one example, a desired response is to inhibit or reduce or prevent MPV infection. The MPV infection does not need to be completely eliminated or reduced or prevented for the method to be effective. For example, administration of a therapeutically effective amount of the agent can decrease the MPV infection (for example, as measured by infection of cells, or by number or percentage of subjects infected by MPV) by a desired amount, for example by at least 10%, at least 20%, at least 50%, at least 60%, at least 70%, at least 80%, at least 90%, at least 95%, at least 98%, or even at least 100% (elimination or prevention of detectable MPV infection, as compared to a suitable control.

It is understood that to obtain a protective immune response against a pathogen can require multiple administrations of the immunogenic composition. Thus, a therapeutically effective amount encompasses a fractional dose that contributes in combination with previous or subsequent administrations to attaining a protective immune response. For example, a therapeutically effective amount of an agent can be administered in a single dose, or in several doses, for example daily, during a course of treatment (such as a prime-boost vaccination treatment). However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Transmembrane domain: An amino acid sequence that inserts into a lipid bilayer, such as the lipid bilayer of a cell or virus or virus-like particle. A transmembrane domain can be used to anchor an antigen to a membrane. In some examples a transmembrane domain is a MPV F transmembrane domain. Exemplary MPV F transmembrane domains are familiar to the person of ordinary skill in the art, and provided herein, for example as residues 491-513 of SEQ ID NO: 2.

Treating or preventing a disease: Inhibiting the full development of a disease or condition, for example, in a subject who is at risk of or has a disease such as an MPV infection. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

The term "reduces" is a relative term, such that an agent reduces a disease or condition if the disease or condition is quantitatively diminished following administration of the agent, or if it is diminished following administration of the agent, as compared to a reference agent. Similarly, the term "prevents" does not necessarily mean that an agent completely eliminates the disease or condition, so long as at least one characteristic of the disease or condition is eliminated. Thus, an immunogenic composition that reduces or prevents an infection, can, but does not necessarily completely, eliminate such an infection, so long as the infection is measurably diminished, for example, by at least about 50%, such as by at least about 70%, or about 80%, or even by about 90% the infection in the absence of the agent, or in comparison to a reference agent.

Under conditions sufficient for: A phrase that is used to describe any environment that permits a desired activity.

Vaccine: A pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In one specific, non-limiting example, a vaccine reduces the severity of the symptoms associated with MPV infection and/or decreases the viral load compared to a control. In another non-limiting example, a vaccine reduces MPV infection compared to a control.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. A replication deficient viral vector is a vector that requires complementation of one or more regions of the viral genome required for replication due to a deficiency in at least one replication-essential gene function. For example, such that the viral vector does not replicate in typical host cells, especially those in a human patient that could be infected by the viral vector in the course of a therapeutic method.

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) *Biophys. J.* 60:1445-1456; and Hagensee et al. (1994) *J. Virol.* 68:4503-4505; Vincente, *J Invertebr Pathol.,* 2011; Schneider-Ohrum and Ross, *Curr. Top. Microbiol. Immunol.,* 354: 53073, 2012).

II. Description of Several Embodiments

The MPV F trimer is understood to undergo dramatic structural rearrangement between its prefusion and postfusion conformations. In the prefusion conformation, the MPV F trimer includes a "cap" at its membrane distal apex, with the three protomers of the F trimer coming together, and the N-terminus of the $F_1$ polypeptide (which includes the fusion peptide that is inserted in to target cell membrane) buried in the core of the F protein trimer. In the postfusion conformation, F protein trimer forms a cylindrical shape, with rearrangements of the fusion peptide extending distally.

Recombinant MPV F proteins are provided that are stabilized or "locked" in the prefusion conformation. Using structure-guided design, positions of the MPV F protein were targeted for modification (e.g., amino acid substitution) to hinder or prevent a trimer of the recombinant MPV F proteins from transitioning from the prefusion conformation to the postfusion conformation. Such proteins have utility, for example, as immunogens to induce a neutralizing immune response to MPV.

A. Immunogens

1. Native hMPV Sequences

MPV can be classified into two group: A and B. Groups A and B include subgroups A1, A2, B1, and B2, based mainly on sequence variability of the attachment (G) and fusion (F) proteins. The disclosed recombinant MPV F proteins can be derived from any group (such as Group A or Group B) or subgroup of MPV, such as subgroup A1, A2, B1, or B2. Exemplary native hMPV F protein sequences and a corresponding GenBank or Uniprot Accession Number (which are incorporated by reference herein in its entirety) are set forth in Table 1.

TABLE 1

Exemplary Native hMPV F sequences

| Strain | Sub Group | F sequence |
|---|---|---|
| NL/1/00 | A1 | MSWKVVIIFSLLITPQHGLKESYLEESCSTITEGYLSVLRTGWYTNVFTLEVGDVENLTCADGPS<br>LIKTELDLTKSALRELRTVSADQLAREEQIENPRQSRFVLGAIALGVATAAAVTAGVAIAKTIRL<br>ESEVTAIKNALKKTNEAVSTLGNGVRVLATAVRELKDFVSKNLTRAINKNKCDIADLKMAVSFSQ<br>FNRRFLNVVRQFSDNAGITPAISLDLMTDAELARAVSNMPTSAGQIKLMLENRAMVRRKGFGFLI<br>GVYGSSVIYMVQLPIFGVIDTPCWIVKAAPSCSGKKGNYACLLREDQGWYCQNAGSTVYYPNEKD<br>CETRGDHVFCDTAAGINVAEQSKECNINISTTNYPCKVSTGRHPISMVALSPLGALVACYKGVSC<br>SIGSNRVGIIKQLNKGCSYITNQDADTVTIDNTVYQLSKVEGEQHVIKGRPVSSSFDPVKFPEDQ<br>FNVALDQVFESIENSQALVDQSNRILSSAEKGNTGFIIVIILIAVLGSTMILVSVFIIIKKTKKP<br>TGAPPELSGVTNNGFIPHN (SEQ ID NO: 1, GenBank: AAK62968.2) |
| CAN97-83 | A2 | MSWKVVIIFSLLITPQHGLKESYLEESCSTITEGYLSVLRTGWYTNVFTLEVGDVENLTCSDGPS<br>LIKTELDLTKSALRELKTVSADQLAREEQIENPRQSRFVLGAIALGVATAAAVTAGVAIAKTIRL<br>ESEVTAIKNALKTTNEAVSTLGNGVRVLATAVRELKDFVSKNLTRAINKNKCDIDDLKMAVSFSQ<br>FNRRFLNVVRQFSDNAGITPAISLDLMTDAELARAVSNMPTSAGQIKLMLENRAMVRRKGFGILI<br>GVYGSSVIYMVQLPIFGVIDTPCWIVKAAPSCSGKKGNYACLLREDQGWYCQNAGSTVYYPNEKD<br>CETRGDHVFCDTAAGINVAEQSKECNINISTTNYPCKVSTGRHPISMVALSPLGALVACYKGVSC<br>SIGSNRVGIIKQLNKGCSYITNQDADTVTIDNTVYQLSKVEGEQHVIKGRPVSSSFDPIKFPEDQ<br>FNVALDQVFENIENSQALVDQSNRILSSAEKGNTGFIIVIILIAVLGSSMILVSIFIIIKKTKKP<br>TGAPPELSGVTNNGFIPHS (SEQ ID NO: 2, Uniprot Q6WB98) |
| NL/17/00 | A2 | MSWKVVIIFSLLITPQHGLKESYLEESCSTITEGYLSVLRTGWYTNVFTLEVGDVENLTCSDGPS<br>LIKTELDLTKSALRELKTVSADQLAREEQIENPRQSRFVLGAIALGVATAAAVTAGVAIAKTIRL<br>ESEVTAIKNALKTTNEAVSTLGNGVRVLATAVRELKDFVSKNLTRAINKNKCDIDDLKMAVSFSQ<br>FNRRFLNVVRQFSDNAGITPAISLDLMTDAELARAVSNMPTSAGQIKLMLENRAMVRRKGFGILI<br>GVYGSSVIYTVQLPIFGVIDTPCWIVKAAPSCSEKKGNYACLLREDQGWYCQNAGSTVYYPNEKD<br>CETRGDHVFCDTAAGINVAEQSKECNINISTTNYPCKVSTGRHPISMVALSPLGALVACYKGVSC<br>SIGSNRVGIIKQLNKGCSYITNQDADTVTIDNTVYQLSKVEGEQHVIKGRPVSSSFDPIKFPEDQ<br>FNVALDQVFENIENSQALVDQSNRILSSAEKGNTGFIIVIILIAVLGSSMILVSIFIIIKKTKKP<br>TGAPPELSGVTNNGFIPHS (SEQ ID NO: 3, GenBank: AY304360.1) |
| NCL174 | A2 | MSWKVVIIFSLLITPQHSLKESYLEESCSTITEGYLSVLRTGWYTNVFTLEVGDVENLTCADGPS<br>LIKTELDLTKSALRELKPVSADQLAREEQIENPRQSRFVLGAIALGVATAAAVTAGVAIAKTIRL<br>ESEVTAIKNALKKTNEAVSTLGNGVRVLATAVRELKDFVSKNLTRAINKNKCDIDDLKMAVSFSQ |

TABLE 1-continued

Exemplary Native hMPV F sequences

| Strain | Sub Group | F sequence |
|---|---|---|
| | | FNRRFLNVVRQFSDNAGITPAISLDLMTDAELARAVSNMPTAAGQIKLMLENRAMVRRKGFGILI GVYGSSVIYMVQLPIFGVIDTPCWIVKAAPSCSEKKGNYACLLREDQGWYCQNAGSTVYYPNEKD CETRGDHVFCDTAAGINVAEQSKECNINISTTNYPCKVSTGRHPISMVALSPLGALVACYKGVSC SIGSNRVGIIKQLNKGCSYITNQDADTVTIDNTVYQLSKVEGEQHVIKGRPVSSSFDPVKFPEDQ FNVALDQVFENIENSQALVDQSNRILSSAEKGNTGFIIVIILIAVLGSSMILVSVFIIIKKTRKP TGAPPELSGVTNNGFIPHS (SEQ ID NO: 4, Uniprot G0ZRI7) |
| NL/1/99 | B1 | MSWKVMIIISLLITPQHGLKESYLEESCSTITEGYLSVLRTGWYTNVFTLEVGDVENLTCTDGPS LIKTELDLTKSALRELKTVSADQLAREEQIENPRQSRFVLGAIALGVATAAAVTAGIAIAKTIRL ESEVNAIKGALKQTNEAVSTLGNGVRVLATAVRELKEFVSKNLTSAINRNKCDIADLKMAVSFSQ FNRRFLNVVRQFSDNAGITPAISLDLMTDAELARAVSYMPTSAGQIKLMLENRAMVRRKGFGILI GVYGSSVIYMVQLPIFGVIDTPCWIIKAAPSCSEKNGNYACLLREDQGWYCKNAGSTVYYPNEKD CETRGDHVFCDTAAGINVAEQSRECNINISTTNYPCKVSTGRHPISMVALSPLGALVACYKGVSC SIGSNWVGIIKQLPKGCSYITNQDADTVTIDNTVYQLSKVEGEQHVIKGRPVSSSFDPIKFPEDQ FNVALDQVFESIENSQALVDQSNKILNSAEKGNTGFIIVVILVAVLGLTMISVSIIIIIKKTRKP TGAPPELNGVTNGGFIPHS (SEQ ID NO: 5, GenBank: AY304361.1) |
| NDL00-1 | B1 | MSWKVVIIFSLLITPQHGLKESYLEESCSTITEGYLSVLRTGWYTNVFTLEVGDVENLTCADGPS LIKTELDLTKSALRELRTVSADQLAREEQIENPRQSRFVLGAIALGVATAAAVTAGVAIAKTIRL ESEVTAIKNALKKTNEAVSTLGNGVRVLATAVRELKDFVSKNLTRAINKNKCDIADLKMAVSFSQ FNRRFLNVVRQFSDNAGITPAISLDLMTDAELARAVSNMPTSAGQIKLMLENRAMVRRKGFGFLI GVYGSSVIYMVQLPIFGVIDTPCWIVKAAPSCSGKKGNYACLLREDQGWYCQNAGSTVYYPNEKD CETRGDHVFCDTAAGINVAEQSKECNINISTTNYPCKVSTGRHPISMVALSPLGALVACYKGVSC SIGSNRVGIIKQLNKGCSYITNQDADTVTIDNTVYQLSKVEGEQHVIKGRPVSSSFDPVKFPEDQ FNVALDQVFESIENSQALVDQSNRILSSAEKGNTGFIIVIILIAVLGSTMILVSVFIIIKKTKKP TGAPPELSGVTNNGFIPHN (SEQ ID NO: 6, GenBank: AAK62968.2) |
| CAN98-75 | B2 | MSWKVMIIISLLITPQHGLKESYLEESCSTITEGYLSVLRTGWYTNVFTLEVGDVENLTCTDGPS LIKTELDLTKSALRELKTVSADQLAREEQIENPRQSRFVLGAIALGVATAAAVTAGIAIAKTIRL ESEVNAIKGALKTTNEAVSTLGNGVRVLATAVRELKEFVSKNLTSAINKNKCDIADLKMAVSFSQ FNRRFLNVVRQFSDNAGITPAISLDLMTDAELARAVSYMPTSAGQIKLMLENRAMVRRKGFGILI GVYGSSVIYMVQLPIFGVIDTPCWIIKAAPSCSEKDGNYACLLREDQGWYCKNAGSTVYYPNKKD CETRGDHVFCDTAAGINVAEQSRECNINISTTNYPCKVSTGRHPISMVALSPLGALVACYKGVSC SIGSNRVGIIKQLPKGCSYITNQDADTVTIDNTVYQLSKVEGEQHVIKGRPVSSSFDPIKFPEDQ FNVALDQVFESIENSQALVDQSNKILNSAEKGNTGFIIVIILIAVLGLTMISVSIIIIIKKTRKP TGAPPELNGVTNGGFIPHS (SEQ ID NO: 7, Uniprot: Q6WBA7) |

As illustrated in Table 1, the hMPV F protein exhibits remarkable sequence conservation, with sequence identify of about 90% across hMPV subgroups. In view of the conservation and breadth of knowledge of MPV F sequences, the person of ordinary skill in the art can easily identify corresponding MPV F amino acid positions between different MPV F strains and subgroups. The numbering of amino acid substitutions disclosed herein is made with reference to the F protein sequence of the CAN98-75 hMPV strain (SEQ ID NO: 7), unless context indicates otherwise.

For illustration purposes, the signal peptide, $F_2$ polypeptide, $F_1$, $F_1$ ectodomain, transmembrane domain, and cytosolic domain of the MPV F protein from the CAN97-83 strain (SEQ ID NO: 2), are set forth as follows:

Signal peptide (SEQ ID NO: 2 residues 1-18):
MSWKVVIIFSLLITPQHG $F_2$ polypeptide (SEQ ID NO: 2 residues 20-102):
KESYLEESCSTITEGYLSVLRTGWYTNVFTLEVGDVENLTCSDGPSLIKT

ELDLTKSALRELKTVSADQLAREEQIENPRQSR $F_1$ (SEQ ID NO: 2 residues 103-539):
FVLGAIALGVATAAAVTAGVAIAKTIRLESEVTAIKNALKTTNEAVSTLG

NGVRVLATAVRELKDFVSKNLTRAINKNKCDIDDLKMAVSFSQFNRRFLN

VVRQFSDNAGITPAISLDLMTDAELARAVSNMPTSAGQIKLMLENRAMVR

-continued

RKGFGILIGVYGSSVIYMVQLPIFGVIDTPCWIVKAAPSCSGKKGNYACL

LREDQGWYCQNAGSTVYYPNEKDCETRGDHVFCDTAAGINVAEQSKECNI

NISTTNYPCKVSTGRHPISMVALSPLGALVACYKGVSCSIGSNRVGIIKQ

LNKGCSYITNQDADTVTIDNTVYQLSKVEGEQHVIKGRPVSSSFDPIKFP

EDQFNVALDQVFENIENSQALVDQSNRILSSAEKGNTGFIIVIILIAVLG

SSMILVSIFIIIKKTKKPTGAPPELSGVTNNGFIPHS $F_1$ ectodomain (SEQ ID NO: 2 residues 103-490):
FVLGAIALGVATAAAVTAGVAIAKTIRLESEVTAIKNALKTTNEAVSTLG

NGVRVLATAVRELKDFVSKNLTRAINKNKCDIDDLKMAVSFSQFNRRFLN

VVRQFSDNAGITPAISLDLMTDAELARAVSNMPTSAGQIKLMLENRAMVR

RKGFGILIGVYGSSVIYMVQLPIFGVIDTPCWIVKAAPSCSGKKGNYACL

LREDQGWYCQNAGSTVYYPNEKDCETRGDHVFCDTAAGINVAEQSKECNI

NISTTNYPCKVSTGRHPISMVALSPLGALVACYKGVSCSIGSNRVGIIKQ

LNKGCSYITNQDADTVTIDNTVYQLSKVEGEQHVIKGRPVSSSFDPIKFP

EDQFNVALDQVFENIENSQALVDQSNRILSSAEKGNTG

-continued

```
F1 Transmembrane domain
(SEQ ID NO: 2 residues 491-513):
FIIVIILIAVLGSSMILVSIFII

F1 cytosolic domain
(SEQ ID NO: 2 residues 515-539):
IKKTKKPTGAPPELSGVTNNGFIPHS
```

2. Recombinant MPV F Proteins and Immunogenic Fragments Thereof

Isolated immunogens are disclosed herein that include a recombinant MPV F protein or immunogenic fragment thereof that is modified from a native form (e.g., by introduction of one or more amino acid substitutions) to be stabilized in the prefusion conformation.

In several embodiments, the immunogen includes a recombinant MPV F protein that is stabilized in the prefusion conformation by one or more amino acid substitutions. The recombinant MPV F protein typically includes a protein complex of $F_1$-$F_2$ protomers, which can trimerize to form a trimeric MPV F protein. The $F_1$-$F_2$ protomer can include separate $F_1$ and $F_2$ polypeptide chains, or can include $F_1$ and $F_2$ polypeptide chains that are linked (e.g., by a peptide linker) to form a single polypeptide chain (e.g., as described in the "single chain" section below). In several embodiments, the recombinant MPV F protein is membrane anchored by linkage to a transmembrane domain (e.g., the C-terminus of an $F_1$ ectodomain included in the MPV F protein can be linked to a transmembrane domain).

The recombinant MPV F protein includes an $F_2$ polypeptide and an $F_1$ ectodomain. The $F_2$ polypeptide typically does not include a signal peptide (for example, the $F_2$ protein typically does not include $F_2$ residues 1-18), as the signal peptide is proteolytically cleaved during cellular processing. In embodiments including a soluble recombinant MPV F protein, the $F_1$ ectodomain (e.g., MPV F positions 103-485) is not linked to a transmembrane domain. However, in embodiments including a membrane anchored recombinant MPV F protein the $F_1$ ectodomain can be linked to a transmembrane domain (such as, but not limited to, an MPV F transmembrane domain).

In several embodiments, the recombinant MPV F protein includes a $F_2$ polypeptide and a $F_1$ ectodomain, wherein the N-terminal residue of the $F_2$ polypeptide is one of MPV F positions 8-30;

the C-terminal residue of the $F_2$ polypeptide is one of MPV F positions 90-102;

the N-terminal residue of the $F_1$ ectodomain is one of MPV F positions 103-130; and/or the C-terminal residue of the $F_1$ ectodomain is one of MPV F positions 470-550.

In some embodiments, the $F_2$ polypeptide comprises or consists of MPV F protein positions 30-90, and the $F_1$ ectodomain comprises or consists of MPV F protein positions 130-470. In additional embodiments, the $F_2$ polypeptide comprises or consists of MPV F protein positions 30-90, and the F1 ectodomain comprises or consists of MPV F protein positions 103-470. In further embodiments, the $F_2$ polypeptide comprises or consists of MPV F protein positions 20-102, and the F1 ectodomain comprises or consists of MPV F protein positions 103-485.

Native MPV F sequences include a protease cleavage site (e.g., RQSR, SEQ ID NO: 8) leading to proteolytic cleavage between positions 102 and 103 (with reference to SEQ ID NO: 7), that separates $F_2$ and $F_1$. In several embodiments, an MPV F protein is provided that includes an enhanced cleavage site (e.g., a canonical furin cleavage site sequence of R—X—(R/K)—R) leading to proteolytic between $F_2$ and $F_1$ proteins. The enhanced cleavage cite can include, for example, substitution of six arginine resides for the four residues of the native cleavage site (e.g., RQSR (SEQ ID NO: 8) to RRRRRR (SEQ ID NO: 9). As used herein, reference to "R6" indicates that a MPV F protein includes the RRRRRR (SEQ ID NO: 9) substitution for the native cleavage site. Alternative cleavage sites include, but are not limited to, RRRR (SEQ ID NO: 10), RAKR (SEQ ID NO: 82), or RKAR (SEQ ID NO: 11) sequences.

Stabilization of the recombinant MPV F protein or immunogenic fragment in the prefusion conformation preserves at least one epitope that is specific to the pre-fusion conformation. Thus, the disclosed recombinant MPV F proteins can be specifically bound by an antibody that is specific for the prefusion conformation of MPV F, such as MPE8 antibody. In several examples, the recombinant MPV F protein specifically binds to an antibody (such as MPE8 antibody) that specifically binds to the prefusion conformation of MPV F ectodomain trimer with a dissociation constant of less than about $10^{-6}$ Molar, such as less than about $10^{-7}$ Molar, $10^{-8}$ Molar, or less than $10^{-9}$ Molar. Specific binding can be determined by methods known in the art. The determination of specific binding may readily be made by using or adapting routine procedures, such as ELISA, immunocompetition, surface plasmon resonance, or other immunosorbant assays (described in many standard texts, including Harlow and Lane, *Using Antibodies: A Laboratory Manual*, CSHL, New York, 1999).

The stabilizing modifications provided herein are targeted modifications that stabilize the recombinant MPV F protein in the prefusion conformation. Guided by the structural features identified in the prefusion conformation, several modes of stabilizing the MPV F ectodomain trimer in this conformation are available, including (but not limited to) amino acid substitutions that introduce one or more non-natural disulfide bonds, fill cavities within the MPV F ectodomain trimer, prevent structural rearrangements, introduce N-linked glycosylation sites, and combinations thereof. Corresponding mutations are discussed in more detail below.

a) Non-Natural Disulfide Bonds and Cavity Filling Substitutions to Stabilize the MPV F Prefusion Conformation In several embodiments, the recombinant MPV F protein includes one or more non-natural disulfide bonds that stabilize the MPV F protein in the prefusion conformation. A non-natural disulfide bond is one that does not occur in a native MPV F protein, and is introduced by protein engineering (e.g., by including one or more substituted cysteine residues that form the non-natural disulfide bond). For example, in some embodiments, any of the disclosed recombinant MPV F proteins can be stabilized in a prefusion conformation by any one of 1, 2, 3, 4, 5, 6, 7, 8, 9, or 10 non-natural disulfide bonds.

The cysteine residues that form the disulfide bond can be introduced into a native MPV F sequence by one or more amino acid substitutions. For example, in some embodiments, a single amino acid substitution introduces a cysteine that forms a disulfide bond with a cysteine residue present in the native MPV F sequence. Alternately, two cysteine residues can be introduced into a native MPV F sequence to form the disulfide bond. The location of the cysteine (or cysteines) of the non-natural disulfide bond can be determined by the person of ordinary skill in the art using the disclosed structure of the MPV F ectodomain trimer in a prefusion conformation.

The amino acid positions of the cysteines are typically within a sufficiently close distance for formation of a disulfide bond in the prefusion conformation of the MPV F protein trimer. Methods of using three-dimensional structure data to determine if two residues are within a sufficiently close distance to one another for disulfide bond formation are known (see, e.g., Peterson et al., *Protein engineering,* 12:535-548, 1999 and Dombkowski, *Bioinformatics,* 19:1852-1853, 3002 (disclosing DISULFIDE BY DESIGN™), each of which is incorporated by reference herein). Residues can be selected manually, based on the three dimensional structure of the MPV F trimer in a prefusion conformation provided herein, or a software, such as DISULFIDEBYDESIGN™, can be used. Without being bound by theory, ideal distances for formation of a disulfide bond are generally considered to be about ~5.6 Å for Cα-Cα distance, ~2.02 Å for Sγ-Sγ distance, and 3.5-4.25 Å for Cβ-Cβ distance (using the optimal rotomer). The person of ordinary skill in the art will appreciate that variations from these distances are included when selecting residues in a three dimensional structure that can be substituted for cysteines for introduction of a disulfide bond. For example, in some embodiments the selected residues have a Cα-Cα distance of less than 7.0 Å and/or a Cβ-Cβ distance of less than 4.7 Å. In some embodiments the selected residues have a Cα-Cα distance of from 2.0-8.0 Å and/or a Cβ-Cβ distance of from 2.0-6.0 Å.

In some embodiments, the recombinant MPV F protein can include one or more cysteine substitutions that introduce a non-native intra-protomer disulfide bond that, alone or in combination with other modifications, can stabilize the MPV F protein in a prefusion conformation. For example, the recombinant MPV F protein can include one or more cysteine substitutions that introduce a non-native intra-protomer disulfide bond between:

residues 103-120 and residues 335-345;

residues 107-118 and residues 335-342;

residues of α-helix 3 (residues 117-129) and residues of β-strand 6 (residues 256-261);

residues of α-helix 2 and residues adjacent to the cleavage site (residues 87-102) with α-helix 3 (residues 117-127);

residues 102-113 and residues of α-helix 3 (residues 117-127); or residues 102-113 and residues of α-helix 2 and residues adjacent to the cleavage site (residues 87-102);

wherein the non-native intra-protomer disulfide bond, alone or in combination with other modifications, can stabilize the MPV F protein in a prefusion conformation.

In some embodiments, the recombinant MPV F protein can include one or more cysteine substitutions that introduce a non-native inter-protomer disulfide bond that, alone or in combination with other modifications, can stabilize the MPV F protein in a prefusion conformation. For example, the recombinant MPV F protein can include one or more cysteine substitutions that introduce a non-native inter-protomer disulfide bond between:

residues 337-341 and residues 421-426;

residues 112-120 and residues 424-432;

residues 150-156 with the addition of a glycine residue and residues 392-400;

residues 112-120 and residues 370-377;

residues 365-375 and residues 455-465;

residues 365-375 and residues 105-115; or residues 60-70 and residues 175-185;

wherein the non-native inter-protomer disulfide bond, alone or in combination with other modifications, can stabilize the MPV F protein in a prefusion conformation.

In some embodiments, the $F_1$ polypeptide in the recombinant MPV F protein can include a pair of cysteine substitutions that can form a non-natural disulfide bond to stabilize MPV F protein (e.g., a trimer of the F protein) in the prefusion conformation. In one non-limiting embodiment, the recombinant MPV F protein can a non-natural disulfide bond between cysteine substitutions at positions 113 and 339 (e.g., A113C and A339C substitutions) that stabilizes the recombinant MPV F protein in the prefusion conformation. In additional embodiments, the recombinant MPV F protein can include cysteine substitutions at positions 113 and 339 (e.g., A113C and A339C substitutions) and further include one or more additional mutations as disclosed herein. Non-limiting examples of mutations that can be combined with the cysteine substitutions at positions 113 and 339 include cavity filling substitutions at positions 160 or 177, or both positions 160 and 177 (such as T160F, I177L, or T160F and I177L substitution). The recombinant MPV F protein can further be linked to additional protein segments as described herein, such as a foldon domain to stabilize the membrane proximal region, or a protein nanoparticle subunit.

Exemplary amino acid sequences of recombinant MPV F proteins including A113C/A338C or A113C/A339C substitutions are provided as SEQ ID NOs: 12 and 13, respectively.

```
MPV F ectodomain A113C/A338C
(F residues 19-485) (SEQ ID NO: 12):
LKESYLEESCSTITEGYLSVLRTGWYTNVFTLEVGDVENLTCTDGPSLIK

TELDLTKSALRELKTVSADQLAREEQIENPRQSRFVLGAIALGVcTAAAV

TAGIAIAKTIRLESEVNAIKGALKTTNEAVSTLGNGVRVLATAVRELKEF

VSKNLTSAINKNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKDGNYACLLREDQGWYCKNAGSTV

YYPNDKDCETRGDHVFCDTcAGINVAEQSRECNINISTTNYPCKVSTGRH

PISMVALSPLGALVACYKGVSCSIGSNRVGIIKQLPKGCSYITNQDADTV

TIDNTVYQLSKVEGEQHVIKGRPVSSSFDPIKFPEDQFNVALDQVFESIE

NSQALVDQSNKILNSAE
```

```
MPV F ectodomain A113C/A339C
(F residues 19-485) (SEQ ID NO: 13):
LKESYLEESCSTITEGYLSVLRTGWYTNVFTLEVGDVENLTCTDGPSLIK

TELDLTKSALRELKTVSADQLAREEQIENPRQSRFVLGAIALGVcTAAAV

TAGIAIAKTIRLESEVNAIKGALKTTNEAVSTLGNGVRVLATAVRELKEF

VSKNLTSAINKNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKDGNYACLLREDQGWYCKNAGSTV

YYPNDKDCETRGDHVFCDTAcGINVAEQSRECNINISTTNYPCKVSTGRH

PISMVALSPLGALVACYKGVSCSIGSNRVGIIKQLPKGCSYITNQDADTV

TIDNTVYQLSKVEGEQHVIKGRPVSSSFDPIKFPEDQFNVALDQVFESIE

NSQALVDQSNKILNSAE
```

In several embodiments, the recombinant MPV F protein can be stabilized in the prefusion conformation by one or more amino acid substitutions that reduce the volume of an internal cavity present in the prefusion conformation of the MPV F protein trimer. For example, cavities can be filled by substituting amino acids with large side chains for those with small side chains. The cavities can be intra-protomer cavities, or inter-protomer cavities. Exemplary amino acids with large side-chains that can be substituted into the MPV F sequence include phenylalanine, leucine, tryptophan, tyrosine, histidine, or methionine.

Analysis of the MPV F structure provided herein reveals at least two cavities that can be filled with one or more cavity filling amino acid substitutions to stabilize the MPF F protein in a prefusion conformation, as follows:

The Threonine 160 cavity. This is a cavity formed at the top by β-strands 4 (residues 146-151) and 5 (residues 155-160), at the bottom by α-helix 7 (residues 225-233) including residues E208 and R211 and Y215 that are located adjacent to Thr160. In addition, β-strands 3, 6, and 7 form a β-sheet that encloses the cavity on the inner region of the HMPV F molecule. Cavity filling substitutions at residues T160, V162, and/or L157 can be used to fill the T160 cavity to stabilize the MPV F protein in a prefusion conformation.

The Isoleucine 177 cavity. This is a cavity formed by α-helix 5 (residues 165-178) and a loop region encompassing residues 52-61 and the two long α-helices, alpha helix 1 (66-91) and alpha helix 5 (residues 188-211) located in the membrane proximal region of the F glycoprotein. Cavity filling substitutions at residues I177, L58, V169, A54, and/or V55 can be used to fill the I177 cavity to stabilize the MPV F protein in a prefusion conformation.

In some embodiments, the recombinant MPV F protein can include a cavity filling amino acid substitution at position 160, position 177, or both positions 160 and 177, that stabilizes the MPV F protein in the prefusion conformation. The recombinant MPV F protein can further be linked to additional protein segments as described herein, such as a foldon domain to stabilize the membrane proximal region, or a protein nanoparticle subunit.

An exemplary amino acid sequence of an F protein ectodomain including T160F/I177L substitutions is provided as: SEQ ID NO: 14.

```
MPV F T160F/I177L (F residues 19-485)
(SEQ ID NO: 14):
LKESYLEESCSTITEGYLSVLRTGWYTNVFTLEVGDVENLTCTDGPSLIK

TELDLTKSALRELKTVSADQLAREEQIENPRQSRFVLGAIALGVATAAAV

TAGIAIAKTIRLESEVNAIKGALKTTNEAVSTLGNGVRVLAfAVRELKEF

VSKNLTSA1NKNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKDGNYACLLREDQGWYCKNAGSTV

YYPNDKDCETRGDHVFCDTAAGINVAEQSRECNINISTTNYPCKVSTGRH

PISMVALSPLGALVACYKGVSCSIGSNRVGIIKQLPKGCSYITNQDADTV

TIDNTVYQLSKVEGEQHVIKGRPVSSSFDPIKFPEDQFNVALDQVFESIE

NSQALVDQSNKILNSAE
```

In an additional embodiment, the recombinant MPV F protein can include a cavity filling amino acid substitution at position 160, position 177, or both positions 160 and 177, and can further includes a non-natural disulfide bond between cysteine substitutions at positions 113 and 339 or 113 and 338, that stabilize the MPV F ectodomain in the prefusion conformation. The recombinant MPV F protein can further be linked to additional protein segments as described herein, such as a foldon domain to stabilize the membrane proximal region, or a protein nanoparticle subunit.

Exemplary amino acid sequences of recombinant MPV F proteins including A113C/A339C substitutions and T160F and I177L substitution are provided as follows:

```
MPV F A113C/A339C/T160F/I177L
(F residues 19-485) (SEQ ID NO: 15):
LKESYLEESCSTITEGYLSVLRTGWYTNVFTLEVGDVENLTCTDGPSLIK

TELDLTKSALRELKTVSADQLAREEQIENPRQSRFVLGAIALGVcTAAAV

TAGIAIAKTIRLESEVNAIKGALKTTNEAVSTLGNGVRVLAfAVRELKEF

VSKNLTSA1NKNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKDGNYACLLREDQGWYCKNAGSTV

YYPNDKDCETRGDHVFCDTAcGINVAEQSRECNINISTTNYPCKVSTGRH

PISMVALSPLGALVACYKGVSCSIGSNRVGIIKQLPKGCSYITNQDADTV

TIDNTVYQLSKVEGEQHVIKGRPVSSSFDPIKFPEDQFNVALDQVFESIE

NSQALVDQSNKILNSAE

NL/1/00 A113C/A339C/T160F/I177L
(SEQ ID NO: 178):
LKESYLEESCSTITEGYLSVLRTGWYTNVFTLEVGDVENLTCADGPSLIK

TELDLTKSALRELRTVSADQLAREEQIENPRQSRFVLGAIALGVCTAAAV

TAGVAIAKTIRLESEVTAIKNALKKTNEAVSTLGNGVRVLAFAVRELKDF

VSKNLTRALNKNKCDIADLKMAVSFSQFNRRFLNVVRQFSDNAGITPAIS

LDLMTDAELARAVSNMPTSAGQIKLMLENRAMVRRKGFGFLIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPVKFPEDQFNVALDQVFESIE

NSQALVDQSNRILSSAE

CAN97-83 A113C/A339C/T160F/I177L
(SEQ ID NO: 179):
LKESYLEESCSTITEGYLSVLRTGWYTNVFTLEVGDVENLTCSDGPSLIK

TELDLTKSALRELKTVSADQLAREEQIENPRQSRFVLGAIALGVCTAAAV

TAGVAIAKTIRLESEVTAIKNALKTTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTSAGQIKLMLENRAMVRRKGFGILIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPIKFPEDQFNVALDQVFENIE

NSQALVDQSNRILSSAE

NL/17/00 A113C/A339C/T160F/I177L
(SEQ ID NO: 180):
LKESYLEESCSTITEGYLSVLRTGWYTNVFTLEVGDVENLTCSDGPSLIK

TELDLTKSALRELKTVSADQLAREEQIENPRQSRFVLGAIALGVCTAAAV
```

-continued

TAGVAIAKTIRLESEVTAIKNALKTTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTSAGQIKLMLENRAMVRRKGFGILIGVYGSSVI

YTVQLPIFGVIDTPCWIVKAAPSCSEKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPIKFPEDQFNVALDQVFENIE

NSQALVDQSNRILSSAE

NCL174 A113C/A339C/T160F/I177L
(SEQ ID NO: 181):
LKESYLEESCSTITEGYLSVLRTGWYTNVFTLEVGDVENLTCADGPSLIK

TELDLTKSALRELKPVSADQLAREEQIENPRQSRFVLGAIALGVCTAAAV

TAGVAIAKTIRLESEVTAIKNALKKTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTAAGQIKLMLENRAMVRRKGFGILIGVYGSSVI

YMVQLPIFGVIDTPCWIVKAAPSCSEKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPVKFPEDQFNVALDQVFENIE

NSQALVDQSNRILSSAE

NL/1/99 A113C/A339C/T160F/I177L
(SEQ ID NO: 182):
LKESYLEESCSTITEGYLSVLRTGWYTNVFTLEVGDVENLTCTDGPSLIK

TELDLTKSALRELKTVSADQLAREEQIENPRQSRFVLGAIALGVCTAAAV

TAGIAIAKTIRLESEVNAIKGALKQTNEAVSTLGNGVRVLAFAVRELKEF

VSKNLTSALNRNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKNGNYACLLREDQGWYCKNAGSTV

YYPNEKDCETRGDHVFCDTACGINVAEQSRECNINISTTNYPCKVSTGRH

PISMVALSPLGALVACYKGVSCSIGSNWVGIIKQLPKGCSYITNQDADTV

TIDNTVYQLSKVEGEQHVIKGRPVSSSFDPIKFPEDQFNVALDQVFESIE

NSQALVDQSNKILNSAE

NDL00-1 A113C/A339C/T160F/I177L
(SEQ ID NO: 183):
LKESYLEESCSTITEGYLSVLRTGWYTNVFTLEVGDVENLTCADGPSLIK

TELDLTKSALRELRTVSADQLAREEQIENPRQSRFVLGAIALGVCTAAAV

TAGVAIAKTIRLESEVTAIKNALKKTNEAVSTLGNGVRVLAFAVRELKDF

VSKNLTRALNKNKCDIADLKMAVSFSQFNRRFLNVVRQFSDNAGITPAIS

LDLMTDAELARAVSNMPTSAGQIKLMLENRAMVRRKGFGFLIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPVKFPEDQFNVALDQVFESIE

NSQALVDQSNRILSSAE

-continued

CAN98-75 A113C/A339C/T160F/I177L
(SEQ ID NO: 184):
LKESYLEESCSTITEGYLSVLRTGWYTNVFTLEVGDVENLTCTDGPSLIK

TELDLTKSALRELKTVSADQLAREEQIENPRQSRFVLGAIALGVCTAAAV

TAGIAIAKTIRLESEVNAIKGALKTTNEAVSTLGNGVRVLAFAVRELKEF

VSKNLTSALNKNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKDGNYACLLREDQGWYCKNAGSTV

YYPNKKDCETRGDHVFCDTACGINVAEQSRECNINISTTNYPCKVSTGRH

PISMVALSPLGALVACYKGVSCSIGSNRVGIIKQLPKGCSYITNQDADTV

TIDNTVYQLSKVEGEQHVIKGRPVSSSFDPIKFPEDQFNVALDQVFESIE

NSQALVDQSNKILNSAE

In any of the recombinant MPV F proteins including A113C/A339C/T160F/I177L substitutions for stabilization in the prefusion conformation (such as any one of SEQ ID NOs: 15 or 178-184), the recombinant MPV F protein can further include additional amino acid substitutions for stabilization in the prefusion conformation (such as introduction of a proline residue by substitution at one of positions 183-189 to prevent elongation of the α7 helix, for example a D183P substitution, a A185P substitution, or a D186 substitution), or one or more mutations to remove N-glycan sequons at N57 and/or N172 (such as a N57Q substitution and/or a N172Q substitution). Further, the recombinant MPV F protein can include any of the above mutations for stabilization in the prefusion conformation and can further be linked to a C-terminal trimerization domain, such as a foldon domain, and/or an oligomerization peptide.

In some embodiments, the recombinant MPV F protein can include a pair of cysteine substitutions that can form a non-natural interprotomer disulfide bond to stabilize a trimer of the MPV F protein in the prefusion conformation. In one non-limiting embodiment, the recombinant MPV F protein trimer can include an interprotomer disulfide between cysteine residues introduced by cysteine substitutions at positions 120 and 426 (e.g., A120C and Q426C substitutions) or positions 120 and 428 (e.g., A120C and S428C substitutions) that stabilizes the recombinant MPV F protein in the prefusion conformation. In additional embodiments, the recombinant MPV F protein can include the cysteine substitutions at positions 120 and 426 (e.g., A120C and Q426C substitutions) or positions 120 and 428 (e.g., A120C and S428C substitutions) and can further include one or more additional mutations as disclosed herein. Non-limiting examples of additional mutations that can be combined with the cysteine substitutions at positions 120 and 426 (e.g., A120C and Q426C substitutions) or positions 120 and 428 (e.g., A120C and S428C substitutions) include cysteine substitutions at positions 113 and 339, and cavity filling substitutions at positions 160 or 177, or both positions 160 and 177 (such as T160F, I177L, or T160F and I177L substitution). The recombinant MPV F protein can further be linked to additional protein segments as described herein, such as a foldon domain to stabilize the membrane proximal region, or a protein nanoparticle subunit.

Exemplary amino acid sequences of recombinant MPV F proteins including A120C/Q426C or A120C/S428C substitutions (in addition to A113C, A339C, T160F, and I177L substitutions) are provided as follows:

NL/1/00 A113C/A339C/T160F/I177L A120C-Q426C
(SEQ ID NO: 101):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TCGVAIAKTIRLESEVTAIKNALKKTNEAVSTLGNGVRVLAFAVRELKDF
VSKNLTRALNKNKCDIADLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYCLSKVEGEQHVIKGRPVSSSFDPVKFPEDQFNVALDQVFESIE
NSQALVDQSNRILSSAE

CAN97-83 A113C/A339C/T160F/I177L A120C-Q426C
(SEQ ID NO: 102):
LKESYLEESCSTITEGYLSVLRTGWYTNVFTLEVGDVENLTCSDGPSLIK
TELDLTKSALRELKTVSADQLAREEQIENPRQSRFVLGAIALGVCTAAAV
TCGVAIAKTIRLESEVTAIKNALKTTNEAVSTLGNGVRVLAFAVRELKDF
VSKNLTRALNKNKCDIDDLKMAVSFSQFNRRFLNVVRQFSDNAGITPAIS
LDLMTDAELARAVSNMPTSAGQIKLMLENRAMVRRKGFGILIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYCLSKVEGEQHVIKGRPVSSSFDPIKFPEDQFNVALDQVFENIE
NSQALVDQSNRILSSAE

NL/17/00 A113C/A339C/T160F/I177L A120C-Q426C
(SEQ ID NO: 103):
LKESYLEESCSTITEGYLSVLRTGWYTNVFTLEVGDVENLTCSDGPSLIK
TELDLTKSALRELKTVSADQLAREEQIENPRQSRFVLGAIALGVCTAAAV
TCGVAIAKTIRLESEVTAIKNALKTTNEAVSTLGNGVRVLAFAVRELKDF
VSKNLTRALNKNKCDIDDLKMAVSFSQFNRRFLNVVRQFSDNAGITPAIS
LDLMTDAELARAVSNMPTSAGQIKLMLENRAMVRRKGFGILIGVYGSSVI
YTVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYCLSKVEGEQHVIKGRPVSSSFDPIKFPEDQFNVALDQVFENIE
NSQALVDQSNRILSSAE

NCL174 A113C/A339C/T160F/I177L A120C-Q426C
(SEQ ID NO: 104):
LKESYLEESCSTITEGYLSVLRTGWYTNVFTLEVGDVENLTCADGPSLIK
TELDLTKSALRELKPVSADQLAREEQIENPRQSRFVLGAIALGVCTAAAV
TCGVAIAKTIRLESEVTAIKNALKKTNEAVSTLGNGVRVLAFAVRELKDF
VSKNLTRALNKNKCDIDDLKMAVSFSQFNRRFLNVVRQFSDNAGITPAIS
LDLMTDAELARAVSNMPTAAGQIKLMLENRAMVRRKGFGILIGVYGSSVI
YMVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH

-continued

PISMVALSPLGALVACYKGVSCSIGSNRVGIIKQLNKGCSYITNQDADTV
TIDNTVYCLSKVEGEQHVIKGRPVSSSFDPVKFPEDQFNVALDQVFENIE
NSQALVDQSNRILSSAE

NL/1/99 A113C/A339C/T160F/I177L A120C-Q426C
(SEQ ID NO: 105):
LKESYLEESCSTITEGYLSVLRTGWYTNVFTLEVGDVENLTCTDGPSLIK
TELDLTKSALRELKTVSADQLAREEQIENPRQSRFVLGAIALGVCTAAAV
TCGIAIAKTIRLESEVNAIKGALKQTNEAVSTLGNGVRVLAFAVRELKEF
VSKNLTSALNRNKCDIADLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKNGNYACLLREDQGWYCKNAGSTV
YYPNEKDCETRGDHVFCDTACGINVAEQSRECNINISTTNYPCKVSTGRH
PISMVALSPLGALVACYKGVSCSIGSNWVGIIKQLPKGCSYITNQDADTV
TIDNTVYCLSKVEGEQHVIKGRPVSSSFDPIKFPEDQFNVALDQVFESIE
NSQALVDQSNKILNSAE

NDL00-1 A113C/A339C/T160F/I177L A120C-Q426C
(SEQ ID NO: 106):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TCGVAIAKTIRLESEVTAIKNALKKTNEAVSTLGNGVRVLAFAVRELKDF
VSKNLTRALNKNKCDIADLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYCLSKVEGEQHVIKGRPVSSSFDPVKFPEDQFNVALDQVFESIE
NSQALVDQSNRILSSAE

CAN98-75 A113C/A339C/T160F/I177L A120C-Q426C
(SEQ ID NO: 107):
LKESYLEESCSTITEGYLSVLRTGWYTNVFTLEVGDVENLTCTDGPSLIK
TELDLTKSALRELKTVSADQLAREEQIENPRQSRFVLGAIALGVCTAAAV
TCGIAIAKTIRLESEVNAIKGALKTTNEAVSTLGNGVRVLAFAVRELKEF
VSKNLTSALNKNKCDIADLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKDGNYACLLREDQGWYCKNAGSTV
YYPNKKDCETRGDHVFCDTACGINVAEQSRECNINISTTNYPCKVSTGRH
PISMVALSPLGALVACYKGVSCSIGSNRVGIIKQLPKGCSYITNQDADTV
TIDNTVYCLSKVEGEQHVIKGRPVSSSFDPIKFPEDQFNVALDQVFESIE
NSQALVDQSNKILNSAE

NL/1/00 A113C/A339C/T160F/I177L A120C-S428C
(SEQ ID NO: 108):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TCGVAIAKTIRLESEVTAIKNALKKTNEAVSTLGNGVRVLAFAVRELKDF

-continued

VSKNLTRALNKNKCDIADLKMAVSFSQFNRRFLNVVRQFSDNAGITPAIS

LDLMTDAELARAVSNMPTSAGQIKLMLENRAMVRRKGFGFLIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLCKVEGEQHVIKGRPVSSSFDPVKFPEDQFNVALDQVFESIE

NSQALVDQSNRILSSAE

CAN97-83 A113C/A339C/T160F/I177L A120C-S428C
(SEQ ID NO: 109):
LKESYLEESCSTITEGYLSVLRTGWYTNVFTLEVGDVENLTCSDGPSLIK

TELDLTKSALRELKTVSADQLAREEQIENPRQSRFVLGAIALGVCTAAAV

TCGVAIAKTIRLESEVTAIKNALKTTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTSAGQIKLMLENRAMVRRKGFGILIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLCKVEGEQHVIKGRPVSSSFDPIKFPEDQFNVALDQVFENIE

NSQALVDQSNRILSSAE

NL/17/00 A113C/A339C/T160F/I177L A120C-S428C
(SEQ ID NO: 110):
LKESYLEESCSTITEGYLSVLRTGWYTNVFTLEVGDVENLTCSDGPSLIK

TELDLTKSALRELKTVSADQLAREEQIENPRQSRFVLGAIALGVCTAAAV

TCGVAIAKTIRLESEVTAIKNALKTTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTSAGQIKLMLENRAMVRRKGFGILIGVYGSSVI

YTVQLPIFGVIDTPCWIVKAAPSCSEKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLCKVEGEQHVIKGRPVSSSFDPIKFPEDQFNVALDQVFENIE

NSQALVDQSNRILSSAE

NCL174 A113C/A339C/T160F/I177L A120C-S428C
(SEQ ID NO: 111):
LKESYLEESCSTITEGYLSVLRTGWYTNVFTLEVGDVENLTCADGPSLIK

TELDLTKSALRELKPVSADQLAREEQIENPRQSRFVLGAIALGVCTAAAV

TCGVAIAKTIRLESEVTAIKNALKKTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTAAGQIKLMLENRAMVRRKGFGILIGVYGSSVI

YMVQLPIFGVIDTPCWIVKAAPSCSEKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLCKVEGEQHVIKGRPVSSSFDPVKFPEDQFNVALDQVFENIE

NSQALVDQSNRILSSAE

-continued

NL/1/99 A113C/A339C/T160F/I177L A120C-S428C
(SEQ ID NO: 112):
LKESYLEESCSTITEGYLSVLRTGWYTNVFTLEVGDVENLTCTDGPSLIK

TELDLTKSALRELKTVSADQLAREEQIENPRQSRFVLGAIALGVCTAAAV

TCGIAIAKTIRLESEVNAIKGALKQTNEAVSTLGNGVRVLAFAVRELKEF

VSKNLTSALNRNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKNGNYACLLREDQGWYCKNAGSTV

YYPNEKDCETRGDHVFCDTACGINVAEQSRECNINISTTNYPCKVSTGRH

PISMVALSPLGALVACYKGVSCSIGSNWVGIIKQLPKGCSYITNQDADTV

TIDNTVYQLCKVEGEQHVIKGRPVSSSFDPIKFPEDQFNVALDQVFESIE

NSQALVDQSNKILNSAE

NDL00-1 A113C/A339C/T160F/I177L A120C-S428C
(SEQ ID NO: 113):
LKESYLEESCSTITEGYLSVLRTGWYTNVFTLEVGDVENLTCADGPSLIK

TELDLTKSALRELRTVSADQLAREEQIENPRQSRFVLGAIALGVCTAAAV

TCGVAIAKTIRLESEVTAIKNALKKTNEAVSTLGNGVRVLAFAVRELKDF

VSKNLTRALNKNKCDIADLKMAVSFSQFNRRFLNVVRQFSDNAGITPAIS

LDLMTDAELARAVSNMPTSAGQIKLMLENRAMVRRKGFGFLIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLCKVEGEQHVIKGRPVSSSFDPVKFPEDQFNVALDQVFESIE

NSQALVDQSNRILSSAE

CAN98-75 A113C/A339C/T160F/I177L A120C-S428C
(SEQ ID NO: 114):
LKESYLEESCSTITEGYLSVLRTGWYTNVFTLEVGDVENLTCTDGPSLIK

TELDLTKSALRELKTVSADQLAREEQIENPRQSRFVLGAIALGVCTAAAV

TCGIAIAKTIRLESEVNAIKGALKTTNEAVSTLGNGVRVLAFAVRELKEF

VSKNLTSALNKNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKDGNYACLLREDQGWYCKNAGSTV

YYPNKKDCETRGDHVFCDTACGINVAEQSRECNINISTTNYPCKVSTGRH

PISMVALSPLGALVACYKGVSCSIGSNRVGIIKQLPKGCSYITNQDADTV

TIDNTVYQLCKVEGEQHVIKGRPVSSSFDPIKFPEDQFNVALDQVFESIE

NSQALVDQSNKILNSAE

In any of the recombinant MPV F proteins including A113C/A339C/T160F/I177L/A120C and Q426C or S428C substitutions for stabilization in the prefusion conformation (such as any one of SEQ ID NOs: 101-114), the recombinant MPV F protein can further include additional amino acid substitutions for stabilization in the prefusion conformation (such as introduction of a proline residue by substitution at one of positions 183-189 to prevent elongation of the α7 helix, for example a D183P substitution, a A185P substitution, or a D186 substitution), or one or more mutations to remove N-glycan sequons at N57 and/or N172 (such as a N57Q substitution and/or a N172Q substitution). Further, the recombinant MPV F protein can include any of the above mutations for stabilization in the prefusion conformation and can further be linked to a C-terminal trimerization domain, such as a foldon domain, and/or an oligomerization peptide.

b) Proline Substitutions to Prevent α7 Helix Formation

In several embodiments, the recombinant MPV F protein can include one or more proline substitutions to prevent or reduce formation of the α7 helix. The α7 helix forms in the post-fusion MPV F conformation, but not the prefusion MPV F conformation; thus prevention of α7 helix formation can stabilize the MPV F protein in its prefusion conformation. In some embodiments, the recombinant MPV F protein can include one or more proline substitutions at positions 183-189 for stabilization in the prefusion conformation. In some embodiments, the recombinant MPV F protein can include a D183P substitution, a A185 substitution, and/or a D186 substitution for stabilization in the prefusion conformation. Non-limiting examples of recombinant MPV F protein sequences including one or more proline substitutions for prevention of α7 helix formation are set forth below.

NL/1/00 A113C/A339C/T160F/I177L D183P
(SEQ ID NO: 115):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCPIADLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAE

CAN97-83 A113C/A339C/T160F/I177L D183P
(SEQ ID NO: 116):
LKESYLEESCSTITEGYLSVLRTGWYTNVFTLEVGDVENLTCSDGPSLIK
TELDLTKSALRELKTVSADQLAREEQIENPRQSRFVLGAIALGVCTAAAV
TAGVAIAKTIRLESEVTAIKNALKTTNEAVSTLGNGVRVLAFAVRELKDF
VSKNLTRALNKNKCPIDDLKMAVSFSQFNRRFLNVVRQFSDNAGITPAIS
LDLMTDAELARAVSNMPTSAGQIKLMLENRAMVRRKGFGILIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAE

NL/17/00 A113C/A339C/T160F/I177L D183P
(SEQ ID NO: 117):
LKESYLEESCSTITEGYLSVLRTGWYTNVFTLEVGDVENLTCSDGPSLIK
TELDLTKSALRELKTVSADQLAREEQIENPRQSRFVLGAIALGVCTAAAV
TAGVAIAKTIRLESEVTAIKNALKTTNEAVSTLGNGVRVLAFAVRELKDF
VSKNLTRALNKNKCPIDDLKMAVSFSQFNRRFLNVVRQFSDNAGITPAIS

-continued

LDLMTDAELARAVSNMPTSAGQIKLMLENRAMVRRKGFGILIGVYGSSVI
YTVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAE

NCL174 A113C/A339C/T160F/I177L D183P
(SEQ ID NO: 118):
LKESYLEESCSTITEGYLSVLRTGWYTNVFTLEVGDVENLTCADGPSLIK
TELDLTKSALRELKPVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCPIDDLKMAVSFSQFNRRFLNVVRQFSDNAGITPAIS
LDLMTDAELARAVSNMPTAAGQIKLMLENRAMVRRKGFGILIGVYGSSVI
YMVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFENIE
NSQALVDQSNRILSSAE

NL/1/99 A113C/A339C/T160F/I177L D183P
(SEQ ID NO: 119):
LKESYLEESCSTITEGYLSVLRTGWYTNVFTLEVGDVENLTCTDGPSLIK
TELDLTKSALRELKTVSADQLAREEQIENPRQSRFVLGAIALGVCTAAAV
TAGIAIAKTIRLESEVNAIKGALKQTNEAVSTLGNGVRVLAFAVRELKEF
VSKNLTSALNRNKCPIADLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKNGNYACLLREDQGWYCKNAGSTV
YYPNEKDCETRGDHVFCDTACGINVAEQSRECNINISTTNYPCKVSTGRH
PISMVALSPLGALVACYKGVSCSIGSNWVGIIKQLPKGCSYITNQDADTV
TIDNTVYQLSKVEGEQHVIKGRPVSSSFDPIKFPEDQFNVALDQVFESIE
NSQALVDQSNKILNSAE

NDL00-1 A113C/A339C/T160F/I177L D183P
(SEQ ID NO: 120):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCPIADLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAE

-continued

CAN98-75 A113C/A339C/T160F/I177L D183P
(SEQ ID NO: 121):
LKESYLEESCSTITEGYLSVLRTGWYTNVFTLEVGDVENLTCTDGPSLIK
TELDLTKSALRELKTVSADQLAREEQIENPRQSRFVLGAIALGVCTAAAV
TAGIAIAKTIRLESEVNAIKGALKTTNEAVSTLGNGVRVLAFAVRELKEF
VSKNLTSALNKNKCPIADLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKDGNYACLLREDQGWYCKNAGSTV
YYPNKKDCETRGDHVFCDTACGINVAEQSRECNINISTTNYPCKVSTGRH
PISMVALSPLGALVACYKGVSCSIGSNRVGIIKQLPKGCSYITNQDADTV
TIDNTVYQLSKVEGEQHVIKGRPVSSSFDPIKFPEDQFNVALDQVFESIE
NSQALVDQSNKILNSAE

NL/1/00 A113C/A339C/T160F/I177L A185P
(SEQ ID NO: 122):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIPDLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAE

CAN97-83 A113C/A339C/T160F/I177L D185P
(SEQ ID NO: 123):
LKESYLEESCSTITEGYLSVLRTGWYTNVFTLEVGDVENLTCSDGPSLIK
TELDLTKSALRELKTVSADQLAREEQIENPRQSRFVLGAIALGVCTAAAV
TAGVAIAKTIRLESEVTAIKNALKTTNEAVSTLGNGVRVLAFAVRELKDF
VSKNLTRALNKNKCDIPDLKMAVSFSQFNRRFLNVVRQFSDNAGITPAIS
LDLMTDAELARAVSNMPTSAGQIKLMLENRAMVRRKGFGILIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAE

NL/17/00 A113C/A339C/T160F/I177L D185P
(SEQ ID NO: 124):
LKESYLEESCSTITEGYLSVLRTGWYTNVFTLEVGDVENLTCSDGPSLIK
TELDLTKSALRELKTVSADQLAREEQIENPRQSRFVLGAIALGVCTAAAV
TAGVAIAKTIRLESEVTAIKNALKTTNEAVSTLGNGVRVLAFAVRELKDF
VSKNLTRALNKNKCDIPDLKMAVSFSQFNRRFLNVVRQFSDNAGITPAIS
LDLMTDAELARAVSNMPTSAGQIKLMLENRAMVRRKGFGILIGVYGSSVI
YTVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAE

NCL174 A113C/A339C/T160F/I177L D185P
(SEQ ID NO: 125):
LKESYLEESCSTITEGYLSVLRTGWYTNVFTLEVGDVENLTCADGPSLIK
TELDLTKSALRELKPVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIPDLKMAVSFSQFNRRFLNVVRQFSDNAGITPAIS
LDLMTDAELARAVSNMPTAAGQIKLMLENRAMVRRKGFGILIGVYGSSVI
YMVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFENIE
NSQALVDQSNRILSSAE

NL/1/99 A113C/A339C/T160F/I177L A185P
(SEQ ID NO: 126):
LKESYLEESCSTITEGYLSVLRTGWYTNVFTLEVGDVENLTCTDGPSLIK
TELDLTKSALRELKTVSADQLAREEQIENPRQSRFVLGAIALGVCTAAAV
TAGIAIAKTIRLESEVNAIKGALKQTNEAVSTLGNGVRVLAFAVRELKEF
VSKNLTSALNRNKCDIPDLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKNGNYACLLREDQGWYCKNAGSTV
YYPNEKDCETRGDHVFCDTACGINVAEQSRECNINISTTNYPCKVSTGRH
PISMVALSPLGALVACYKGVSCSIGSNWVGIIKQLPKGCSYITNQDADTV
TIDNTVYQLSKVEGEQHVIKGRPVSSSFDPIKFPEDQFNVALDQVFESIE
NSQALVDQSNKILNSAE

NDL00-1 A113C/A339C/T160F/I177L A185P
(SEQ ID NO: 127):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIPDLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAE

CAN98-75 A113C/A339C/T160F/I177L A185P
(SEQ ID NO: 128):
LKESYLEESCSTITEGYLSVLRTGWYTNVFTLEVGDVENLTCTDGPSLIK
TELDLTKSALRELKTVSADQLAREEQIENPRQSRFVLGAIALGVCTAAAV
TAGIAIAKTIRLESEVNAIKGALKTTNEAVSTLGNGVRVLAFAVRELKEF

-continued

VSKNLTSALNKNKCDIPDLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKDGNYACLLREDQGWYCKNAGSTV
YYPNKKDCETRGDHVFCDTACGINVAEQSRECNINISTTNYPCKVSTGRH
PISMVALSPLGALVACYKGVSCSIGSNRVGIIKQLPKGCSYITNQDADTV
TIDNTVYQLSKVEGEQHVIKGRPVSSSFDPIKFPEDQFNVALDQVFESIE
NSQALVDQSNKILNSAE

NL/1/00 A113C/A339C/T160F/I177L D186P (SEQ ID NO: 129):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIAPLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAE

CAN97-83 A113C/A339C/T160F/I177L D186P (SEQ ID NO: 130):
LKESYLEESCSTITEGYLSVLRTGWYTNVFTLEVGDVENLTCSDGPSLIK
TELDLTKSALRELKTVSADQLAREEQIENPRQSRFVLGAIALGVCTAAAV
TAGVAIAKTIRLESEVTAIKNALKTTNEAVSTLGNGVRVLAFAVRELKDF
VSKNLTRALNKNKCDIDPLKMAVSFSQFNRRFLNVVRQFSDNAGITPAIS
LDLMTDAELARAVSNMPTSAGQIKLMLENRAMVRRKGFGILIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAE

NL/17/00 A113C/A339C/T160F/I177L D186P (SEQ ID NO: 131):
LKESYLEESCSTITEGYLSVLRTGWYTNVFTLEVGDVENLTCSDGPSLIK
TELDLTKSALRELKTVSADQLAREEQIENPRQSRFVLGAIALGVCTAAAV
TAGVAIAKTIRLESEVTAIKNALKTTNEAVSTLGNGVRVLAFAVRELKDF
VSKNLTRALNKNKCDIDPLKMAVSFSQFNRRFLNVVRQFSDNAGITPAIS
LDLMTDAELARAVSNMPTSAGQIKLMLENRAMVRRKGFGILIGVYGSSVI
YTVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAE

-continued

NCL174 A113C/A339C/T160F/I177L D186P (SEQ ID NO: 132):
LKESYLEESCSTITEGYLSVLRTGWYTNVFTLEVGDVENLTCADGPSLIK
TELDLTKSALRELKPVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIDPLKMAVSFSQFNRRFLNVVRQFSDNAGITPAIS
LDLMTDAELARAVSNMPTAAGQIKLMLENRAMVRRKGFGILIGVYGSSVI
YMVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFENIE
NSQALVDQSNRILSSAE

NL/1/99 A113C/A339C/T160F/I177L D186P (SEQ ID NO: 133):
LKESYLEESCSTITEGYLSVLRTGWYTNVFTLEVGDVENLTCTDGPSLIK
TELDLTKSALRELKTVSADQLAREEQIENPRQSRFVLGAIALGVCTAAAV
TAGIAIAKTIRLESEVNAIKGALKQTNEAVSTLGNGVRVLAFAVRELKEF
VSKNLTSALNRNKCDIAPLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKNGNYACLLREDQGWYCKNAGSTV
YYPNEKDCETRGDHVFCDTACGINVAEQSRECNINISTTNYPCKVSTGRH
PISMVALSPLGALVACYKGVSCSIGSNWVGIIKQLPKGCSYITNQDADTV
TIDNTVYQLSKVEGEQHVIKGRPVSSSFDPIKFPEDQFNVALDQVFESIE
NSQALVDQSNKILNSAE

NDL00-1 A113C/A339C/T160F/I177L D186P (SEQ ID NO: 134):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIAPLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAE

CAN98-75 A113C/A339C/T160F/I177L D186P (SEQ ID NO: 135):
LKESYLEESCSTITEGYLSVLRTGWYTNVFTLEVGDVENLTCTDGPSLIK
TELDLTKSALRELKTVSADQLAREEQIENPRQSRFVLGAIALGVCTAAAV
TAGIAIAKTIRLESEVNAIKGALKTTNEAVSTLGNGVRVLAFAVRELKEF
VSKNLTSALNKNKCDIAPLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKDGNYACLLREDQGWYCKNAGSTV
YYPNKKDCETRGDHVFCDTACGINVAEQSRECNINISTTNYPCKVSTGRH

-continued

PISMVALSPLGALVACYKGVSCSIGSNRVGIIKQLPKGCSYITNQDADTV

TIDNTVYQLSKVEGEQHVIKGRPVSSSFDPIKFPEDQFNVALDQVFESIE

NSQALVDQSNKILNSAE

In any of the embodiments disclosed above for recombinant MPV F proteins including introduction of a proline residue by substitution at one of positions 183-189 to prevent elongation of the α7 helix (such as any one of SEQ ID NOs: 115-135), the recombinant MPV F protein can further include additional amino acid substitutions for stabilization in the prefusion conformation, such as introduction of an additional non-native disulfide bond by A120C/Q426C substitution or A120C/S428C substitutions. Further, in any of the embodiments disclosed above for recombinant MPV F proteins including introduction of a proline residue by substitution at one of positions 183-189 to prevent elongation of the α7 helix (such as any one of SEQ ID NOs: 115-135), the recombinant MPV F protein can include deletion of the N57 or N172 N-glycan sequon to increase immunogenicity of the MPV F protein. Further, the recombinant MPV F protein can include any of the above mutations for stabilization in the prefusion conformation and can further be linked to a C-terminal trimerization domain, such as a foldon domain, and/or an oligomerization peptide.

c) Removal of Fusion Peptide

In several embodiments, the recombinant MPV F protein can be modified to include a deletion of the fusion peptide (residues 103-123). Deletion of the fusion peptide can further stabilize the MPV F protein in its prefusion conformation by restricting the conformational changes MPV F can undergo and also removing the possibility of fusion peptide-fusion peptide aggregation. Non-limiting examples of recombinant MPV F protein sequences including deletion of the fusion peptide are set forth below.

NL/1/00 T160F/I177L (SEQ ID NO: 185):
LKESYLEESCSTITEGYLSVLRTGWYTNVFTLEVGDVENLTCADGPSLIK

TELDLTKSALRELRTVSADQLAREEQIENPRQSRIAKTIRLESEVTAIKN

ALKKTNEAVSTLGNGVRVLAFAVRELKDFVSKNLTRALNKNKCDIADLKM

AVSFSQFNRRFLNVVRQFSDNAGITPAISLDLMTDAELARAVSNMPTSAG

QIKLMLENRAMVRRKGFGFLIGVYGSSVIYMVQLPIFGVIDTPCWIVKAA

PSCSGKKGNYACLLREDQGWYCQNAGSTVYYPNEKDCETRGDHVFCDTAA

GINVAEQSKECNINISTTNYPCKVSTGRHPISMVALSPLGALVACYKGVS

CSIGSNRVGIIKQLNKGCSYITNQDADTVTIDNTVYQLSKVEGEQHVIKG

RPVSSSFDPVKFPEDQFNVALDQVFESIENSQALVDQSNRILSSAE

CAN97-83 T160F/I177L (SEQ ID NO: 186):
LKESYLEESCSTITEGYLSVLRTGWYTNVFTLEVGDVENLTCSDGPSLIK

TELDLTKSALRELKTVSADQLAREEQIENPRQSRIAKTIRLESEVTAIKN

ALKTTNEAVSTLGNGVRVLAFAVRELKDFVSKNLTRALNKNKCDIDDLKM

AVSFSQFNRRFLNVVRQFSDNAGITPAISLDLMTDAELARAVSNMPTSAG

QIKLMLENRAMVRRKGFGILIGVYGSSVIYMVQLPIFGVIDTPCWIVKAA

PSCSGKKGNYACLLREDQGWYCQNAGSTVYYPNEKDCETRGDHVFCDTAA

GINVAEQSKECNINISTTNYPCKVSTGRHPISMVALSPLGALVACYKGVS

-continued

CSIGSNRVGIIKQLNKGCSYITNQDADTVTIDNTVYQLSKVEGEQHVIKG

RPVSSSFDPIKFPEDQFNVALDQVFENIENSQALVDQSNRILSSAE

NL/17/00 T160F/I177L (SEQ ID NO: 187):
LKESYLEESCSTITEGYLSVLRTGWYTNVFTLEVGDVENLTCSDGPSLIK

TELDLTKSALRELKTVSADQLAREEQIENPRQSRIAKTIRLESEVTAIKN

ALKTTNEAVSTLGNGVRVLAFAVRELKDFVSKNLTRALNKNKCDIDDLKM

AVSFSQFNRRFLNVVRQFSDNAGITPAISLDLMTDAELARAVSNMPTSAG

QIKLMLENRAMVRRKGFGILIGVYGSSVIYTVQLPIFGVIDTPCWIVKAA

PSCSEKKGNYACLLREDQGWYCQNAGSTVYYPNEKDCETRGDHVFCDTAA

GINVAEQSKECNINISTTNYPCKVSTGRHPISMVALSPLGALVACYKGVS

CSIGSNRVGIIKQLNKGCSYITNQDADTVTIDNTVYQLSKVEGEQHVIKG

RPVSSSFDPIKFPEDQFNVALDQVFENIENSQALVDQSNRILSSAE

NCL174 T160F/I177L (SEQ ID NO: 188):
LKESYLEESCSTITEGYLSVLRTGWYTNVFTLEVGDVENLTCADGPSLIK

TELDLTKSALRELKPVSADQLAREEQIENPRQSRIAKTIRLESEVTAIKN

ALKKTNEAVSTLGNGVRVLAFAVRELKDFVSKNLTRALNKNKCDIDDLKM

AVSFSQFNRRFLNVVRQFSDNAGITPAISLDLMTDAELARAVSNMPTAAG

QIKLMLENRAMVRRKGFGILIGVYGSSVIYMVQLPIFGVIDTPCWIVKAA

PSCSEKKGNYACLLREDQGWYCQNAGSTVYYPNEKDCETRGDHVFCDTAA

GINVAEQSKECNINISTTNYPCKVSTGRHPISMVALSPLGALVACYKGVS

CSIGSNRVGIIKQLNKGCSYITNQDADTVTIDNTVYQLSKVEGEQHVIKG

RPVSSSFDPVKFPEDQFNVALDQVFENIENSQALVDQSNRILSSAE

NL/1/99 T160F/I177L (SEQ ID NO: 189):
LKESYLEESCSTITEGYLSVLRTGWYTNVFTLEVGDVENLTCTDGPSLIK

TELDLTKSALRELKTVSADQLAREEQIENPRQSRIAKTIRLESEVNAIKG

ALKQTNEAVSTLGNGVRVLAFAVRELKEFVSKNLTSALNRNKCDIADLKM

AVSFSQFNRRFLNVVRQFSDNAGITPAISLDLMTDAELARAVSYMPTSAG

QIKLMLENRAMVRRKGFGILIGVYGSSVIYMVQLPIFGVIDTPCWIIKAA

PSCSEKNGNYACLLREDQGWYCKNAGSTVYYPNEKDCETRGDHVFCDTAA

GINVAEQSRECNINISTTNYPCKVSTGRHPISMVALSPLGALVACYKGVS

CSIGSNWVGIIKQLPKGCSYITNQDADTVTIDNTVYQLSKVEGEQHVIKG

RPVSSSFDPIKFPEDQFNVALDQVFESIENSQALVDQSNKILNSAE

NDL00-1 T160F/I177L (SEQ ID NO: 190):
LKESYLEESCSTITEGYLSVLRTGWYTNVFTLEVGDVENLTCADGPSLIK

TELDLTKSALRELRTVSADQLAREEQIENPRQSRIAKTIRLESEVTAIKN

ALKKTNEAVSTLGNGVRVLAFAVRELKDFVSKNLTRALNKNKCDIADLKM

AVSFSQFNRRFLNVVRQFSDNAGITPAISLDLMTDAELARAVSNMPTSAG

QIKLMLENRAMVRRKGFGFLIGVYGSSVIYMVQLPIFGVIDTPCWIVKAA

PSCSGKKGNYACLLREDQGWYCQNAGSTVYYPNEKDCETRGDHVFCDTAA

GINVAEQSKECNINISTTNYPCKVSTGRHPISMVALSPLGALVACYKGVS

CSIGSNRVGIIKQLNKGCSYITNQDADTVTIDNTVYQLSKVEGEQHVIKG

RPVSSSFDPVKFPEDQFNVALDQVFESIENSQALVDQSNRILSSAE

-continued

CAN98-75 T160F/I177L (SEQ ID NO: 191):
LKESYLEESCSTITEGYLSVLRTGWYTNVFTLEVGDVENLTCTDGPSLIK
TELDLTKSALRELKTVSADQLAREEQIENPRQSRIAKTIRLESEVNAIKG
ALKTTNEAVSTLGNGVRVLAFAVRELKEFVSKNLTSALNKNKCDIADLKM
AVSFSQFNRRFLNVVRQFSDNAGITPAISLDLMTDAELARAVSYMPTSAG
QIKLMLENRAMVRRKGFGILIGVYGSSVIYMVQLPIFGVIDTPCWIIKAA
PSCSEKDGNYACLLREDQGWYCKNAGSTVYYPNKKDCETRGDHVFCDTAA
GINVAEQSRECNINISTTNYPCKVSTGRHPISMVALSPLGALVACYKGVS
CSIGSNRVGIIKQLPKGCSYITNQDADTVTIDNTVYQLSKVEGEQHVIKG
RPVSSSFDPIKFPEDQFNVALDQVFESIENSQALVDQSNKILNSAE

In any of the embodiments disclosed above for recombinant MPV F proteins including deletion of the fusion peptide (such as any one of SEQ ID NOs: 185-191), the recombinant MPV F protein can further include additional amino acid substitutions for stabilization in the prefusion conformation, such as introduction of a proline residue by substitution at one of positions 183-189 to prevent elongation of the α7 helix. Further, in any of the embodiments disclosed above for recombinant MPV F proteins including deletion of the fusion peptide (such as any one of SEQ ID NOs: 185-191), the recombinant MPV F protein can include deletion of the N57 or N172 N-glycan sequon to increase immunogenicity of the MPV F protein. Further, the recombinant MPV F protein can include any of the above mutations for stabilization in the prefusion conformation and can further be linked to a C-terminal trimerization domain, such as a foldon domain, and/or an oligomerization peptide.

d) Removal of N-Linked Glycans at N57 and/or N172 to Improve Immunogenicity

In several embodiments, the recombinant MPV F protein can include one or more amino acid substitutions to remove the native N-linked glycan sequons at position N57 and/or N172. In some embodiments, the removal of one or both of these sequons prevents N-glycosylation at these residues which can improve the immunogenicity of the resulting MPV F protein. To remove the N-linked glycan sequon, the sequon (Asn-X-Ser/Thr, where X is any amino acid except Pro) is modified, for example by introducing an N-to-Q substitution. In some embodiments, the recombinant MPV F protein can comprise one or more of: a N57Q substitution, a N172Q substitution, N57Q and N172Q substitutions, a T59A substitution, a T174A substitution, or T59A substitution and T174A substitutions, to remove N57 and/or N172 N-glycan sequons. Non-limiting examples of recombinant MPV F protein sequences including one or more mutations for stabilization in the prefusion conformation and further including amino acid substitutions to remove the N57, or the N57 and N172, N-glycan sequons are set forth below:

NL/1/00 A113C/A339C/T160F/I177L N57Q
(SEQ ID NO: 1 36):
LKESYLEESCSTITEGYLSVLRTGWYTNVFTLEVGDVEQLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIADLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAE

CAN97-83 A113C/A339C/T160F/I177L N57Q
(SEQ ID NO: 137):
LKESYLEESCSTITEGYLSVLRTGWYTNVFTLEVGDVEQLTCSDGPSLIK
TELDLTKSALRELKTVSADQLAREEQIENPRQSRFVLGAIALGVCTAAAV
TAGVAIAKTIRLESEVTAIKNALKTTNEAVSTLGNGVRVLAFAVRELKDF
VSKNLTRALNKNKCDIDDLKMAVSFSQFNRRFLNVVRQFSDNAGITPAIS
LDLMTDAELARAVSNMPTSAGQIKLMLENRAMVRRKGFGILIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAE

NL/17/00 A113C/A339C/T160F/I177L N57Q
(SEQ ID NO: 138):
LKESYLEESCSTITEGYLSVLRTGWYTNVFTLEVGDVEQLTCSDGPSLIK
TELDLTKSALRELKTVSADQLAREEQIENPRQSRFVLGAIALGVCTAAAV
TAGVAIAKTIRLESEVTAIKNALKTTNEAVSTLGNGVRVLAFAVRELKDF
VSKNLTRALNKNKCDIDDLKMAVSFSQFNRRFLNVVRQFSDNAGITPAIS
LDLMTDAELARAVSNMPTSAGQIKLMLENRAMVRRKGFGILIGVYGSSVI
YTVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAE

NCL174 A113C/A339C/T160F/I177L N57Q
(SEQ ID NO: 139):
LKESYLEESCSTITEGYLSVLRTGWYTNVFTLEVGDVEQLTCADGPSLIK
TELDLTKSALRELKPVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIDDLKMAVSFSQFNRRFLNVVRQFSDNAGITPAIS
LDLMTDAELARAVSNMPTAAGQIKLMLENRAMVRRKGFGILIGVYGSSVI
YMVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFENIE
NSQALVDQSNRILSSAE

-continued

NL/1/99 A113C/A339C/T160F/I177L N57Q (SEQ ID NO: 140):
LKESYLEESCSTITEGYLSVLRTGWYTNVFTLEVGDVEQLTCTDGPSLIK
TELDLTKSALRELKTVSADQLAREEQIENPRQSRFVLGAIALGVCTAAAV
TAGIAIAKTIRLESEVNAIKGALKQTNEAVSTLGNGVRVLAFAVRELKEF
VSKNLTSALNRNKCDIADLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKNGNYACLLREDQGWYCKNAGSTV
YYPNEKDCETRGDHVFCDTACGINVAEQSRECNINISTTNYPCKVSTGRH
PISMVALSPLGALVACYKGVSCSIGSNWVGIIKQLPKGCSYITNQDADTV
TIDNTVYQLSKVEGEQHVIKGRPVSSSFDPIKFPEDQFNVALDQVFESIE
NSQALVDQSNKILNSAE

NDL00-1 A113C/A339C/T160F/I177L N57Q (SEQ ID NO: 141):
LKESYLEESCSTITEGYLSVLRTGWYTNVFTLEVGDVEQLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIADLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAE

CAN98-75 A113C/A339C/T160F/I177L N57Q (SEQ ID NO: 142):
LKESYLEESCSTITEGYLSVLRTGWYTNVFTLEVGDVEQLTCTDGPSLIK
TELDLTKSALRELKTVSADQLAREEQIENPRQSRFVLGAIALGVCTAAAV
TAGIAIAKTIRLESEVNAIKGALKTTNEAVSTLGNGVRVLAFAVRELKEF
VSKNLTSALNKNKCDIADLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKDGNYACLLREDQGWYCKNAGSTV
YYPNKKDCETRGDHVFCDTACGINVAEQSRECNINISTTNYPCKVSTGRH
PISMVALSPLGALVACYKGVSCSIGSNRVGIIKQLPKGCSYITNQDADTV
TIDNTVYQLSKVEGEQHVIKGRPVSSSFDPIKFPEDQFNVALDQVFESIE
NSQALVDQSNKILNSAE

NL/1/00 A113C/A339C/T160F/I177L N57Q/N172Q (SEQ ID NO: 143):
LKESYLEESCSTITEGYLSVLRTGWYTNVFTLEVGDVEQLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKQLTRALNKNKCDIADLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAE

CAN97-83 A113C/A339C/T160F/I177L N57Q/N172Q (SEQ ID NO: 144):
LKESYLEESCSTITEGYLSVLRTGWYTNVFTLEVGDVEQLTCSDGPSLIK
TELDLTKSALRELKTVSADQLAREEQIENPRQSRFVLGAIALGVCTAAAV
TAGVAIAKTIRLESEVTAIKNALKTTNEAVSTLGNGVRVLAFAVRELKDF
VSKQLTRALNKNKCDIDDLKMAVSFSQFNRRFLNVVRQFSDNAGITPAIS
LDLMTDAELARAVSNMPTSAGQIKLMLENRAMVRRKGFGILIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAE

NL/17/00 A113C/A339C/T160F/I177L N57Q/N172Q (SEQ ID NO: 145):
LKESYLEESCSTITEGYLSVLRTGWYTNVFTLEVGDVEQLTCSDGP
SLIKTELDLTKSALRELKTVSADQLAREEQIENPRQSRFVLGAIALGV
CTAAAVTAGVAIAKTIRLESEVTAIKNALKTTNEAVSTLGNGVRVLAFAV
RELKDFVSKQLTRALNKNKCDIDDLKMAVSFSQFNRRFLNVVRQFSDNAG
ITPAISLDLMTDAELARAVSNMPTSAGQIKLMLENRAMVRRKGFGILIGV
YGSSVIYTVQLPIFGVIDTPCWIVKAAPSCSEKKGNYACLLREDQGWYCQ
NAGSTVYYPNEKDCETRGDHVFCDTACGINVAEQSKECNINISTTNYPCK
VSTGRHPISMVALSPLGALVACYKGVSCSIGSNRVGIIKQLNKGCSYITN
QDADTVTIDNTVYQLSKVEGEQHVIKGRPVSSSFDPIKFPEDQFNVALDQ
VFENIENSQALVDQSNRILSSAE

NCL174 A113C/A339C/T160F/I1 77L N57Q/N172Q (SEQ ID NO: 146):
LKESYLEESCSTITEGYLSVLRTGWYTNVFTLEVGDVEQLTCADGPSLIK
TELDLTKSALRELKPVSADQLAREEQIENPRQSRFVLGAIALGVCTAAAV
TAGVAIAKTIRLESEVTAIKNALKKTNEAVSTLGNGVRVLAFAVRELKDF
VSKQLTRALNKNKCDIDDLKMAVSFSQFNRRFLNVVRQFSDNAGITPAIS
LDLMTDAELARAVSNMPTAAGQIKLMLENRAMVRRKGFGILIGVYGSSVI
YMVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFENIE
NSQALVDQSNRILSSAE

NL/1/99 A113C/A339C/T160F/I177L N57Q/N172Q (SEQ ID NO: 147):
LKESYLEESCSTITEGYLSVLRTGWYTNVFTLEVGDVEQLTCTDGPSLIK
TELDLTKSALRELKTVSADQLAREEQIENPRQSRFVLGAIALGVCTAAAV
TAGIAIAKTIRLESEVNAIKGALKQTNEAVSTLGNGVRVLAFAVRELKEF

-continued

VSKQLTSALNRNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKNGNYACLLREDQGWYCKNAGSTV

YYPNEKDCETRGDHVFCDTACGINVAEQSRECNINISTTNYPCKVSTGRH

PISMVALSPLGALVACYKGVSCSIGSNWVGIIKQLPKGCSYITNQDADTV

TIDNTVYQLSKVEGEQHVIKGRPVSSSFDPIKFPEDQFNVALDQVFESIE

NSQALVDQSNKILNSAE

NDL00-1 A113C/A339C/T160F/I177L N57Q/N172Q
(SEQ ID NO: 148):
LKESYLEESCSTITEGYLSVLRTGWYTNVFTLEVGDVEQLTCADGPSLIK

TELDLTKSALRELRTVSADQLAREEQIENPRQSRFVLGAIALGVCTAAAV

TAGVAIAKTIRLESEVTAIKNALKKTNEAVSTLGNGVRVLAFAVRELKDF

VSKQLTRALNKNKCDIADLKMAVSFSQFNRRFLNVVRQFSDNAGITPAIS

LDLMTDAELARAVSNMPTSAGQIKLMLENRAMVRRKGFGFLIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPVKFPEDQFNVALDQVFESIE

NSQALVDQSNRILSSAE

CAN98-75 A113C/A339C/T160F/I177L N57Q/N172Q
(SEQ ID NO: 149):
LKESYLEESCSTITEGYLSVLRTGWYTNVFTLEVGDVEQLTCTDGPSLIK

TELDLTKSALRELKTVSADQLAREEQIENPRQSRFVLGAIALGVCTAAAV

TAGIAIAKTIRLESEVNAIKGALKTTNEAVSTLGNGVRVLAFAVRELKEF

VSKQLTSALNKNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKDGNYACLLREDQGWYCKNAGSTV

YYPNKKDCETRGDHVFCDTACGINVAEQSRECNINISTTNYPCKVSTGRH

PISMVALSPLGALVACYKGVSCSIGSNRVGIIKQLPKGCSYITNQDADTV

TIDNTVYQLSKVEGEQHVIKGRPVSSSFDPIKFPEDQFNVALDQVFESIE

NSQALVDQSNKILNSAE

In any of the embodiments disclosed above for recombinant MPV F proteins including deletion of the N57 or N172 N-glycan sequons (such as any one of SEQ ID NOs: 136-149), the recombinant MPV F protein can further include additional amino acid substitutions for stabilization in the prefusion conformation, such as introduction of a proline residue by substitution at one of positions 183-189 to prevent elongation of the α7 helix (for example a D183P substitution, a A185P substitution, or a D186 substitution), and/or introduction of an additional non-native disulfide bond by A120C/Q426C substitutions or A120C/S428C substitutions. Further, the recombinant MPV F protein can include any of the above mutations for stabilization in the prefusion conformation and can further be linked to a C-terminal trimerization domain, such as a foldon domain, and/or an oligomerization peptide.

e) Addition of N-Linked Glycosylation Sites

In several embodiments, the recombinant MPV F protein can include one or more N-linked glycosylation sites introduced onto the membrane proximal portion of the trimer (for example, within 20 residues of the c-terminal residue of the F1 polypeptide) to mask non-neutralizing epitopes present on this portion of the trimer. Such mutations are typically utilized in soluble embodiments of the recombinant MPV F protein. To create an N-linked glycosylation site, the sequence Asn-X-Ser/Thr (where X is any amino acid except Pro) can to be introduced. This can be accomplished by substitution of a Ser/Thr amino acid two residues C-terminal to a native Asn residue, or by substitution of an Asn amino acid two residues N-terminal to a native Ser/Thr residue, or by substitution of both an Asn and Ser/Thr residue separated by one non-proline amino acid. In some embodiments, the recombinant MPV F protein comprises one or more amino acid substitutions that introduce an N-linked glycosylation site near the C-terminus of the $F_1$ ectodomain. In some embodiments, the recombinant MPV F protein can include one or more non-native N-linked glycosylation sites between positions 468-478, such as positions 468-476. For example, the recombinant MPV F protein can include one or more non-native N-linked glycosylation sites at positions 468, 472, 474, 475, and/or 476. In some embodiments, the native MPV F sequence (for example, 468-ENSQALVDQSN-478, residues 468-478 of SEQ ID NO: 1) can be mutated to include one or more non-native N-linked glycosylation sites as set forth below (non-native glycosylation sequons are underlined):

468- ENSQALVDNST-478 (Q476N/V478T, SEQ ID NO: 51)

468- ENSQALVNQSN-478 (D475N, SEQ ID NO: 52)

468- ENSQALNDTSN-478 (V474N/Q476T, SEQ ID NO: 53)

468- ENSQNLTDQSN-478 (A472N/V474T, SEQ ID NO: 54)

468- NNSQALVDQSN-478 (E468N, SEQ ID NO: 55)

468- ENSQNLTDNST-478 (A472N/V474T, Q476N/V478T, SEQ ID NO: 56)

468- NNSQNLTDNST-478 (E468N, A472N/V474T, Q476N/V478T, SEQ ID NO: 57)

468- NNSQALVDNST-478 (E468N, Q476N/V478T, SEQ ID NO: 58)

468- NNSQNLTDQSN-478 (E468N, A472N/V474T, SEQ ID NO: 59)

468- ENSQNLTNQSN-478 (A472N/V474T, D475N, SEQ ID NO: 60)

-continued

468- NNSQNLTNQSN-478 (E468N, A472N/V474T, D475N, SEQ ID NO: 61)

468- NNSQALVNQSN-478 (E468N, D475N, SEQ ID NO: 62)

468- NNSQNLTDQSN-478 (E468N, A472N/V474T, SEQ ID NO: 63)

468- NNSQALVDNST-478 (E468N, Q476N/V478T, SEQ ID NO: 64)

f) Chimeric F Proteins

In some embodiments, the recombinant MPV F protein can include sequences from multiple strains of MPV. For example, the recombinant MPV F protein can include a $F_2$ sequence from a first MPV strain and a $F_1$ sequence from a second MPV strain.

g) Single Chain MPV F Proteins

In some embodiments, the recombinant MPV F protein is a single chain MPV F protein, which includes a single polypeptide chain including the $F_2$ polypeptide and the $F_1$ ectodomain. Native MPV F sequences include a protease cleavage site approximately at position 102 (e.g., $RQSR_{102}$), which is cleaved by a cellular protease to generate separate $F_2$ and $F_1$ polypeptides. The disclosed single chain proteins do not include the cleavage site separating the $F_2$ and $F_1$ polypeptides; therefore, when produced in cells, the F polypeptide is not cleaved into separate $F_2$ and $F_1$ polypeptides.

Single chain MPV F proteins can be generated by mutating the protease cleavage site to prevent cleave and formation of separate $F_2$ and $F_1$ polypeptide chains and join the $F_2$ and $F_1$ polypeptides directly to form the single chain MPV F protein or indirectly via a linker, such as a peptide linker. Non-limiting examples of peptide linkers that can be used include glycine, serine, and glycine-serine linkers, such as a G, S, GG, GS, SG, GGG, GSG, GSK, SQSD (SEQ ID NO: 16), STST (SEQ ID NO: 17), GGGG (SEQ ID NO: 18), SGGG (SEQ ID NO: 19), GGGGG (SEQID NO: 20), GGGGGGG (SEQ ID NO: 21), GGSGG (SEQ ID NO: 22), and GGSGGSG (SEQ ID NO: 23). In some embodiments, the single chain MPV F protein can include a heterologous peptide linker between one of MPV F residues 98 and 103, 98 and 104, 98 and 105, 98 and 106, 98 and 107, 99 and 103, 99 and 104, 99 and 105, 99 and 106, 99 and 107, 100 and 103, 100 and 104, 100 and 105, 100 and 106, 100 and 107, 101 and 103, 101 and 104, 101 and 105, 101 and 106, or 101 and 107. Any amino acid substitution or insertion can be used that effectively prevents cleavage of MPV F into separate $F_2$ and $F_1$ polypeptide chains, and also allows folding of the MPV F ectodomain into its prefusion conformation. Exemplary sequences of positions 95-106 or 95-110 that can be used to make a single chain MPV F protein are provided below (peptide linker sequence is shown in lower case):

95-IENP - sqsd - FVLG-106 (SEQ ID NO: 24)

95-IENP - stst - FVLG-106 (SEQ ID NO: 25)

95-IENP - gggg - FVLG-106 (SEQ ID NO: 26)

95-IENPRQ - sggg - FVLG-106 (SEQ ID NO: 27)

95-IENPRQS - ggggg - FVLG-106 (SEQ ID NO: 28)

95-IENPRQS - ggggggg - FVLG-106 (SEQ ID NO: 29)

95-IENP - gsg - FVLG-106 (SEQ ID NO: 30)

95-IENP - gsk - FVLG-106 (SEQ ID NO: 83)

-continued

95-IEN - ggsgg - AIAL-110 (SEQ ID NO: 31)

95-IEN - ggsggsg - AIAL-110 (SEQ ID NO: 32)

It is noted that position 113 of SEQ ID NOs: 31 and 32 above is shown as an alanine, however, in several embodiments, this residue can be substituted for a cysteine residue.

Any of the stabilizing mutations (or combinations thereof) disclosed herein can be included in the single chain MPV F protein as long as the single chain MPV F protein retains the MPV F prefusion conformation. For example, in some embodiments, the single chain MPV F protein can include cysteine substitutions at positions 113 and 339 (such as A113C and A339C substitutions) that form a non-natural disulfide bond and/or cavity filling substitutions at positions 160 and/or 177 (such as T160F and I177L substitutions). The single chain MPV F proteins can be incorporated into any embodiment disclosed herein in which the cleaved MPV F proteins can be used. For example, the single chain MPV F proteins can be linked to a protein nanoparticle subunit to generate a protein nanoparticle including the single chain MPV F protein.

h) Stabilization of the Membrane Proximal Region

In several embodiments, the recombinant MPV F protein can include one or more modifications that stabilize the membrane proximal region, for example, to maintain a soluble (e.g., without transmembrane domain) MPV F protein trimer in a trimeric configuration. Non-limiting examples include addition of a trimerization domain, a transmembrane domain (e.g., for applications including a membrane-anchored MPV F protein antigen), or one or more cysteine residues that can form inter-protomer non-natural disulfide bonds. It will be understood that these modifications are not strictly necessary to stabilize a recombinant MPV F protein in a prefusion conformation, but that, in some instances, they can be combined with other prefusion stabilizing modifications, such as those described above.

(1) Trimerization Domains

In several embodiments, the recombinant MPV F protein can be linked to a trimerization domain. For example the C-terminus of the $F_1$ protein included in the recombinant MPV F protein can be linked to the trimerization domain. The trimerization domain promotes trimerization of the three protomers of the recombinant MPV F protein. Non-limiting examples of exogenous multimerization domains that promote stable trimers of soluble recombinant proteins include: the GCN4 leucine zipper (Harbury et al. 1993 *Science* 262:1401-1407), the trimerization motif from the lung surfactant protein (Hoppe et al. 1994 *FEBS Lett* 344: 191-195), collagen (McAlinden et al. 2003 *J Biol Chem* 278:42200-42207), and the phage T4 fibritin foldon (Miroshnikov et al. 1998 *Protein Eng* 11:329-414), any of which can be linked to the recombinant MPV F protein (e.g., by linkage to the C-terminus of the $F_1$ polypeptide) to promote trimerization of the recombinant MPV F protein, as long as the recombinant MPV F protein retains specific binding activity for a prefusion conformation specific antibody (e.g., MPE8), and/or includes a MPV F prefusion conformation.

In some examples, the recombinant MPV F protein can be linked to a foldon domain, for example, the recombinant MPV F protein can include a $F_1$ polypeptide with a foldon domain linked to its C-terminus. In specific examples, the foldon domain is a T4 fibritin foldon domain such as the amino acid sequence S (SEQ ID NO: 33), which adopts a β-propeller conformation, and can fold and trimerize in an autonomous way (Tao et al. 1997 *Structure* 5:789-798). Modified foldon domains can also be used, such as a foldon domain including an amino acid sequence set forth as GYIPEAPRDGQCYVRCDGEWVLLSTF (SEQ ID NO: 34), GYIPECPRDGQAYVCKDGEWVLLSTF (SEQ ID NO: 35), GYIPEAPRDGQCYCRKDGEWVLLSTF (SEQ ID NO: 36), or GYIPEAPRDGQACVRKDGECVLLSTF (SEQ ID NO: 37). These modified foldon domains include amino acid substitutions that add two cysteine residues for formation of stabilizing disulfide bonds. In some embodiments, any of the disclosed recombinant MPV F proteins can be linked to a modified foldon domain as described herein.

Typically, the heterologous trimerization domain is positioned C-terminal to the $F_1$ ectodomain. Optionally, the multimerization domain is connected to the $F_1$ ectodomain protein via a linker, such as an amino acid linker. Exemplary linkers are provided herein and are known in the art; non-limiting examples include Gly or Gly-Ser linkers, such as the amino acid sequence: GGSGGSGGS; SEQ ID NO: 38. Numerous conformationally neutral linkers are known in the art that can be used in this context without disrupting the conformation of the recombinant MPV F protein. Some embodiments include a protease cleavage site for removing the trimerization domain from the MPV F protein, such as, but not limited to, a thrombin site between the $F_1$ ectodomain and the trimerization domain. A non-limiting example of a cleavable trimerization domain sequence is provided as: GGGLVPRGSGGYIPEAPRDGQAYVRKDGEWVLLSTFL (SEQ ID NO: 39), which includes a protease cleavage site N-terminal to a foldon domain.

In non-limiting embodiments, the recombinant MPV F protein can include an $F_1$ ectodomain that is linked to a trimerization domain at its C-terminus, for example, as set forth as SEQ ID NOs: 80-81.

```
hMPV B2 Fd with a foldon trimerization domain and
cavity filling mutations (T160F, I177L) that
stabilizes the prefusion conformation:
                                      (SEQ ID NO: 80)
MSWKVMIIISLLITPQHGLKESYLEESCSTITEGYLSVLRTGWYTNVFTL

EVGDVENLTCTDGPSLIKTELDLTKSALRELKTVSADQLAREEQIENPRQ

SRFVLGAIALGVATAAAVTAGIAIAKTIRLESEVNAIKGALKTTNEAVST

LGNGVRVLAFAVRELKEFVSKNLTSALNKNKCDIADLKMAVSFSQFNRRF

LNVVRQFSDNAGITPAISLDLMTDAELARAVSYMPTSAGQIKLMLENRAM

VRRKGFGILIGVYGSSVIYMVQLPIFGVIDTPCWIIKAAPSCSEKDGNYA

CLLREDQGWYCKNAGSTVYYPNDKDCETRGDHVFCDTAAGINVAEQSREC

NINISTTNYPCKVSTGRHPISMVALSPLGALVACYKGVSCSIGSNRVGII

KQLPKGCSYITNQDADTVTIDNTVYQLSKVEGEQHVIKGRPVSSSFDPIK

FPEDQFNVALDQVFESIENSQALVDQSNKILNSAESAIGG
```

-continued

```
hMPV B2 with A113C and A339C mutations and a
foldon-trimerization domain that stabilize the
prefusion conformation:
                                      (SEQ ID NO: 81)
MSWKVMIIISLLITPQHGLKESYLEESCSTITEGYLSVLRTGWYTNVFTL

EVGDVENLTCTDGPSLIKTELDLTKSALRELKTVSADQLAREEQIENPRQ

SRFVLGAIALGVcTAAAVTAGIAIAKTIRLESEVNAIKGALKTTNEAVST

LGNGVRVLATAVRELKEFVSKNLTSAINKNKCDIADLKMAVSFSQFNRRF

LNVVRQFSDNAGITPAISLDLMTDAELARAVSYMPTSAGQIKLMLENRAM

VRRKGFGILIGVYGSSVIYMVQLPIFGVIDTPCWIIKAAPSCSEKDGNYA

CLLREDQGWYCKNAGSTVYYPNDKDCETRGDHVFCDTAcGINVAEQSREC

NINISTTNYPCKVSTGRHPISMVALSPLGALVACYKGVSCSIGSNRVGII

KQLPKGCSYITNQDADTVTIDNTVYQLSKVEGEQHVIKGRPVSSSFDPIK

FPEDQFNVALDQVFESIENSQALVDQSNKILNSAESAIGGYIPEAPRDGQ

AYVRKDGEWVLLSTFLGGLVPRGSHHHHHHSAWSHPQFEK
```

Any of the recombinant MPV F proteins described herein can be linked to a foldon domain to promote trimerization of the MPV F protein. For example, the C-terminal residue of a F1 ectodomain of a MPV F protein as described herein can be linked to a foldon domain (such as a foldon domain comprising an amino acid sequence set forth as SEQ ID NO: 33) to promote trimerization of the MPV F protein. In some embodiments, the C-terminal residue of any one of SEQ ID NOs: 12-15, 101-149, or 178-191 can be linked to a foldon domain by a peptide linker or can be directly linked. In some embodiments, the MPV F protein can comprises an amino acid sequence set forth as any one of SEQ ID NOs: 12-15, 101-149, or 178-191 (or an amino acid sequence at least 90% identical to any one of SEQ ID NOs: 12-15, 101-149, or 178-191), and the C-terminal residue of the F1 ectodomain of the MPV F portion can be linked (for example, by a peptide linker) to a foldon domain comprising an amino acid sequence set forth as SEQ ID NO: 33.

(2) Disulfide Bonds

In several embodiments, the recombinant MPV F protein can include a $F_1$ ectodomain including one or more disulfide bonds near the C-terminus of the ectodomain that are used to maintain the MPV F protein trimer in a trimeric configuration. For example, the soluble recombinant MPV F ectodomain can be stabilized in a trimeric configuration without the use of a foldon domain, for example, by incorporation of a C-terminal "cysteine zipper" domain. The cysteine zipper domain is similar in structure to a leucine zipper domain, and includes a coiled-coil domain with cysteine residues in place of the corresponding leucine residues of the coiled-coil domain of a leucine zipper. In several embodiments, the C-terminal non-native elongated cysteine zipper domain includes a coiled-coil domain including inter-protomer disulfide bonds between three, four, or five rings of di-cysteine motifs. The cysteine residues that form the disulfide bond can be introduced into the recombinant MPV F protein by one or more amino acid substitutions, or a peptide including the cysteine residues can be linked to the recombinant MPV F protein, for example, the peptide including the cysteine residues can be linked to the C-terminus of the $F_1$ ectodomain.

In embodiments including a cysteine zipper domain, the domain can comprise a coiled-coil domain with three parallel α-helices, each based on a portion of the membrane proximal α helix of the native MPV F ectodomain beginning at approximately position 480. The cysteine zipper domain included on the disclosed recombinant MPV F ectodomains is present on the C-terminal portion of the F ectodomain. In some embodiments, the cysteine zipper domain can be extended to include additional C-terminal helical positions in place of a portion of the native transmembrane domain, and also mutated to include the cysteine residues in the rings of di-cysteine motifs. Cysteine residues are introduced into the sequence of the cysteine zipper domain to allow for formation of inter-protomer disulfide bonds between the α-helices of the coiled-coil, thereby "locking" the three α-helices in the trimeric configuration.

In some embodiments, the recombinant MPV F protein includes cysteine substitutions at positions 480 and 481, or 487 and 488, or 480, 481, 487, and 488, that introduce non-natural disulfide bonds that to maintain a MPV F protein trimer in a trimeric configuration. In further embodiments, the recombinant MPV F protein can include a peptide with a di-cysteine motif, such as peptides including the sequence set forth as one of CCTTTGICCTTTNICCTT (SEQ ID NO: 40), CCHNVNAGKSTTN (SEQ ID NO: 41), CCHNVNACCSTTN (SEQ ID NO: 42). The peptide can be linked to the C-terminus of the $F_1$ ectodomain of the recombinant MPV F protein, for example, at one of MPV F positions 480-490. Thus, non-limiting examples of polypeptide sequences that can be linked to the MPV F protein includes (with linkage at position 480 of the MPV F protein):

(SEQ ID NO: 43)
480-CCSSAEKGNTG (SEQ ID NO: 44)
480-CCSSAEKCCTG (SEQ ID NO: 45)
480-CCHNVNAGKSTTN (SEQ ID NO: 46)
480-CCHNVNACCSTTN (SEQ ID NO: 84)
480-ILSSAEKCCTTTGICCTTTNICCTT

-continued (SEQ ID NO: 85)
480-CCSSAEKCCTTTGICCTTTNICCTT (SEQ ID NO: 86)
480-ILSSAEKCCTTTGICCTTVNACCSTTNICCTT (SEQ ID NO: 87)
480-CCSSAEKCCTTTGICCTTVNACCSTTNICCTT (SEQ ID NO: 88)
480-ILHNVNACCSTTNICCTTTNICCTT (SEQ ID NO: 89)
480-CCHNVNACCSTTNICCTTTNICCTT (SEQ ID NO: 90)
480-ILHNVNACCSTTNICCTTVNACCSTTNICCTT (SEQ ID NO: 91)
480-CCHNVNACCSTTNICCTTVNACCSTTNICCTT In some embodiments, use of a cysteine ring can be combined with other modalities to stabilize the membrane proximal region of the MPV F protein trimer in trimeric form, or for other purposes. For example, the recombinant MPV F protein can include cysteine substitutions that can form a cysteine zipper domain, and further include a trimerization domain and/or purification tags. The trimerization domain can be separated from the cysteine ring by one or more protease cleavage sites that facilitate removal of the trimerization domain if desired. In some embodiments, a peptide including the sequences of such stabilization elements can be linked to the C-terminus of the $F_1$ ectodomain of the recombinant MPV F protein, for example, at one of MPV F positions 480-490. A non-limiting example of a polypeptide sequence that can be included C-terminal to the coiled-coil domain on the $F_1$ ectodomain is set forth as: LVPRGSGGYIPEAPRDGQAYVRKDGEWVLLSTFLGGHHHHHHSAWSHPQFEK, SEQ ID NO: 92 (with thrombin cleavage site, His tag, Strep Tag II, and foldon domain bolded and separated by GG linkers).

Non-limiting examples of polypeptide sequences that can be linked to the MPV F protein include (with linkage at position 480):

(SEQ ID NO: 47)
480-CCSSAEKGNTGGGLVPRGSGGYIPEAPRDGQAYVRKDGEWVLLSTFLGGHHHHHHSAWSHPQFEK (SEQ ID NO: 48)
480-CCSSAEKCCTGGGLVPRGSGGYIPEAPRDGQAYVRKDGEWVLLSTFLGGHHHHHHSAWSHPQFEK (SEQ ID NO: 93)
480-ILSSAEKCCTTTGICCTTTNICCTTGGLVPRGSGGYIPEAPRDGQAYVRKDGEWVLLSTFLGGHHHHHHSAWSHPQFEK (SEQ ID NO: 94)
480-CCSSAEKCCTTTGICCTTTNICCTTGGLVPRGSGGYIPEAPRDGQAYVRKDGEWVLLSTFLGGHHHHHHSAWSHPQFEK (SEQ ID NO: 95)
480-ILSSAEKCCTTTGICCTTVNACCSTTNICCTTGGLVPRGSGGYIPEAPRDGQAYVRKDGEWVLLSTFLGGHHHHHHSAWSHPQFEK (SEQ ID NO: 96)
480-CCSSAEKCCTTTGICCTTVNACCSTTNICCTTGGLVPRGSGGYIPEAPRDGQAYVRKDGEWVLLSTFLGGHHHHHHSAWSHPQFEK (SEQ ID NO: 49)
480-CCHNVNAGKSTTNGGLVPRGSGGYIPEAPRDGQAYVRKDGEWVLLSTFLGGHHHHHHSAWSHPQFEK (SEQ ID NO: 50)
480-CCHNVNACCSTTNGGLVPRGSGGYIPEAPRDGQAYVRKDGEWVLLSTFLGGHHHHHHSAWSHPQFEK (SEQ ID NO: 97)
480-ILHNVNACCSTTNICCTTTNICCTTGGLVPRGSGGYIPEAPRDGQAYVRKDGEWVLLSTFLGGHHHHHHSAWSHPQFEK

-continued (SEQ ID NO: 98)
480-CCHNVNACCSTTNICCTTTNICCTTGGLVPRGSGGYIPEAPRDGQAYVRKDGEWVLLSTFLGGHHHHHHSAWSHPQFEK (SEQ ID NO: 99)
480-ILHNVNACCSTTNICCTTVNACCSTTNICCTTGGLVPRGSGGYIPEAPRDGQAYVRKDGEWVLLSTFLGGHHHHHHSAWSHPQFEK (SEQ ID NO: 100)
480-CCHNVNACCSTTNICCTTVNACCSTTNICCTTGGLVPRGSGGYIPEAPRDGQAYVRKDGEWVLLSTFLGGHHHHHHSAWSHPQFEK (3) Membrane Anchor In some embodiments, the recombinant MPV F protein is a membrane anchored protein, for example, the recombinant MPV F protein can be linked to a transmembrane domain. The transmembrane domain can be linked to any portion of the recombinant MPV F protein, as long as the presence of the transmembrane domain does not disrupt the structure of the MPV F ectodomain, or its ability to induce an immune response to MPV F protein. In a non-limiting example, the transmembrane domain can be linked to the C-terminal residue of a $F_1$ ectodomain included in the recombinant MPV F protein. One or more peptide linkers (such as a Gly-Ser linker) can be included between the transmembrane domain and the $F_1$ ectodomain. The transmembrane domain can be linked to a recombinant MPV F protein including any of the stabilizing mutations provided herein. For example, the transmembrane domain can be linked to the C-terminal residue of a $F_1$ ectodomain included in a recombinant MPV F protein including A113C/A339C substitutions and/or T160F, I177L, or T160F and I177L substitutions.

Non-limiting examples of transmembrane domains for use with the disclosed embodiments include a transmembrane domain from a MPV F protein (e.g., FIIVIILIAVLGSSMILVSIFII, SEQ ID NO: 68), an Influenza A Hemagglutinin™ domain (ILAIYSTVASSLVLLVSLGAISF, SEQ ID NO: 69), and an Influenza A Neuraminidase™ domain (IITIGSICMVVGIISLILQIGNIISIWVS, SEQ ID NO: 70).

j) Oligomerization Peptides

In some embodiments, the recombinant MPV F protein can include a C-terminal hydrophobic oligomerization peptide to promote oligomerization of the MPV F protein. In several embodiments, the recombinant MPV F protein can include a C-terminal trimerization domain (such as a foldon domain) and further include an oligomerization peptide at or near the C-terminus of the trimerization domain. In several embodiments the hydrophobic oligomerization peptide can comprise the amino acid sequence set forth as: FLGFLLGV (SEQ ID NO: 150). The oligomerization peptide can be linked to the C-terminus of the MPV F protein, or the trimerization domain (such as a foldon domain) using a peptide linker. The oligomerization peptides on the MPV F protein self-assemble, thereby allowing formation of nanoparticle-sized oligomers of the recombinant MPV F protein. Different subgroups (such as human subgroup A and human subgroup B) of the recombinant MPV F protein can be mixed into the particles by producing recombinant MPV F proteins with the oligomerization domain from different subgroups, and then mixing the different recombinant MPV F proteins. Non-limiting examples of linker+peptide oligomerization domain sequences that can be used with the disclosed recombinant MPV F proteins include:

Np3
(SEQ ID NO: 151)
GGGGSSGGSSGGFLGFLLGVGSAIASGVAV

Np6
(SEQ ID NO: 152)
GGGGSSGGFLGFLLGV

Np8
(SEQ ID NO: 153)
GGGGSSGGSSGGSSGGSSGGFLGFLLGV

Np6v1
(SEQ ID NO: 154)
GGGSGGFLGFLLGV

Np6v2
(SEQ ID NO: 155)
GGGGFLGFLLGV

Np6v3
(SEQ ID NO: 156)
GGGGSSGGFLGFLLGVGSFLGFLLGV

Non-limiting examples of recombinant MPV F protein sequence including one or more mutations for stabilization in the prefusion conformation and further including a foldon trimerization domain and a peptide oligomerization domain are set forth below.

NL/1/00 A113C/A339C/T160F/I177L Fd np3
(SEQ ID NO: 157):
LKESYLEESCSTITEGYLSVLRTGWYTNVFTLEVGDVENLTCADGPSLIK

TELDLTKSALRELRTVSADQLAREEQIENPRQSRFVLGAIALGVCTAAAV

TAGVAIAKTIRLESEVTAIKNALKKTNEAVSTLGNGVRVLAFAVRELKDF

VSKNLTRALNKNKCDIADLKMAVSFSQFNRRFLNVVRQFSDNAGITPAIS

LDLMTDAELARAVSNMPTSAGQIKLMLENRAMVRRKGFGFLIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPVKFPEDQFNVALDQVFESIE

NSQALVDQSNRILSSAESAIGGYIPEAPRDGQAYVRKDGEWVLLSTFLGG

GGSSGGSSGGFLGFLLGVGSAIASGVAV

CAN97-83 A113C/A339C/T160F/I177L Fd np3
(SEQ ID NO: 158):
LKESYLEESCSTITEGYLSVLRTGWYTNVFTLEVGDVENLTCSDGPSLIK

TELDLTKSALRELKTVSADQLAREEQIENPRQSRFVLGAIALGVCTAAAV

TAGVAIAKTIRLESEVTAIKNALKTTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTSAGQIKLMLENRAMVRRKGFGILIGVYGSSVI

-continued

YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAESAIGGYIPEAPRDGQAYVRKDGEWVLLSTFLGG
GGSSGGSSGGFLGFLLGVGSAIASGVAV

NL/17/00 A113C/A339C/T160F/I177L Fd np3
(SEQ ID NO: 159):
LKESYLEESCSTITEGYLSVLRTGWYTNVFTLEVGDVENLTCSDGPSLIK
TELDLTKSALRELKTVSADQLAREEQIENPRQSRFVLGAIALGVCTAAAV
TAGVAIAKTIRLESEVTAIKNALKTTNEAVSTLGNGVRVLAFAVRELKDF
VSKNLTRALNKNKCDIDDLKMAVSFSQFNRRFLNVVRQFSDNAGITPAIS
LDLMTDAELARAVSNMPTSAGQIKLMLENRAMVRRKGFGILIGVYGSSVI
YTVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPIKFPEDQFNVALDQVFENIE
NSQALVDQSNRILSSAESAIGGYIPEAPRDGQAYVRKDGEWVLLSTFLGG
GGSSGGSSGGFLGFLLGVGSAIASGVAV

NCL174 A113C/A339C/T160F/I177L Fd np3
(SEQ ID NO: 160):
LKESYLEESCSTITEGYLSVLRTGWYTNVFTLEVGDVENLTCADGPSLIK
TELDLTKSALRELKPVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIDDLKMAVSFSQFNRRFLNVVRQFSDNAGITPAIS
LDLMTDAELARAVSNMPTAAGQIKLMLENRAMVRRKGFGILIGVYGSSVI
YMVQLPIFGVIDTPCWIVKAAPSCSEKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFENIE
NSQALVDQSNRILSSAESAIGGYIPEAPRDGQAYVRKDGEWVLLSTFLGG
GGSSGGSSGGFLGFLLGVGSAIASGVAV

NL/1/99 A113C/A339C/T160F/I177L Fd np3
(SEQ ID NO: 161):
LKESYLEESCSTITEGYLSVLRTGWYTNVFTLEVGDVENLTCTDGPSLIK
TELDLTKSALRELKTVSADQLAREEQIENPRQSRFVLGAIALGVCTAAAV
TAGIAIAKTIRLESEVNAIKGALKQTNEAVSTLGNGVRVLAFAVRELKEF
VSKNLTSALNRNKCDIADLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKNGNYACLLREDQGWYCKNAGSTV
YYPNEKDCETRGDHVFCDTACGINVAEQSRECNINISTTNYPCKVSTGRH
PISMVALSPLGALVACYKGVSCSIGSNWVGIIKQLPKGCSYITNQDADTV
TIDNTVYQLSKVEGEQHVIKGRPVSSSFDPIKFPEDQFNVALDQVFESIE

-continued

NSQALVDQSNKILNSAESAIGGYIPEAPRDGQAYVRKDGEWVLLSTFLGG
GGSSGGSSGGFLGFLLGVGSAIASGVAV

NDL00-1 A113C/A339C/T160F/I177L Fd np3
(SEQ ID NO: 162):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIADLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAESAIGGYIPEAPRDGQAYVRKDGEWVLLSTFLGG
GGSSGGSSGGFLGFLLGVGSAIASGVAV

CAN98-75 A113C/A339C/T160F/I177L Fd np3
(SEQ ID NO: 163):
LKESYLEESCSTITEGYLSVLRTGWYTNVFTLEVGDVENLTCTDGPSLIK
TELDLTKSALRELKTVSADQLAREEQIENPRQSRFVLGAIALGVCTAAAV
TAGIAIAKTIRLESEVNAIKGALKTTNEAVSTLGNGVRVLAFAVRELKEF
VSKNLTSALNKNKCDIADLKMAVSFSQFNRRFLNVVRQFSDNAGITPAIS
LDLMTDAELARAVSYMPTSAGQIKLMLENRAMVRRKGFGILIGVYGSSVI
YMVQLPIFGVIDTPCWIIKAAPSCSEKDGNYACLLREDQGWYCKNAGSTV
YYPNKKDCETRGDHVFCDTACGINVAEQSRECNINISTTNYPCKVSTGRH
PISMVALSPLGALVACYKGVSCSIGSNRVGIIKQLPKGCSYITNQDADTV
TIDNTVYQLSKVEGEQHVIKGRPVSSSFDPIKFPEDQFNVALDQVFESIE
NSQALVDQSNKILNSAESAIGGYIPEAPRDGQAYVRKDGEWVLLSTFLGG
GGSSGGSSGGFLGFLLGVGSAIASGVAV

NL/1/00 A113C/A339C/T160F/I177L Fd np6
(SEQ ID NO: 164):
LKESYLEESCSTITEGYLSVLRTGWYTNVFTLEVGDVENLTCADGPSLIK
TELDLTKSALRELRTVSADQLAREEQIENPRQSRFVLGAIALGVCTAAAV
TAGVAIAKTIRLESEVTAIKNALKKTNEAVSTLGNGVRVLAFAVRELKDF
VSKNLTRALNKNKCDIADLKMAVSFSQFNRRFLNVVRQFSDNAGITPAIS
LDLMTDAELARAVSNMPTSAGQIKLMLENRAMVRRKGFGFLIGVYGSSVI
YMVQLPIFGVIDTPCWIVKAAPSCSGKKGNYACLLREDQGWYCQNAGSTV
YYPNEKDCETRGDHVFCDTACGINVAEQSKECNINISTTNYPCKVSTGRH
PISMVALSPLGALVACYKGVSCSIGSNRVGIIKQLNKGCSYITNQDADTV
TIDNTVYQLSKVEGEQHVIKGRPVSSSFDPVKFPEDQFNVALDQVFESIE
NSQALVDQSNRILSSAESAIGGYIPEAPRDGQAYVRKDGEWVLLSTFLGG
GGSSGGFLGFLLGV

-continued

CAN97-83 A113C/A339C/T160F/I177L Fd np6
(SEQ ID NO: 165):
LKESYLEESCSTITEGYLSVLRTGWYTNVFTLEVGDVENLTCSDGPSLIK

TELDLTKSALRELKTVSADQLAREEQIENPRQSRFVLGAIALGVCTAAAV

TAGVAIAKTIRLESEVTAIKNALKTTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTSAGQIKLMLENRAMVRRKGFGILIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPIKFPEDQFNVALDQVFENIE

NSQALVDQSNRILSSAESAIGGYIPEAPRDGQAYVRKDGEWVLLSTFLGG

GGSSGGFLGFLLGV

NL/17/00 A113C/A339C/T160F/I177L Fd np6
(SEQ ID NO: 166):
LKESYLEESCSTITEGYLSVLRTGWYTNVFTLEVGDVENLTCSDGPSLIK

TELDLTKSALRELKTVSADQLAREEQIENPRQSRFVLGAIALGVCTAAAV

TAGVAIAKTIRLESEVTAIKNALKTTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTSAGQIKLMLENRAMVRRKGFGILIGVYGSSVI

YTVQLPIFGVIDTPCWIVKAAPSCSEKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPIKFPEDQFNVALDQVFENIE

NSQALVDQSNRILSSAESAIGGYIPEAPRDGQAYVRKDGEWVLLSTFLGG

GGSSGGFLGFLLGV

NCL174 A113C/A339C/T160F/I177L Fd np6
(SEQ ID NO: 167):
LKESYLEESCSTITEGYLSVLRTGWYTNVFTLEVGDVENLTCADGPSLIK

TELDLTKSALRELKPVSADQLAREEQIENPRQSRFVLGAIALGVCTAAAV

TAGVAIAKTIRLESEVTAIKNALKKTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTAAGQIKLMLENRAMVRRKGFGILIGVYGSSVI

YMVQLPIFGVIDTPCWIVKAAPSCSEKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPVKFPEDQFNVALDQVFENIE

NSQALVDQSNRILSSAESAIGGYIPEAPRDGQAYVRKDGEWVLLSTFLGG

GGSSGGFLGFLLGV

NL/1/99 A113C/A339C/T160F/I177L Fd np6
(SEQ ID NO: 168):
LKESYLEESCSTITEGYLSVLRTGWYTNVFTLEVGDVENLTCTDGPSLIK

TELDLTKSALRELKTVSADQLAREEQIENPRQSRFVLGAIALGVCTAAAV

TAGIAIAKTIRLESEVNAIKGALKQTNEAVSTLGNGVRVLAFAVRELKEF

VSKNLTSALNRNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKNGNYACLLREDQGWYCKNAGSTV

YYPNEKDCETRGDHVFCDTACGINVAEQSRECNINISTTNYPCKVSTGRH

PISMVALSPLGALVACYKGVSCSIGSNWVGIIKQLPKGCSYITNQDADTV

TIDNTVYQLSKVEGEQHVIKGRPVSSSFDPIKFPEDQFNVALDQVFESIE

NSQALVDQSNKILNSAESAIGGYIPEAPRDGQAYVRKDGEWVLLSTFLGG

GGSSGGFLGFLLGV

NDL00-1 A113C/A339C/T160F/I177L Fd np6
(SEQ ID NO: 169):
LKESYLEESCSTITEGYLSVLRTGWYTNVFTLEVGDVENLTCADGPSLIK

TELDLTKSALRELRTVSADQLAREEQIENPRQSRFVLGAIALGVCTAAAV

TAGVAIAKTIRLESEVTAIKNALKKTNEAVSTLGNGVRVLAFAVRELKDF

VSKNLTRALNKNKCDIADLKMAVSFSQFNRRFLNVVRQFSDNAGITPAIS

LDLMTDAELARAVSNMPTSAGQIKLMLENRAMVRRKGFGFLIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPVKFPEDQFNVALDQVFESIE

NSQALVDQSNRILSSAESAIGGYIPEAPRDGQAYVRKDGEWVLLSTFLGG

GGSSGGFLGFLLGV

CAN98-75 A113C/A339C/T160F/I177L Fd np6
(SEQ ID NO: 170):
LKESYLEESCSTITEGYLSVLRTGWYTNVFTLEVGDVENLTCTDGPSLIK

TELDLTKSALRELKTVSADQLAREEQIENPRQSRFVLGAIALGVCTAAAV

TAGIAIAKTIRLESEVNAIKGALKTTNEAVSTLGNGVRVLAFAVRELKEF

VSKNLTSALNKNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKDGNYACLLREDQGWYCKNAGSTV

YYPNKKDCETRGDHVFCDTACGINVAEQSRECNINISTTNYPCKVSTGRH

PISMVALSPLGALVACYKGVSCSIGSNRVGIIKQLPKGCSYITNQDADTV

TIDNTVYQLSKVEGEQHVIKGRPVSSSFDPIKFPEDQFNVALDQVFESIE

NSQALVDQSNKILNSAESAIGGYIPEAPRDGQAYVRKDGEWVLLSTFLGG

GGSSGGFLGFLLGV

NL/1/00 A113C/A339C/T160F/I177L Fd np8
(SEQ ID NO: 171):
LKESYLEESCSTITEGYLSVLRTGWYTNVFTLEVGDVENLTCADGPSLIK

TELDLTKSALRELRTVSADQLAREEQIENPRQSRFVLGAIALGVCTAAAV

TAGVAIAKTIRLESEVTAIKNALKKTNEAVSTLGNGVRVLAFAVRELKDF

VSKNLTRALNKNKCDIADLKMAVSFSQFNRRFLNVVRQFSDNAGITPAIS

LDLMTDAELARAVSNMPTSAGQIKLMLENRAMVRRKGFGFLIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

-continued

TIDNTVYQLSKVEGEQHVIKGRPVSSSFDPVKFPEDQFNVALDQVFESIE

NSQALVDQSNRILSSAESAIGGYIPEAPRDGQAYVRKDGEWVLLSTFLGG

GGSSGGSSGGSSGGSSGGFLGFLLGV

CAN97-83 A113C/A339C/T160F/I177L Fd np8
(SEQ ID NO: 172):
LKESYLEESCSTITEGYLSVLRTGWYTNVFTLEVGDVENLTCSDGPSLIK

TELDLTKSALRELKTVSADQLAREEQIENPRQSRFVLGAIALGVCTAAAV

TAGVAIAKTIRLESEVTAIKNALKTTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTSAGQIKLMLENRAMVRRKGFGILIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPIKFPEDQFNVALDQVFENIE

NSQALVDQSNRILSSAESAIGGYIPEAPRDGQAYVRKDGEWVLLSTFLGG

GGSSGGSSGGSSGGSSGGFLGFLLGV

NL/17/00 A113C/A339C/T160F/I177L Fd np8
(SEQ ID NO: 173):
LKESYLEESCSTITEGYLSVLRTGWYTNVFTLEVGDVENLTCSDGPSLIK

TELDLTKSALRELKTVSADQLAREEQIENPRQSRFVLGAIALGVCTAAAV

TAGVAIAKTIRLESEVTAIKNALKTTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTSAGQIKLMLENRAMVRRKGFGILIGVYGSSVI

YTVQLPIFGVIDTPCWIVKAAPSCSEKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPIKFPEDQFNVALDQVFENIE

NSQALVDQSNRILSSAESAIGGYIPEAPRDGQAYVRKDGEWVLLSTFLGG

GGSSGGSSGGSSGGSSGGFLGFLLGV

NCL174 A113C/A339C/T160F/I177L Fd np8
(SEQ ID NO: 174):
LKESYLEESCSTITEGYLSVLRTGWYTNVFTLEVGDVENLTCADGPSLIK

TELDLTKSALRELKPVSADQLAREEQIENPRQSRFVLGAIALGVCTAAAV

TAGVAIAKTIRLESEVTAIKNALKKTNEAVSTLGNGVRVLAFAVRELKDF

VSKNLTRALNKNKCDIDDLKMAVSFSQFNRRFLNVVRQFSDNAGITPAIS

LDLMTDAELARAVSNMPTAAGQIKLMLENRAMVRRKGFGILIGVYGSSVI

YMVQLPIFGVIDTPCWIVKAAPSCSEKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPVKFPEDQFNVALDQVFENIE

NSQALVDQSNRILSSAESAIGGYIPEAPRDGQAYVRKDGEWVLLSTFLGG

GGSSGGSSGGSSGGSSGGFLGFLLGV

-continued

NL/1/99 A113C/A339C/T160F/I177L Fd np8
(SEQ ID NO: 175):
LKESYLEESCSTITEGYLSVLRTGWYTNVFTLEVGDVENLTCTDGPSLIK

TELDLTKSALRELKTVSADQLAREEQIENPRQSRFVLGAIALGVCTAAAV

TAGIAIAKTIRLESEVNAIKGALKQTNEAVSTLGNGVRVLAFAVRELKEF

VSKNLTSALNRNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKNGNYACLLREDQGWYCKNAGSTV

YYPNEKDCETRGDHVFCDTACGINVAEQSRECNINISTTNYPCKVSTGRH

PISMVALSPLGALVACYKGVSCSIGSNWVGIIKQLPKGCSYITNQDADTV

TIDNTVYQLSKVEGEQHVIKGRPVSSSFDPIKFPEDQFNVALDQVFESIE

NSQALVDQSNKILNSAESAIGGYIPEAPRDGQAYVRKDGEWVLLSTFLGG

GGSSGGSSGGSSGGSSGGFLGFLLGV

NDL00-1 A113C/A339C/T160F/I177L Fd np8
(SEQ ID NO: 176):
LKESYLEESCSTITEGYLSVLRTGWYTNVFTLEVGDVENLTCADGPSLIK

TELDLTKSALRELRTVSADQLAREEQIENPRQSRFVLGAIALGVCTAAAV

TAGVAIAKTIRLESEVTAIKNALKKTNEAVSTLGNGVRVLAFAVRELKDF

VSKNLTRALNKNKCDIADLKMAVSFSQFNRRFLNVVRQFSDNAGITPAIS

LDLMTDAELARAVSNMPTSAGQIKLMLENRAMVRRKGFGFLIGVYGSSVI

YMVQLPIFGVIDTPCWIVKAAPSCSGKKGNYACLLREDQGWYCQNAGSTV

YYPNEKDCETRGDHVFCDTACGINVAEQSKECNINISTTNYPCKVSTGRH

PISMVALSPLGALVACYKGVSCSIGSNRVGIIKQLNKGCSYITNQDADTV

TIDNTVYQLSKVEGEQHVIKGRPVSSSFDPVKFPEDQFNVALDQVFESIE

NSQALVDQSNRILSSAESAIGGYIPEAPRDGQAYVRKDGEWVLLSTFLGG

GGSSGGSSGGSSGGSSGGFLGFLLGV

CAN98-75 A113C/A339C/T160F/I177L Fd np8
(SEQ ID NO: 177):
LKESYLEESCSTITEGYLSVLRTGWYTNVFTLEVGDVENLTCTDGPSLIK

TELDLTKSALRELKTVSADQLAREEQIENPRQSRFVLGAIALGVCTAAAV

TAGIAIAKTIRLESEVNAIKGALKTTNEAVSTLGNGVRVLAFAVRELKEF

VSKNLTSALNKNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKDGNYACLLREDQGWYCKNAGSTV

YYPNKKDCETRGDHVFCDTACGINVAEQSRECNINISTTNYPCKVSTGRH

PISMVALSPLGALVACYKGVSCSIGSNRVGIIKQLPKGCSYITNQDADTV

TIDNTVYQLSKVEGEQHVIKGRPVSSSFDPIKFPEDQFNVALDQVFESIE

NSQALVDQSNKILNSAESAIGGYIPEAPRDGQAYVRKDGEWVLLSTFLGG

GGSSGGSSGGSSGGSSGGFLGFLLGV k) Additional Description

In some embodiments, the recombinant MPV F protein or immunogenic fragment is not stabilized in the prefusion conformation by non-specific crosslinking, for example glutaraldehyde crosslinking of membrane bound MPV F trimers. In some embodiments, the recombinant MPV F protein does not include an amino acid substitution at positions 329, 330, or 331, such as a R329K, G330A, D331A. D331E, and/or D331R substitution.

In several embodiments, the recombinant MPV F protein is soluble in aqueous solution. In some embodiments, the recombinant MPV F protein dissolves to a concentration of at least 0.5 mg/ml (such as at least 1.0 mg/ml, 1.5 mg/ml, 2.0 mg/ml, 3.0 mg/ml, 4.0 mg/ml or at least 5.0 mg/ml) in aqueous solution (such as phosphate buffered saline (pH 7.4) or 350 mM NaCl (pH 7.0)) at room temperature (e.g., 20-22 degrees Celsius) and remains dissolved for at least 12 hours (such as at least 24 hours, at least 48 hours, at least one week, at least two weeks, at least one month, or more time). In another embodiment, the recombinant MPV F protein dissolves to a concentration of at least 0.5 mg/ml (such as at least 1.0 mg/ml, 1.5 mg/ml, 2.0 mg/ml, 3.0 mg/ml, 4.0 mg/ml or at least 5.0 mg/ml) in aqueous solution (such as phosphate buffered saline (pH 7.4) or 350 mM NaCl (pH 7.0)) at 4° C. and remains dissolved for at least 12 hours (such as at least 24 hours, at least 48 hours, at least one week, at least two weeks, at least one month, or more time). In one embodiment, the phosphate buffered saline includes NaCl (137 mM), KCl (2.7 mM), $Na_2HPO_4$ (10 mM), $KH_2PO_4$ (1.8 mM) at pH 7.4. In some embodiments, the phosphate buffered saline further includes $CaCl_2$ (1 mM) and $MgCl_2$ (0.5 mM).

The person of skill in the art is familiar with methods of determining if a protein remains in solution over time. For example, the concentration of the protein dissolved in an aqueous solution can be tested over time using standard methods.

In some embodiments, the recombinant MPV F protein, when incubated in an aqueous solution, forms a population of recombinant MPV F proteins stabilized in a prefusion conformation, wherein at least 70% (such as at least 80%, or at least 90% or at least 95% or at least 98%) of the recombinant MPV F proteins in the population specifically bind to an antibody that specifically binds to the prefusion, but not post-fusion, form of the MPV F protein (such as a MPE8 antibody) after incubation for (a) one hour in aqueous solution (such as PBS (pH 7.4) or 350 mM NaCl (pH 7.0)) at 50° C.;

(b) one hour in aqueous solution (such as PBS (pH 7.4) or 350 mM NaCl (pH 7.0)) at 60° C.;

(c) one hour in aqueous solution (such as PBS (pH 7.4) or 350 mM NaCl (pH 7.0)) at 25° C.;

(d) one hour in aqueous solution (such as PBS (pH 7.4) or 350 mM NaCl (pH 7.0)) at 25° C.;

(e) one hour in aqueous solution (such as PBS (pH 7.4) or 350 mM NaCl (pH 7.0)) at 25° C.;

(f) one hour in aqueous solution (such as PBS (pH 7.4) or 350 mM NaCl (pH 7.0)) at 25° C.; or (g) one week in aqueous solution (such as PBS (pH 7.4) or 350 mM NaCl (pH 7.0)) at 4° C.;

(h) one month in aqueous solution (such as PBS (pH 7.4) or 350 mM NaCl (pH 7.0)) at 4° C.;

(i) ten freeze-thaw cycles in 350 mM NaCl pH 7.0; or (j) ten freeze-thaw cycles in 350 mM NaCl pH 7.0;

(k) a combination of two or more of (a)-(j); wherein

In some embodiments, the recombinant MPV F protein, when incubated in an aqueous solution, forms a population of recombinant MPV F proteins stabilized in a prefusion conformation, wherein at least 70% (such as at least 80%, or at least 90% or at least 95% or at least 98%) of the recombinant MPV F proteins in the population specifically bind to an antibody that specifically binds to the prefusion, but not post-fusion, form of the MPV F protein (such as a MPE8 antibody) after ten freeze-thaw cycles in 350 mM NaCl pH 7.0.

Several embodiments include a multimer of the recombinant MPV F protein or immunogenic fragment thereof, for example, a multimer including 2, 3, 4, 5, 6, 7, 8, 9, or 10, or more of the recombinant MPV F proteins or immunogenic fragment thereof.

It is understood in the art that some variations can be made in the amino acid sequence of a protein without affecting the activity of the protein. Such variations include insertion of amino acid residues, deletions of amino acid residues, and substitutions of amino acid residues. These variations in sequence can be naturally occurring variations or they can be engineered through the use of genetic engineering technique known to those skilled in the art. Examples of such techniques are found in see, e.g., Sambrook et al. (Molecular Cloning: A Laboratory Manual, 4$^{th}$ ed., Cold Spring Harbor, N.Y., 2012) and Ausubel et al. (In Current Protocols in Molecular Biology, John Wiley & Sons, New York, through supplement 104, 2013, both of which are incorporated herein by reference in their entirety.

The recombinant MPV F protein can include modifications of the native MPV sequence, such as amino acid substitutions, deletions or insertions, glycosylation and/or covalent linkage to unrelated proteins (e.g., a protein tag), as long as the recombinant MPV F protein can form a trimer that is stabilized in the prefusion conformation. MPV F proteins from the different subgroups, as well as nucleic acid sequences encoding such proteins and methods for the manipulation and insertion of such nucleic acid sequences into vectors, are disclosed herein and known in the art.

In some embodiments a recombinant MPV F protein includes a $F_2$ polypeptide and a $F_1$ ectodomain including amino acid sequences at least 75% (for example at least 85%, 90%, 95%, 96%, 97%, 98% or 99%) identical to a corresponding native MPV $F_2$ or $F_1$ ectodomain polypeptide sequence (e.g., a native $F_2$ or $F_1$ ectodomain polypeptide sequence from a subgroup A1, A2, B1, or B2 MPV F protein), such the sequence of a MPV F protein set forth as one of SEQ ID NOs: 1-7.

In additional embodiments, a recombinant MPV F protein includes a $F_2$ polypeptide and/or a $F_1$ ectodomain including one or more amino acid substitutions compared to a corresponding native MPV F sequence. For example, in some embodiments, the $F_2$ polypeptide, $F_1$ ectodomain, or both, can include up to 20 (such as up to 1, 2, 3, 4, 5, 6, 7, 8, 9, 10, 11, 12, 13, 14, 15, 16, 17, 18, or 19) amino acid substitutions compared to a native MPV $F_1$ polypeptide sequence (e.g., a native $F_2$ or $F_1$ ectodomain protein sequence from a subgroup A1, A2, B1, or B2 MPV F protein), such the sequence of a MPV F protein set forth as one of SEQ ID NOs: 1-7. The simplest modifications involve the substitution of one or more amino acids for amino acids having similar biochemical properties. These so-called conservative substitutions are likely to have minimal impact on the activity of the resultant protein.

Conservative amino acid substitution tables providing functionally similar amino acids are well known to one of ordinary skill in the art.

In certain embodiments, an immunogen provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the immunogen to be improved or altered, whether the immunogen derivative will be used in a therapy under defined conditions, etc.

The recombinant MPV F protein included in the disclosed trimers can be derivatized or linked to another molecule (such as another peptide or protein). In general, the recombinant MPV F protein is derivatized such that the binding to broadly neutralizing antibodies to a trimer of the recombinant MPV F protein, such as MPE8, is not affected adversely by the derivatization or labeling. For example, the recombinant MPV F protein can be functionally linked (by chemical coupling, genetic fusion, non-covalent association or otherwise) to one or more other molecular entities, such as an antibody or protein or detection tag.

Some of the sequences of recombinant MPV F proteins provided herein include the sequence of protease cleavage sites (such as thrombin sites), protein tags (such as a His tag, a Strep Tag II, a Avi tag, etc.), signal peptides, that the person of ordinary skill in the art will understand would not be included in an isolated immunogen including a recombinant MPV F protein immunogen. The person of ordinary skill in the art will recognize such sequences, and when appropriate, understand that these tags or protease cleavage sites are not included in a disclosed recombinant MPV F protein.

Reference to "any one of SEQ ID NOs: 12-15, 80-81, 101-149, or 157-191," refers to any one of SEQ ID NOs: 12, 13, 14, 15, 80, 81, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, or 191. Reference to "any one of SEQ ID NOs: 12-15, 101-149, or 178-191," refers to any one of SEQ ID NOs: 12, 13, 14, 15, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 178, 179, 180, 181, 182, 183, 184, 185, 186, 187, 188, 189, 190, or 191.

B. Protein Nanoparticles Including Recombinant MPV F Proteins

In some embodiments a protein nanoparticle is provided that includes one or more of the disclosed immunogens (e.g., a MPV F ectodomain stabilized in a prefusion conformation, or an immunogenic fragment thereof). Such a protein nanoparticle can specifically bind to one or more MPV F prefusion conformation specific antibodies, such as the MPE8 antibody. Non-limiting example of nanoparticles include ferritin nanoparticles, encapsulin nanoparticles, Sulfur Oxygenase Reductase (SOR) nanoparticles, and lumazine synthase nanoparticles, which are comprised of an assembly of monomeric subunits including ferritin proteins, encapsulin proteins, SOR proteins, and lumazine synthase proteins respectively. To construct protein nanoparticles including a MPV F proteins stabilized in a prefusion conformation or immunogenic fragment thereof, the MPV F protein or fragment can be linked to a subunit of the protein nanoparticle (such as a ferritin protein, an encapsulin protein, a SOR protein, or a lumazine synthase protein). The fusion protein self-assembles into a nanoparticle under appropriate conditions.

In several embodiments, the protein nanoparticle comprises two or more of the recombinant MPV F proteins, wherein the two or more recombinant MPV F proteins are from at least two different strains of MPV.

In some embodiments, a disclosed recombinant MPV F protein stabilized in a prefusion conformation or immunogenic fragment thereof can be linked to a ferritin subunit to construct a ferritin nanoparticle. Ferritin nanoparticles and their use for immunization purposes (e.g., for immunization against influenza antigens) have been disclosed in the art (see, e.g., Kanekiyo et al., Nature, 499:102-106, 2013, incorporated by reference herein in its entirety). Ferritin is a globular protein that is found in all animals, bacteria, and plants, and which acts primarily to control the rate and location of polynuclear $Fe(III)_2O_3$ formation through the transportation of hydrated iron ions and protons to and from a mineralized core. The globular form of the ferritin nanoparticle is made up of monomeric subunits, which are polypeptides having a molecule weight of approximately 17-20 kDa. An example of the amino acid sequence of one such monomeric subunit is represented by:

(SEQ ID NO: 71)

```
ESQVRQQFSKDIEKLLNEQVNKEMQSSNLYMSMSSWCYTHSLDGAGLFLF
DHAAEEYEHAKKLIIFLNENNVPVQLTSISAPEHKFEGLTQIFQKAYEHE
QHISESINNIVDHAIKSKDHATFNFLQWYVAEQHEEEVLFKDILDKIELI
GNENHGLYLADQYVKGIAKSRKS
```

Each monomeric subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, D & E' from the N-terminus respectively. The N-terminal sequence lies adjacent to the capsid three-fold axis and extends to the surface, while the E helices pack together at the four-fold axis with the C-terminus extending into the capsid core. The consequence of this packing creates two pores on the capsid surface. It is expected that one or both of these pores represent the point by which the hydrated iron diffuses into and out of the capsid. Following production, these monomeric subunit proteins self-assemble into the globular ferritin protein. Thus, the globular form of ferritin comprises 24 monomeric, subunit proteins, and has a capsid-like structure having 432 symmetry. Methods of constructing ferritin nanoparticles are known to the person of ordinary skill in the art and are further described herein (see, e.g., Zhang, Int. *J. Mol. Sci.,* 12:5406-5421, 2011, which is incorporated herein by reference in its entirety).

In specific examples, the ferritin polypeptide is *E. coli* ferritin, *Helicobacter pylori* ferritin, human light chain ferritin, bullfrog ferritin or a hybrid thereof, such as *E. coli*- human hybrid ferritin, *E. coli*-bullfrog hybrid ferritin, or human-bullfrog hybrid ferritin. Exemplary amino acid sequences of ferritin polypeptides and nucleic acid sequences encoding ferritin polypeptides for use to make a ferritin nanoparticle including a recombinant MPV F protein or immunogenic fragment thereof can be found in GENBANK®, for example at accession numbers ZP_03085328, ZP_06990637, EJB64322.1, AAA35832, NP_000137 AAA49532, AAA49525, AAA49524 and AAA49523, which are specifically incorporated by reference herein in their entirety as available Jun. 20, 2014. In some embodiments, a disclosed recombinant MPV F protein stabilized in a prefusion conformation or immunogenic fragment thereof can be linked to a ferritin subunit including an amino acid sequence at least 80% (such as at least 85%, at least 90%, at least 95%, or at least 97%) identical to amino acid sequence set forth as SEQ ID NO: 71.

In additional embodiments, any of the disclosed recombinant MPV F proteins stabilized in a prefusion conformation or immunogenic fragments thereof can be linked to a lumazine synthase subunit to construct a lumazine synthase nanoparticle. The globular form of lumazine synthase nanoparticle is made up of monomeric subunits; an example of the sequence of one such monomeric subunit is provides as the amino acid sequence set forth as:

```
                                        (SEQ ID NO: 72)
MQIYEGKLTAEGLRFGIVASRFNHALVDRLVEGAIDAIVRHGGREEDITL

VRVPGSWEIPVAAGELARKEDIDAVIAIGVLIRGATPHFDYIASEVSKGL

ADLSLELRKPITFGVITADTLEQAIERAGTKHGNKGWEAALSAIEMANLF

KSLR.
```

In some embodiments, a disclosed recombinant MPV F protein stabilized in a prefusion conformation or immunogenic fragment thereof can be linked to a lumazine synthase subunit including an amino acid sequence at least 80% (such as at least 85%, at least 90%, at least 95%, or at least 97%) identical to amino acid sequence set forth as SEQ ID NO: 72.

In additional embodiments, a disclosed recombinant MPV F protein stabilized in a prefusion conformation or immunogenic fragment thereof can be linked to an encapsulin subunit to construct an encapsulin nanoparticle. The globular form of the encapsulin nanoparticle is made up of monomeric subunits; an example of the sequence of one such monomeric subunit is provides as the amino acid sequence set forth as

```
                                        (SEQ ID NO: 73)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF.
```

In some embodiments, a disclosed recombinant MPV F protein stabilized in a prefusion conformation or immunogenic fragment thereof can be linked to an encapsulin subunit including an amino acid sequence at least 80% (such as at least 85%, at least 90%, at least 95%, or at least 97%) identical to amino acid sequence set forth as SEQ ID NO: 73.

Encapsulin proteins are a conserved family of bacterial proteins also known as linocin-like proteins that form large protein assemblies that function as a minimal compartment to package enzymes. The encapsulin assembly is made up of monomeric subunits, which are polypeptides having a molecule weight of approximately 30 kDa. Following production, the monomeric subunits self-assemble into the globular encapsulin assembly including 60 monomeric subunits. Methods of constructing encapsulin nanoparticles are known to the person of ordinary skill in the art, and further described herein (see, for example, Sutter et al., Nature Struct. and Mol. Biol., 15:939-947, 2008, which is incorporated by reference herein in its entirety). In specific examples, the encapsulin polypeptide is bacterial encapsulin, such as *E. coli* or *Thermotoga maritime* encapsulin.

In additional embodiments, a disclosed recombinant MPV F protein stabilized in a prefusion conformation or immunogenic fragment thereof can be linked to a Sulfur Oxygenase Reductase (SOR) subunit to construct a recombinant SOR nanoparticle. In some embodiments, the SOR subunit can include the amino acid sequence set forth as

```
                                        (SEQ ID NO: 74)
MEFLKRSFAPLTEKQWQEIDNRAREIFKTQLYGRKFVDVEGPYGWEYAAH

PLGEVEVLSDENEVVKWGLRKSLPLIELRATFTLDLWELDNLERGKPNVD

LSSLEETVRKVAEFEDEVIFRGCEKSGVKGLLSFEERKIECGSTPKDLLE

AIVRALSIFSKDGIEGPYTLVINTDRWINFLKEEAGHYPLEKRVEECLRG

GKIITTPRIEDALVVSERGGDFKLILGQDLSIGYEDREKDAVRLFITETF

TFQVVNPEALILLKF.
```

In some embodiments, a disclosed recombinant MPV F protein stabilized in a prefusion conformation or immunogenic fragment thereof can be linked to a SOR subunit including an amino acid sequence at least 80% (such as at least 85%, at least 90%, at least 95%, or at least 97%) identical to amino acid sequence set forth as SEQ ID NO: 74.

SOR proteins are microbial proteins (for example from the thermoacidophilic archaeon *Acidianus ambivalens* that form 24 subunit protein assemblies. Methods of constructing SOR nanoparticles are known to the person of ordinary skill in the art (see, e.g., Urich et al., Science, 311:996-1000, 2006, which is incorporated by reference herein in its entirety). An example of an amino acid sequence of a SOR protein for use to make SOR nanoparticles is set forth in Urich et al., Science, 311:996-1000, 2006, which is incorporated by reference herein in its entirety.

In some examples, the disclosed recombinant MPV F protein stabilized in a prefusion conformation or immunogenic fragment thereof can be linked to the N- or C-terminus, or placed within an internal loop of a ferritin, encapsulin, SOR, or lumazine synthase subunit, for example with a linker, such as a Ser-Gly linker. When the constructs have been made in HEK 293 Freestyle cells, the fusion proteins are secreted from the cells and self-assembled into nanoparticles. The nanoparticles can be purified using known techniques, for example by a few different chromatography procedures, e.g. Mono Q (anion exchange) followed by size exclusion (SUPEROSE® 6) chromatography.

Several embodiments include a monomeric subunit of a ferritin, encapsulin, SOR, or lumazine synthase protein, or any portion thereof which is capable of directing self-assembly of monomeric subunits into the globular form of the protein. Amino acid sequences from monomeric subunits of any known ferritin, encapsulin, SOR, or lumazine synthase protein can be used to produce fusion proteins with the disclosed recombinant MPV F protein or immunogenic fragment thereof, so long as the monomeric subunit is capable of self-assembling into a nanoparticle displaying recombinant MPV F protein or immunogenic fragment thereof on its surface.

The fusion proteins need not comprise the full-length sequence of a monomeric subunit polypeptide of a ferritin, encapsulin, SOR, or lumazine synthase protein. Portions, or regions, of the monomeric subunit polypeptide can be utilized so long as the portion comprises amino acid sequences that direct self-assembly of monomeric subunits into the globular form of the protein.

In some embodiments, it may be useful to engineer mutations into the amino acid sequence of the monomeric ferritin, encapsulin, SOR, or lumazine synthase subunits. For example, it may be useful to alter sites such as enzyme recognition sites or glycosylation sites in order to give the fusion protein beneficial properties (e.g., half-life).

It will be understood by those skilled in the art that fusion of any of the disclosed recombinant MPV F proteins stabilized in a prefusion conformation or immunogenic fragments thereof to the ferritin, encapsulin, SOR, or lumazine synthase protein should be done such that the disclosed recombinant MPV F proteins stabilized in a prefusion conformation or immunogenic fragments thereof does not interfere with self-assembly of the monomeric ferritin, encapsulin, SOR, or lumazine synthase subunits into the globular protein, and that the ferritin, encapsulin, SOR, or lumazine synthase subunits do not interfere with the ability of the disclosed recombinant MPV F proteins stabilized in a prefusion conformation or immunogenic fragments thereof to elicit an immune response to MPV. In some embodiments, the ferritin, encapsulin, SOR, or lumazine synthase protein and disclosed recombinant MPV F proteins stabilized in a prefusion conformation or immunogenic fragments thereof can be joined together directly without affecting the activity of either portion. In other embodiments, the ferritin, encapsulin, SOR, or lumazine synthase protein and the disclosed recombinant MPV F proteins stabilized in a prefusion conformation or immunogenic fragments thereof can be joined using a linker (also referred to as a spacer) sequence. The linker sequence is designed to position the ferritin, encapsulin, SOR, or lumazine synthase portion of the fusion protein and the recombinant MPV F protein stabilized in a prefusion conformation or immunogenic fragments thereof can be linked to an portion of the fusion protein, with regard to one another, such that the fusion protein maintains the ability to assemble into nanoparticles, and also elicit an immune response to MPV. In several embodiments, the linker sequences comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. One example of such a linker sequence is SGG. Amino acids can be added or subtracted as needed. Those skilled in the art are capable of determining appropriate linker sequences for construction of protein nanoparticles.

The disclosed recombinant MPV F proteins stabilized in a prefusion conformation or immunogenic fragments thereof can be linked to ferritin, encapsulin, SOR, or lumazine synthase subunits can self-assemble into multi-subunit protein nanoparticles, termed ferritin nanoparticles, encapsulin nanoparticles, SOR nanoparticles, and lumazine synthase nanoparticles, respectively. The nanoparticles including a disclosed recombinant MPV F protein stabilized in a prefusion conformation or immunogenic fragment thereof have substantially the same structural characteristics as the native ferritin, encapsulin, SOR, or lumazine synthase nanoparticles that do not include the disclosed recombinant MPV F protein or immunogenic fragment thereof. That is, they contain 24, 60, 24, or 60 subunits (respectively) and have similar corresponding symmetry.

C. Virus-Like Particles

In some embodiments, a virus-like particle (VLP) is provided that includes a disclosed immunogen (e.g., a recombinant MPV F protein or immunogenic fragment thereof). VLPs lack the viral components that are required for virus replication and thus represent a highly attenuated form of a virus. The VLP can display a polypeptide (e.g., a recombinant MPV F protein) that is capable of eliciting an immune response to MPV when administered to a subject. Virus like particles and methods of their production are known and familiar to the person of ordinary skill in the art, and viral proteins from several viruses are known to form VLPs, including human papillomavirus, MPV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rotavirus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Virol. 70: 5422-9 (1996)), hepatitis E virus (Li et al., J. Virol. 71: 7207-13 (1997)), and Newcastle disease virus. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

D. Polynucleotides and Expression

Polynucleotides encoding a disclosed immunogen (e.g., a MPV F ectodomain stabilized in a prefusion conformation, or an immunogenic fragment thereof), or protein nanoparticles (or a subunit thereof) or vectors, disclosed herein are also provided. These polynucleotides include DNA, cDNA and RNA sequences which encode the antigen. One of skill in the art can readily use the genetic code to construct a variety of functionally equivalent nucleic acids, such as nucleic acids which differ in sequence but which encode the same antibody sequence, or encode a conjugate or fusion protein including the nucleic acid sequence.

Non-limiting examples of polynucleotide sequences encoding MPV F proteins stabilized in a prefusion conformation are provided as SEQ ID NOs: 97-99, which encode MPV F with A113C/A339C, T160F/I177L, or A113C/A339C/T160F/I177L substitutions, respectively.

MPV F with T160F/I177L (SEQ ID NO: 65):
atgagttggaaagtgatgattattattagcctgctgattaccccccagca cggactgaaggagtcttatctggaggagtcttgctcaacaatcactgagg gctacctgagcgtcctgcgcacagggtggtatactaacgtgtttaccctg gaagtgggcgatgtcgaaaatctgacctgtacagacgggcctagcctgat caagacagagctggatctgactaaaagcgccctgcgggaactgaagaccg tgtccgctgaccagctggcaagagaggaacagatcgagaacccacgacag agccgattcgtgctgggagctattgcactgggagtggcaaccgccgctgc agtcacagcaggaatcgcaattgctaaaactatccgcctggagagtgaag tgaacgccattaagggagctctgaaaaccacaaacgaagctgtgtctacc ctggggaatggagtgagagtcctggcatttgccgtcagggagctgaagga attcgtgtctaaaaatctgacaagtgccctgaacaagaacaagtgcgaca tcgcagatctgaagatggccgtgagcttctcccagtttaaccggagattt ctgaatgtggtccggcagttctctgataacgctggcatcactccagcaat tagtctggacctgatgaccgatgccgagctggctagggcagtgtcataca tgcccaccagcgctggccagatcaaactgatgctggaaaatcgcgcaatg gtcaggcgcaagggctttgggatcctgattggagtgtacggcagcagcgt gatctacatggtccagctgcctatcttcggcgtgattgacacaccatgct ggatcatcaaggccgctccctcttgtagtgagaaggatgggaactacgca tgcctgctgagagaagaccagggatggtattgtaaaaacgccggctccac tgtgtactatccaaatgacaaggattgtgagacacgaggagaccacgtct tttgcgatactgcagccggcatcaacgtggctgagcagagtcgcgaatgt aacatcaacatctcaactaccaactacccctgcaaagtctctacaggccg gcatcctatcagcatggtggcactgtctccactgggagcactggtggctt gctataagggcgtctcatgtagcattggctccaatagagtggggatcatt aagcagctgcccaaaggctgctcttacatcaccaaccaggacgccgatac tgtgaccattgataatacagtctatcagctgagcaaagtggagggggaac agcacgtcatcaagggaaggcctgtgtctagttcattcgacccaattaag tttcccgaggatcagttcaacgtggccctggaccaggtcttcgagagcat cgaaaattcccaggctctggtggaccagtccaacaaaattctgaattccg cagagtctgccatcggcgggtacattcccgaagcccctcgcgatgggcag gcttatgtccgaaaggacggagagtgggtgctgctgtcaacctttctggg aggactggtgccaaggggaagccaccatcaccatcaccatagtgcctggt cacatcctcagttcgaaaagtgatga MPV F with A113C/A339C (SEQ ID NO: 66):
atgtcctggaaagtgatgattattattagcctgctgattacaccacagca cggcctgaaagagtcctatctggaagagagttgttcaacaatcactgagg gctacctgagcgtcctgcgcacagggtggtatactaacgtgtttaccctg gaagtgggcgatgtcgaaaatctgacctgtacagacgggcctagcctgat caagacagagctggatctgactaaaagcgccctgcgggaactgaagaccg tgtccgctgaccagctggcaagagaggaacagatcgagaacccacgacag agccgattcgtgctgggagctattgcactgggagtgtgcaccgccgctgc -continued agtcacagcaggaatcgcaattgctaaaacaatccgcctggagagtgaag tgaacgccattaagggagctctgaaaaccacaaacgaagctgtgtctacc ctggggaatggagtgagagtcctggcaacagccgtcagggagctgaagga atttgtgtctaaaaatctgactagtgccatcaacaagaacaagtgcgaca ttgcagatctgaagatggccgtgagcttctcccagtttaaccggagattt ctgaatgtggtccggcagttctctgataacgctggcatcactccagcaat tagtctggacctgatgaccgatgccgagctggctagggcagtgtcataca tgcccaccagcgctggccagatcaaactgatgctggaaaatcgcgcaatg gtcaggcgcaagggctttgggatcctgattggagtgtacggcagctccgt gatctatatggtccagctgcctatcttcggcgtgattgacacaccatgct ggatcatcaaggccgctccctcttgtagtgagaaggatgggaactacgca tgcctgctgagagaagaccagggatggtattgtaaaaacgccggctccac tgtgtactatccaaatgacaaggattgtgagacacgaggagaccacgtct tttgcgatactgcatgcggcatcaacgtggctgagcagagtcgcgaatgt aacatcaacatctcaactaccaactacccctgcaaagtctctacaggccg gcatcctatcagcatggtggcactgtctccactgggagcactggtggctt gctataagggcgtctcatgtagcattggctccaatagagtggggatcatt aagcagctgcccaaaggctgctcttacatcactaaccaggacgccgatac tgtgaccattgataataccgtctatcagctgagcaaagtggagggggaac agcacgtcatcaagggaaggcctgtgtctagttcattcgacccaattaag tttcccgaggatcagttcaacgtggccctggaccaggtcttcgagagcat cgaaaattcccaggctctggtggaccagtccaacaaaattctgaattccg cagagtctgccatcggcgggtacattcccgaagcccctcgcgatgggcag gcttatgtccgaaaggacggagagtgggtgctgctgtcaacctttctggg aggactggtgccaaggggaagccaccatcaccatcaccatagtgcctggt cacatcctcagttcgaaaagtgatga MPV F with A113C/A339C/T 160F/I177L
(SEQ ID NO: 67):
atgagttggaaagtgatgattattattagcctgctgattacc ccccagcacggactgaaggagtcttatctggaggagtcttg ctcaacaatcactgagggctacctgagcgtcctgcgcaca gggtggtatactaacgtgtttaccctggaagtgggcgatgtcgaaaatct gacctgtacagacgggcctagcctgatcaagacagagctggatctgacta aaagcgccctgcgggaactgaagaccgtgtccgctgaccagctggcaaga gaggaacagatcgagaacccacgacagagccgattcgtgctgggagctat tgcactgggagtgtgcaccgccgctgcagtcacagcaggaatcgcaattg ctaaaactatccgcctggagagtgaagtgaacgccattaagggagctctg aaaaccacaaacgaagctgtgtctaccctggggaatggagtgagagtcct ggcatttgccgtcagggagctgaaggaattcgtgtctaaaaatctgacaa gtgccctgaacaagaacaagtgcgacatcgcagatctgaagatggccgtg agcttctcccagtttaaccggagatttctgaatgtggtccggcagttctc -continued

```
tgataacgctggcatcactccagcaattagtctggacctgatgaccgatg
ccgagctggctagggcagtgtcatacatgcccaccagcgctggccagatc
aaactgatgctggaaaatcgcgcaatggtcaggcgcaagggctttgggat
cctgattggagtgtacggcagcagcgtgatctacatggtccagctgccta
tcttcggcgtgattgacacaccatgctggatcatcaaggccgctccctct
tgtagtgagaaggatgggaactacgcatgcctgctgagagaagaccaggg
atggtattgtaaaaacgccggctccactgtgtactatccaaatgacaagg
attgtgagacacgaggagaccacgtcttttgcgatactgcatgcggcatc
aacgtggctgagcagagtcgcgaatgtaacatcaacatctcaactaccaa
ctacccctgcaaagtctctacaggccggcatcctatcagcatggtggcac
tgtctccactgggagcactggtggcttgctataagggcgtctcatgtagc
attggctccaatagagtggggatcattaagcagctgcccaaaggctgctc
ttacatcaccaaccaggacgccgatactgtgaccattgataatacagtct
atcagctgagcaaagtggagggggaacagcacgtcatcaagggaaggcct
gtgtctagttcattcgacccaattaagtttcccgaggatcagttcaacgt
ggccctggaccaggtcttcgagagcatcgaaaattcccaggctctggtgg
accagtccaacaaaattctgaattccgcagagtctgccatcggcgggtac
attcccgaagcccctcgcgatgggcaggcttatgtccgaaaggacggaga
gtgggtgctgctgtcaacctttctgggaggactggtgccaaggggaagcc
accatcaccatcaccatagtgcctggtcacatcctcagttcgaaaagtga
tga
```

In several embodiments, the nucleic acid molecule encodes a precursor of a disclosed recombinant MPV F protein or immunogenic fragment thereof, that, when expressed in an appropriate cell, is processed into a disclosed recombinant MPV F protein or immunogenic fragment thereof. For example, the nucleic acid molecule can encode a recombinant MPV F protein including a N-terminal signal sequence for entry into the cellular secretory system that is proteolytically cleaved in the during processing of the MPV F protein in the cell. In some embodiments, the signal peptide includes the amino acid sequence set forth as residues 1-18 of SEQ ID NO: 7.

Exemplary nucleic acids can be prepared by cloning techniques. Examples of appropriate cloning and sequencing techniques, and instructions sufficient to direct persons of skill through many cloning exercises are known (see, e.g., Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

The polynucleotides encoding a recombinant MPV F proteins stabilized in a prefusion conformation, fragments thereof, and protein nanoparticles (or a subunit thereof) can include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

Polynucleotide sequences encoding recombinant MPV F proteins stabilized in a prefusion conformation, fragments thereof, and protein nanoparticles (or a subunit thereof) can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

DNA sequences encoding the recombinant MPV F proteins stabilized in a prefusion conformation, fragments thereof, and protein nanoparticles (or a subunit thereof) can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, e.g., Helgason and Miller (Eds.), 2012, Basic Cell Culture Protocols (Methods in Molecular Biology), $4^{th}$ Ed., Humana Press). Examples of commonly used mammalian host cell lines are VERO and HeLa cells, CHO cells, and W138, BHK, and COS cell lines, although cell lines may be used, such as cells designed to provide higher expression, desirable glycosylation patterns, or other features. In some embodiments, the host cells include HEK293 cells or derivatives thereof, such as $GnTI^{-/-}$ cells (ATCC® No. CRL-3022), or HEK-293F cells.

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Viral Expression Vectors, Springer press, Muzyczka ed., 2011). One of skill in the art can readily use an expression systems such as plasmids and vectors of use in producing proteins in cells including higher eukaryotic cells such as the COS, CHO, HeLa and myeloma cell lines.

In one non-limiting example, a disclosed immunogen is expressed using the pVRC8400 vector (described in Barouch et al., J. Virol, 79, 8828-8834, 2005, which is incorporated by reference herein).

Modifications can be made to a nucleic acid encoding a recombinant MPV F protein stabilized in a prefusion conformation, fragment thereof, and protein nanoparticle (or a subunit thereof) described herein without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

In addition to recombinant methods, the recombinant MPV F proteins stabilized in a prefusion conformation, fragments thereof, and protein nanoparticles (or a subunit thereof) can also be constructed in whole or in part using protein synthesis methods known in the art.

E. Viral Vectors

The nucleic acid molecules encoding the disclosed immunogens (e.g., a recombinant MPV F protein stabilized in a prefusion conformation or an immunogenic fragment thereof) can be included in a viral vector, for example for expression of the antigen in a host cell, or for immunization of a subject as disclosed herein. In some embodiments, the viral vectors are administered to a subject as part of a prime-boost vaccination. In several embodiments, the viral vectors are included in a vaccine, such as a primer vaccine or a booster vaccine for use in a prime-boost vaccination.

In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

A number of viral vectors have been constructed, that can be used to express the disclosed antigens, including polyoma, i.e., SV40 (Madzak et al., 1992, *J. Gen. Virol.,* 73:15331536), adenovirus (Berkner, 1992, *Cur. Top. Microbiol. Immunol.,* 158:39-6; Berliner et al., 1988, *Bio Techniques,* 6:616-629; Gorziglia et al., 1992, *J. Virol.,* 66:4407-4412; Quantin et al., 1992, *Proc. Natl. Acad. Sci. USA,* 89:2581-2584; Rosenfeld et al., 1992, *Cell,* 68:143-155; Wilkinson et al., 1992, *Nucl. Acids Res.,* 20:2233-2239; Stratford-Perricaudet et al., 1990, *Hum. Gene Ther.,* 1:241-256), vaccinia virus (Mackett et al., 1992, *Biotechnology,* 24:495-499), adeno-associated virus (Muzyczka, 1992, Curr. Top. *Microbiol. Immunol.,* 158:91-123; On et al., 1990, *Gene,* 89:279-282), herpes viruses including HSV and EBV (Margolskee, 1992, *Curr. Top. Microbiol. Immunol.,* 158:67-90; Johnson et al., 1992, *J. Virol.,* 66:29522965; Fink et al., 1992, *Hum. Gene Ther.* 3:11-19; Breakfield et al., 1987, *Mol. Neurobiol.,* 1:337-371; Fresse et al., 1990, *Biochem. Pharmacol.,* 40:2189-2199), Sindbis viruses (H. Herweijer et al., 1995, *Human Gene Therapy* 6:1161-1167; U.S. Pat. Nos. 5,091,309 and 5,2217,879), alphaviruses (S. Schlesinger, 1993, *Trends Biotechnol.* 11:18-22; I. Frolov et al., 1996, *Proc. Nat. Acad. Sci. USA* 93:11371-11377) and retroviruses of avian (Brandyopadhyay et al., 1984, *Mol. Cell Biol.,* 4:749-754; Petropouplos et al., 1992, *J. Virol.,* 66:3391-3397), murine (Miller, 1992, *Curr. Top. Microbiol. Immunol.,* 158:1-24; Miller et al., 1985, *Mol. Cell Biol.,* 5:431-437; Sorge et al., 1984, *Mol. Cell Biol.,* 4:1730-1737; Mann et al., 1985, *J. Virol.,* 54:401-407), and human origin (Page et al., 1990, *J. Virol.,* 64:5370-5276; Buchschalcher et al., 1992, *J. Virol.,* 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In some embodiments, a nucleic acid molecule encoding a recombinant MPV F protein stabilized in a prefusion conformation as described herein can be included in a recombinant paramyxovirus vector (such as an inactivated or attenuated recombinant paramyxovirus vector). The recombinant paramyxovirus vector typically includes a genome comprising a heterologous gene encoding the ectodomain of the recombinant MPV F protein linked to a TM and CT of an envelope protein from the paramyxovirus (or alternatively the native MPV F TM and CT domains can be used) to allow for expression of the MPV F ectodomain on the paramyxovirus envelope. For example, the recombinant paramyxovirus can be a recombinant parainfluenza virus (PIV) comprising a genome comprising a heterologous gene encoding the ectodomain of an MPV F protein linked to the TM and CT of the F protein from the PIV.

In non-limiting examples, the recombinant paramyxovirus can be a recombinant HPIV1, a HPIV2, a HPIV3, a BPIV3, a PIV5, a Sendai virus, or a NDV, or a chimera thereof, for example. General methods of generating a recombinant paramyxovirus including a genome including a heterologous gene are known to the person of ordinary skill in the art, as are viral sequences and reagents for use in such methods. Non-limiting examples of methods of generating a recombinant PIV vector (such as a recombinant HPIV1, HPIV2, HPIV3, or H/BPIV3 vector) including a heterologous gene, methods of attenuating the vectors (e.g., by recombinant or chemical means), as well as viral sequences and reagents for use in such methods are provided in US Patent Publications 2012/0045471; 2010/0119547; 2009/0263883; 2009/0017517; 8084037; 6,410,023; 8,367,074; 7,951,383; 7,820,182; 7704509; 7632508; 7622123; 7250171; 7208161; 7201907; 7192593, and Newman et al. 2002. Virus genes 24:77-92, Tang et al., 2003. J Virol, 77(20):10819-10828; each of which is incorporated by reference herein in its entirety. Non-limiting examples of methods of generating a recombinant NDV vector including a heterologous gene, as well as viral sequences and reagents for use in such methods are provided in US Patent Publications 2012/0064112; and Basavarajappa et al. 2014 Vaccine, 32: 3555-3563, and McGinnes et al., J. Virol., 85: 366-377, 2011, each of which is incorporated by reference herein in its entirety. Non-limiting examples of methods of generating a recombinant Sendai vector including a heterologous gene, as well as viral sequences and reagents for use in such methods are provided in US Patent Publications 20140186397, and Jones et al., *Vaccine,* 30:959-968, 2012, each of which is incorporated by reference herein in its entirety.

In some embodiments, the viral vector can include an adenoviral vector that expresses a disclosed recombinant MPV F protein or immunogenic fragment thereof. Adenovirus from various origins, subtypes, or mixture of subtypes can be used as the source of the viral genome for the adenoviral vector. Non-human adenovirus (e.g., simian, chimpanzee, gorilla, avian, canine, ovine, or bovine adenoviruses) can be used to generate the adenoviral vector. For example, a simian adenovirus can be used as the source of the viral genome of the adenoviral vector. A simian adenovirus can be of serotype 1, 3, 7, 11, 16, 18, 19, 20, 27, 33, 38, 39, 48, 49, 50, or any other simian adenoviral serotype. A simian adenovirus can be referred to by using any suitable abbreviation known in the art, such as, for example, SV, SAdV, SAV or sAV. In some examples, a simian adenoviral vector is a simian adenoviral vector of serotype 3, 7, 11, 16, 18, 19, 20, 27, 33, 38, or 39. In one example, a chimpanzee serotype C Ad3 vector is used (see, e.g., Peruzzi et al., Vaccine, 27:1293-1300, 2009). Human adenovirus can be used as the source of the viral genome for the adenoviral vector. Human adenovirus can be of various subgroups or serotypes. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22, 23, 24, 25, 26, 27, 28, 29, 30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. The person of ordinary skill in the art is familiar with replication competent and deficient adenoviral vectors (including singly and multiply replication deficient adenoviral vectors). Examples of replication-deficient adenoviral vectors, including multiply replication-deficient adenoviral vectors, are disclosed in U.S. Pat. Nos. 5,837,511; 5,851,806; 5,994,106; 6,127,175; 6,482,616; and 7,195,896, and International Patent Application Nos. WO 94/28152, WO 95/02697, WO 95/16772, WO 95/34671, WO 96/22378, WO 97/12986, WO 97/21826, and WO 03/022311.

F. Compositions

The disclosed immunogens (for example, a recombinant MPV F protein or immunogenic fragment thereof, or a protein nanoparticle including such proteins), or nucleic acid molecule encoding an immunogen, can be included in a pharmaceutical composition (including therapeutic and prophylactic formulations), often combined together with one or more pharmaceutically acceptable vehicles and, optionally, other therapeutic ingredients (for example, antibiotics or antiviral drugs). In several embodiments, pharmaceutical compositions including one or more of the disclosed immunogens are immunogenic compositions.

Such pharmaceutical compositions can be administered to subjects by a variety of administration modes known to the person of ordinary skill in the art, for example, intramuscular, subcutaneous, intravenous, intra-arterial, intra-articular, intraperitoneal, or parenteral routes.

To formulate the pharmaceutical compositions, the disclosed immunogens (for example, a recombinant MPV F protein or immunogenic fragment thereof, or a protein nanoparticle including such proteins), or nucleic acid molecule encoding an immunogen, can be combined with various pharmaceutically acceptable additives, as well as a base or vehicle for dispersion of the conjugate. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, TWEEN® 80), solubility enhancing agents (for example, cyclodextrins and derivatives thereof), stabilizers (for example, serum albumin), and reducing agents (for example, glutathione) can be included. Adjuvants, such as aluminum hydroxide (ALHYDROGEL®, available from Brenntag Biosector, Copenhagen, Denmark and AMPHOGEL®, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The disclosed immunogens (for example, a recombinant MPV F protein or immunogenic fragment thereof, or a protein nanoparticle including such proteins), or nucleic acid molecule encoding an immunogen can be dispersed in a base or vehicle, which can include a hydrophilic compound having a capacity to disperse the antigens, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films, for examples for direct application to a mucosal surface.

The disclosed immunogens (for example, a recombinant MPV F protein or immunogenic fragment thereof, or a protein nanoparticle including such proteins), or nucleic acid molecule encoding an immunogen can be combined with the base or vehicle according to a variety of methods, and release of the antigens can be by diffusion, disintegration of the vehicle, or associated formation of water channels. In some circumstances, the disclosed immunogens (for example, a recombinant MPV F protein or immunogenic fragment thereof, or a protein nanoparticle including such proteins), or nucleic acid molecule encoding an immunogen is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The pharmaceutical compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the immunogenic compositions can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the disclosed antigens can be brought about by including in the composition an agent which delays absorption, for example, monostearate salts and gelatin.

In certain embodiments, the disclosed immunogens (for example, a recombinant MPV F protein or immunogenic fragment thereof, or a protein nanoparticle including such proteins), or nucleic acid molecule encoding an immunogen can be administered in a time-release formulation, for example in a composition that includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the disclosed antigen and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body. Numerous systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the conjugate in the required amount in an appropriate solvent with one or a combination of ingredients enumerated herein, as required, followed by filtered sterilization. Generally, dispersions are prepared by incorporating the disclosed antigen and/or other biologically active agent into a sterile vehicle that contains a basic dispersion medium and the required other ingredients from those enumerated herein. In the case of sterile powders, methods of preparation include vacuum drying and freeze-drying which yields a powder of the disclosed antigen plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

Actual methods for preparing administrable compositions will be known or apparent to those skilled in the art and are described in more detail in such publications as *Remingtons Pharmaceutical Sciences,* 19th Ed., Mack Publishing Company, Easton, Pa., 1995.

In several embodiments, the compositions include an adjuvant. The person of ordinary skill in the art is familiar with adjuvants, for example, those that can be included in an immunogenic composition. It will be appreciated that the choice of adjuvant can be different in these different applications, and the optimal adjuvant and concentration for each situation can be determined empirically by those of skill in the art.

The pharmaceutical composition typically contains a therapeutically effective amount of a disclosed immunogen (for example, a recombinant MPV F protein or immunogenic fragment thereof, or a protein nanoparticle including such proteins), or nucleic acid molecule encoding an immunogen, or viral vector can be prepared by conventional techniques. Preparation of immunogenic compositions, including those for administration to human subjects, is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757. Typically, the amount of antigen in each dose of the immunogenic composition is selected as an amount which induces an immune response without significant, adverse side effects.

The amount of the disclosed immunogen (for example, a recombinant MPV F protein or immunogenic fragment thereof, or a protein nanoparticle including such proteins), or nucleic acid molecule encoding an immunogen, or viral vector can vary depending upon the specific antigen employed, the route and protocol of administration, and the target population, for example. For protein therapeutics, typically, each human dose will comprise 1-1000 μg of protein, such as from about 1 μg to about 100 μg, for example, from about 1 μg to about 50 μg, such as about 1 μg, about 2 μg, about 5 μg, about 10 μg, about 15 μg, about 20 μg, about 25 μg, about 30 μg, about 40 μg, or about 50 μg. The amount utilized in an immunogenic composition is selected based on the subject population (e.g., infant or elderly). An optimal amount for a particular composition can be ascertained by standard studies involving observation of antibody titers and other responses in subjects. It is understood that a therapeutically effective amount of a disclosed immunogen, such as a recombinant MPV F protein or fragment thereof, protein nanoparticle, viral vector, or nucleic acid molecule in a immunogenic composition, can include an amount that is ineffective at eliciting an immune response by administration of a single dose, but that is effective upon administration of multiple dosages, for example in a prime-boost administration protocol.

In some embodiments, the composition can be provided as a sterile composition. In more embodiments, the composition can be provided in unit dosage form for use to induce an immune response in a subject, for example, to prevent MPV infection in the subject. A unit dosage form contains a suitable single preselected dosage for administration to a subject, or suitable marked or measured multiples of two or more preselected unit dosages, and/or a metering mechanism for administering the unit dose or multiples thereof. In other embodiments, the composition further includes an adjuvant.

G. Therapeutic Methods

The disclosed immunogens (for example, recombinant MPV F proteins and immunogenic fragments thereof, polynucleotides encoding same, protein nanoparticles, vectors, and viral-like particles) can be used in methods of preventing, inhibiting and treating an MPV infection, as well as methods of inducing an immune response to MPV. In several embodiments, a therapeutically effective amount of an immunogenic composition including one or more of the disclosed immunogens can be administered to a subject in order to generate an immune response to MPV.

In some embodiments, a subject is selected for treatment that has, or is at risk for developing, an MPV infection, for example because of exposure or the possibility of exposure to MPV. Following administration of a therapeutically effective amount of a disclosed immunogen, the subject can be monitored for MPV infection, symptoms associated with MPV infection, or both.

Typical subjects intended for treatment with the therapeutics and methods of the present disclosure include humans, as well as non-human primates and other animals. Because nearly all humans are infected with MPV by the age of 5, the entire birth cohort is included as a relevant population for immunization. This could be done, for example, by beginning an immunization regimen anytime from birth to 6 months of age, from 6 months of age to 5 years of age, in pregnant women (or women of child-bearing age) to protect their infants by passive transfer of antibody, family members of newborn infants or those still in utero, and subjects greater than 50 years of age.

Subjects at greatest risk of MPV infection with severe symptoms (e.g. requiring hospitalization) include children with prematurity, bronchopulmonary dysplasia, and congenital heart disease are most susceptible to severe disease. During childhood and adulthood, disease is milder but can be associated with lower airway disease and is commonly complicated by sinusitis. Disease severity increases in the institutionalized elderly (e.g., humans over 65 years old). Severe disease also occurs in persons with severe combined immunodeficiency disease or following bone marrow or lung transplantation. (See, e.g., Edwards et al., New Eng. J. Med., 368, 633-643, 2013, which is incorporated by reference herein). Thus, these subjects can be selected for administration of the disclosed immunogens, or a nucleic acid or a viral vector encoding, expressing or including an immunogen.

To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize MPV infection. These and other routine methods allow the clinician to select patients in need of therapy using the methods and pharmaceutical compositions of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

The administration of a disclosed immunogen can be for prophylactic or therapeutic purpose. When provided prophylactically, the immunogen can be provided in advance of any symptom, for example in advance of infection. The prophylactic administration serves to prevent or ameliorate any subsequent infection. In some embodiments, the methods can involve selecting a subject at risk for contracting MPV infection, and administering a therapeutically effective amount of a disclosed immunogen to the subject. The immunogen can be provided prior to the anticipated exposure to MPV so as to attenuate the anticipated severity, duration or extent of an infection and/or associated disease symptoms, after exposure or suspected exposure to the virus, or after the actual initiation of an infection. When provided therapeutically, the disclosed immunogens are provided at or after the onset of a symptom of MPV infection, or after diagnosis of MPV infection. Treatment of MPV by inhibiting MPV replication or infection can include delaying and/or reducing signs or symptoms of MPV infection in a subject. In some examples, treatment using the methods disclosed herein prolongs the time of survival of the subject.

An immunogenic composition including one or more of the disclosed immunogens can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-MPV immune response, such as an immune response to MPV F protein. Separate immunogenic compositions that elicit the anti-MPV immune response can be combined in a polyvalent immunogenic composition administered to a subject in a single immunization step, or they can be administered separately (in monovalent immunogenic compositions) in a coordinate (or prime-boost) immunization protocol.

In one embodiment, a suitable immunization regimen includes at least two separate inoculations with one or more immunogenic compositions, with a second inoculation being administered more than about two, about three to eight, or about four, weeks following the first inoculation. A third inoculation can be administered several months after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory." The adequacy of the vaccination parameters chosen, e.g., formulation, dose, regimen and the like, can be determined by taking aliquots of serum from the subject and assaying antibody titers during the course of the immunization program. Alternatively, the T cell populations can be monitored by conventional methods. In addition, the clinical condition of the subject can be monitored for the desired effect, e.g., prevention of MPV infection or improvement in disease state (e.g., reduction in viral load). If such monitoring indicates that vaccination is sub-optimal, the subject can be boosted with an additional dose of immunogenic composition, and the vaccination parameters can be modified in a fashion expected to potentiate the immune response. Thus, for example, the dose of the disclosed immunogen (e.g., recombinant MPV F protein with A113C/A339C/T160F/I177L substitutions or immunogenic fragment thereof, polynucleotides encoding same, protein nanoparticles, viral-like particles, or vectors) can be increased or the route of administration can be changed.

It is contemplated that there can be several boosts, and that each boost can be a different disclosed immunogen. It is also contemplated in some examples that the boost may be the same immunogen as another boost, or the prime.

The prime and boost can be administered as a single dose or multiple doses, for example two doses, three doses, four doses, five doses, six doses or more can be administered to a subject over days, weeks or months. Multiple boosts can also be given, such one to five (e.g., 1, 2, 3, 4 or 5 boosts), or more. Different dosages can be used in a series of sequential inoculations. For example a relatively large dose in a primary inoculation and then a boost with relatively smaller doses. The immune response against the selected antigenic surface can be generated by one or more inoculations of a subject.

In some embodiments, the prime composition administered to the subject includes (or encodes) a recombinant MPV F protein that is a group A MPV F protein stabilized in a prefusion conformation, and the boost composition administered to the subject includes (or encodes) a recombinant MPV F protein that is a group B MPVF protein stabilized in a prefusion conformation. In some embodiments, the prime composition administered to the subject includes (or encodes) a recombinant MPV F protein that is a group B MPV F protein stabilized in a prefusion conformation, and the boost composition administered to the subject includes (or encodes) a recombinant MPV F protein that is a group A MPV F protein stabilized in a prefusion conformation.

In some embodiments, the methods include administering a composition including a recombinant group A MPV F protein stabilized in a prefusion conformation and a recombinant group B MPV F protein stabilized in a prefusion conformation once, or more than one (such as in a prime-boost protocol) as a series of injections.

In some embodiments, the prime and boost compositions administered to the subject each include (or encode) a first recombinant MPV F protein that is a group A MPV F protein stabilized in a prefusion conformation, and a second recombinant MPV F protein that is a group B MPV F protein stabilized in a prefusion conformation. In several embodiments, the prime and boost compositions administered to the subject each include (or encode) a mixture (such as about a 1:1, 1:2, 2:1, 2:3, 3:2, 1:3, 3:1, 1:4, 4:1, 3:5, 5:3, 1:5, 5:1, 5:7, 7:5 mixture), of first and second recombinant MPV F proteins that are group A or group B MPV F proteins stabilized in a prefusion conformation, respectively.

In some embodiments, the method can include DNA-protein, DNA-protein nanoparticle, or protein-protein nanoparticle, prime-boost vaccination protocol to a subject, including administering a therapeutically effective amount of a recombinant MPV F protein stabilized in a prefusion conformation or immunogenic fragment thereof, a nucleic acid molecule encoding the recombinant MPV F protein or immunogenic fragment, or a protein nanoparticle including the recombinant MPV F protein or immunogenic fragment. For example the method can include administration of a prime including the nucleic acid molecule encoding the recombinant MPV F protein and a boost including the recombinant MPV F protein. The method can include two or more administrations of the nucleic acid molecule or the protein.

Immunization protocols using a DNA plasmid prime and ferritin nanoparticle boost are known to the person of ordinary skill in the art (see, e.g., Wei et al., Science, 329(5995):1060-4, 2010, which is incorporated by reference herein in its entirety).

Upon administration of a disclosed immunogen (or a prime-boost regimen of disclosed immunogens), the immune system of the subject typically responds to the immunogenic composition by producing antibodies specific for MPV F protein. Such a response signifies that an immunologically effective dose was delivered to the subject.

An immunologically effective dosage can be achieved by single or multiple administrations (including, for example, multiple administrations per day), daily, or weekly administrations of the immunogen. For each particular subject, specific dosage regimens can be evaluated and adjusted over time according to the individual need and professional judgment of the person administering or supervising the administration of the immunogenic composition. In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including, for example, a MPV F protein. The methods of using immunogenic compositions, and the related compositions and methods of the disclosure are also useful in increasing resistance to, preventing, ameliorating, and/or treating infection and disease caused by MPV in animal hosts, and other, in vitro applications.

In several embodiments, a disclosed immunogen can be administered to the subject simultaneously with the administration of an adjuvant. In other embodiments, the immunogen can be administered to the subject after the administration of an adjuvant and within a sufficient amount of time to induce the immune response.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

Dosage can be varied by the attending clinician to maintain a desired concentration at a target site (for example, systemic circulation). Higher or lower concentrations can be selected based on the mode of delivery, for example, trans-epidermal, rectal, oral, pulmonary, or intranasal delivery versus intravenous or subcutaneous delivery. The actual dosage of disclosed immunogen will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

A non-limiting range for a therapeutically effective amount of the disclosed immunogen (e.g., recombinant MPV F protein or immunogenic fragment thereof, polynucleotides encoding same, protein nanoparticles, viral-like particles, or vectors) within the methods and immunogenic compositions of the disclosure can be about 0.0001 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight. In some embodiments, the dosage includes a set amount of a disclosed immunogen (e.g., recombinant MPV F protein or immunogenic fragment thereof, polynucleotides encoding same, protein nanoparticles, viral-like particles, or vectors) such as from about 1-300 μg, for example, a dosage of about 1, 2, 3, 4, 5, 6, 7, 8, 9, 10, 15, 20, 30, 40, 50, 60, 70, 80, 90, 100, 150, 200, 250, or about 300 μg.

The dosage and number of doses will depend on the setting, for example, in an adult or anyone primed by prior MPV infection or immunization, a single dose may be a sufficient booster. In naïve subjects, in some examples, at least two doses would be given, for example, at least three doses. In some embodiments, an annual boost is given, for example, along with an annual influenza vaccination.

Actual methods for preparing administrable compositions will be known or apparent to those skilled in the art and are described in more detail in such publications as *Remingtons Pharmaceutical Sciences,* $19^{th}$ Ed., Mack Publishing Company, Easton, Pa., 1995.

Following immunization of a subject, serum can be collected from the subject at appropriate time points, frozen, and stored for neutralization testing. Methods to assay for neutralization activity are known to the person of ordinary skill in the art and are further described herein, and include, but are not limited to, plaque reduction neutralization (PRNT) assays, microneutralization assays, flow cytometry based assays, single-cycle infection assays. In some embodiments, the serum neutralization activity can be assayed using a panel of MPV pseudoviruses. Virus-neutralizing (VN) antibody titres were determined in serum samples by a PRVN assay as described previously (de Graaf et al., *J. Virol Methods,* 143: 169-174, 2007). In brief, serum samples were diluted and incubated for 60 min at 37° C. with approximately 50 p.f.u. of NL/1/00 or NL/1/99, expressing the enhanced green fluorescent protein. Subsequently, the virus-serum mixtures were added to Vero-118 cells in 24-well plates and incubated at 37° C., After 2 h, the supernatants were replaced by a mixture of equal amounts of infection medium and 2% methyl cellulose. Six days later, fluorescent plaques were counted using a Typhoon 9410 Variable Node Imager (GE Healthcare). VN antibody titres were expressed as the dilution resulting in 50% reduction of the number of plaques, calculated according to the method of Reed & Muench, *Am. J. Hyg.,* 27, 493-497, 1938.

In some embodiments, administration of a therapeutically effective amount of one or more of the disclosed immunogens to a subject (e.g., by a prime-boost administration of a DNA vector encoding a disclosed immunogen (prime) followed by a protein nanoparticle including a disclosed immunogen (boost)) induces a neutralizing immune response in the subject. In several embodiments, the neutralizing immune response can be detected using a pseudovirus neutralization assay against a panel of MPV pseudoviruses including MPV F proteins from different MPV strains. In one example, the panel can include pseudoviruses including F proteins from MPV strains from subgroup A1 (NL/1/00), subgroup A2 (CAN97-83, NL/17/00, NCL174), subgroup B1 (NL/1/99, NDL00-1), or subgroup B2 (CAN98-75).

In some embodiments, administration of a therapeutically effective amount of one or more of the disclosed immunogen to a subject (e.g., by a prime-boost administration of a DNA vector encoding a disclosed immunogen (prime) followed by a protein nanoparticle including a disclosed immunogen (boost)) induces a neutralizing immune response in the subject, wherein serum from the subject neutralizes, with an $ID_{50}\geq40$, at least 30% (such as at least 40%, at least 50%, at least 60%, at least 70%, at least 80%, or at least 90%) of pseudoviruses is a panel of pseudoviruses including F proteins from MPV strains from subgroup A1 (NL/1/00), subgroup A2 (CAN97-83, NL/17/00, NCL174), subgroup B1 (NL/1/99, NDL00-1),or subgroup B2 (CAN98-75).

In some embodiments, administration of a therapeutically effective amount of one or more of the disclosed immunogens to a subject induces a neutralizing immune response in the subject. In one non-limiting example, the neutralizing immune response can be detected using a pseudovirus neutralization assay against a panel of MPV pseudoviruses including MPV F proteins from different MPV strains. In some embodiments, administration of the therapeutically effective amount of one or more disclosed immunogens to a subject induces a neutralizing immune response in the subject, wherein serum from the subject neutralizes, with an $ID_{50}\geq40$, at least 50% (such as at least 60%, at least 70%, at least 80%, or at least 90%) of pseudoviruses in a panel of pseudoviruses including the MPV F proteins listed in Table 1.

One approach to administration of nucleic acids is direct immunization with plasmid DNA, such as with a mammalian expression plasmid. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In some embodiments, a plasmid DNA vaccine is used to express a disclosed immunogen in a subject. For example, a nucleic acid molecule encoding a recombinant MPV F protein stabilized in a prefusion conformation can be administered to a subject to induce an immune response to MPV F protein. In some embodiments, the nucleic acid molecule can be included on a plasmid vector for DNA immunization, such as the pVRC8400 vector (described in Barouch et al., J. Virol, 79, 8828-8834, 2005, which is incorporated by reference herein).

In another approach to using nucleic acids for immunization, a disclosed recombinant MPV F protein or immunogenic fragment thereof can also be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (*Bacillus* Calmette Guerin) provides another vector for expression of the peptides (see Stover, *Nature* 351:456-460, 1991).

In one embodiment, a nucleic acid encoding a disclosed recombinant MPV f protein or immunogenic fragment thereof, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites. Dosages for injection are usually around 0.5 μg/kg to about 50 mg/kg, and typically are about 0.005 mg/kg to about 5 mg/kg (see, e.g., U.S. Pat. No. 5,589,466).

In certain embodiments, the immunogen can be administered sequentially with other anti-MPV therapeutic agents, such as before or after the other agent. One of ordinary skill in the art would know that sequential administration can mean immediately following or after an appropriate period of time, such as hours, days, weeks, months, or even years later.

H. Immunodiagnostic Methods

In addition to the therapeutic methods provided above, any of the disclosed immunogens (for example, disclosed recombinant MPV F protein or immunogenic fragment thereof) can be utilized to produce antigen specific immunodiagnostic reagents, for example, for serosurveillance. Immunodiagnostic reagents can be designed from any of the antigenic polypeptide described herein. For example, in the case of the disclosed immunogens, the presence of serum antibodies to MPV is monitored using the isolated immunogens disclosed herein, such as to detect an MPV infection and/or the presence of antibodies that specifically bind to MPV F in a prefusion conformation.

Methods are further provided for a diagnostic assay to monitor MPV induced disease in a subject and/or to monitor the response of the subject to immunization with one or more of the disclosed antigens. By "MPV induced disease" is intended any disease caused, directly or indirectly, by MPV. An example of an MPV induced disease is pneumonia.

The method includes contacting a disclosed immunogen with a sample of bodily fluid from the subject, and detecting binding of antibodies in the sample to the disclosed immunogens. In addition, the detection of the MPV F binding antibody also allows the response of the subject to immunization with the disclosed antigen to be monitored. In still other embodiments, the titer of the MPV F binding antibodies can be determined. The binding can be detected by any means known to one of skill in the art, including the use of labeled secondary antibodies that specifically bind the antibodies from the sample. Labels include radiolabels, enzymatic labels, and fluorescent labels. In other embodiments, a disclosed immunogen is used to isolate antibodies present in a subject or biological sample obtained from a subject.

Generally, the method includes contacting a sample from a subject, such as, but not limited to a blood, serum, plasma, urine or sputum sample from the subject with one or more of the disclosed recombinant MPV F proteins or immunogenic fragments thereof (including a polymeric form thereof) and detecting binding of antibodies in the sample to the disclosed immunogens. The binding can be detected by any means known to one of skill in the art, including the use of labeled secondary antibodies that specifically bind the antibodies from the sample. Labels include radiolabels, enzymatic labels, and fluorescent labels.

I. Kits

Any immunodiagnostic or therapeutic reagents can be provided as components of a kit. Optionally, such a kit includes additional components including packaging, instructions and various other reagents, such as buffers, substrates, antibodies or ligands, such as control antibodies or ligands, and detection reagents. The kit can include a container and a label or package insert on or associated with the container. Suitable containers include, for example, bottles, vials, syringes, etc. The containers may be formed from a variety of materials such as glass or plastic. The container typically holds a composition including one or more of the disclosed recombinant MPV F proteins, immunogenic fragments thereof, protein nanoparticles, polynucleotides encoding a recombinant MPV F protein or immunogenic fragment, vectors or compositions, which is effective for treating, preventing, diagnosing, monitoring MPV infection or immune response. In several embodiments the container may have a sterile access port (for example the container may be an intravenous solution bag or a vial having a stopper pierceable by a hypodermic injection needle). The label or package insert indicates that the composition is used for treating the particular condition.

The label or package insert typically will further include instructions for use of an antigen, or a nucleic acid or a viral vector encoding, expressing or including the antigen, for example, in a method of treating or preventing a MPV infection. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. The kits may additionally include buffers and other reagents routinely used for the practice of a particular method. Such kits and appropriate contents are well known to those of skill in the art.

III. Examples

The following examples are provided to illustrate particular features of certain embodiments, but the scope of the claims should not be limited to those features exemplified.

Example 1

Prefusion MPV F Structure and Stabilization

The fusion (F) glycoprotein of human metapneumovirus (hMPV) exists in at least two conformations, a metastable prefusion state and a stable postfusion state. Both states share several epitopes targeted by neutralizing antibodies, but the predominant target of hMPV-neutralizing antibodies elicited by natural infection is thought to reside on the prefusion conformation of F. An atomic-level structure for the MPV F trimer in complex with the DS7 antibody (which neutralizes MPV infection) has been previously disclosed (see, e.g., Wen et al., *Nat. Struct. Mol. Biol.,* 19, 461-463, 2012, which is incorporated by reference herein in its entirety). The three-dimensional coordinates for the structure of the MPV F trimer in complex with the DS7 antibody are deposited as PDB Accession No. 4DAG, which is incorporated by reference herein. The DS7 antibody specifically binds to an epitope on MPV F that is present in both the pre- and post-fusion forms of the MPV F protein trimer. The previously published structure was believed to show the MPV F protein in its prefusion conformation. Surprisingly, a detailed analysis of this published structure revealed that the conformation of the membrane-distal aspect of the MPV F protein (a potential immunodominant site of vaccine interest) was incorrect. Correction of errors through re-refinement of the deposited coordinates of the structure was used to obtain a corrected structural model of the prefusion form of the hMPV F glycoprotein. In the re-refined structure, there are two glycan sites (N57 and N172) in the Domain II membrane distal region adjacent to the "antigenic site Ø" of MPV F protein, and both of these glycan sites can be clearly built in the electron density of the re-refined structure. The three-dimensional coordinates of the re-refined structure are provided in Table 1 of U.S. Provisional Patent Application No. 62/096,744, filed Dec. 24, 2014, which is incorporated by reference herein in its entirety. The re-refined structure provides a different structure for the membrane-distal apex of the prefusion F trimer, which is believed to be an immunodominant site (see FIG. 18).

The re-refined MPV F structure was compared with the previously determined structure of respiratory syncytial virus (RSV) F protein in its prefusion conformation (deposited in PDB as Nos. 4MMU and 4JHW, each of which is incorporated by reference herein in its entirety) (see FIGS. 1-3, and 14). FIGS. 1A-2B illustrate that the RSV and MPV F structures are part of the viral type I fusion glycoprotein family and display similarity in sequence residue number, secondary, tertiary and quaternary structure. The membrane distal apex of the RSV F protein in its prefusion conformation includes the "antigenic site Ø," which is known to be a target of neutralizing antibodies (see, McLellan et al., *Science,* 340, 1113-1117, 2013). The RSV F monomer consists of three large domains, (i) a membrane proximal α-10 helix, (ii) a β-sheet rich DII domain and (iii) a large membrane distal α-helix rich region where antigenic site Ø is found. The published structure for the HMPV F molecule (4DAG) did not contain structural definition of the α-10 helix but gave a model for the DII domain and parts of the DIII domain. Comparison of the HMPV structure with the RSV F molecule indicated that the DII region and parts of the DIII region had significant structural similarity.

Figure 15:
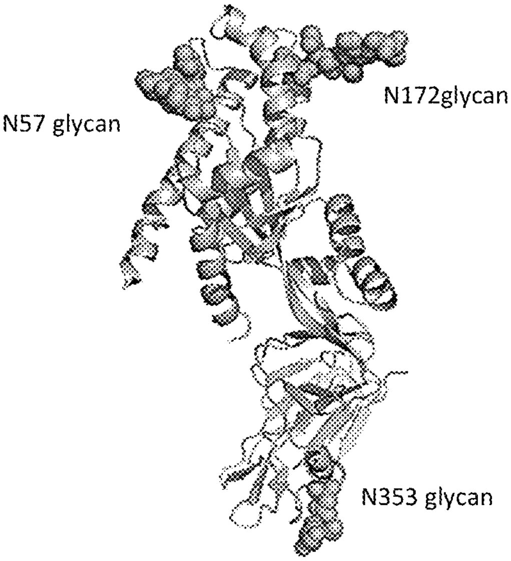

At the primary amino acid sequence level, the $F_1/F_2$ ectodomain sequences of the MPV and RSV F proteins share only 37.5% identity (see FIG. 5). Additionally, as illustrated in FIG. 5, the sequence of the membrane distal apex of RSV in its prefusion conformation ("antigenic site Ø") is only 27% identical to the corresponding sequence of MPV F protein. Given these differences, it is not surprising that there are substantial differences in the three dimensional structure of the prefusion conformation of the two F proteins, even though MPV and RSV are from the same family of Paramyxoviridae. The extracellular domain of both F glycoproteins is ~470 amino acids in length with similar tertiary domain organization in common with the RSV F molecule including the membrane proximal α-10 helix, the DII domain and the membrane distal DIII domain. The molecules have a root mean square deviation (rmsd) of 2.13 Å when 351 carbon-alpha atoms are aligned. Analysis of the membrane distal DII region spanning residues 40 to 278 in HMPV F (49-308 in RSV F) gives a rmsd of 1.59 Å over 184 carbon-alpha atoms. Major differences between the two glycoproteins include the F1-F2 cleavage site topology and the location of surface glycans on the F glycoprotein (see FIGS. 14 and 15). The HMPV cleavage into F1 and F2 occurs at just one site whereas the RSV cleavage occurs at two sites and results in the removal of a short 27 amino acid peptide. The HMPV fusion peptide is located on the surface of the molecule while the RSV fusion peptide is located in a central cavity of the molecule (see FIG. 14). The glycosylation pattern on the F molecules also differs with HMPV having conserved glycans located at residues 57, 172 and 353 compared to residue 27, 70 and 500 seen in the case of RSV. HMPV residues 57 and 172 are located in the DII region within the equivalent region of the prefusion specific antigenic site Ø of RSV (see FIG. 15).

Figure 16:
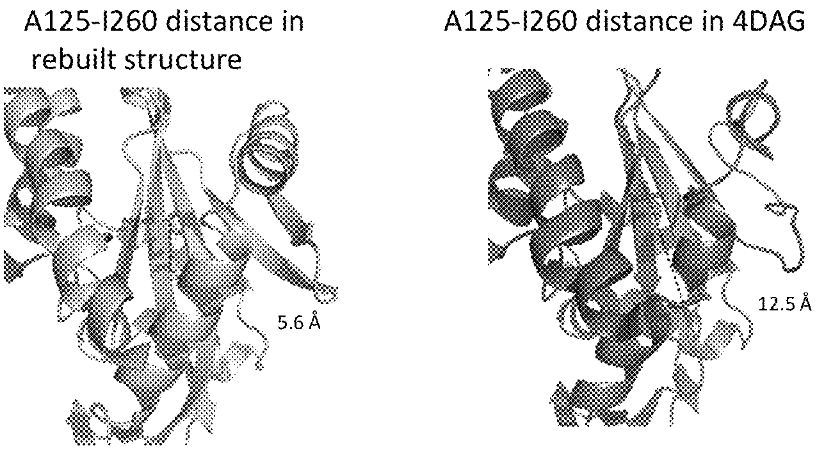

RSV fusion glycoprotein has been stabilized in a prefusion conformation using four mutations, S155C, S290C (DS) and S190F, V207L (Cav1). Sequence alignment of HMPV F with RSV F indicates that the equivalent residues on the HMPV F molecule are A125C, I260C and T160F, I177L. However, in the published 4DAG structure, the A125 and I260 C-beta atoms face in opposite directions and are located 12.8 Å apart in distance with a number of residues located in space between these residues (see FIG. 16). Thr160 faces the opposite direction from the equivalent cavity utilized by RSV F S190F and residue I177 is not built in the 4DAG structure. Thus, it was expected that the mutations used to stabilize the RSV F protein in a prefusion conformation could not be used to stabilize the MPV F protein in a prefusion conformation.

In the rebuilt structure (FIGS. 1-3, 16), T160 is shifted in space to face towards the equivalent S190F cavity and a T160F mutation can clearly be modeled. I177 is modeled to be located in a helical region equivalent to the V207 from RSV and a I177L mutation fills the adjacent cavity. In addition, A125 and I260 C-beta atoms face towards each other at a distance of 5.7 Å. Insertion of the A125C and I260C mutations in combination with the Foldon in HMPV F resulted in reduced expression of the HMPV F glycoprotein and reduced binding of the prefusion-specific antibody MPE8 as observed by ELISA binding after small-scale expression: MPE8 (0.125), DS7 (1.3827), 234 (1.0107), 338 (1.1195).

Figure 17:
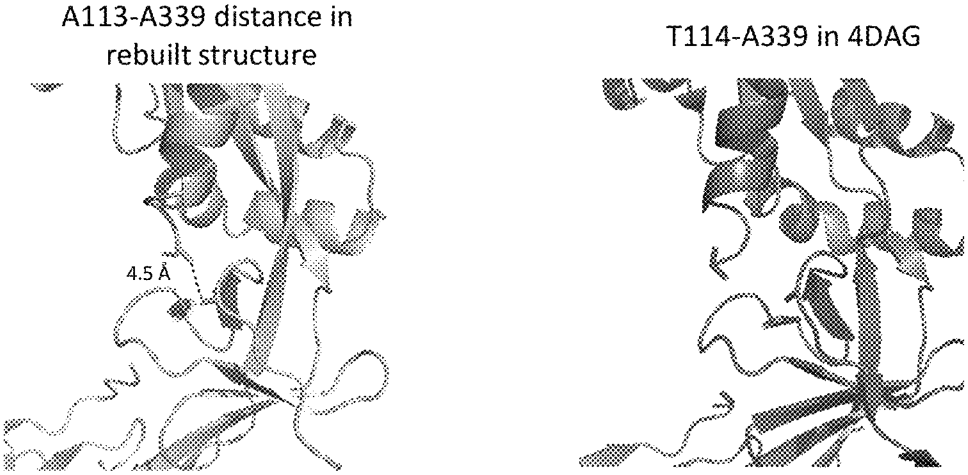

The mutations A113C, A339C in the context of the HMPV F Fd molecule provide increased stability as evidenced by full MPE8 binding after the HMPV F A113C, A339C+Fd molecule has been heated for 1 hour at 60° C. No other molecule with designed mutations displays this increased temperature stability. In the published 4DAG structure, the A113 residue is not modeled in the structure while in the rebuilt structure, the Cβ-Cβ distance is 4.5 Å (see FIG. 17). In addition, the A113 residue does not have an analogous equivalent in the RSV F mature molecule, since this residue aligns with those found in the pep27 that is removed during RSV F processing.

In summary, based on the previous HMPV structure (4DAG), the four mutations (A113C, A339C and T160F, I177L) identified as stabilizing are particularly unexpected, they are either not present in the model or there is sufficient error in their atomic location.

Example 2

MPV F Proteins Stabilized in a Prefusion Conformation

Figure 6:
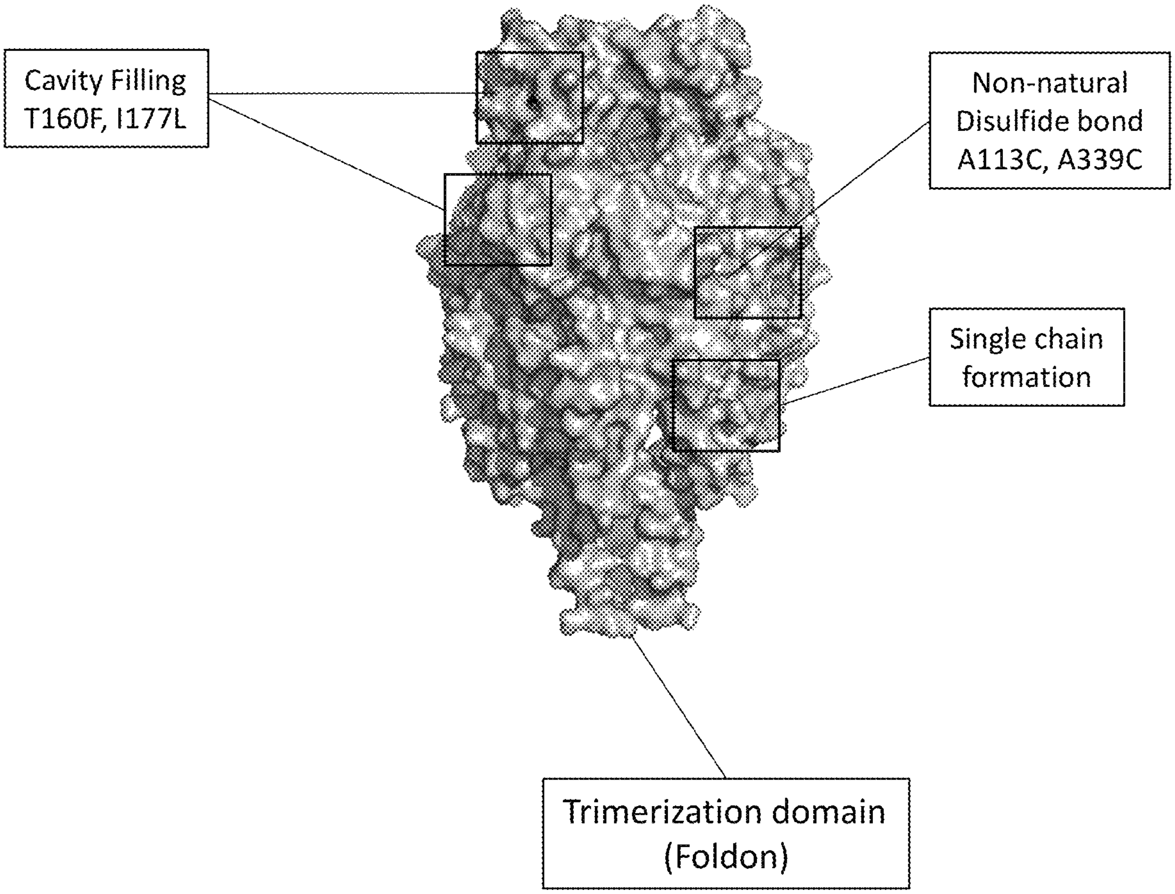
FIG. 6 is a surface diagram of the re-refined MPV F protein that illustrates exemplary stabilizing modifications of the MPV F protein used in recombinant MPV F proteins disclosed herein that are stabilized in a prefusion conformation. The illustrated substitutions include the A113C/A339C substitutions that can be used to introduce a non-natural disulfide bond that stabilizes the MPV F protein in its prefusion conformation, as well as the T160F and I177L cavity filling amino acid substitutions that also can be used to stabilize the MPV F protein in its prefusion conformation.

The re-refined atomic-level structure of the hMPV F protein provides new vistas for vaccine design. Based on the new structure, MPV F mutants were designed that are "locked" in the prefusion conformation. As illustrated in FIG. 6, the mutants include:

1. Introduction of a non-natural disulfide bond between residues 113 and 339 that stabilizes the hMPV F protein in its prefusion conformation. The non-natural disulfide bond can be introduced into the MPV F protein by A113C and A339C amino acid substitutions.

2. Introduction of cavity-filling amino acid substitutions at positions 160 and 177 of the MPV F protein. The substitutions can include T160F and I177L substitutions.

MPV F proteins including the T160F/I177L cavity filling substitutions were produced and purified by transient transfection in Expi293F cells using TrueFect-Max (United BioSystems, MD). The culture supernatant was harvested 5 days post transfection and centrifuged at 10,000 g to remove cell debris. The culture supernatants were sterile-filtered prior to buffer exchange and concentrated using tangential flow filtration. HMPV F glycoprotein variants was purified by nickel-(Roche) and streptactinII-affinity (IBA lifesciences) chromatography, and relevant fractions containing the HMPV F protein was pooled and concentrated. The 6×His- and StreptagII-purification tags were removed by digestion with thrombin and following overnight digestion at 4° C., MPV F was further purified by size-exclusion chromatography.

Figure 7:
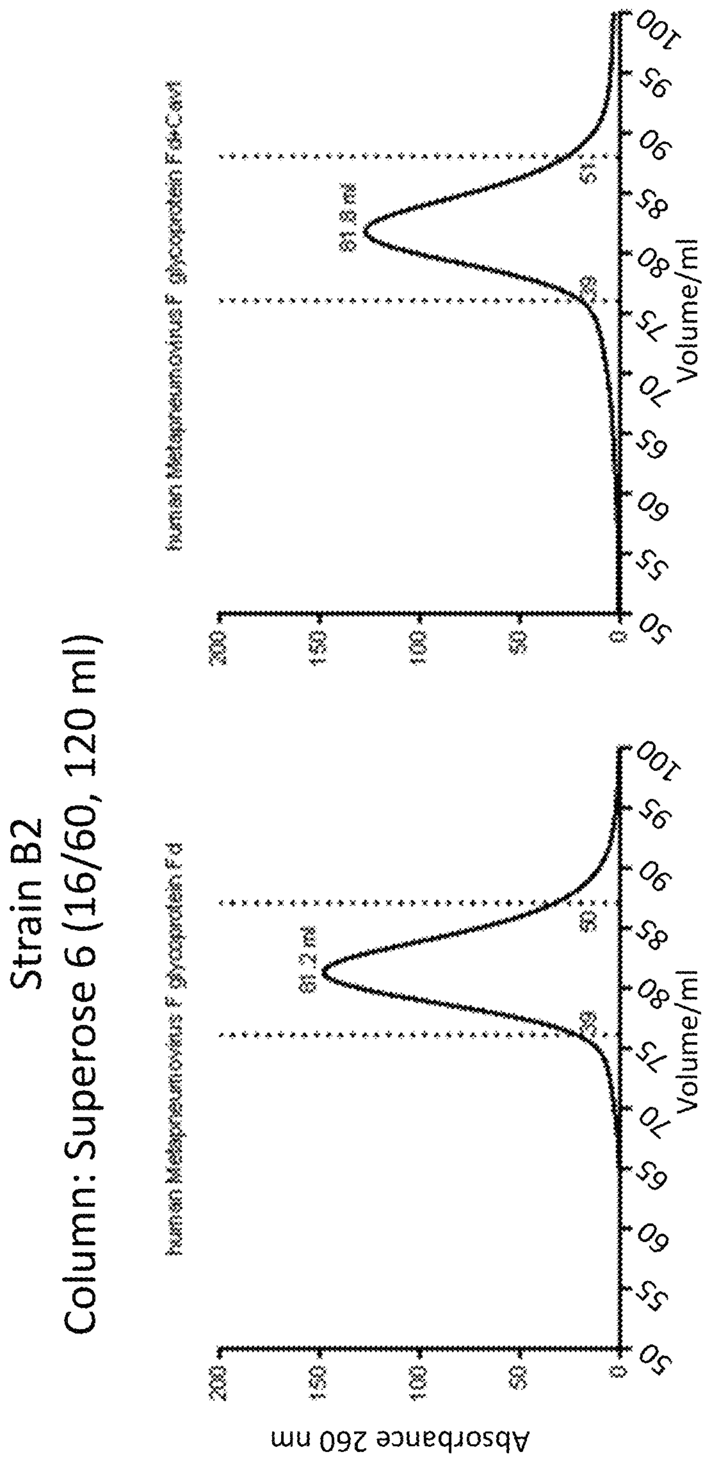
FIG. 7 shows a set of graphs illustrating elution profiles a native MPV F ectodomain (residues 19-484) linked to a foldon trimerization domain (Fd) and a recombinant MPV F protein (residues 19-484) with the T160F/I177L substitutions linked to a foldon trimerization domain (Fd+Cav1) passed over a Superose 6 purification column.
Figure 8:
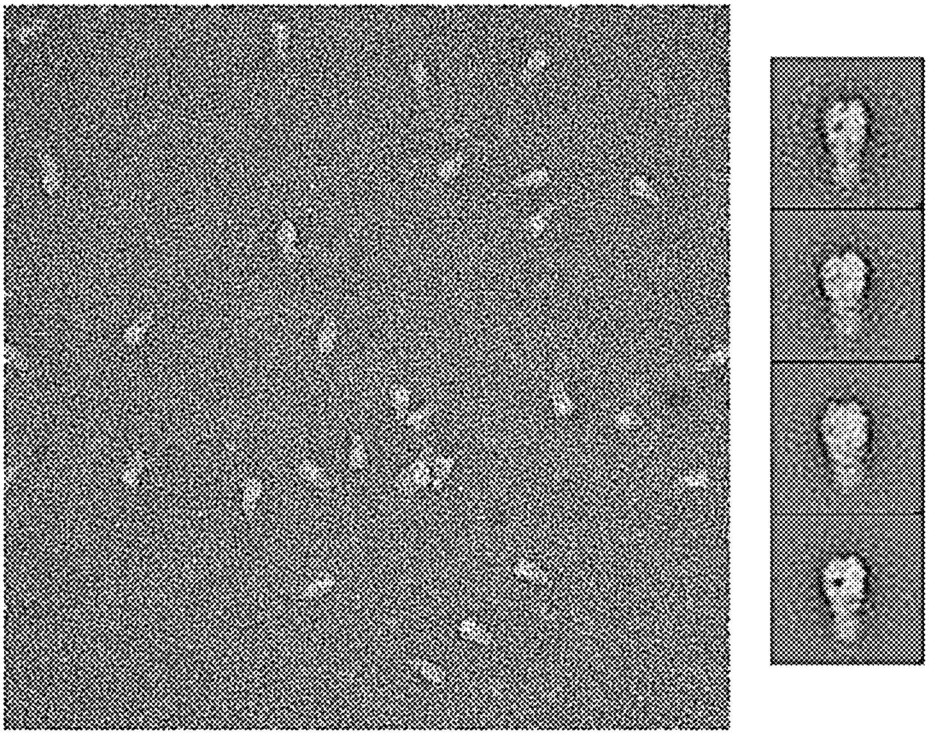
FIG. 8 shows a set of electron micrograph images illustrating that purified MPV F proteins including the T160F/I177L cavity filling substitutions are in the prefusion conformation. The electron micrograph image illustrates reference free classification of 1429 particles. The classes are similar and appear to be of the pre-fusion conformation

FIG. 7 shows the eluate profile of a superose column used to purify a native MPV F ectodomain (residues18-484) linked to a foldon trimerization domain (Fd) and a recombinant MPV F protein (residues 18-484) with the T160F/I177L substitutions linked to a foldon trimerization domain (Fd+Cav1). The purified Fd-Cav1 MPV F ectodomains were examined by electron microscopy (FIG. 8), showing that the purification proteins are homogenous, and in the prefusion conformation.

Figure 9:
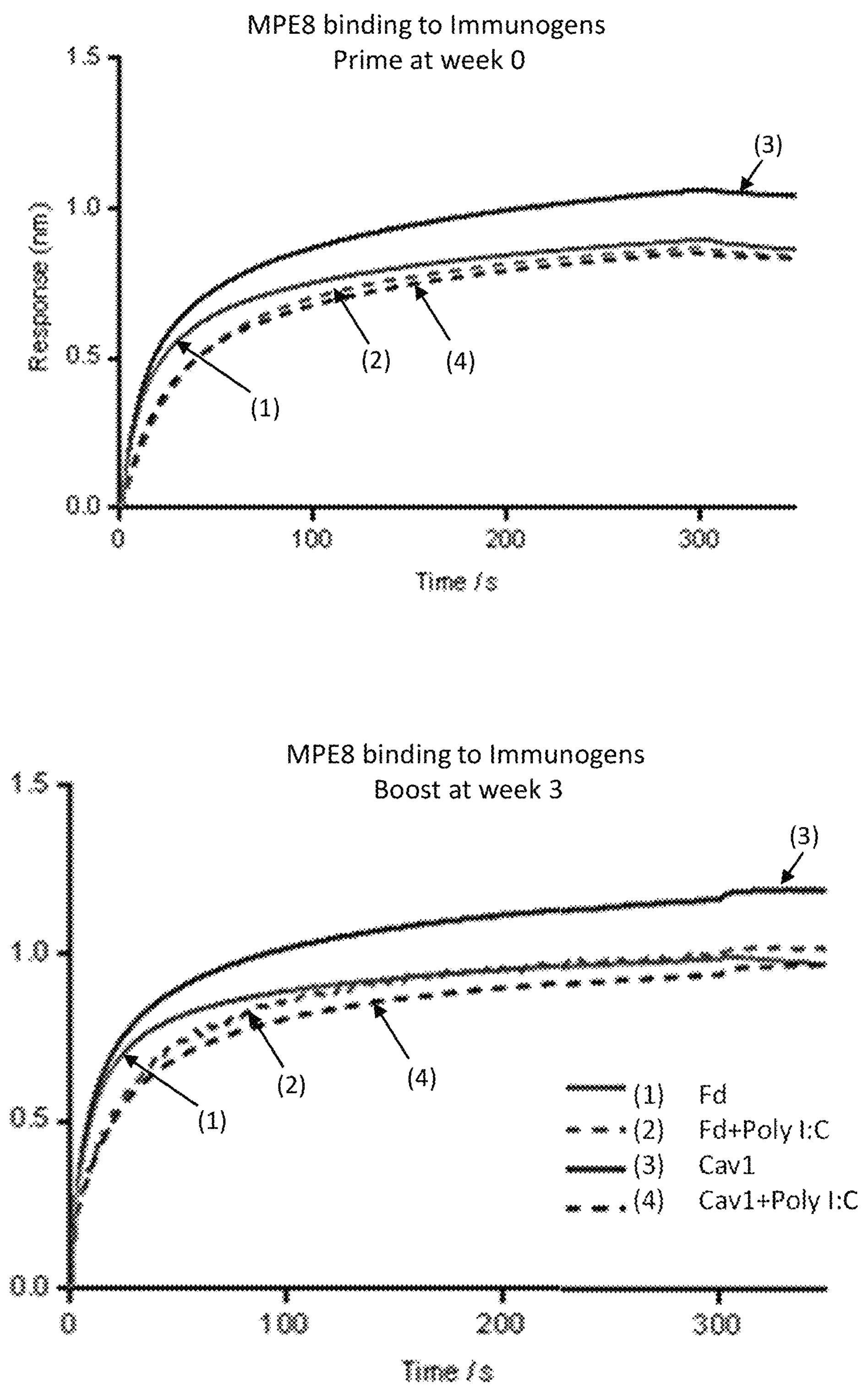
FIG. 9 is a set of graphs illustrating the antigenic properties of the MPV F protein linked to the Fd domain and MPV F protein with the T160F/I177L cavity filling substitutions and the stabilizing Fd domain in the presence of 1:2.5 w/w of the adjuvant Poly I:C as assessed by the pre-fusion specific antibody MPE8 using Octet Biolayer Interferometry. The immunogens in the presence of the adjuvant are highly similar to un-adjuvanted proteins and display high affinity to MPE8.
Figure 13:
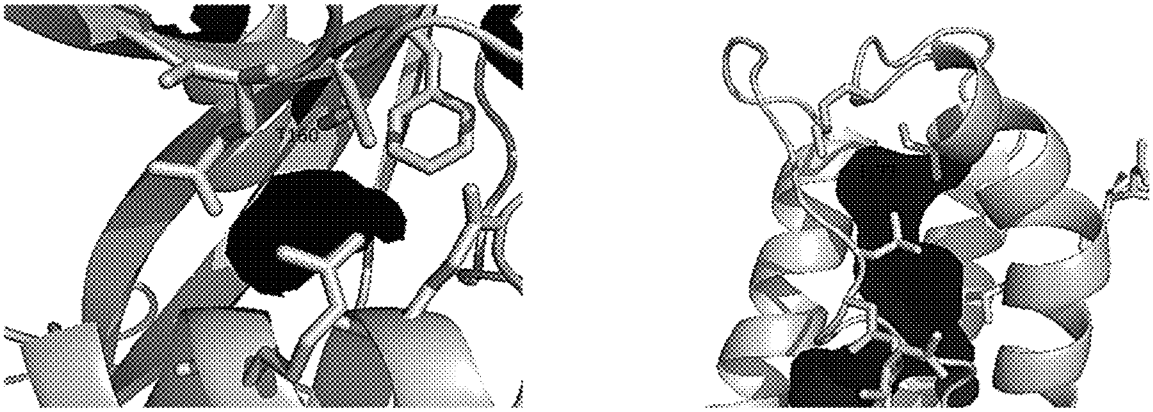
Figure 14:
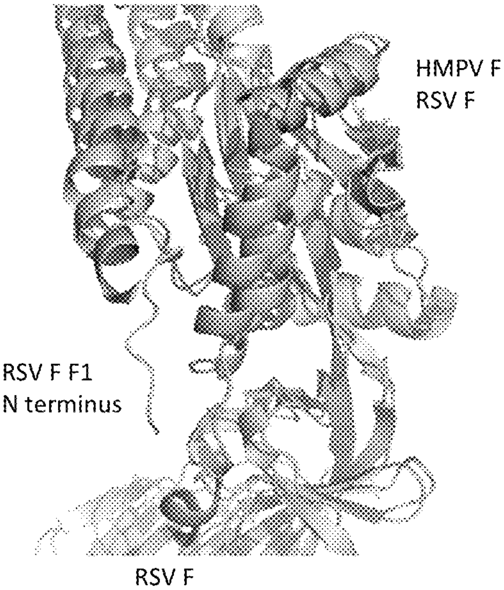

The purified MPV F proteins were administered to an animal model to assay for immunogenicity (FIGS. 9 and 10). HMPV F molecules stabilized with foldon (Fd) or T160F, I177L+Fd (Cav1) were mixed with Poly I:C adjuvant (InvivoGen) and assayed for reactivity to MPE8 by biolayer interferometry. Briefly, MPE8 IgG was loaded onto an anti-human capture assay probe and dipped into HMPV F protein either mixed with adjuvant or with PBS. MPE8 IgG binding is shown by a displacement of the white light interference pattern as measured in wavelength (nanometer).

Immunogens Fd and Cav1 showed very similar binding to MPE8 IgG in the presence of the adjuvant Poly I:C as compared to unadjuvanted samples.

Immunogenicity of stabilized HMPV F variants. HMPV F glycoprotein variants stabilized in the pre-fusion form with Foldon (Fd) or Foldon with cavity-filling mutations (Cav1) can elicit neutralizing antibodies against HMPV strain CAN97-83 in golden (Syrian) hamsters (Mesocricetus auratus, HsdHan:AURA). Neutralization titers of sera from hamsters immunized intramuscularly with 20 μg protein and 50 μg Poly I:C of adjuvant per animal are shown (5 hamsters/group) for the Fd and Cav1 groups and a third group that were inoculated intranasally with rHMPV-SHs (lot 102A) with an inoculum of ($5\times10^6$ PFU/ml) to a group of 6 hamsters followed by a later Cav1 intramuscular injection. Neutralization titers from individual hamsters are shown as individual colored dots. The immunization type is indicated below the x-axis shown in days and the limit of detection for the plaque-reducing neutralization assay is indicated by a dotted line (FIG. 10). The neutralization titers elicited by the immunization scheme indicate that both Fd and Cav1 are immunogenic and can elicit neutralization against HMPV strains. The neutralization titers elicited by Fd and Cav1 are ~4-fold lower than seen with natural infection. The Cav1 immunogen can boost the neutralizing response seen in animals that have been naturally infected by approximately four-fold.

Additionally, MPV F proteins including the A113C/A339C substitutions were produced and purified as described above. To examine antigenicity, purified MPV F ectodomain with native sequence (Fd), or with the A113C/A339C substitutions (DS), each linked to a foldon trimerization domain, were assayed for binding to the MPE8, DS7, 234, and 338 monoclonal antibodies. The MPE8 antibody specifically binds to the prefusion conformation, but not the post-fusion conformation, of MPV F, whereas the DS7, 234, and 338 monoclonal antibodies do not discriminate between the pre- and post-fusion conformations. Specific binding activity was assayed following initial purification, and also after incubation at 4° C. for 1.5 weeks, or incubation at 50° C., 60° C., or 70° C. for 1 hour (FIG. 11). A 96-well microplate-formatted transient gene expression approach was used to achieve high-throughput expression of various HMPV F proteins as described previously (McLellan et al., *Science,* 340, 1113-1117, 2013). Briefly, 24 h prior to transfection HEK 293T cells were seeded in each well of a 96-well microplate at a density of $2.5\times10^5$ cells/ml in expression medium (high glucose DMEM supplemented with 10% ultra-low IgG fetal bovine serum and 1×-non-essential amino acids), and incubated at 37° C., 5% $CO_2$ for 20 h. Plasmid DNA and TrueFect-Max (United BioSystems, MD) were mixed and added to the growing cells, and the 96-well plate incubated at 37° C., 5% $CO_2$. One day post transfection, enriched medium (high glucose DMEM plus 25% ultra-low IgG fetal bovine serum, 2× non-essential amino acids, 1× glutamine) was added to each well, and the 96-well plate was returned to the incubator for continuous culture. On day five post transfection, supernatants with the expressed HMPV F variants were harvested and tested by ELISA for binding to DS7, 234, 338 and MPE8 antibodies using $Ni^{2+}$-NTA microplates at room temperature. Supernatant samples were also heated for 1 h using a temperature plate at either 50° C., 60° C., or 70° C. and then cooled to room temperature and assessed for binding to DS7, 234, 338 and MPE8 antibodies using $Ni^{2+}$-NTA microplates at room temperature. After incubating a sample of the harvested supernatants at 4° C. for 1.5 weeks, ELISA assays were repeated at room temperature.

Following the 60° C. incubation, the DS mutant maintained binding to the MPE8 antibody, but MPV F protein with a native ectodomain (Fd) sequence did not bind to MPE8. This data indicated that the DS mutation stabilizes the MPV F ectodomain in its prefusion conformation.

Additional immunogenicity assays were performed in hamsters (FIG. 19). Four groups of Syrian golden hamsters were initially immunized with prefusion MPV F CAN98-75 protein (this immunogen contains the A113C-A339C mutations, the T160F and I177L mutations, and a Foldon trimerization domain), postfusion MPV F CAN97-83 protein (this immunogen does not contain any prefusion-stabilizing mutations and is not linked to a Foldon domain) intramuscularly, or intranasally with HMPV-75 or HMPV-83 virus at day zero. The sequences of the prefusion MPV F CAN98-75 protein and postfusion MPV F CAN97-83 protein are as follows:

```
prefusion MPV F CAN98-75
                                        (SEQ ID NO: 192)
LKESYLEESCSTITEGYLSVLRTGWYTNVFTLEVGDVENLTCTDGPSLIK

TELDLTKSALRELKTVSADQLAREEQIENPRKARFVLGAIALGVCTAAAV

TAGIAIAKTIRLESEVNAIKGALKTTNEAVSTLGNGVRVLAFAVRELKEF

VSKNLTSALNKNKCDIADLKMAVSFSQFNRRFLNVVRQFSDNAGITPAIS

LDLMTDAELARAVSYMPTSAGQIKLMLENRAMVRRKGFGILIGVYGSSVI

YMVQLPIFGVIDTPCWIIKAAPSCSEKDGNYACLLREDQGWYCKNAGSTV

YYPNDKDCETRGDHVFCDTACGINVAEQSRECNINISTTNYPCKVSTGRH

PISMVALSPLGALVACYKGVSCSIGSNRVGIIKQLPKGCSYITNQDADTV

TIDNTVYQLSKVEGEQHVIKGRPVSSSFDPIKFPEDQFNVALDQVFESIE

NSQALVDQSNKILNSAESAIGGYIPEAPRDGQAYVRKDGEWVLLSTFLGG

LVPR

postfusion MPV F CAN97-83
                                        (SEQ ID NO: 193)
LKESYLEESCSTITEGYLSVLRTGWYTNVFTLEVGDVENLTCSDGPSLIK

TELDLTKSALRELKTVSADQLAREEQIENPRQSRIAKTIRLESEVTAIKN

ALKTTNEAVSTLGNGVRVLATAVRELKDFVSKNLTRAINKNKCDIDDLKM

AVSFSQFNRRFLNVVRQFSDNAGITPAISLDLMTDAELARAVSNMPTSAG

QIKLMLENRAMVRRKGFGILIGVYGSSVIYMVQLPIFGVIDTPCWIVKAA

PSCSGKKGNYACLLREDQGWYCQNAGSTVYYPNEKDCETRGDHVFCDTAA

GINVAEQSKECNINISTTNYPCKVSTGRHPISMVALSPLGALVACYKGVS

CSIGSNRVGIIKQLNKGCSYITNQDADTVTIDNTVYQLSKVEGEQHVIKG

RPVSSSFDPIKFPEDQFNVALDQVFENIENSQALVDQSNRILSSAEGGLV

PR
```

The two subunit protein immunization groups were boosted at day 23 and day 98 with the homologous proteins (animals initially treated with prefusion MPV F CAN98-75 were boosted with prefusion MPV F CAN98-75; animals initially treated with postfusion MPV F CAN97-83 were boosted with postfusion MPV F CAN97-83). The HMPV-75 virus intranasal group did not receive any boost. The rHMPV-83 intranasal virus group received a boost with prefusion CAN98-75 protein at day 98. All immunized animals were assessed for neutralization against both CAN97-83 and CAN98-75 strains. For all protein immunizations, 10 μg of protein was provided at 0.1 mg/ml concentration with adjuvant Poly I:C (Invivogen).

FIG. 19 shows the results of neutralization assays. Neutralization titers of sera from individual hamsters for CAN98-75 (subgroup B HPMV, upper graph) and CAN97-83 (subgroup A HPMV, lower graph) are shown. Neutralization was determined using a plaque reduction assay, as described above. The limit of detection for the plaque-reducing neutralization assay is indicated by a dotted line.

The Prefusion MPV F CAN98-75 (subgroup B) gave log 2 neutralization titers of ~7 against the subgroup B virus (CAN98-75) which is comparable to the titers generated following viral infection with either subgroup A or subgroup B virus. Boosting of the subgroup A virus infection with prefusion HMP F subgroup B protein led to a noticeable boost of titers to log 2-10. The postfusion MPV F protein from subgroup A failed to give any measurable neutralization titers against the subgroup B virus.

The Prefusion MPV F CAN98-75 (subgroup B) gave log 2 neutralization titers of ~7 against the subgroup A virus (CAN97-83). The postfusion MPV F subgroup A gave log 2 titers ranging from ~5-10. The MPV F subgroup B virus infection gave no detectable neutralization titers against the heterologous A strain. The subgroup A intranasal virus immunization gave titers ranging from log 2 8-12 which were boosted by the heterologous prefusion MPV F molecule.

The elicited neutralization titers using the indicated immunization protocols indicate that the prefusion MPV protein is immunogenic and can elicit neutralization activity against subgroup A and subgroup B HMPV strains, and is particularly effective when used to boost immunity following natural MPV infection.

Example 3

Immunization of Subjects

This example describes exemplary procedures for the immunization of a subject (such as a human or non-human primate) with the disclosed immunogens, and measurement of the corresponding immune response.

In some examples, a nucleic acid molecule encoding a disclosed immunogen (e.g., a recombinant MPV F protein comprising A113C, A339C, T160F, and I177L substitutions) can be cloned into expression vector CMV/R. The expression vectors are then transfected into 293F cells using 293Fectin (Invitrogen, Carlsbad, Calif.). Seven days after transfection, cell culture supernatant is harvested and passed over either a MPE8 antibody affinity column. After washing with PBS, bound proteins were eluted with 3M $MgCl_2$, 10 mM Tris pH 8.0. The eluate was concentrated to less than 5 ml with Centricon-70 and applied to a Superdex 200 column, equilibrated in 5 mM HEPES, pH 7.5, 150 mM NaCl, 0.02% azide. The peak corresponding to trimeric MPV F is identified, pooled, and concentrated or flash-frozen in liquid nitrogen and stored at −80° C. Some proteins are purified using HiTrap IMAC HP Column (GE, Piscataway, N.J.), and subsequent gel-filtration using SUPERDEX™ 200 (GE). In some examples the 6× His tag is cleaved off using 3C protease (Novagen, Madison, Wis.).

For vaccinations with the disclosed immunogens, the subject is immunized with polyIC-LC as the adjuvant. Five subjects in each group are vaccinated with 100 μg of protein and 500 μg polyIC-LC in 1 ml intramuscularly in the Quadriceps muscle for example at week 0, 4, 20. Sera are collected for example at week 2 (Post-1), 6 (Post-2), 24 (Post-3), and subsequently analyzed for their neutralization activities against a panel of MPV strains, and the profile of antibodies that mediate the neutralization.

The purified immunogens can also be used to probe anti-sera from the subjects for existence of MPV neutralizing antibodies in the anti-sera, such as antibodies that compete for binding to the recombinant MPV F protein trimer with MPE8 antibody.

It will be apparent that the precise details of the methods or compositions described may be varied or modified without departing from the spirit of the described embodiments. We claim all such modifications and variations that fall within the scope and spirit of the claims below.

We claim:

1. A method for generating an immune response to MPV F protein in a subject, comprising administering to the subject an effective amount of a recombinant metapneumovirus (MPV) F protein or immunogenic fragment thereof stabilized in a prefusion conformation by one or more amino acid substitutions compared to a native MPV F protein sequence, wherein the recombinant MPV F protein comprises a $F_2$ polypeptide and a $F_1$ ectodomain, wherein the one or more amino acid substitutions introduce one or more non-native intra- or inter-protomer disulfide bonds that, alone or in combination with other modifications, stabilize the MPV F protein in the prefusion conformation.

2. The method of claim 1, wherein the recombinant MPV F protein comprises a non-natural disulfide bond between A113C and A339C substitutions that stabilizes the recombinant MPV F protein in the prefusion conformation, wherein the amino acid positions correspond to a reference MPV F sequence set forth as SEQ ID NO: 7.

3. The method of claim 1, wherein the recombinant MPV F protein comprises:

a non-natural disulfide bond between A120C and Q426C substitutions that stabilizes the recombinant MPV F protein in the prefusion conformation; or a non-natural disulfide bond between A120C and Q428C substitutions that stabilizes the recombinant MPV F protein in the prefusion conformation; and wherein the amino acid positions correspond to a reference MPV F sequence set forth as SEQ ID NO: 7.

4. The method of claim 1, wherein the recombinant MPV F protein comprises one or more cavity filling amino acid substitutions that reduce the volume of a threonine 160 cavity and/or an isoleucine 177 cavity, wherein the amino acid positions correspond to a reference MPV F sequence set forth as SEQ ID NO: 7.

5. The method of claim 4, wherein the recombinant MPV F protein comprises:

one or more cavity filling amino acid substitutions at positions 160, 162, and/or 157 to reduce the volume of the threonine 160 cavity; and/or one or more cavity filling amino acid substitutions at positions 177, 58, 169, 54, and/or 55 to reduce the volume of the isoleucine 177 cavity; and wherein the amino acid positions correspond to a reference MPV F sequence set forth as SEQ ID NO: 7.

6. The method of claim 4, wherein the cavity filling amino acid substitution comprises a F, L, W, Y, H, or M substitution.

7. The method of claim 4, wherein the recombinant MPV F protein comprises a T160F substitution, a I177L substitution, or T160F and I177L substitutions that stabilize the recombinant MPV F protein in the prefusion conformation, wherein the amino acid positions correspond to a reference MPV F sequence set forth as SEQ ID NO: 7.

8. The method of claim 1, wherein the recombinant MPV F protein comprises a non-natural disulfide bond between A113C and A339C substitutions, and T160F and I177L cavity filling substitutions, that stabilize the recombinant MPV F protein in the prefusion conformation, wherein the amino acid positions correspond to a reference MPV F sequence set forth as SEQ ID NO: 7.

9. The method of claim 8, wherein the recombinant MPV F protein further comprises one or more additional amino acid substitutions.

10. The method of claim 1, wherein the recombinant MPV F protein comprises a proline amino acid substitution at one of positions 183-189 that reduces or prevents formation of an $\alpha 7$ helix to stabilize the MPV F protein in the prefusion conformation, wherein the amino acid positions correspond to a reference MPV F sequence set forth as SEQ ID NO: 7.

11. The method of claim 10, comprising the A185P substitution.

12. The method of claim 1, wherein the recombinant MPV F protein is not glycosylated at N57, N172, or N57 and N172, wherein the amino acid positions correspond to a reference MPV F sequence set forth as SEQ ID NO: 7.

13. The method of claim 12, wherein the recombinant MPV F protein comprises one of:

a N57Q substitution;

a N172Q substitution;

a N57Q substitution and a N172Q substitution, a T59A substitution;

a T174A substitution; or a T59A substitution and a T174A substitution;

to remove N57 and/or N172 N-glycan sequons; and wherein the amino acid positions correspond to a reference MPV F sequence set forth as SEQ ID NO: 7.

14. The method of claim 1, wherein the recombinant MPV F protein comprises:

one or more cysteine substitutions that introduce the non-native intra-protomer disulfide bond between the amino acids of:

any one of positions 103-120 and any one of positions 335-345;

any one of positions 107-118 and any one of positions 335-342;

any one of positions of α-helix 3 (residues 117-129) and any one of positions of β-strand 6 (residues 256-261);

any one of positions of α-helix 2 and any one of positions adjacent to the cleavage site (residues 87-102) with α-helix 3 (residues 117-127);

any one of positions 102-113 and any one of positions of α-helix 3 (residues 117-127); or any one of positions 102-113 and any one of positions of α-helix 2 and residues adjacent to the cleavage site (residues 87-102); and/or one or more cysteine substitutions that introduce the non-native inter-protomer disulfide bond between the amino acids of:

any one of positions 337-341 and any one of positions 421-426;

any one of positions 112-120 and any one of positions 424-432;

any one of positions 150-156 with the addition of a glycine residue, and any one of positions 392-400;

any one of positions 112-120 and any one of positions 370-377;

any one of positions 365-375 and any one of positions 455-465;

any one of positions 365-375 and any one of positions 105-115; or any one of positions 60-70 and any one of positions 175-185;

wherein the positions correspond to the amino acids positions of a reference MPV F protein sequence set forth as SEQ ID NO: 7.

15. The method of claim 1, wherein the recombinant MPV F protein comprises one of the following combinations of substitutions:

A113C, A339C, and D183P;
A113C, A339C, and A185P;
A113C, A339C, and D186P;
A113C, A339C, T160F, I177L, and D183P;
A113C, A339C, T160F, I177L, and A185P;
A113C, A339C, T160F, I177L, and D186P;
A113C, A339C, A120C, Q426C, T160F, I177L, and D183P;
A113C, A339C, A120C, Q428C, T160F, I177L, and D183P;
A113C, A339C, A120C, Q426C, T160F, I177L, and A185P;
A113C, A339C, A120C, Q428C, T160F, I177L, and A185P;
A113C, A339C, A120C, Q426C, T160F, I177L, and D186P;
A113C, A339C, A120C, Q428C, T160F, I177L, and D186P;
A113C, A339C, D183P, and N57Q;
A113C, A339C, A185P, and N57Q;
A113C, A339C, D186P, and N57Q;
A113C, A339C, T160F, I177L, D183P, and N57Q;
A113C, A339C, T160F, I177L, A185P, and N57Q;
A113C, A339C, T160F, I177L, D186P, and N57Q;
A113C, A339C, A120C, Q426C, T160F, I177L, D183P, and N57Q;
A113C, A339C, A120C, Q428C, T160F, I177L, D183P, and N57Q;
A113C, A339C, A120C, Q426C, T160F, I177L, A185P, and N57Q;
A113C, A339C, A120C, Q428C, T160F, I177L, A185P, and N57Q;
A113C, A339C, A120C, Q426C, T160F, I177L, D186P, and N57Q;
A113C, A339C, A120C, Q428C, T160F, I177L, D186P, and N57Q;
A113C, A339C, D183P, and N172Q;
A113C, A339C, A185P, and N172Q;
A113C, A339C, D186P, and N172Q;
A113C, A339C, T160F, I177L, D183P, and N172Q;
A113C, A339C, T160F, I177L, A185P, and N172Q;
A113C, A339C, T160F, I177L, D186P, and N172Q;
A113C, A339C, A120C, Q426C, T160F, I177L, D183P, and N172Q;
A113C, A339C, A120C, Q428C, T160F, I177L, D183P, and N172Q;
A113C, A339C, A120C, Q426C, T160F, I177L, A185P, and N172Q;
A113C, A339C, A120C, Q428C, T160F, I177L, A185P, and N172Q;
A113C, A339C, A120C, Q426C, T160F, I177L, D186P, and N172Q;
A113C, A339C, A120C, Q428C, T160F, I177L, D186P, and N172Q;
A113C, A339C, D183P, N57Q, and N172Q;
A113C, A339C, A185P, N57Q, and N172Q;
A113C, A339C, D186P, N57Q, and N172Q;
A113C, A339C, T160F, I177L, D183P, N57Q, and N172Q;
A113C, A339C, T160F, I177L, A185P, N57Q, and N172Q;
A113C, A339C, T160F, I177L, D186P, N57Q, and N172Q;
A113C, A339C, A120C, Q426C, T160F, I177L, D183P, N57Q, and N172Q;
A113C, A339C, A120C, Q428C, T160F, I177L, D183P, N57Q, and N172Q;
A113C, A339C, A120C, Q426C, T160F, I177L, A185P, N57Q, and N172Q;
A113C, A339C, A120C, Q428C, T160F, I177L, A185P, N57Q, and N172Q;
A113C, A339C, A120C, Q426C, T160F, I177L, D186P, N57Q, and N172Q;
A113C, A339C, A120C, Q428C, T160F, I177L, D186P, N57Q, and N172Q;
A113C, A339C, D183P, and T59A;
A113C, A339C, A185P, and T59A;
A113C, A339C, D186P, and T59A;
A113C, A339C, T160F, I177L, D183P, and T59A;
A113C, A339C, T160F, I177L, A185P, and T59A;
A113C, A339C, T160F, I177L, D186P, and T59A;
A113C, A339C, A120C, Q426C, T160F, I177L, D183P, and T59A;
A113C, A339C, A120C, Q428C, T160F, I177L, D183P, and T59A;
A113C, A339C, A120C, Q426C, T160F, I177L, A185P, and T59A;
A113C, A339C, A120C, Q428C, T160F, I177L, A185P, and T59A;

A113C, A339C, A120C, Q426C, T160F, I177L, D186P, and T59A;

A113C, A339C, A120C, Q428C, T160F, I177L, D186P, and T59A;

A113C, A339C, D183P, and T174A;

A113C, A339C, A185P, and T174A;

A113C, A339C, D186P, and T174A;

A113C, A339C, T160F, I177L, D183P, and T174A;

A113C, A339C, T160F, I177L, A185P, and T174A;

A113C, A339C, T160F, I177L, D186P, and T174A;

A113C, A339C, A120C, Q426C, T160F, I177L, D183P, and T174A;

A113C, A339C, A120C, Q428C, T160F, I177L, D183P, and T174A;

A113C, A339C, A120C, Q426C, T160F, I177L, A185P, and T174A;

A113C, A339C, A120C, Q428C, T160F, I177L, A185P, and T174A;

A113C, A339C, A120C, Q426C, T160F, I177L, D186P, and T174A;

A113C, A339C, A120C, Q428C, T160F, I177L, D186P, and T174A;

A113C, A339C, D183P, T59A, and T174A;

A113C, A339C, A185P, T59A, and T174A;

A113C, A339C, D186P, T59A, and T174A;

A113C, A339C, T160F, I177L, D183P, T59A, and T174A;

A113C, A339C, T160F, I177L, A185P, T59A, and T174A;

A113C, A339C, T160F, I177L, D186P, T59A, and T174A;

A113C, A339C, A120C, Q426C, T160F, I177L, D183P, T59A, and T174A;

A113C, A339C, A120C, Q428C, T160F, I177L, D183P, T59A, and T174A;

A113C, A339C, A120C, Q426C, T160F, I177L, A185P, T59A, and T174A;

A113C, A339C, A120C, Q428C, T160F, I177L, A185P, T59A, and T174A;

A113C, A339C, A120C, Q426C, T160F, I177L, D186P, T59A, and T174A; or

A113C, A339C, A120C, Q428C, T160F, I177L, D186P, T59A, and T174A;

to stabilize the recombinant MPV F protein in the prefusion conformation; and wherein the amino acid positions correspond to a reference MPV F sequence set forth as SEQ ID NO: 7.

16. The method of claim 1, wherein:

the N-terminal residue of the $F_2$ polypeptide is one of MPV F positions 8-30;

the C-terminal residue of the $F_2$ polypeptide is one of MPV F positions 90-102;

the N-terminal residue of the $F_1$ ectodomain is one of MPV F positions 103-130; and/or the C-terminal residue of the $F_1$ ectodomain is one of MPV F positions 470-550, and wherein the positions correspond to a reference MPV F sequence set forth as SEQ ID NO: 7.

17. The method of claim 1, wherein the recombinant MPV F protein further comprises a deletion of residues 103-123 to remove a fusion peptide of the F1 ectodomain, wherein the amino acid positions correspond to a reference MPV F sequence set forth as SEQ ID NO: 7.

18. The method of claim 1, wherein the $F_2$ polypeptide and/or the $F_1$ ectodomain comprises an amino acid sequence at least 80% identical to a corresponding $F_2$ polypeptide or $F_1$ ectodomain from a human A1, A2, B1, or B2 strain of MPV.

19. The method of claim 1, wherein the recombinant MPV F protein is a human subgroup A or human subgroup B MPV F protein.

20. The method of claim 1, wherein the native MPV F protein sequence comprises the amino acid sequence set forth as SEQ ID NO: 1 (NL/1/00), SEQ ID NO: 2 (CAN97-83), SEQ ID NO: 3 (NL/17/00), SEQ ID NO: 4 (NCL174), SEQ ID NO: 5 (NL/1/99), SEQ ID NO: 6 (NDLOO-1), or SEQ ID NO: 7 (CAN98-75).

21. The method of claim 1, wherein the recombinant MPV F protein comprises the amino acid sequence set forth as any one of SEQ ID NOs: 12-13, 15, 80-81, 101-149, or 157-184, or an amino acid sequence at least 90% identical to any one of SEQ ID NOs: 12-13, 15, 80-81, 101-149, or 157-184.

22. The method of claim 1, wherein the recombinant MPV F protein further comprises one or more amino acid substitutions that introduce an enhanced furin cleavage site between the $F_2$ polypeptide and the $F_1$ ectodomain.

23. The method of claim 22, wherein the enhanced furin cleavage site comprises the amino acid sequence set forth as RRRRRR (SEQ ID NO: 9).

24. The method of claim 1, wherein the recombinant MPV F protein is a single chain MPV F protein and further comprises one or more amino acid substitutions to remove a protease cleavage site between the F2 polypeptide and the F1 ectodomain, and the $F_2$ polypeptide and $F_1$ ectodomain are linked by a heterologous peptide linker, or are directly linked.

25. The method of claim 24, wherein the heterologous peptide linker joins MPV F positions 97 and 107, 98 and 103, 98 and 107, 100 and 103, or 101 and 103, wherein the amino acid positions correspond to a reference MPV F sequence set forth as SEQ ID NO: 7.

26. The method of claim 1, wherein the recombinant MPV F protein forms a trimer of recombinant MPV F proteins stabilized in the prefusion conformation.

27. The method of claim 1, wherein a C-terminal residue of the $F_1$ ectodomain is linked to a trimerization domain by a peptide linker or is directly linked.

28. The method of claim 27, wherein the trimerization domain is a foldon domain.

29. The method of claim 28, wherein the foldon domain comprises or consists of the amino acid sequence set forth as SEQ ID NO: 33.

30. The method of claim 27, wherein the recombinant MPV F protein comprises or consists of an amino acid sequence at least 90% identical to SEQ ID NO: 192.

31. The method of claim 30, wherein the recombinant MPV F protein comprises or consists of the amino acid sequence set forth as SEQ ID NO: 192.

32. The method of claim 1, wherein the C-terminus of the $F_1$ ectodomain of the MPV F protein is linked to a transmembrane domain by a peptide linker, or is directly linked.

33. The method of claim 1, wherein the C-terminus of the $F_1$ ectodomain of the MPV F protein is linked to a self-assembling protein nanoparticle subunit by a peptide linker, or is directly linked.

34. The method of claim 33, wherein the self-assembling protein nanoparticle subunit is a ferritin nanoparticle subunit or a lumazine synthase nanoparticle subunit.

35. The method of claim 1, comprising a prime-boost administration of the recombinant MPV F protein or immunogenic fragment thereof.

36. The method of claim 1, wherein the immune response inhibits MPV infection.

* * * * *

SEQUENCE LISTING

```
<160> NUMBER OF SEQ ID NOS: 193

<210> SEQ ID NO 1
<211> LENGTH: 539
<212> TYPE: PRT
<213> ORGANISM: Metapneumovirus

<400> SEQUENCE: 1

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95
```

```
Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Phe Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Thr Met Ile Leu Val Ser Val Phe Ile
            500                 505                 510
```

```
Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535


<210> SEQ ID NO 2
<211> LENGTH: 539
<212> TYPE: PRT
<213> ORGANISM: Metapneumovirus

<400> SEQUENCE: 2

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350
```

```
Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Ser
    530                 535
```

<210> SEQ ID NO 3
<211> LENGTH: 539
<212> TYPE: PRT
<213> ORGANISM: Metapneumovirus

<400> SEQUENCE: 3

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
```

180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Thr Asp
210 215 220

Ala Glu Leu Ala Arg Ala Val Ser Asn Met Pro Thr Ser Ala Gly Gln
225 230 235 240

Ile Lys Leu Met Leu Glu Asn Arg Ala Met Val Arg Arg Lys Gly Phe
245 250 255

Gly Ile Leu Ile Gly Val Tyr Gly Ser Ser Val Ile Tyr Thr Val Gln
260 265 270

Leu Pro Ile Phe Gly Val Ile Asp Thr Pro Cys Trp Ile Val Lys Ala
275 280 285

Ala Pro Ser Cys Ser Glu Lys Lys Gly Asn Tyr Ala Cys Leu Leu Arg
290 295 300

Glu Asp Gln Gly Trp Tyr Cys Gln Asn Ala Gly Ser Thr Val Tyr Tyr
305 310 315 320

Pro Asn Glu Lys Asp Cys Glu Thr Arg Gly Asp His Val Phe Cys Asp
325 330 335

Thr Ala Ala Gly Ile Asn Val Ala Glu Gln Ser Lys Glu Cys Asn Ile
340 345 350

Asn Ile Ser Thr Thr Asn Tyr Pro Cys Lys Val Ser Thr Gly Arg His
355 360 365

Pro Ile Ser Met Val Ala Leu Ser Pro Leu Gly Ala Leu Val Ala Cys
370 375 380

Tyr Lys Gly Val Ser Cys Ser Ile Gly Ser Asn Arg Val Gly Ile Ile
385 390 395 400

Lys Gln Leu Asn Lys Gly Cys Ser Tyr Ile Thr Asn Gln Asp Ala Asp
405 410 415

Thr Val Thr Ile Asp Asn Thr Val Tyr Gln Leu Ser Lys Val Glu Gly
420 425 430

Glu Gln His Val Ile Lys Gly Arg Pro Val Ser Ser Ser Phe Asp Pro
435 440 445

Ile Lys Phe Pro Glu Asp Gln Phe Asn Val Ala Leu Asp Gln Val Phe
450 455 460

Glu Asn Ile Glu Asn Ser Gln Ala Leu Val Asp Gln Ser Asn Arg Ile
465 470 475 480

Leu Ser Ser Ala Glu Lys Gly Asn Thr Gly Phe Ile Ile Val Ile Ile
485 490 495

Leu Ile Ala Val Leu Gly Ser Ser Met Ile Leu Val Ser Ile Phe Ile
500 505 510

Ile Ile Lys Lys Thr Lys Lys Pro Thr Gly Ala Pro Pro Glu Leu Ser
515 520 525

Gly Val Thr Asn Asn Gly Phe Ile Pro His Ser
530 535

<210> SEQ ID NO 4
<211> LENGTH: 539
<212> TYPE: PRT
<213> ORGANISM: Metapneumovirus

<400> SEQUENCE: 4

Met Ser Trp Lys Val Val Ile Ile Phe Ser Leu Leu Ile Thr Pro Gln
1 5 10 15

```
His Ser Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Lys Pro Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ala Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
```

-continued

```
        435                 440                 445

Val Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Val Phe Ile
            500                 505                 510

Ile Ile Lys Lys Thr Arg Lys Pro Thr Gly Ala Pro Pro Glu Leu Ser
        515                 520                 525

Gly Val Thr Asn Asn Gly Phe Ile Pro His Ser
    530                 535


<210> SEQ ID NO 5
<211> LENGTH: 539
<212> TYPE: PRT
<213> ORGANISM: Metapneumovirus

<400> SEQUENCE: 5

Met Ser Trp Lys Val Met Ile Ile Ile Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Thr Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Ile Ala Ile Ala Lys Thr Ile
        115                 120                 125

Arg Leu Glu Ser Glu Val Asn Ala Ile Lys Gly Ala Leu Lys Gln Thr
    130                 135                 140

Asn Glu Ala Val Ser Thr Leu Gly Asn Gly Val Arg Val Leu Ala Thr
145                 150                 155                 160

Ala Val Arg Glu Leu Lys Glu Phe Val Ser Lys Asn Leu Thr Ser Ala
                165                 170                 175

Ile Asn Arg Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Tyr Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270
```

-continued

Leu Pro Ile Phe Gly Val Ile Asp Thr Pro Cys Trp Ile Ile Lys Ala
275 280 285

Ala Pro Ser Cys Ser Glu Lys Asn Gly Asn Tyr Ala Cys Leu Leu Arg
290 295 300

Glu Asp Gln Gly Trp Tyr Cys Lys Asn Ala Gly Ser Thr Val Tyr Tyr
305 310 315 320

Pro Asn Glu Lys Asp Cys Glu Thr Arg Gly Asp His Val Phe Cys Asp
325 330 335

Thr Ala Ala Gly Ile Asn Val Ala Glu Gln Ser Arg Glu Cys Asn Ile
340 345 350

Asn Ile Ser Thr Thr Asn Tyr Pro Cys Lys Val Ser Thr Gly Arg His
355 360 365

Pro Ile Ser Met Val Ala Leu Ser Pro Leu Gly Ala Leu Val Ala Cys
370 375 380

Tyr Lys Gly Val Ser Cys Ser Ile Gly Ser Asn Trp Val Gly Ile Ile
385 390 395 400

Lys Gln Leu Pro Lys Gly Cys Ser Tyr Ile Thr Asn Gln Asp Ala Asp
405 410 415

Thr Val Thr Ile Asp Asn Thr Val Tyr Gln Leu Ser Lys Val Glu Gly
420 425 430

Glu Gln His Val Ile Lys Gly Arg Pro Val Ser Ser Ser Phe Asp Pro
435 440 445

Ile Lys Phe Pro Glu Asp Gln Phe Asn Val Ala Leu Asp Gln Val Phe
450 455 460

Glu Ser Ile Glu Asn Ser Gln Ala Leu Val Asp Gln Ser Asn Lys Ile
465 470 475 480

Leu Asn Ser Ala Glu Lys Gly Asn Thr Gly Phe Ile Ile Val Val Ile
485 490 495

Leu Val Ala Val Leu Gly Leu Thr Met Ile Ser Val Ser Ile Ile Ile
500 505 510

Ile Ile Lys Lys Thr Arg Lys Pro Thr Gly Ala Pro Pro Glu Leu Asn
515 520 525

Gly Val Thr Asn Gly Gly Phe Ile Pro His Ser
530 535

<210> SEQ ID NO 6
<211> LENGTH: 539
<212> TYPE: PRT
<213> ORGANISM: Metapneumovirus

<400> SEQUENCE: 6

Met Ser Trp Lys Val Val Ile Ile Phe Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Glu Val Gly Asp Val Glu Asn Leu Thr Cys Ala Asp Gly Pro
50 55 60

Ser Leu Ile Lys Thr Glu Leu Asp Leu Thr Lys Ser Ala Leu Arg Glu
65 70 75 80

Leu Arg Thr Val Ser Ala Asp Gln Leu Ala Arg Glu Glu Gln Ile Glu
85 90 95

Asn Pro Arg Gln Ser Arg Phe Val Leu Gly Ala Ile Ala Leu Gly Val
100 105 110

```
Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Phe Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Thr Met Ile Leu Val Ser Val Phe Ile
            500                 505                 510

Ile Ile Lys Lys Thr Lys Lys Pro Thr Gly Ala Pro Pro Glu Leu Ser
        515                 520                 525
```

Gly Val Thr Asn Asn Gly Phe Ile Pro His Asn
530 535

<210> SEQ ID NO 7
<211> LENGTH: 539
<212> TYPE: PRT
<213> ORGANISM: Metapneumovirus

<400> SEQUENCE: 7

Met Ser Trp Lys Val Met Ile Ile Ile Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Glu Val Gly Asp Val Glu Asn Leu Thr Cys Thr Asp Gly Pro
50 55 60

Ser Leu Ile Lys Thr Glu Leu Asp Leu Thr Lys Ser Ala Leu Arg Glu
65 70 75 80

Leu Lys Thr Val Ser Ala Asp Gln Leu Ala Arg Glu Glu Gln Ile Glu
85 90 95

Asn Pro Arg Gln Ser Arg Phe Val Leu Gly Ala Ile Ala Leu Gly Val
100 105 110

Ala Thr Ala Ala Ala Val Thr Ala Gly Ile Ala Ile Ala Lys Thr Ile
115 120 125

Arg Leu Glu Ser Glu Val Asn Ala Ile Lys Gly Ala Leu Lys Thr Thr
130 135 140

Asn Glu Ala Val Ser Thr Leu Gly Asn Gly Val Arg Val Leu Ala Thr
145 150 155 160

Ala Val Arg Glu Leu Lys Glu Phe Val Ser Lys Asn Leu Thr Ser Ala
165 170 175

Ile Asn Lys Asn Lys Cys Asp Ile Ala Asp Leu Lys Met Ala Val Ser
180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Thr Asp
210 215 220

Ala Glu Leu Ala Arg Ala Val Ser Tyr Met Pro Thr Ser Ala Gly Gln
225 230 235 240

Ile Lys Leu Met Leu Glu Asn Arg Ala Met Val Arg Arg Lys Gly Phe
245 250 255

Gly Ile Leu Ile Gly Val Tyr Gly Ser Ser Val Ile Tyr Met Val Gln
260 265 270

Leu Pro Ile Phe Gly Val Ile Asp Thr Pro Cys Trp Ile Ile Lys Ala
275 280 285

Ala Pro Ser Cys Ser Glu Lys Asp Gly Asn Tyr Ala Cys Leu Leu Arg
290 295 300

Glu Asp Gln Gly Trp Tyr Cys Lys Asn Ala Gly Ser Thr Val Tyr Tyr
305 310 315 320

Pro Asn Lys Lys Asp Cys Glu Thr Arg Gly Asp His Val Phe Cys Asp
325 330 335

Thr Ala Ala Gly Ile Asn Val Ala Glu Gln Ser Arg Glu Cys Asn Ile
340 345 350

Asn Ile Ser Thr Thr Asn Tyr Pro Cys Lys Val Ser Thr Gly Arg His
355 360 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Lys Ile
465                 470                 475                 480

Leu Asn Ser Ala Glu Lys Gly Asn Thr Gly Phe Ile Ile Val Ile Ile
                485                 490                 495

Leu Ile Ala Val Leu Gly Leu Thr Met Ile Ser Val Ser Ile Ile Ile
            500                 505                 510

Ile Ile Lys Lys Thr Arg Lys Pro Thr Gly Ala Pro Pro Glu Leu Asn
        515                 520                 525

Gly Val Thr Asn Gly Gly Phe Ile Pro His Ser
    530                 535

<210> SEQ ID NO 8
<211> LENGTH: 4
<212> TYPE: PRT
<213> ORGANISM: Artificial Sequence
<220> FEATURE:
<223> OTHER INFORMATION: Protease Cleavage Sequence

<400> SEQUENCE: 8

Arg Gln Ser Arg
1

<210> SEQ ID NO 9
<211> LENGTH: 6
<212> TYPE: PRT
<213> ORGANISM: Artificial Sequence
<220> FEATURE:
<223> OTHER INFORMATION: Protease Cleavage Sequence

<400> SEQUENCE: 9

Arg Arg Arg Arg Arg Arg
1               5

<210> SEQ ID NO 10
<211> LENGTH: 4
<212> TYPE: PRT
<213> ORGANISM: Artificial Sequence
<220> FEATURE:
<223> OTHER INFORMATION: Protease Cleavage Sequence

<400> SEQUENCE: 10

Arg Arg Arg Arg
1

<210> SEQ ID NO 11
<211> LENGTH: 4
<212> TYPE: PRT
<213> ORGANISM: Artificial Sequence
<220> FEATURE:

<223> OTHER INFORMATION: Protease Cleavage Sequence

<400> SEQUENCE: 11

Arg Lys Ala Arg
1

<210> SEQ ID NO 12
<211> LENGTH: 467
<212> TYPE: PRT
<213> ORGANISM: Artificial Sequence
<220> FEATURE:
<223> OTHER INFORMATION: Recombinant MPV F protein

<400> SEQUENCE: 12

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Thr Ala Val
    130                 135                 140

Arg Glu Leu Lys Glu Phe Val Ser Lys Asn Leu Thr Ser Ala Ile Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Asp Lys Asp Cys Glu Thr Arg Gly Asp His Val Phe Cys Asp Thr Cys
305                 310                 315                 320

Ala Gly Ile Asn Val Ala Glu Gln Ser Arg Glu Cys Asn Ile Asn Ile
                325                 330                 335
```

```
Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
            405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu
465


<210> SEQ ID NO 13
<211> LENGTH: 467
<212> TYPE: PRT
<213> ORGANISM: Artificial Sequence
<220> FEATURE:
<223> OTHER INFORMATION: Recombinant MPV F protein

<400> SEQUENCE: 13

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Thr Ala Val
    130                 135                 140

Arg Glu Leu Lys Glu Phe Val Ser Lys Asn Leu Thr Ser Ala Ile Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220
```

```
Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Asp Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu
465


<210> SEQ ID NO 14
<211> LENGTH: 467
<212> TYPE: PRT
<213> ORGANISM: Artificial Sequence
<220> FEATURE:
<223> OTHER INFORMATION: Recombinant MPV F protein

<400> SEQUENCE: 14

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Ala Thr
                85                  90                  95

Ala Ala Ala Val Thr Ala Gly Ile Ala Ile Ala Lys Thr Ile Arg Leu
            100                 105                 110
```

Glu Ser Glu Val Asn Ala Ile Lys Gly Ala Leu Lys Thr Thr Asn Glu
115 120 125

Ala Val Ser Thr Leu Gly Asn Gly Val Arg Val Leu Ala Phe Ala Val
130 135 140

Arg Glu Leu Lys Glu Phe Val Ser Lys Asn Leu Thr Ser Ala Leu Asn
145 150 155 160

Lys Asn Lys Cys Asp Ile Ala Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Tyr Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Ile Lys Ala Ala Pro
260 265 270

Ser Cys Ser Glu Lys Asp Gly Asn Tyr Ala Cys Leu Leu Arg Glu Asp
275 280 285

Gln Gly Trp Tyr Cys Lys Asn Ala Gly Ser Thr Val Tyr Tyr Pro Asn
290 295 300

Asp Lys Asp Cys Glu Thr Arg Gly Asp His Val Phe Cys Asp Thr Ala
305 310 315 320

Ala Gly Ile Asn Val Ala Glu Gln Ser Arg Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Pro Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Lys Ile Leu Asn
450 455 460

Ser Ala Glu
465

<210> SEQ ID NO 15
<211> LENGTH: 467
<212> TYPE: PRT
<213> ORGANISM: Artificial Sequence
<220> FEATURE:
<223> OTHER INFORMATION: Recombinant MPV F protein

<400> SEQUENCE: 15

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Asp Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415
```

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Lys Ile Leu Asn
450 455 460

Ser Ala Glu
465

<210> SEQ ID NO 16
<211> LENGTH: 4
<212> TYPE: PRT
<213> ORGANISM: Artificial Sequence
<220> FEATURE:
<223> OTHER INFORMATION: Peptide Linker Sequence

<400> SEQUENCE: 16

Ser Gln Ser Asp
1

<210> SEQ ID NO 17
<211> LENGTH: 4
<212> TYPE: PRT
<213> ORGANISM: Artificial Sequence
<220> FEATURE:
<223> OTHER INFORMATION: Peptide linker sequence

<400> SEQUENCE: 17

Ser Thr Ser Thr
1

<210> SEQ ID NO 18
<211> LENGTH: 4
<212> TYPE: PRT
<213> ORGANISM: Artificial Sequence
<220> FEATURE:
<223> OTHER INFORMATION: Peptide linker sequence

<400> SEQUENCE: 18

Gly Gly Gly Gly
1

<210> SEQ ID NO 19
<211> LENGTH: 4
<212> TYPE: PRT
<213> ORGANISM: Artificial Sequence
<220> FEATURE:
<223> OTHER INFORMATION: Peptide Linker Sequence

<400> SEQUENCE: 19

Ser Gly Gly Gly
1

<210> SEQ ID NO 20
<211> LENGTH: 5
<212> TYPE: PRT
<213> ORGANISM: Artificial Sequence
<220> FEATURE:
<223> OTHER INFORMATION: Peptide Linker Sequence

<400> SEQUENCE: 20

Gly Gly Gly Gly Gly
1 5

<210> SEQ ID NO 21

-continued

<211> LENGTH: 7
<212> TYPE: PRT
<213> ORGANISM: Artificial Sequence
<220> FEATURE:
<223> OTHER INFORMATION: Peptide Linker Sequence

<400> SEQUENCE: 21

Gly Gly Gly Gly Gly Gly Gly
1 5

<210> SEQ ID NO 22
<211> LENGTH: 5
<212> TYPE: PRT
<213> ORGANISM: Artificial Sequence
<220> FEATURE:
<223> OTHER INFORMATION: Peptide Linker Sequence

<400> SEQUENCE: 22

Gly Gly Ser Gly Gly
1 5

<210> SEQ ID NO 23
<211> LENGTH: 7
<212> TYPE: PRT
<213> ORGANISM: Artificial Sequence
<220> FEATURE:
<223> OTHER INFORMATION: Peptide Linker Sequence

<400> SEQUENCE: 23

Gly Gly Ser Gly Gly Ser Gly
1 5

<210> SEQ ID NO 24
<211> LENGTH: 12
<212> TYPE: PRT
<213> ORGANISM: Artificial Sequence
<220> FEATURE:
<223> OTHER INFORMATION: Recombinant MPV F protein sequence

<400> SEQUENCE: 24

Ile Glu Asn Pro Ser Gln Ser Asp Phe Val Leu Gly
1 5 10

<210> SEQ ID NO 25
<211> LENGTH: 12
<212> TYPE: PRT
<213> ORGANISM: Artificial Sequence
<220> FEATURE:
<223> OTHER INFORMATION: Recombinant MPV F protein sequence

<400> SEQUENCE: 25

Ile Glu Asn Pro Ser Thr Ser Thr Phe Val Leu Gly
1 5 10

<210> SEQ ID NO 26
<211> LENGTH: 12
<212> TYPE: PRT
<213> ORGANISM: Artificial Sequence
<220> FEATURE:
<223> OTHER INFORMATION: Recombinant MPV F protein sequence

<400> SEQUENCE: 26

Ile Glu Asn Pro Gly Gly Gly Gly Phe Val Leu Gly
1 5 10

<210> SEQ ID NO 27
<211> LENGTH: 14

<212> TYPE: PRT
<213> ORGANISM: Artificial Sequence
<220> FEATURE:
<223> OTHER INFORMATION: Recombinant MPV F protein sequence

<400> SEQUENCE: 27

Ile Glu Asn Pro Arg Gln Ser Gly Gly Gly Phe Val Leu Gly
1 5 10

<210> SEQ ID NO 28
<211> LENGTH: 16
<212> TYPE: PRT
<213> ORGANISM: Artificial Sequence
<220> FEATURE:
<223> OTHER INFORMATION: Recombinant MPV F protein sequence

<400> SEQUENCE: 28

Ile Glu Asn Pro Arg Gln Ser Gly Gly Gly Gly Gly Phe Val Leu Gly
1 5 10 15

<210> SEQ ID NO 29
<211> LENGTH: 18
<212> TYPE: PRT
<213> ORGANISM: Artificial Sequence
<220> FEATURE:
<223> OTHER INFORMATION: Recombinant MPV F protein sequence

<400> SEQUENCE: 29

Ile Glu Asn Pro Arg Gln Ser Gly Gly Gly Gly Gly Gly Gly Phe Val
1 5 10 15

Leu Gly

<210> SEQ ID NO 30
<211> LENGTH: 11
<212> TYPE: PRT
<213> ORGANISM: Artificial Sequence
<220> FEATURE:
<223> OTHER INFORMATION: Recombinant MPV F protein sequence

<400> SEQUENCE: 30

Ile Glu Asn Pro Gly Ser Gly Phe Val Leu Gly
1 5 10

<210> SEQ ID NO 31
<211> LENGTH: 12
<212> TYPE: PRT
<213> ORGANISM: Artificial Sequence
<220> FEATURE:
<223> OTHER INFORMATION: Recombinant MPV F protein sequence

<400> SEQUENCE: 31

Ile Glu Asn Gly Gly Ser Gly Gly Ala Ile Ala Leu
1 5 10

<210> SEQ ID NO 32
<211> LENGTH: 14
<212> TYPE: PRT
<213> ORGANISM: Artificial Sequence
<220> FEATURE:
<223> OTHER INFORMATION: Recombinant MPV F protein sequence

<400> SEQUENCE: 32

Ile Glu Asn Gly Gly Ser Gly Gly Ser Gly Ala Ile Ala Leu
1 5 10

<210> SEQ ID NO 33

```
<211> LENGTH: 26
<212> TYPE: PRT
<213> ORGANISM: Artificial Sequence
<220> FEATURE:
<223> OTHER INFORMATION: Trimerization domain

<400> SEQUENCE: 33

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe
            20                  25


<210> SEQ ID NO 34
<211> LENGTH: 26
<212> TYPE: PRT
<213> ORGANISM: Artificial Sequence
<220> FEATURE:
<223> OTHER INFORMATION: Trimerization domain

<400> SEQUENCE: 34

Gly Tyr Ile Pro Glu Ala Pro Arg Asp Gly Gln Cys Tyr Val Arg Cys
1               5                   10                  15

Asp Gly Glu Trp Val Leu Leu Ser Thr Phe
            20                  25


<210> SEQ ID NO 35
<211> LENGTH: 26
<212> TYPE: PRT
<213> ORGANISM: Artificial Sequence
<220> FEATURE:
<223> OTHER INFORMATION: Trimerization domain

<400> SEQUENCE: 35

Gly Tyr Ile Pro Glu Cys Pro Arg Asp Gly Gln Ala Tyr Val Cys Lys
1               5                   10                  15

Asp Gly Glu Trp Val Leu Leu Ser Thr Phe
            20                  25


<210> SEQ ID NO 36
<211> LENGTH: 26
<212> TYPE: PRT
<213> ORGANISM: Artificial Sequence
<220> FEATURE:
<223> OTHER INFORMATION: Trimerization domain

<400> SEQUENCE: 36

Gly Tyr Ile Pro Glu Ala Pro Arg Asp Gly Gln Cys Tyr Cys Arg Lys
1               5                   10                  15

Asp Gly Glu Trp Val Leu Leu Ser Thr Phe
            20                  25


<210> SEQ ID NO 37
<211> LENGTH: 26
<212> TYPE: PRT
<213> ORGANISM: Artificial Sequence
<220> FEATURE:
<223> OTHER INFORMATION: Trimerization domain

<400> SEQUENCE: 37

Gly Tyr Ile Pro Glu Ala Pro Arg Asp Gly Gln Ala Cys Val Arg Lys
1               5                   10                  15

Asp Gly Glu Cys Val Leu Leu Ser Thr Phe
            20                  25
```

-continued

<210> SEQ ID NO 38
<211> LENGTH: 9
<212> TYPE: PRT
<213> ORGANISM: Artificial Sequence
<220> FEATURE:
<223> OTHER INFORMATION: Peptide Linker Sequence

<400> SEQUENCE: 38

Gly Gly Ser Gly Gly Ser Gly Gly Ser
1 5

<210> SEQ ID NO 39
<211> LENGTH: 37
<212> TYPE: PRT
<213> ORGANISM: Artificial Sequence
<220> FEATURE:
<223> OTHER INFORMATION: Trimerization domain

<400> SEQUENCE: 39

Gly Gly Gly Leu Val Pro Arg Gly Ser Gly Gly Tyr Ile Pro Glu Ala
1 5 10 15

Pro Arg Asp Gly Gln Ala Tyr Val Arg Lys Asp Gly Glu Trp Val Leu
20 25 30

Leu Ser Thr Phe Leu
35

<210> SEQ ID NO 40
<211> LENGTH: 18
<212> TYPE: PRT
<213> ORGANISM: Artificial Sequence
<220> FEATURE:
<223> OTHER INFORMATION: Cysteine ring domain

<400> SEQUENCE: 40

Cys Cys Thr Thr Thr Gly Ile Cys Cys Thr Thr Thr Asn Ile Cys Cys
1 5 10 15

Thr Thr

<210> SEQ ID NO 41
<211> LENGTH: 13
<212> TYPE: PRT
<213> ORGANISM: Artificial Sequence
<220> FEATURE:
<223> OTHER INFORMATION: Cysteine ring domain

<400> SEQUENCE: 41

Cys Cys His Asn Val Asn Ala Gly Lys Ser Thr Thr Asn
1 5 10

<210> SEQ ID NO 42
<211> LENGTH: 13
<212> TYPE: PRT
<213> ORGANISM: Artificial Sequence
<220> FEATURE:
<223> OTHER INFORMATION: Cysteine ring domain

<400> SEQUENCE: 42

Cys Cys His Asn Val Asn Ala Cys Cys Ser Thr Thr Asn
1 5 10

<210> SEQ ID NO 43
<211> LENGTH: 11
<212> TYPE: PRT
<213> ORGANISM: Artificial Sequence
<220> FEATURE:
<223> OTHER INFORMATION: Cysteine ring domain

<400> SEQUENCE: 43

Cys Cys Ser Ser Ala Glu Lys Gly Asn Thr Gly
1 5 10

<210> SEQ ID NO 44
<211> LENGTH: 11
<212> TYPE: PRT
<213> ORGANISM: Artificial Sequence
<220> FEATURE:
<223> OTHER INFORMATION: Cysteine ring domain

<400> SEQUENCE: 44

Cys Cys Ser Ser Ala Glu Lys Cys Cys Thr Gly
1 5 10

<210> SEQ ID NO 45
<211> LENGTH: 13
<212> TYPE: PRT
<213> ORGANISM: Artificial Sequence
<220> FEATURE:
<223> OTHER INFORMATION: Cysteine ring domain

<400> SEQUENCE: 45

Cys Cys His Asn Val Asn Ala Gly Lys Ser Thr Thr Asn
1 5 10

<210> SEQ ID NO 46
<211> LENGTH: 13
<212> TYPE: PRT
<213> ORGANISM: Artificial Sequence
<220> FEATURE:
<223> OTHER INFORMATION: Cysteine ring domain

<400> SEQUENCE: 46

Cys Cys His Asn Val Asn Ala Cys Cys Ser Thr Thr Asn
1 5 10

<210> SEQ ID NO 47
<211> LENGTH: 65
<212> TYPE: PRT
<213> ORGANISM: Artificial Sequence
<220> FEATURE:
<223> OTHER INFORMATION: Cysteine ring domain

<400> SEQUENCE: 47

Cys Cys Ser Ser Ala Glu Lys Gly Asn Thr Gly Gly Gly Leu Val Pro
1 5 10 15

Arg Gly Ser Gly Gly Tyr Ile Pro Glu Ala Pro Arg Asp Gly Gln Ala
20 25 30

Tyr Val Arg Lys Asp Gly Glu Trp Val Leu Leu Ser Thr Phe Leu Gly
35 40 45

Gly His His His His His His Ser Ala Trp Ser His Pro Gln Phe Glu
50 55 60

Lys
65

<210> SEQ ID NO 48
<211> LENGTH: 65
<212> TYPE: PRT
<213> ORGANISM: Artificial Sequence
<220> FEATURE:
<223> OTHER INFORMATION: Cysteine ring domain

<400> SEQUENCE: 48

-continued

Cys Cys Ser Ser Ala Glu Lys Cys Cys Thr Gly Gly Gly Leu Val Pro
1 5 10 15

Arg Gly Ser Gly Gly Tyr Ile Pro Glu Ala Pro Arg Asp Gly Gln Ala
20 25 30

Tyr Val Arg Lys Asp Gly Glu Trp Val Leu Leu Ser Thr Phe Leu Gly
35 40 45

Gly His His His His His His Ser Ala Trp Ser His Pro Gln Phe Glu
50 55 60

Lys
65

<210> SEQ ID NO 49
<211> LENGTH: 67
<212> TYPE: PRT
<213> ORGANISM: Artificial Sequence
<220> FEATURE:
<223> OTHER INFORMATION: Cysteine ring domain

<400> SEQUENCE: 49

Cys Cys His Asn Val Asn Ala Gly Lys Ser Thr Thr Asn Gly Gly Leu
1 5 10 15

Val Pro Arg Gly Ser Gly Gly Tyr Ile Pro Glu Ala Pro Arg Asp Gly
20 25 30

Gln Ala Tyr Val Arg Lys Asp Gly Glu Trp Val Leu Leu Ser Thr Phe
35 40 45

Leu Gly Gly His His His His His His Ser Ala Trp Ser His Pro Gln
50 55 60

Phe Glu Lys
65

<210> SEQ ID NO 50
<211> LENGTH: 67
<212> TYPE: PRT
<213> ORGANISM: Artificial Sequence
<220> FEATURE:
<223> OTHER INFORMATION: Cysteine ring domain

<400> SEQUENCE: 50

Cys Cys His Asn Val Asn Ala Cys Cys Ser Thr Thr Asn Gly Gly Leu
1 5 10 15

Val Pro Arg Gly Ser Gly Gly Tyr Ile Pro Glu Ala Pro Arg Asp Gly
20 25 30

Gln Ala Tyr Val Arg Lys Asp Gly Glu Trp Val Leu Leu Ser Thr Phe
35 40 45

Leu Gly Gly His His His His His His Ser Ala Trp Ser His Pro Gln
50 55 60

Phe Glu Lys
65

<210> SEQ ID NO 51
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 51

Glu Asn Ser Gln Ala Leu Val Asp Asn Ser Thr
1 5 10

<210> SEQ ID NO 52
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 52

Glu Asn Ser Gln Ala Leu Val Asn Gln Ser Asn
1 5 10

<210> SEQ ID NO 53
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 53

Glu Asn Ser Gln Ala Leu Asn Asp Thr Ser Asn
1 5 10

<210> SEQ ID NO 54
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 54

Glu Asn Ser Gln Asn Leu Thr Asp Gln Ser Asn
1 5 10

<210> SEQ ID NO 55
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 55

Asn Asn Ser Gln Ala Leu Val Asp Gln Ser Asn
1 5 10

<210> SEQ ID NO 56
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 56

Glu Asn Ser Gln Asn Leu Thr Asp Asn Ser Thr
1 5 10

<210> SEQ ID NO 57
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 57

Asn Asn Ser Gln Asn Leu Thr Asp Asn Ser Thr
1 5 10

-continued

<210> SEQ ID NO 58
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 58

Asn Asn Ser Gln Ala Leu Val Asp Asn Ser Thr
1 5 10

<210> SEQ ID NO 59
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 59

Asn Asn Ser Gln Asn Leu Thr Asp Gln Ser Asn
1 5 10

<210> SEQ ID NO 60
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 60

Glu Asn Ser Gln Asn Leu Thr Asn Gln Ser Asn
1 5 10

<210> SEQ ID NO 61
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 61

Asn Asn Ser Gln Asn Leu Thr Asn Gln Ser Asn
1 5 10

<210> SEQ ID NO 62
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 62

Asn Asn Ser Gln Ala Leu Val Asn Gln Ser Asn
1 5 10

<210> SEQ ID NO 63
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 63

Asn Asn Ser Gln Asn Leu Thr Asp Gln Ser Asn
1 5 10

<210> SEQ ID NO 64

<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 64

Asn Asn Ser Gln Ala Leu Val Asp Asn Ser Thr
1 5 10

<210> SEQ ID NO 65
<211> LENGTH: 1626
<212> TYPE: DNA
<213> ORGANISM: Artificial Sequence
<220> FEATURE:
<223> OTHER INFORMATION: Recombinant MPV F sequence

<400> SEQUENCE: 65
atgagttgga aagtgatgat tattattagc ctgctgatta ccccccagca cggactgaag 60
gagtcttatc tggaggagtc ttgctcaaca atcactgagg gctacctgag cgtcctgcgc 120
acagggtggt atactaacgt gtttaccctg gaagtgggcg atgtcgaaaa tctgacctgt 180
acagacgggc ctagcctgat caagacagag ctggatctga ctaaaagcgc cctgcgggaa 240
ctgaagaccg tgtccgctga ccagctggca agagaggaac agatcgagaa cccacgacag 300
agccgattcg tgctgggagc tattgcactg ggagtggcaa ccgccgctgc agtcacagca 360
ggaatcgcaa ttgctaaaac tatccgcctg gagagtgaag tgaacgccat taagggagct 420
ctgaaaacca caaacgaagc tgtgtctacc ctggggaatg gagtgagagt cctggcattt 480
gccgtcaggg agctgaagga attcgtgtct aaaaatctga caagtgccct gaacaagaac 540
aagtgcgaca tcgcagatct gaagatggcc gtgagcttct cccagtttaa ccggagattt 600
ctgaatgtgg tccggcagtt ctctgataac gctggcatca ctccagcaat tagtctggac 660
ctgatgaccg atgccgagct ggctagggca gtgtcataca tgcccaccag cgctggccag 720
atcaaactga tgctggaaaa tcgcgcaatg gtcaggcgca agggctttgg gatcctgatt 780
ggagtgtacg gcagcagcgt gatctacatg gtccagctgc ctatcttcgg cgtgattgac 840
acaccatgct ggatcatcaa ggccgctccc tcttgtagtg agaaggatgg gaactacgca 900
tgcctgctga gagaagacca gggatggtat tgtaaaaacg ccggctccac tgtgtactat 960
ccaaatgaca aggattgtga gacacgagga gaccacgtct tttgcgatac tgcagccggc 1020
atcaacgtgg ctgagcagag tcgcgaatgt aacatcaaca tctcaactac caactacccc 1080
tgcaaagtct ctacaggccg gcatcctatc agcatggtgg cactgtctcc actgggagca 1140
ctggtggctt gctataaggg cgtctcatgt agcattggct ccaatagagt ggggatcatt 1200
aagcagctgc ccaaaggctg ctcttacatc accaaccagg acgccgatac tgtgaccatt 1260
gataatacag tctatcagct gagcaaagtg gagggggaac agcacgtcat caagggaagg 1320
cctgtgtcta gttcattcga cccaattaag tttcccgagg atcagttcaa cgtggccctg 1380
gaccaggtct tcgagagcat cgaaaattcc caggctctgg tggaccagtc caacaaaatt 1440
ctgaattccg cagagtctgc catcggcggg tacattcccg aagcccctcg cgatgggcag 1500
gcttatgtcc gaaaggacgg agagtgggtg ctgctgtcaa cctttctggg aggactggtg 1560
ccaaggggaa gccaccatca ccatcaccat agtgcctggt cacatcctca gttcgaaaag 1620
tgatga 1626

<210> SEQ ID NO 66

<211> LENGTH: 1626
<212> TYPE: DNA
<213> ORGANISM: Artificial Sequence
<220> FEATURE:
<223> OTHER INFORMATION: Recombinant MPV F sequence

<400> SEQUENCE: 66
atgtcctgga aagtgatgat tattattagc ctgctgatta caccacagca cggcctgaaa 60
gagtcctatc tggaagagag ttgttcaaca atcactgagg gctacctgag cgtcctgcgc 120
acagggtggt atactaacgt gtttaccctg gaagtgggcg atgtcgaaaa tctgacctgt 180
acagacgggc ctagcctgat caagacagag ctggatctga ctaaaagcgc cctgcgggaa 240
ctgaagaccg tgtccgctga ccagctggca agagaggaac agatcgagaa cccacgacag 300
agccgattcg tgctgggagc tattgcactg ggagtgtgca ccgccgctgc agtcacagca 360
ggaatcgcaa ttgctaaaac aatccgcctg gagagtgaag tgaacgccat taagggagct 420
ctgaaaacca caaacgaagc tgtgtctacc ctggggaatg gagtgagagt cctggcaaca 480
gccgtcaggg agctgaagga atttgtgtct aaaaatctga ctagtgccat caacaagaac 540
aagtgcgaca ttgcagatct gaagatggcc gtgagcttct cccagtttaa ccggagattt 600
ctgaatgtgg tccggcagtt ctctgataac gctggcatca ctccagcaat tagtctggac 660
ctgatgaccg atgccgagct ggctagggca gtgtcataca tgcccaccag cgctggccag 720
atcaaactga tgctggaaaa tcgcgcaatg gtcaggcgca agggctttgg gatcctgatt 780
ggagtgtacg gcagctccgt gatctatatg gtccagctgc ctatcttcgg cgtgattgac 840
acaccatgct ggatcatcaa ggccgctccc tcttgtagtg agaaggatgg gaactacgca 900
tgcctgctga gagaagacca gggatggtat tgtaaaaacg ccggctccac tgtgtactat 960
ccaaatgaca aggattgtga gacacgagga gaccacgtct tttgcgatac tgcatgcggc 1020
atcaacgtgg ctgagcagag tcgcgaatgt aacatcaaca tctcaactac caactacccc 1080
tgcaaagtct ctacaggccg gcatcctatc agcatggtgg cactgtctcc actgggagca 1140
ctggtggctt gctataaggg cgtctcatgt agcattggct ccaatagagt ggggatcatt 1200
aagcagctgc ccaaaggctg ctcttacatc actaaccagg acgccgatac tgtgaccatt 1260
gataataccg tctatcagct gagcaaagtg gagggggaac agcacgtcat caagggaagg 1320
cctgtgtcta gttcattcga cccaattaag tttcccgagg atcagttcaa cgtggccctg 1380
gaccaggtct tcgagagcat cgaaaattcc caggctctgg tggaccagtc caacaaaatt 1440
ctgaattccg cagagtctgc catcggcggg tacattcccg aagcccctcg cgatgggcag 1500
gcttatgtcc gaaaggacgg agagtgggtg ctgctgtcaa cctttctggg aggactggtg 1560
ccaaggggaa gccaccatca ccatcaccat agtgcctggt cacatcctca gttcgaaaag 1620
tgatga 1626

<210> SEQ ID NO 67
<211> LENGTH: 1626
<212> TYPE: DNA
<213> ORGANISM: Artificial Sequence
<220> FEATURE:
<223> OTHER INFORMATION: Recombinant MPV F sequence

<400> SEQUENCE: 67
atgagttgga aagtgatgat tattattagc ctgctgatta ccccccagca cggactgaag 60
gagtcttatc tggaggagtc ttgctcaaca atcactgagg gctacctgag cgtcctgcgc 120
acagggtggt atactaacgt gtttaccctg gaagtgggcg atgtcgaaaa tctgacctgt 180

```
acagacgggc ctagcctgat caagacagag ctggatctga ctaaaagcgc cctgcgggaa    240
ctgaagaccg tgtccgctga ccagctggca agagaggaac agatcgagaa cccacgacag    300
agccgattcg tgctgggagc tattgcactg ggagtgtgca ccgccgctgc agtcacagca    360
ggaatcgcaa ttgctaaaac tatccgcctg gagagtgaag tgaacgccat taagggagct    420
ctgaaaacca caaacgaagc tgtgtctacc ctggggaatg gagtgagagt cctggcattt    480
gccgtcaggg agctgaagga attcgtgtct aaaaatctga caagtgccct gaacaagaac    540
aagtgcgaca tcgcagatct gaagatggcc gtgagcttct cccagtttaa ccggagattt    600
ctgaatgtgg tccggcagtt ctctgataac gctggcatca ctccagcaat tagtctggac    660
ctgatgaccg atgccgagct ggctagggca gtgtcataca tgcccaccag cgctggccag    720
atcaaactga tgctggaaaa tcgcgcaatg gtcaggcgca agggctttgg gatcctgatt    780
ggagtgtacg gcagcagcgt gatctacatg gtccagctgc ctatcttcgg cgtgattgac    840
acaccatgct ggatcatcaa ggccgctccc tcttgtagtg agaaggatgg gaactacgca    900
tgcctgctga gagaagacca gggatggtat tgtaaaaacg ccggctccac tgtgtactat    960
ccaaatgaca aggattgtga gacacgagga gaccacgtct tttgcgatac tgcatgcggc   1020
atcaacgtgg ctgagcagag tcgcgaatgt aacatcaaca tctcaactac caactacccc   1080
tgcaaagtct ctacaggccg gcatcctatc agcatggtgg cactgtctcc actgggagca   1140
ctggtggctt gctataaggg cgtctcatgt agcattggct ccaatagagt ggggatcatt   1200
aagcagctgc ccaaaggctg ctcttacatc accaaccagg acgccgatac tgtgaccatt   1260
gataatacag tctatcagct gagcaaagtg gaggggggaac agcacgtcat caagggaagg   1320
cctgtgtcta gttcattcga cccaattaag tttcccgagg atcagttcaa cgtggccctg   1380
gaccaggtct tcgagagcat cgaaaattcc caggctctgg tggaccagtc caacaaaatt   1440
ctgaattccg cagagtctgc catcggcggg tacattcccg aagcccctcg cgatgggcag   1500
gcttatgtcc gaaaggacgg agagtgggtg ctgctgtcaa cctttctggg aggactggtg   1560
ccaaggggaa gccaccatca ccatcaccat agtgcctggt cacatcctca gttcgaaaag   1620
tgatga                                                               1626
```

<210> SEQ ID NO 68
<211> LENGTH: 23
<212> TYPE: PRT
<213> ORGANISM: Artificial Sequence
<220> FEATURE:
<223> OTHER INFORMATION: transmembrane domain

<400> SEQUENCE: 68

```
Phe Ile Ile Val Ile Ile Leu Ile Ala Val Leu Gly Ser Ser Met Ile
1               5                   10                  15

Leu Val Ser Ile Phe Ile Ile
            20
```

<210> SEQ ID NO 69
<211> LENGTH: 23
<212> TYPE: PRT
<213> ORGANISM: Artificial Sequence
<220> FEATURE:
<223> OTHER INFORMATION: transmembrane domain

<400> SEQUENCE: 69

```
Ile Leu Ala Ile Tyr Ser Thr Val Ala Ser Ser Leu Val Leu Leu Val
1               5                   10                  15
```

```
Ser Leu Gly Ala Ile Ser Phe
            20


<210> SEQ ID NO 70
<211> LENGTH: 29
<212> TYPE: PRT
<213> ORGANISM: Artificial Sequence
<220> FEATURE:
<223> OTHER INFORMATION: transmembrane domain

<400> SEQUENCE: 70

Ile Ile Thr Ile Gly Ser Ile Cys Met Val Val Gly Ile Ile Ser Leu
1               5                   10                  15

Ile Leu Gln Ile Gly Asn Ile Ile Ser Ile Trp Val Ser
            20                  25


<210> SEQ ID NO 71
<211> LENGTH: 173
<212> TYPE: PRT
<213> ORGANISM: Artificial Sequence
<220> FEATURE:
<223> OTHER INFORMATION: Protein nanoparticle subunit

<400> SEQUENCE: 71

Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30

Met Ser Ser Trp Cys Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170


<210> SEQ ID NO 72
<211> LENGTH: 154
<212> TYPE: PRT
<213> ORGANISM: Artificial Sequence
<220> FEATURE:
<223> OTHER INFORMATION: Protein nanoparticle subunit

<400> SEQUENCE: 72

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30
```

```
Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150


<210> SEQ ID NO 73
<211> LENGTH: 265
<212> TYPE: PRT
<213> ORGANISM: Artificial Sequence
<220> FEATURE:
<223> OTHER INFORMATION: Protein nanoparticle subunit

<400> SEQUENCE: 73

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240
```

```
Ala Val Arg Leu Phe Ile Thr Glu Thr Phe Thr Phe Gln Val Val Asn
                245                 250                 255

Pro Glu Ala Leu Ile Leu Leu Lys Phe
            260                 265
```

<210> SEQ ID NO 74
<211> LENGTH: 265
<212> TYPE: PRT
<213> ORGANISM: Artificial Sequence
<220> FEATURE:
<223> OTHER INFORMATION: Protein nanoparticle subunit

<400> SEQUENCE: 74

```
Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys
            180                 185                 190

Arg Val Glu Glu Cys Leu Arg Gly Gly Lys Ile Ile Thr Thr Pro Arg
        195                 200                 205

Ile Glu Asp Ala Leu Val Val Ser Glu Arg Gly Gly Asp Phe Lys Leu
    210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265
```

<210> SEQ ID NO 75
<211> LENGTH: 496
<212> TYPE: PRT
<213> ORGANISM: Artificial Sequence
<220> FEATURE:
<223> OTHER INFORMATION: Recombinant RSV F sequence

<400> SEQUENCE: 75

```
Gln Asn Ile Thr Glu Glu Phe Tyr Gln Ser Thr Cys Ser Ala Val Ser
1               5                   10                  15
```

-continued

```
Lys Gly Tyr Leu Ser Ala Leu Arg Thr Gly Trp Tyr Thr Ser Val Ile
            20                  25                  30

Thr Ile Glu Leu Ser Asn Ile Lys Glu Asn Lys Cys Asn Gly Thr Asp
        35                  40                  45

Ala Lys Val Lys Leu Ile Lys Gln Glu Leu Asp Lys Tyr Lys Asn Ala
    50                  55                  60

Val Thr Glu Leu Gln Leu Leu Met Gln Ser Thr Pro Ala Thr Asn Asn
65                  70                  75                  80

Arg Ala Phe Leu Gly Phe Leu Leu Gly Val Gly Ser Ala Ile Ala Ser
                85                  90                  95

Gly Val Ala Val Cys Lys Val Leu His Leu Glu Gly Glu Val Asn Lys
            100                 105                 110

Ile Lys Ser Ala Leu Leu Ser Thr Asn Lys Ala Val Val Ser Leu Ser
        115                 120                 125

Asn Gly Val Ser Val Leu Thr Phe Lys Val Leu Asp Leu Lys Asn Tyr
    130                 135                 140

Ile Asp Lys Gln Leu Leu Pro Ile Leu Asn Lys Gln Ser Cys Ser Ile
145                 150                 155                 160

Ser Asn Ile Glu Thr Val Ile Glu Phe Gln Gln Lys Asn Asn Arg Leu
                165                 170                 175

Leu Glu Ile Thr Arg Glu Phe Ser Val Asn Ala Gly Val Thr Thr Pro
            180                 185                 190

Val Ser Thr Tyr Met Leu Thr Asn Ser Glu Leu Leu Ser Leu Ile Asn
        195                 200                 205

Asp Met Pro Ile Thr Asn Asp Gln Lys Lys Leu Met Ser Asn Asn Val
    210                 215                 220

Gln Ile Val Arg Gln Gln Ser Tyr Ser Ile Met Cys Ile Ile Lys Glu
225                 230                 235                 240

Glu Val Leu Ala Tyr Val Val Gln Leu Pro Leu Tyr Gly Val Ile Asp
                245                 250                 255

Thr Pro Cys Trp Lys Leu His Thr Ser Pro Leu Cys Thr Thr Asn Thr
            260                 265                 270

Lys Glu Gly Ser Asn Ile Cys Leu Thr Arg Thr Asp Arg Gly Trp Tyr
        275                 280                 285

Cys Asp Asn Ala Gly Ser Val Ser Phe Phe Pro Gln Ala Glu Thr Cys
    290                 295                 300

Lys Val Gln Ser Asn Arg Val Phe Cys Asp Thr Met Asn Ser Leu Thr
305                 310                 315                 320

Leu Pro Ser Glu Val Asn Leu Cys Asn Val Asp Ile Phe Asn Pro Lys
                325                 330                 335

Tyr Asp Cys Lys Ile Met Thr Ser Lys Thr Asp Val Ser Ser Ser Val
            340                 345                 350

Ile Thr Ser Leu Gly Ala Ile Val Ser Cys Tyr Gly Lys Thr Lys Cys
        355                 360                 365

Thr Ala Ser Asn Lys Asn Arg Gly Ile Ile Lys Thr Phe Ser Asn Gly
    370                 375                 380

Cys Asp Tyr Val Ser Asn Lys Gly Val Asp Thr Val Ser Val Gly Asn
385                 390                 395                 400

Thr Leu Tyr Tyr Val Asn Lys Gln Glu Gly Lys Ser Leu Tyr Val Lys
                405                 410                 415

Gly Glu Pro Ile Ile Asn Phe Tyr Asp Pro Leu Val Phe Pro Ser Asp
            420                 425                 430
```

```
Glu Phe Asp Ala Ser Ile Ser Gln Val Asn Glu Lys Ile Asn Gln Ser
        435                 440                 445

Leu Ala Phe Ile Arg Lys Ser Asp Glu Leu Leu Ser Ala Ile Gly Gly
    450                 455                 460

Tyr Ile Pro Glu Ala Pro Arg Asp Gly Gln Ala Tyr Val Arg Lys Asp
465                 470                 475                 480

Gly Glu Trp Val Leu Leu Ser Thr Phe Leu Gly Gly Leu Val Pro Arg
                485                 490                 495


<210> SEQ ID NO 76
<211> LENGTH: 122
<212> TYPE: PRT
<213> ORGANISM: Artificial Sequence
<220> FEATURE:
<223> OTHER INFORMATION: antibody heavy chain variable region

<400> SEQUENCE: 76

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Val Ser Ser Ser
            20                  25                  30

Tyr Met Ser Trp Val Arg Gln Thr Pro Gly Lys Gly Leu Glu Trp Ile
        35                  40                  45

Ser Val Phe Tyr Ser Gly Gly Thr Thr Tyr Tyr Ala Asp Ala Val Lys
    50                  55                  60

Gly Arg Phe Ser Ile Ser Met Asp Thr Ser Lys Asn Thr Leu His Leu
65                  70                  75                  80

Gln Met Asn Ser Leu Arg Val Glu Asp Thr Ala Ile Tyr Tyr Cys Ala
                85                  90                  95

Arg Val Leu Ser Arg Ala Ser Gly Met Pro Asp Ala Phe Asp Ile Trp
            100                 105                 110

Gly Pro Gly Thr Met Val Thr Val Ser Ser
        115                 120


<210> SEQ ID NO 77
<211> LENGTH: 108
<212> TYPE: PRT
<213> ORGANISM: Artificial Sequence
<220> FEATURE:
<223> OTHER INFORMATION: antibody light chain variable region

<400> SEQUENCE: 77

Glu Leu Ala Leu Ile Gln Pro Ala Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Ser Trp Tyr Gln Gln Lys Pro Gly Gln Ser Pro Val Leu Val Ile Tyr
        35                  40                  45

Gln Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Thr Leu Thr Val Leu Gly Gln
            100                 105


<210> SEQ ID NO 78
```

<211> LENGTH: 124
<212> TYPE: PRT
<213> ORGANISM: Homo Sapiens

<400> SEQUENCE: 78

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ala Ser Ser Ser Tyr Ser Asp Tyr Ala Asp Ser Ala
    50                  55                  60

Lys Gly Arg Phe Thr Ile Ser Arg Asp Asn Ala Lys Thr Ser Leu Phe
65                  70                  75                  80

Leu Gln Met Asn Ser Leu Arg Ala Glu Asp Thr Ala Ile Tyr Phe Cys
                85                  90                  95

Ala Arg Ala Arg Ala Thr Gly Tyr Ser Ser Ile Thr Pro Tyr Phe Asp
            100                 105                 110

Ile Trp Gly Gln Gly Thr Leu Val Thr Val Ser Ser
        115                 120

<210> SEQ ID NO 79
<211> LENGTH: 110
<212> TYPE: PRT
<213> ORGANISM: Homo Sapiens

<400> SEQUENCE: 79

Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Arg Ser
                85                  90                  95

Leu Ser Gly Val Phe Gly Thr Gly Thr Lys Val Thr Val Leu
            100                 105                 110

<210> SEQ ID NO 80
<211> LENGTH: 490
<212> TYPE: PRT
<213> ORGANISM: Artificial Sequence
<220> FEATURE:
<223> OTHER INFORMATION: Recombinant MPV F sequence

<400> SEQUENCE: 80

Met Ser Trp Lys Val Met Ile Ile Ile Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Thr Asp Gly Pro

```
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Ile Ala Ile Ala Lys Thr Ile
        115                 120                 125

Arg Leu Glu Ser Glu Val Asn Ala Ile Lys Gly Ala Leu Lys Thr Thr
    130                 135                 140

Asn Glu Ala Val Ser Thr Leu Gly Asn Gly Val Arg Val Leu Ala Phe
145                 150                 155                 160

Ala Val Arg Glu Leu Lys Glu Phe Val Ser Lys Asn Leu Thr Ser Ala
                165                 170                 175

Leu Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Tyr Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Ile Lys Ala
        275                 280                 285

Ala Pro Ser Cys Ser Glu Lys Asp Gly Asn Tyr Ala Cys Leu Leu Arg
    290                 295                 300

Glu Asp Gln Gly Trp Tyr Cys Lys Asn Ala Gly Ser Thr Val Tyr Tyr
305                 310                 315                 320

Pro Asn Asp Lys Asp Cys Glu Thr Arg Gly Asp His Val Phe Cys Asp
                325                 330                 335

Thr Ala Ala Gly Ile Asn Val Ala Glu Gln Ser Arg Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Lys Ile
465                 470                 475                 480
```

```
Leu Asn Ser Ala Glu Ser Ala Ile Gly Gly
                485                 490


<210> SEQ ID NO 81
<211> LENGTH: 540
<212> TYPE: PRT
<213> ORGANISM: Artificial Sequence
<220> FEATURE:
<223> OTHER INFORMATION: Recombinant MPV F sequence

<400> SEQUENCE: 81

Met Ser Trp Lys Val Met Ile Ile Ile Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Thr Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Cys Thr Ala Ala Ala Val Thr Ala Gly Ile Ala Ile Ala Lys Thr Ile
        115                 120                 125

Arg Leu Glu Ser Glu Val Asn Ala Ile Lys Gly Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Glu Phe Val Ser Lys Asn Leu Thr Ser Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Tyr Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Ile Lys Ala
        275                 280                 285

Ala Pro Ser Cys Ser Glu Lys Asp Gly Asn Tyr Ala Cys Leu Leu Arg
    290                 295                 300

Glu Asp Gln Gly Trp Tyr Cys Lys Asn Ala Gly Ser Thr Val Tyr Tyr
305                 310                 315                 320

Pro Asn Asp Lys Asp Cys Glu Thr Arg Gly Asp His Val Phe Cys Asp
                325                 330                 335

Thr Ala Cys Gly Ile Asn Val Ala Glu Gln Ser Arg Glu Cys Asn Ile
            340                 345                 350
```

```
Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Lys Ile
465                 470                 475                 480

Leu Asn Ser Ala Glu Ser Ala Ile Gly Gly Tyr Ile Pro Glu Ala Pro
                485                 490                 495

Arg Asp Gly Gln Ala Tyr Val Arg Lys Asp Gly Glu Trp Val Leu Leu
            500                 505                 510

Ser Thr Phe Leu Gly Gly Leu Val Pro Arg Gly Ser His His His His
        515                 520                 525

His His Ser Ala Trp Ser His Pro Gln Phe Glu Lys
    530                 535                 540


<210> SEQ ID NO 82
<211> LENGTH: 4
<212> TYPE: PRT
<213> ORGANISM: Artificial Sequence
<220> FEATURE:
<223> OTHER INFORMATION: protease cleavage sequence

<400> SEQUENCE: 82

Arg Ala Lys Arg
1


<210> SEQ ID NO 83
<211> LENGTH: 11
<212> TYPE: PRT
<213> ORGANISM: Artificial Sequence
<220> FEATURE:
<223> OTHER INFORMATION: Recombinant MPV F sequence

<400> SEQUENCE: 83

Ile Glu Asn Pro Gly Ser Lys Phe Val Leu Gly
1               5                   10


<210> SEQ ID NO 84
<211> LENGTH: 25
<212> TYPE: PRT
<213> ORGANISM: Artificial Sequence
<220> FEATURE:
<223> OTHER INFORMATION: Cysteine ring domain

<400> SEQUENCE: 84

Ile Leu Ser Ser Ala Glu Lys Cys Cys Thr Thr Thr Gly Ile Cys Cys
1               5                   10                  15

Thr Thr Thr Asn Ile Cys Cys Thr Thr
            20                  25
```

<210> SEQ ID NO 85
<211> LENGTH: 25
<212> TYPE: PRT
<213> ORGANISM: Artificial Sequence
<220> FEATURE:
<223> OTHER INFORMATION: Cysteine ring domain

<400> SEQUENCE: 85

Cys Cys Ser Ser Ala Glu Lys Cys Cys Thr Thr Thr Gly Ile Cys Cys
1 5 10 15

Thr Thr Thr Asn Ile Cys Cys Thr Thr
20 25

<210> SEQ ID NO 86
<211> LENGTH: 32
<212> TYPE: PRT
<213> ORGANISM: Artificial Sequence
<220> FEATURE:
<223> OTHER INFORMATION: Cysteine ring domain

<400> SEQUENCE: 86

Ile Leu Ser Ser Ala Glu Lys Cys Cys Thr Thr Thr Gly Ile Cys Cys
1 5 10 15

Thr Thr Val Asn Ala Cys Cys Ser Thr Thr Asn Ile Cys Cys Thr Thr
20 25 30

<210> SEQ ID NO 87
<211> LENGTH: 32
<212> TYPE: PRT
<213> ORGANISM: Artificial Sequence
<220> FEATURE:
<223> OTHER INFORMATION: Cysteine ring domain

<400> SEQUENCE: 87

Cys Cys Ser Ser Ala Glu Lys Cys Cys Thr Thr Thr Gly Ile Cys Cys
1 5 10 15

Thr Thr Val Asn Ala Cys Cys Ser Thr Thr Asn Ile Cys Cys Thr Thr
20 25 30

<210> SEQ ID NO 88
<211> LENGTH: 25
<212> TYPE: PRT
<213> ORGANISM: Artificial Sequence
<220> FEATURE:
<223> OTHER INFORMATION: Cysteine ring domain

<400> SEQUENCE: 88

Ile Leu His Asn Val Asn Ala Cys Cys Ser Thr Thr Asn Ile Cys Cys
1 5 10 15

Thr Thr Thr Asn Ile Cys Cys Thr Thr
20 25

<210> SEQ ID NO 89
<211> LENGTH: 25
<212> TYPE: PRT
<213> ORGANISM: Artificial Sequence
<220> FEATURE:
<223> OTHER INFORMATION: Cysteine ring domain

<400> SEQUENCE: 89

Cys Cys His Asn Val Asn Ala Cys Cys Ser Thr Thr Asn Ile Cys Cys
1 5 10 15

Thr Thr Thr Asn Ile Cys Cys Thr Thr
20 25

<210> SEQ ID NO 90
<211> LENGTH: 32
<212> TYPE: PRT
<213> ORGANISM: Artificial Sequence
<220> FEATURE:
<223> OTHER INFORMATION: Cysteine ring domain

<400> SEQUENCE: 90

```
Ile Leu His Asn Val Asn Ala Cys Cys Ser Thr Thr Asn Ile Cys Cys
1               5                   10                  15

Thr Thr Val Asn Ala Cys Cys Ser Thr Thr Asn Ile Cys Cys Thr Thr
            20                  25                  30
```

<210> SEQ ID NO 91
<211> LENGTH: 32
<212> TYPE: PRT
<213> ORGANISM: Artificial Sequence
<220> FEATURE:
<223> OTHER INFORMATION: Cysteine ring domain

<400> SEQUENCE: 91

```
Cys Cys His Asn Val Asn Ala Cys Cys Ser Thr Thr Asn Ile Cys Cys
1               5                   10                  15

Thr Thr Val Asn Ala Cys Cys Ser Thr Thr Asn Ile Cys Cys Thr Thr
            20                  25                  30
```

<210> SEQ ID NO 92
<211> LENGTH: 52
<212> TYPE: PRT
<213> ORGANISM: Artificial Sequence
<220> FEATURE:
<223> OTHER INFORMATION: Cysteine ring domain

<400> SEQUENCE: 92

```
Leu Val Pro Arg Gly Ser Gly Gly Tyr Ile Pro Glu Ala Pro Arg Asp
1               5                   10                  15

Gly Gln Ala Tyr Val Arg Lys Asp Gly Glu Trp Val Leu Leu Ser Thr
            20                  25                  30

Phe Leu Gly Gly His His His His His His Ser Ala Trp Ser His Pro
        35                  40                  45

Gln Phe Glu Lys
    50
```

<210> SEQ ID NO 93
<211> LENGTH: 79
<212> TYPE: PRT
<213> ORGANISM: Artificial Sequence
<220> FEATURE:
<223> OTHER INFORMATION: Cysteine ring domain

<400> SEQUENCE: 93

```
Ile Leu Ser Ser Ala Glu Lys Cys Cys Thr Thr Thr Gly Ile Cys Cys
1               5                   10                  15

Thr Thr Thr Asn Ile Cys Cys Thr Thr Gly Gly Leu Val Pro Arg Gly
            20                  25                  30

Ser Gly Gly Tyr Ile Pro Glu Ala Pro Arg Asp Gly Gln Ala Tyr Val
        35                  40                  45

Arg Lys Asp Gly Glu Trp Val Leu Leu Ser Thr Phe Leu Gly Gly His
    50                  55                  60

His His His His His Ser Ala Trp Ser His Pro Gln Phe Glu Lys
65                  70                  75
```

<210> SEQ ID NO 94
<211> LENGTH: 79
<212> TYPE: PRT
<213> ORGANISM: Artificial Sequence
<220> FEATURE:
<223> OTHER INFORMATION: Cysteine ring domain

<400> SEQUENCE: 94

```
Cys Cys Ser Ser Ala Glu Lys Cys Cys Thr Thr Thr Gly Ile Cys Cys
1               5                   10                  15

Thr Thr Thr Asn Ile Cys Cys Thr Thr Gly Gly Leu Val Pro Arg Gly
            20                  25                  30

Ser Gly Gly Tyr Ile Pro Glu Ala Pro Arg Asp Gly Gln Ala Tyr Val
        35                  40                  45

Arg Lys Asp Gly Glu Trp Val Leu Leu Ser Thr Phe Leu Gly Gly His
    50                  55                  60

His His His His His Ser Ala Trp Ser His Pro Gln Phe Glu Lys
65                  70                  75
```

<210> SEQ ID NO 95
<211> LENGTH: 86
<212> TYPE: PRT
<213> ORGANISM: Artificial Sequence
<220> FEATURE:
<223> OTHER INFORMATION: Cysteine ring domain

<400> SEQUENCE: 95

```
Ile Leu Ser Ser Ala Glu Lys Cys Cys Thr Thr Thr Gly Ile Cys Cys
1               5                   10                  15

Thr Thr Val Asn Ala Cys Cys Ser Thr Thr Asn Ile Cys Cys Thr Thr
            20                  25                  30

Gly Gly Leu Val Pro Arg Gly Ser Gly Gly Tyr Ile Pro Glu Ala Pro
        35                  40                  45

Arg Asp Gly Gln Ala Tyr Val Arg Lys Asp Gly Glu Trp Val Leu Leu
    50                  55                  60

Ser Thr Phe Leu Gly Gly His His His His His His Ser Ala Trp Ser
65                  70                  75                  80

His Pro Gln Phe Glu Lys
                85
```

<210> SEQ ID NO 96
<211> LENGTH: 86
<212> TYPE: PRT
<213> ORGANISM: Artificial Sequence
<220> FEATURE:
<223> OTHER INFORMATION: Cysteine ring domain

<400> SEQUENCE: 96

```
Cys Cys Ser Ser Ala Glu Lys Cys Cys Thr Thr Thr Gly Ile Cys Cys
1               5                   10                  15

Thr Thr Val Asn Ala Cys Cys Ser Thr Thr Asn Ile Cys Cys Thr Thr
            20                  25                  30

Gly Gly Leu Val Pro Arg Gly Ser Gly Gly Tyr Ile Pro Glu Ala Pro
        35                  40                  45

Arg Asp Gly Gln Ala Tyr Val Arg Lys Asp Gly Glu Trp Val Leu Leu
    50                  55                  60

Ser Thr Phe Leu Gly Gly His His His His His His Ser Ala Trp Ser
65                  70                  75                  80
```

```
His Pro Gln Phe Glu Lys
                85


<210> SEQ ID NO 97
<211> LENGTH: 79
<212> TYPE: PRT
<213> ORGANISM: Artificial Sequence
<220> FEATURE:
<223> OTHER INFORMATION: Cysteine ring domain

<400> SEQUENCE: 97

Ile Leu His Asn Val Asn Ala Cys Cys Ser Thr Thr Asn Ile Cys Cys
1               5                   10                  15

Thr Thr Thr Asn Ile Cys Cys Thr Thr Gly Gly Leu Val Pro Arg Gly
            20                  25                  30

Ser Gly Gly Tyr Ile Pro Glu Ala Pro Arg Asp Gly Gln Ala Tyr Val
        35                  40                  45

Arg Lys Asp Gly Glu Trp Val Leu Leu Ser Thr Phe Leu Gly Gly His
    50                  55                  60

His His His His His Ser Ala Trp Ser His Pro Gln Phe Glu Lys
65                  70                  75


<210> SEQ ID NO 98
<211> LENGTH: 79
<212> TYPE: PRT
<213> ORGANISM: Artificial Sequence
<220> FEATURE:
<223> OTHER INFORMATION: Cysteine ring domain

<400> SEQUENCE: 98

Cys Cys His Asn Val Asn Ala Cys Cys Ser Thr Thr Asn Ile Cys Cys
1               5                   10                  15

Thr Thr Thr Asn Ile Cys Cys Thr Thr Gly Gly Leu Val Pro Arg Gly
            20                  25                  30

Ser Gly Gly Tyr Ile Pro Glu Ala Pro Arg Asp Gly Gln Ala Tyr Val
        35                  40                  45

Arg Lys Asp Gly Glu Trp Val Leu Leu Ser Thr Phe Leu Gly Gly His
    50                  55                  60

His His His His His Ser Ala Trp Ser His Pro Gln Phe Glu Lys
65                  70                  75


<210> SEQ ID NO 99
<211> LENGTH: 86
<212> TYPE: PRT
<213> ORGANISM: Artificial Sequence
<220> FEATURE:
<223> OTHER INFORMATION: Cysteine ring domain

<400> SEQUENCE: 99

Ile Leu His Asn Val Asn Ala Cys Cys Ser Thr Thr Asn Ile Cys Cys
1               5                   10                  15

Thr Thr Val Asn Ala Cys Cys Ser Thr Thr Asn Ile Cys Cys Thr Thr
            20                  25                  30

Gly Gly Leu Val Pro Arg Gly Ser Gly Gly Tyr Ile Pro Glu Ala Pro
        35                  40                  45

Arg Asp Gly Gln Ala Tyr Val Arg Lys Asp Gly Glu Trp Val Leu Leu
    50                  55                  60

Ser Thr Phe Leu Gly Gly His His His His His His Ser Ala Trp Ser
65                  70                  75                  80

His Pro Gln Phe Glu Lys
```

85

<210> SEQ ID NO 100
<211> LENGTH: 86
<212> TYPE: PRT
<213> ORGANISM: Artificial Sequence
<220> FEATURE:
<223> OTHER INFORMATION: Cysteine ring domain

<400> SEQUENCE: 100

Cys Cys His Asn Val Asn Ala Cys Cys Ser Thr Thr Asn Ile Cys Cys
1 5 10 15

Thr Thr Val Asn Ala Cys Cys Ser Thr Thr Asn Ile Cys Cys Thr Thr
20 25 30

Gly Gly Leu Val Pro Arg Gly Ser Gly Gly Tyr Ile Pro Glu Ala Pro
35 40 45

Arg Asp Gly Gln Ala Tyr Val Arg Lys Asp Gly Glu Trp Val Leu Leu
50 55 60

Ser Thr Phe Leu Gly Gly His His His His His His Ser Ala Trp Ser
65 70 75 80

His Pro Gln Phe Glu Lys
85

<210> SEQ ID NO 101
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 101

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ala Asp Gly Pro Ser Leu
35 40 45

Ile Lys Thr Glu Leu Asp Leu Thr Lys Ser Ala Leu Arg Glu Leu Arg
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Cys Gly Val Ala Ile Ala Lys Thr Ile Arg Leu
100 105 110

Glu Ser Glu Val Thr Ala Ile Lys Asn Ala Leu Lys Lys Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Asp Ile Ala Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Cys Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465

<210> SEQ ID NO 102
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 102

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

```
Ala Ala Ala Val Thr Cys Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Cys Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465
```

<210> SEQ ID NO 103
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 103

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ser Asp Gly Pro Ser Leu
35 40 45

Ile Lys Thr Glu Leu Asp Leu Thr Lys Ser Ala Leu Arg Glu Leu Lys
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Cys Gly Val Ala Ile Ala Lys Thr Ile Arg Leu
100 105 110

Glu Ser Glu Val Thr Ala Ile Lys Asn Ala Leu Lys Thr Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Asp Ile Asp Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Thr Val Gln Leu Pro
245 250 255

Ile Phe Gly Val Ile Asp Thr Pro Cys Trp Ile Val Lys Ala Ala Pro
260 265 270

Ser Cys Ser Glu Lys Lys Gly Asn Tyr Ala Cys Leu Leu Arg Glu Asp
275 280 285

Gln Gly Trp Tyr Cys Gln Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Asn Lys Gly Cys Ser Tyr Ile Thr Asn Gln Asp Ala Asp Thr Val
385 390 395 400

Thr Ile Asp Asn Thr Val Tyr Cys Leu Ser Lys Val Glu Gly Glu Gln

```
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 104
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 104

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Lys
    50                  55                  60

Pro Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Cys Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ala Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
```

```
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Cys Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 105
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 105

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Cys Gly Ile Ala Ile Ala Lys Thr Ile Arg Leu
            100                 105                 110

Glu Ser Glu Val Asn Ala Ile Lys Gly Ala Leu Lys Gln Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Arg Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
```

```
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asn Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Trp Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Cys Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu
465


<210> SEQ ID NO 106
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 106

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
```

-continued

```
65                  70                  75                  80

Arg Gln Ser Arg Phe Val Leu Gly Ala Ile Ala Leu Gly Val Cys Thr
                85                  90                  95

Ala Ala Ala Val Thr Cys Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Cys Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465
```

<210> SEQ ID NO 107

<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 107

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Cys Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Lys Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380
```

```
Leu Pro Lys Gly Cys Ser Tyr Ile Thr Asn Gln Asp Ala Asp Thr Val
385                 390                 395                 400

Thr Ile Asp Asn Thr Val Tyr Cys Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu
465
```

<210> SEQ ID NO 108
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 108

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Cys Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270
```

Ser Cys Ser Gly Lys Lys Gly Asn Tyr Ala Cys Leu Leu Arg Glu Asp
275 280 285

Gln Gly Trp Tyr Cys Gln Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Asn Lys Gly Cys Ser Tyr Ile Thr Asn Gln Asp Ala Asp Thr Val
385 390 395 400

Thr Ile Asp Asn Thr Val Tyr Gln Leu Cys Lys Val Glu Gly Glu Gln
405 410 415

His Val Ile Lys Gly Arg Pro Val Ser Ser Ser Phe Asp Pro Val Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Arg Ile Leu Ser
450 455 460

Ser Ala Glu
465

<210> SEQ ID NO 109
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 109

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ser Asp Gly Pro Ser Leu
35 40 45

Ile Lys Thr Glu Leu Asp Leu Thr Lys Ser Ala Leu Arg Glu Leu Lys
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Cys Gly Val Ala Ile Ala Lys Thr Ile Arg Leu
100 105 110

Glu Ser Glu Val Thr Ala Ile Lys Asn Ala Leu Lys Thr Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

```
Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Cys Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 110
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 110

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45
```

```
Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Cys Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Thr Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Cys Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460
```

Ser Ala Glu
465

<210> SEQ ID NO 111
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 111

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ala Asp Gly Pro Ser Leu
35 40 45

Ile Lys Thr Glu Leu Asp Leu Thr Lys Ser Ala Leu Arg Glu Leu Lys
50 55 60

Pro Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Cys Gly Val Ala Ile Ala Lys Thr Ile Arg Leu
100 105 110

Glu Ser Glu Val Thr Ala Ile Lys Asn Ala Leu Lys Lys Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Asp Ile Asp Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ala Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Val Lys Ala Ala Pro
260 265 270

Ser Cys Ser Glu Lys Lys Gly Asn Tyr Ala Cys Leu Leu Arg Glu Asp
275 280 285

Gln Gly Trp Tyr Cys Gln Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile
340 345 350

```
Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Cys Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 112
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 112

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Cys Gly Ile Ala Ile Ala Lys Thr Ile Arg Leu
            100                 105                 110

Glu Ser Glu Val Asn Ala Ile Lys Gly Ala Leu Lys Gln Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Arg Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240
```

Leu Ile Gly Val Tyr Gly Ser Ser Val Ile Tyr Met Val Gln Leu Pro
245 250 255

Ile Phe Gly Val Ile Asp Thr Pro Cys Trp Ile Ile Lys Ala Ala Pro
260 265 270

Ser Cys Ser Glu Lys Asn Gly Asn Tyr Ala Cys Leu Leu Arg Glu Asp
275 280 285

Gln Gly Trp Tyr Cys Lys Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Arg Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Trp Val Gly Ile Ile Lys Gln
370 375 380

Leu Pro Lys Gly Cys Ser Tyr Ile Thr Asn Gln Asp Ala Asp Thr Val
385 390 395 400

Thr Ile Asp Asn Thr Val Tyr Gln Leu Cys Lys Val Glu Gly Glu Gln
405 410 415

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Lys Ile Leu Asn
450 455 460

Ser Ala Glu
465

<210> SEQ ID NO 113
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 113

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ala Asp Gly Pro Ser Leu
35 40 45

Ile Lys Thr Glu Leu Asp Leu Thr Lys Ser Ala Leu Arg Glu Leu Arg
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Cys Gly Val Ala Ile Ala Lys Thr Ile Arg Leu
100 105 110

Glu Ser Glu Val Thr Ala Ile Lys Asn Ala Leu Lys Lys Thr Asn Glu
115 120 125

```
Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Cys Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 114
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 114

Leu Lys Glu Ser Tyr Leu Glu Glu Ser Cys Ser Thr Ile Thr Glu Gly
1               5                   10                  15
```

-continued

```
Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Cys Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Lys Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Cys Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
```

```
        435                 440                 445

Ile Glu Asn Ser Gln Ala Leu Val Asp Gln Ser Asn Lys Ile Leu Asn
    450                 455                 460

Ser Ala Glu
465
```

<210> SEQ ID NO 115
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 115

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Pro Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
```

```
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 116
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 116

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Pro Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
```

```
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 117
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 117

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
```

```
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Pro Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Thr Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465
```

<210> SEQ ID NO 118
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 118

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ala Asp Gly Pro Ser Leu
35 40 45

Ile Lys Thr Glu Leu Asp Leu Thr Lys Ser Ala Leu Arg Glu Leu Lys
50 55 60

Pro Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Val Ala Ile Ala Lys Thr Ile Arg Leu
100 105 110

Glu Ser Glu Val Thr Ala Ile Lys Asn Ala Leu Lys Lys Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Pro Ile Asp Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ala Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Val Lys Ala Ala Pro
260 265 270

Ser Cys Ser Glu Lys Lys Gly Asn Tyr Ala Cys Leu Leu Arg Glu Asp
275 280 285

Gln Gly Trp Tyr Cys Gln Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Asn Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Val Lys
420 425 430

Phe Pro Glu Asp Gln Phe Asn Val Ala Leu Asp Gln Val Phe Glu Asn
435 440 445

Ile Glu Asn Ser Gln Ala Leu Val Asp Gln Ser Asn Arg Ile Leu Ser
450 455 460

Ser Ala Glu
465

<210> SEQ ID NO 119
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 119

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Thr Asp Gly Pro Ser Leu
35 40 45

Ile Lys Thr Glu Leu Asp Leu Thr Lys Ser Ala Leu Arg Glu Leu Lys
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Ile Ala Ile Ala Lys Thr Ile Arg Leu
100 105 110

Glu Ser Glu Val Asn Ala Ile Lys Gly Ala Leu Lys Gln Thr Asn Glu
115 120 125

Ala Val Ser Thr Leu Gly Asn Gly Val Arg Val Leu Ala Phe Ala Val
130 135 140

Arg Glu Leu Lys Glu Phe Val Ser Lys Asn Leu Thr Ser Ala Leu Asn
145 150 155 160

Arg Asn Lys Cys Pro Ile Ala Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Tyr Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Ile Lys Ala Ala Pro
260 265 270

Ser Cys Ser Glu Lys Asn Gly Asn Tyr Ala Cys Leu Leu Arg Glu Asp
275 280 285

Gln Gly Trp Tyr Cys Lys Asn Ala Gly Ser Thr Val Tyr Tyr Pro Asn
290 295 300

```
Glu Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Trp Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu
465


<210> SEQ ID NO 120
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 120

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Pro Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190
```

```
Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 121
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 121

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80
```

Arg Gln Ser Arg Phe Val Leu Gly Ala Ile Ala Leu Gly Val Cys Thr
85 90 95

Ala Ala Ala Val Thr Ala Gly Ile Ala Ile Ala Lys Thr Ile Arg Leu
100 105 110

Glu Ser Glu Val Asn Ala Ile Lys Gly Ala Leu Lys Thr Thr Asn Glu
115 120 125

Ala Val Ser Thr Leu Gly Asn Gly Val Arg Val Leu Ala Phe Ala Val
130 135 140

Arg Glu Leu Lys Glu Phe Val Ser Lys Asn Leu Thr Ser Ala Leu Asn
145 150 155 160

Lys Asn Lys Cys Pro Ile Ala Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Tyr Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Ile Lys Ala Ala Pro
260 265 270

Ser Cys Ser Glu Lys Asp Gly Asn Tyr Ala Cys Leu Leu Arg Glu Asp
275 280 285

Gln Gly Trp Tyr Cys Lys Asn Ala Gly Ser Thr Val Tyr Tyr Pro Asn
290 295 300

Lys Lys Asp Cys Glu Thr Arg Gly Asp His Val Phe Cys Asp Thr Ala
305 310 315 320

Cys Gly Ile Asn Val Ala Glu Gln Ser Arg Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Pro Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Lys Ile Leu Asn
450 455 460

Ser Ala Glu
465

<210> SEQ ID NO 122
<211> LENGTH: 467

<212> TYPE: PRT
<213> ORGANISM: Artificial Sequence
<220> FEATURE:
<223> OTHER INFORMATION: recombinant Metapneumovirus F protein

<400> SEQUENCE: 122

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Pro Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380
```

Leu Asn Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Val Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Arg Ile Leu Ser
450 455 460

Ser Ala Glu
465

<210> SEQ ID NO 123
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 123

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ser Asp Gly Pro Ser Leu
35 40 45

Ile Lys Thr Glu Leu Asp Leu Thr Lys Ser Ala Leu Arg Glu Leu Lys
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Val Ala Ile Ala Lys Thr Ile Arg Leu
100 105 110

Glu Ser Glu Val Thr Ala Ile Lys Asn Ala Leu Lys Thr Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Asp Ile Pro Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Val Lys Ala Ala Pro
260 265 270

```
Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 124
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 124

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160
```

-continued

```
Lys Asn Lys Cys Asp Ile Pro Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Thr Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 125
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 125

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45
```

```
Ile Lys Thr Glu Leu Asp Leu Thr Lys Ser Ala Leu Arg Glu Leu Lys
    50                  55                  60

Pro Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Pro Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ala Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
```

465

<210> SEQ ID NO 126
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 126

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Thr Asp Gly Pro Ser Leu
35 40 45

Ile Lys Thr Glu Leu Asp Leu Thr Lys Ser Ala Leu Arg Glu Leu Lys
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Ile Ala Ile Ala Lys Thr Ile Arg Leu
100 105 110

Glu Ser Glu Val Asn Ala Ile Lys Gly Ala Leu Lys Gln Thr Asn Glu
115 120 125

Ala Val Ser Thr Leu Gly Asn Gly Val Arg Val Leu Ala Phe Ala Val
130 135 140

Arg Glu Leu Lys Glu Phe Val Ser Lys Asn Leu Thr Ser Ala Leu Asn
145 150 155 160

Arg Asn Lys Cys Asp Ile Pro Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Tyr Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Ile Lys Ala Ala Pro
260 265 270

Ser Cys Ser Glu Lys Asn Gly Asn Tyr Ala Cys Leu Leu Arg Glu Asp
275 280 285

Gln Gly Trp Tyr Cys Lys Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Arg Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys

-continued 355 360 365

Gly Val Ser Cys Ser Ile Gly Ser Asn Trp Val Gly Ile Ile Lys Gln
370 375 380

Leu Pro Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Lys Ile Leu Asn
450 455 460

Ser Ala Glu
465

<210> SEQ ID NO 127
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 127

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ala Asp Gly Pro Ser Leu
35 40 45

Ile Lys Thr Glu Leu Asp Leu Thr Lys Ser Ala Leu Arg Glu Leu Arg
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Val Ala Ile Ala Lys Thr Ile Arg Leu
100 105 110

Glu Ser Glu Val Thr Ala Ile Lys Asn Ala Leu Lys Lys Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Asp Ile Pro Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ser Ala Gly Gln Ile Lys
210 215 220

Leu Met Leu Glu Asn Arg Ala Met Val Arg Arg Lys Gly Phe Gly Phe
225 230 235 240

Leu Ile Gly Val Tyr Gly Ser Ser Val Ile Tyr Met Val Gln Leu Pro

```
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 128
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 128

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Phe Ala Val
```

130 135 140

Arg Glu Leu Lys Glu Phe Val Ser Lys Asn Leu Thr Ser Ala Leu Asn
145 150 155 160

Lys Asn Lys Cys Asp Ile Pro Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Tyr Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Ile Lys Ala Ala Pro
260 265 270

Ser Cys Ser Glu Lys Asp Gly Asn Tyr Ala Cys Leu Leu Arg Glu Asp
275 280 285

Gln Gly Trp Tyr Cys Lys Asn Ala Gly Ser Thr Val Tyr Tyr Pro Asn
290 295 300

Lys Lys Asp Cys Glu Thr Arg Gly Asp His Val Phe Cys Asp Thr Ala
305 310 315 320

Cys Gly Ile Asn Val Ala Glu Gln Ser Arg Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Pro Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Lys Ile Leu Asn
450 455 460

Ser Ala Glu
465

<210> SEQ ID NO 129
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 129

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu

```
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Pro Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445
```

Ile Glu Asn Ser Gln Ala Leu Val Asp Gln Ser Asn Arg Ile Leu Ser
    450                 455                 460

Ser Ala Glu
465

<210> SEQ ID NO 130
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 130

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Pro Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

```
Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 131
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 131

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Pro Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220
```

```
Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Thr Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 132
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 132

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Lys
    50                  55                  60

Pro Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110
```

```
Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Pro Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ala Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465
```

<210> SEQ ID NO 133
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 133

-continued

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Gln Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Arg Asn Lys Cys Asp Ile Ala Pro Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asn Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Trp Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415
```

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Lys Ile Leu Asn
450 455 460

Ser Ala Glu
465

<210> SEQ ID NO 134
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 134

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ala Asp Gly Pro Ser Leu
35 40 45

Ile Lys Thr Glu Leu Asp Leu Thr Lys Ser Ala Leu Arg Glu Leu Arg
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Val Ala Ile Ala Lys Thr Ile Arg Leu
100 105 110

Glu Ser Glu Val Thr Ala Ile Lys Asn Ala Leu Lys Lys Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Asp Ile Ala Pro Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ser Ala Gly Gln Ile Lys
210 215 220

Leu Met Leu Glu Asn Arg Ala Met Val Arg Arg Lys Gly Phe Gly Phe
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Val Lys Ala Ala Pro
260 265 270

Ser Cys Ser Gly Lys Lys Gly Asn Tyr Ala Cys Leu Leu Arg Glu Asp
275 280 285

Gln Gly Trp Tyr Cys Gln Asn Ala Gly Ser Thr Val Tyr Tyr Pro Asn
290 295 300

-continued

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Asn Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Val Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Arg Ile Leu Ser
450 455 460

Ser Ala Glu
465

<210> SEQ ID NO 135
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 135

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Thr Asp Gly Pro Ser Leu
35 40 45

Ile Lys Thr Glu Leu Asp Leu Thr Lys Ser Ala Leu Arg Glu Leu Lys
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Ile Ala Ile Ala Lys Thr Ile Arg Leu
100 105 110

Glu Ser Glu Val Asn Ala Ile Lys Gly Ala Leu Lys Thr Thr Asn Glu
115 120 125

Ala Val Ser Thr Leu Gly Asn Gly Val Arg Val Leu Ala Phe Ala Val
130 135 140

Arg Glu Leu Lys Glu Phe Val Ser Lys Asn Leu Thr Ser Ala Leu Asn
145 150 155 160

Lys Asn Lys Cys Asp Ile Ala Pro Leu Lys Met Ala Val Ser Phe Ser
165 170 175

Gln Phe Asn Arg Arg Phe Leu Asn Val Val Arg Gln Phe Ser Asp Asn
180 185 190

```
Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Lys Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu
465


<210> SEQ ID NO 136
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 136

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80
```

-continued

```
Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465
```

<210> SEQ ID NO 137
<211> LENGTH: 467
<212> TYPE: PRT

<213> ORGANISM: Artificial Sequence
<220> FEATURE:
<223> OTHER INFORMATION: recombinant Metapneumovirus F protein

<400> SEQUENCE: 137

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
```

```
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 138
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 138

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Thr Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
```

```
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 139
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 139

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Ala Asp Gly Pro Ser Leu
        35                  40                  45

Ile Lys Thr Glu Leu Asp Leu Thr Lys Ser Ala Leu Arg Glu Leu Lys
    50                  55                  60

Pro Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
```

165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ala Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Val Lys Ala Ala Pro
260 265 270

Ser Cys Ser Glu Lys Lys Gly Asn Tyr Ala Cys Leu Leu Arg Glu Asp
275 280 285

Gln Gly Trp Tyr Cys Gln Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Asn Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Val Lys
420 425 430

Phe Pro Glu Asp Gln Phe Asn Val Ala Leu Asp Gln Val Phe Glu Asn
435 440 445

Ile Glu Asn Ser Gln Ala Leu Val Asp Gln Ser Asn Arg Ile Leu Ser
450 455 460

Ser Ala Glu
465

<210> SEQ ID NO 140
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 140

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Gln Leu Thr Cys Thr Asp Gly Pro Ser Leu
35 40 45

Ile Lys Thr Glu Leu Asp Leu Thr Lys Ser Ala Leu Arg Glu Leu Lys

-continued

```
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Gln Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Arg Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asn Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Trp Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu
465
```

<210> SEQ ID NO 141
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 141

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365
```

```
Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465
```

<210> SEQ ID NO 142
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 142

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255
```

```
Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Lys Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu
465


<210> SEQ ID NO 143
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 143

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140
```

```
Arg Glu Leu Lys Asp Phe Val Ser Lys Gln Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465
```

<210> SEQ ID NO 144
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 144

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30
```

```
Glu Val Gly Asp Val Glu Gln Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Gln Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445
```

-continued

```
Ile Glu Asn Ser Gln Ala Leu Val Asp Gln Ser Asn Arg Ile Leu Ser
    450                 455                 460

Ser Ala Glu
465


<210> SEQ ID NO 145
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 145

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Gln Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Thr Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335
```

```
Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 146
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 146

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Ala Asp Gly Pro Ser Leu
        35                  40                  45

Ile Lys Thr Glu Leu Asp Leu Thr Lys Ser Ala Leu Arg Glu Leu Lys
    50                  55                  60

Pro Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Gln Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ala Ala Gly Gln Ile Lys
    210                 215                 220
```

```
Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 147
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 147

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110
```

Glu Ser Glu Val Asn Ala Ile Lys Gly Ala Leu Lys Gln Thr Asn Glu
115 120 125

Ala Val Ser Thr Leu Gly Asn Gly Val Arg Val Leu Ala Phe Ala Val
130 135 140

Arg Glu Leu Lys Glu Phe Val Ser Lys Gln Leu Thr Ser Ala Leu Asn
145 150 155 160

Arg Asn Lys Cys Asp Ile Ala Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Tyr Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Ile Lys Ala Ala Pro
260 265 270

Ser Cys Ser Glu Lys Asn Gly Asn Tyr Ala Cys Leu Leu Arg Glu Asp
275 280 285

Gln Gly Trp Tyr Cys Lys Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Arg Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Trp Val Gly Ile Ile Lys Gln
370 375 380

Leu Pro Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Lys Ile Leu Asn
450 455 460

Ser Ala Glu
465

<210> SEQ ID NO 148
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 148

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Gln Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
```

```
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 149
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 149

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Gln Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Gln Leu Thr Ser Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Lys Lys Asp Cys Glu Thr Arg Gly Asp His Val Phe Cys Asp Thr Ala
```

```
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu
465


<210> SEQ ID NO 150
<211> LENGTH: 8
<212> TYPE: PRT
<213> ORGANISM: Artificial Sequence
<220> FEATURE:
<223> OTHER INFORMATION: oligomerization peptide

<400> SEQUENCE: 150

Phe Leu Gly Phe Leu Leu Gly Val
1               5


<210> SEQ ID NO 151
<211> LENGTH: 30
<212> TYPE: PRT
<213> ORGANISM: Artificial Sequence
<220> FEATURE:
<223> OTHER INFORMATION: recombinant Metapneumovirus F protein

<400> SEQUENCE: 151

Gly Gly Gly Gly Ser Ser Gly Gly Ser Ser Gly Gly Phe Leu Gly Phe
1               5                   10                  15

Leu Leu Gly Val Gly Ser Ala Ile Ala Ser Gly Val Ala Val
            20                  25                  30


<210> SEQ ID NO 152
<211> LENGTH: 16
<212> TYPE: PRT
<213> ORGANISM: Artificial Sequence
<220> FEATURE:
<223> OTHER INFORMATION: oligomerization peptide

<400> SEQUENCE: 152

Gly Gly Gly Gly Ser Ser Gly Gly Phe Leu Gly Phe Leu Leu Gly Val
1               5                   10                  15


<210> SEQ ID NO 153
<211> LENGTH: 28
<212> TYPE: PRT
<213> ORGANISM: Artificial Sequence
```

```
<220> FEATURE:
<223> OTHER INFORMATION: oligomerization peptide

<400> SEQUENCE: 153

Gly Gly Gly Gly Ser Ser Gly Gly Ser Ser Gly Gly Ser Ser Gly Gly
1               5                   10                  15

Ser Ser Gly Gly Phe Leu Gly Phe Leu Leu Gly Val
            20                  25


<210> SEQ ID NO 154
<211> LENGTH: 14
<212> TYPE: PRT
<213> ORGANISM: Artificial Sequence
<220> FEATURE:
<223> OTHER INFORMATION: oligomerization peptide

<400> SEQUENCE: 154

Gly Gly Gly Ser Gly Gly Phe Leu Gly Phe Leu Leu Gly Val
1               5                   10


<210> SEQ ID NO 155
<211> LENGTH: 12
<212> TYPE: PRT
<213> ORGANISM: Artificial Sequence
<220> FEATURE:
<223> OTHER INFORMATION: oligomerization peptide

<400> SEQUENCE: 155

Gly Gly Gly Gly Phe Leu Gly Phe Leu Leu Gly Val
1               5                   10


<210> SEQ ID NO 156
<211> LENGTH: 26
<212> TYPE: PRT
<213> ORGANISM: Artificial Sequence
<220> FEATURE:
<223> OTHER INFORMATION: oligomerization peptide

<400> SEQUENCE: 156

Gly Gly Gly Gly Ser Ser Gly Gly Phe Leu Gly Phe Leu Leu Gly Val
1               5                   10                  15

Gly Ser Phe Leu Gly Phe Leu Leu Gly Val
            20                  25


<210> SEQ ID NO 157
<211> LENGTH: 528
<212> TYPE: PRT
<213> ORGANISM: Artificial Sequence
<220> FEATURE:
<223> OTHER INFORMATION: recombinant Metapneumovirus F protein

<400> SEQUENCE: 157

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
```

```
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Phe Leu
            500                 505                 510
```

Gly Phe Leu Leu Gly Val Gly Ser Ala Ile Ala Ser Gly Val Ala Val
515 520 525

<210> SEQ ID NO 158
<211> LENGTH: 528
<212> TYPE: PRT
<213> ORGANISM: Artificial Sequence
<220> FEATURE:
<223> OTHER INFORMATION: recombinant Metapneumovirus F protein

<400> SEQUENCE: 158

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ser Asp Gly Pro Ser Leu
35 40 45

Ile Lys Thr Glu Leu Asp Leu Thr Lys Ser Ala Leu Arg Glu Leu Lys
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Val Ala Ile Ala Lys Thr Ile Arg Leu
100 105 110

Glu Ser Glu Val Thr Ala Ile Lys Asn Ala Leu Lys Thr Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Asp Ile Asp Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Val Lys Ala Ala Pro
260 265 270

Ser Cys Ser Gly Lys Lys Gly Asn Tyr Ala Cys Leu Leu Arg Glu Asp
275 280 285

Gln Gly Trp Tyr Cys Gln Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile
340 345 350

```
Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Phe Leu
            500                 505                 510

Gly Phe Leu Leu Gly Val Gly Ser Ala Ile Ala Ser Gly Val Ala Val
        515                 520                 525
```

<210> SEQ ID NO 159
<211> LENGTH: 528
<212> TYPE: PRT
<213> ORGANISM: Artificial Sequence
<220> FEATURE:
<223> OTHER INFORMATION: recombinant Metapneumovirus F protein

<400> SEQUENCE: 159

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190
```

```
Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Thr Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Phe Leu
            500                 505                 510

Gly Phe Leu Leu Gly Val Gly Ser Ala Ile Ala Ser Gly Val Ala Val
        515                 520                 525
```

<210> SEQ ID NO 160
<211> LENGTH: 528
<212> TYPE: PRT
<213> ORGANISM: Artificial Sequence
<220> FEATURE:
<223> OTHER INFORMATION: recombinant Metapneumovirus F protein

<400> SEQUENCE: 160

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30
```

```
Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Lys
    50                  55                  60

Pro Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ala Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Asn
        435                 440                 445
```

```
Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Phe Leu
            500                 505                 510

Gly Phe Leu Leu Gly Val Gly Ser Ala Ile Ala Ser Gly Val Ala Val
        515                 520                 525


<210> SEQ ID NO 161
<211> LENGTH: 528
<212> TYPE: PRT
<213> ORGANISM: Artificial Sequence
<220> FEATURE:
<223> OTHER INFORMATION: recombinant Metapneumovirus F protein

<400> SEQUENCE: 161

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Gln Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Arg Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asn Gly Asn Tyr Ala Cys Leu Leu Arg Glu Asp
        275                 280                 285
```

```
Gln Gly Trp Tyr Cys Lys Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Trp Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Phe Leu
            500                 505                 510

Gly Phe Leu Leu Gly Val Gly Ser Ala Ile Ala Ser Gly Val Ala Val
        515                 520                 525


<210> SEQ ID NO 162
<211> LENGTH: 528
<212> TYPE: PRT
<213> ORGANISM: Artificial Sequence
<220> FEATURE:
<223> OTHER INFORMATION: recombinant Metapneumovirus F protein

<400> SEQUENCE: 162

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125
```

```
Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Phe Leu
            500                 505                 510

Gly Phe Leu Leu Gly Val Gly Ser Ala Ile Ala Ser Gly Val Ala Val
        515                 520                 525
```

<210> SEQ ID NO 163
<211> LENGTH: 528
<212> TYPE: PRT

<213> ORGANISM: Artificial Sequence
<220> FEATURE:
<223> OTHER INFORMATION: recombinant Metapneumovirus F protein

<400> SEQUENCE: 163

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Lys Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
```

385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Lys Ile Leu Asn
450 455 460

Ser Ala Glu Ser Ala Ile Gly Gly Tyr Ile Pro Glu Ala Pro Arg Asp
465 470 475 480

Gly Gln Ala Tyr Val Arg Lys Asp Gly Glu Trp Val Leu Leu Ser Thr
485 490 495

Phe Leu Gly Gly Gly Gly Ser Ser Gly Gly Ser Ser Gly Gly Phe Leu
500 505 510

Gly Phe Leu Leu Gly Val Gly Ser Ala Ile Ala Ser Gly Val Ala Val
515 520 525

<210> SEQ ID NO 164
<211> LENGTH: 514
<212> TYPE: PRT
<213> ORGANISM: Artificial Sequence
<220> FEATURE:
<223> OTHER INFORMATION: recombinant Metapneumovirus F protein

<400> SEQUENCE: 164

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ala Asp Gly Pro Ser Leu
35 40 45

Ile Lys Thr Glu Leu Asp Leu Thr Lys Ser Ala Leu Arg Glu Leu Arg
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Val Ala Ile Ala Lys Thr Ile Arg Leu
100 105 110

Glu Ser Glu Val Thr Ala Ile Lys Asn Ala Leu Lys Lys Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Asp Ile Ala Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ser Ala Gly Gln Ile Lys
210 215 220

Leu Met Leu Glu Asn Arg Ala Met Val Arg Arg Lys Gly Phe Gly Phe

```
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Phe Leu Gly Phe Leu Leu
            500                 505                 510

Gly Val


<210> SEQ ID NO 165
<211> LENGTH: 514
<212> TYPE: PRT
<213> ORGANISM: Artificial Sequence
<220> FEATURE:
<223> OTHER INFORMATION: recombinant Metapneumovirus F protein

<400> SEQUENCE: 165

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80
```

```
Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495
```

Phe Leu Gly Gly Gly Gly Ser Ser Gly Gly Phe Leu Gly Phe Leu Leu
500 505 510

Gly Val

<210> SEQ ID NO 166
<211> LENGTH: 514
<212> TYPE: PRT
<213> ORGANISM: Artificial Sequence
<220> FEATURE:
<223> OTHER INFORMATION: recombinant Metapneumovirus F protein

<400> SEQUENCE: 166

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ser Asp Gly Pro Ser Leu
35 40 45

Ile Lys Thr Glu Leu Asp Leu Thr Lys Ser Ala Leu Arg Glu Leu Lys
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Val Ala Ile Ala Lys Thr Ile Arg Leu
100 105 110

Glu Ser Glu Val Thr Ala Ile Lys Asn Ala Leu Lys Thr Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Asp Ile Asp Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Thr Val Gln Leu Pro
245 250 255

Ile Phe Gly Val Ile Asp Thr Pro Cys Trp Ile Val Lys Ala Ala Pro
260 265 270

Ser Cys Ser Glu Lys Lys Gly Asn Tyr Ala Cys Leu Leu Arg Glu Asp
275 280 285

Gln Gly Trp Tyr Cys Gln Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile

```
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Phe Leu Gly Phe Leu Leu
            500                 505                 510

Gly Val


<210> SEQ ID NO 167
<211> LENGTH: 514
<212> TYPE: PRT
<213> ORGANISM: Artificial Sequence
<220> FEATURE:
<223> OTHER INFORMATION: recombinant Metapneumovirus F protein

<400> SEQUENCE: 167

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Lys
    50                  55                  60

Pro Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190
```

```
Ala Gly Ile Thr Pro Ala Ile Ser Leu Asp Leu Met Thr Asp Ala Glu
        195                 200                 205

Leu Ala Arg Ala Val Ser Asn Met Pro Thr Ala Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Phe Leu Gly Phe Leu Leu
            500                 505                 510

Gly Val


<210> SEQ ID NO 168
<211> LENGTH: 514
<212> TYPE: PRT
<213> ORGANISM: Artificial Sequence
<220> FEATURE:
<223> OTHER INFORMATION: recombinant Metapneumovirus F protein

<400> SEQUENCE: 168

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30
```

-continued

```
Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Gln Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Arg Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asn Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Trp Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
```

```
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Phe Leu Gly Phe Leu Leu
            500                 505                 510

Gly Val


<210> SEQ ID NO 169
<211> LENGTH: 514
<212> TYPE: PRT
<213> ORGANISM: Artificial Sequence
<220> FEATURE:
<223> OTHER INFORMATION: recombinant Metapneumovirus F protein

<400> SEQUENCE: 169

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300
```

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Asn Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Val Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Arg Ile Leu Ser
450 455 460

Ser Ala Glu Ser Ala Ile Gly Gly Tyr Ile Pro Glu Ala Pro Arg Asp
465 470 475 480

Gly Gln Ala Tyr Val Arg Lys Asp Gly Glu Trp Val Leu Leu Ser Thr
485 490 495

Phe Leu Gly Gly Gly Gly Ser Ser Gly Gly Phe Leu Gly Phe Leu Leu
500 505 510

Gly Val

<210> SEQ ID NO 170
<211> LENGTH: 514
<212> TYPE: PRT
<213> ORGANISM: Artificial Sequence
<220> FEATURE:
<223> OTHER INFORMATION: recombinant Metapneumovirus F protein

<400> SEQUENCE: 170

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Thr Asp Gly Pro Ser Leu
35 40 45

Ile Lys Thr Glu Leu Asp Leu Thr Lys Ser Ala Leu Arg Glu Leu Lys
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Ile Ala Ile Ala Lys Thr Ile Arg Leu
100 105 110

Glu Ser Glu Val Asn Ala Ile Lys Gly Ala Leu Lys Thr Thr Asn Glu
115 120 125

Ala Val Ser Thr Leu Gly Asn Gly Val Arg Val Leu Ala Phe Ala Val
130 135 140

```
Arg Glu Leu Lys Glu Phe Val Ser Lys Asn Leu Thr Ser Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Lys Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Phe Leu Gly Phe Leu Leu
            500                 505                 510

Gly Val
```

<210> SEQ ID NO 171
<211> LENGTH: 526
<212> TYPE: PRT
<213> ORGANISM: Artificial Sequence
<220> FEATURE:
<223> OTHER INFORMATION: recombinant Metapneumovirus F protein

<400> SEQUENCE: 171

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

```
His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Ser Ser
            500                 505                 510

Gly Gly Ser Ser Gly Gly Phe Leu Gly Phe Leu Leu Gly Val
        515                 520                 525


<210> SEQ ID NO 172
<211> LENGTH: 526
<212> TYPE: PRT
<213> ORGANISM: Artificial Sequence
<220> FEATURE:
<223> OTHER INFORMATION: recombinant Metapneumovirus F protein

<400> SEQUENCE: 172

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255
```

```
Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Ser Ser
            500                 505                 510

Gly Gly Ser Ser Gly Gly Phe Leu Gly Phe Leu Leu Gly Val
        515                 520                 525


<210> SEQ ID NO 173
<211> LENGTH: 526
<212> TYPE: PRT
<213> ORGANISM: Artificial Sequence
<220> FEATURE:
<223> OTHER INFORMATION: recombinant Metapneumovirus F protein

<400> SEQUENCE: 173

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95
```

```
Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Thr Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Ser Ser
            500                 505                 510
```

```
Gly Gly Ser Ser Gly Gly Phe Leu Gly Phe Leu Leu Gly Val
        515                 520                 525


<210> SEQ ID NO 174
<211> LENGTH: 526
<212> TYPE: PRT
<213> ORGANISM: Artificial Sequence
<220> FEATURE:
<223> OTHER INFORMATION: recombinant Metapneumovirus F protein

<400> SEQUENCE: 174

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Lys
    50                  55                  60

Pro Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ala Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350
```

```
Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Asn
        435                 440                 445

Ile Glu Asn Ser Gln Ala Leu Val Asp Gln Ser Asn Arg Ile Leu Ser
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Ser Ser
            500                 505                 510

Gly Gly Ser Ser Gly Gly Phe Leu Gly Phe Leu Leu Gly Val
        515                 520                 525


<210> SEQ ID NO 175
<211> LENGTH: 526
<212> TYPE: PRT
<213> ORGANISM: Artificial Sequence
<220> FEATURE:
<223> OTHER INFORMATION: recombinant Metapneumovirus F protein

<400> SEQUENCE: 175

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Gln Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Arg Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190
```

```
Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asn Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Trp Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Ser Ser
            500                 505                 510

Gly Gly Ser Ser Gly Gly Phe Leu Gly Phe Leu Leu Gly Val
        515                 520                 525
```

<210> SEQ ID NO 176
<211> LENGTH: 526
<212> TYPE: PRT
<213> ORGANISM: Artificial Sequence
<220> FEATURE:
<223> OTHER INFORMATION: recombinant Metapneumovirus F protein

<400> SEQUENCE: 176

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30
```

```
Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
```

```
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Ser Ser
            500                 505                 510

Gly Gly Ser Ser Gly Gly Phe Leu Gly Phe Leu Leu Gly Val
        515                 520                 525


<210> SEQ ID NO 177
<211> LENGTH: 526
<212> TYPE: PRT
<213> ORGANISM: Artificial Sequence
<220> FEATURE:
<223> OTHER INFORMATION: recombinant Metapneumovirus F protein

<400> SEQUENCE: 177

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
```

```
    290                 295                 300

Lys Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu Ser Ala Ile Gly Gly Tyr Ile Pro Glu Ala Pro Arg Asp
465                 470                 475                 480

Gly Gln Ala Tyr Val Arg Lys Asp Gly Glu Trp Val Leu Leu Ser Thr
                485                 490                 495

Phe Leu Gly Gly Gly Gly Ser Ser Gly Gly Ser Ser Gly Gly Ser Ser
            500                 505                 510

Gly Gly Ser Ser Gly Gly Phe Leu Gly Phe Leu Leu Gly Val
        515                 520                 525


<210> SEQ ID NO 178
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 178

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
```

130 135 140

Arg Glu Leu Lys Asp Phe Val Ser Lys Asn Leu Thr Arg Ala Leu Asn
145 150 155 160

Lys Asn Lys Cys Asp Ile Ala Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ser Ala Gly Gln Ile Lys
210 215 220

Leu Met Leu Glu Asn Arg Ala Met Val Arg Arg Lys Gly Phe Gly Phe
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Val Lys Ala Ala Pro
260 265 270

Ser Cys Ser Gly Lys Lys Gly Asn Tyr Ala Cys Leu Leu Arg Glu Asp
275 280 285

Gln Gly Trp Tyr Cys Gln Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Asn Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Val Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Arg Ile Leu Ser
450 455 460

Ser Ala Glu
465

<210> SEQ ID NO 179
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 179

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu

```
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Asn
        435                 440                 445
```

```
Ile Glu Asn Ser Gln Ala Leu Val Asp Gln Ser Asn Arg Ile Leu Ser
    450                 455                 460

Ser Ala Glu
465


<210> SEQ ID NO 180
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 180

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Asp Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Thr Val Gln Leu Pro
                245                 250                 255

Ile Phe Gly Val Ile Asp Thr Pro Cys Trp Ile Val Lys Ala Ala Pro
            260                 265                 270

Ser Cys Ser Glu Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335
```

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Asn Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Asn
435 440 445

Ile Glu Asn Ser Gln Ala Leu Val Asp Gln Ser Asn Arg Ile Leu Ser
450 455 460

Ser Ala Glu
465

<210> SEQ ID NO 181
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 181

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Ala Asp Gly Pro Ser Leu
35 40 45

Ile Lys Thr Glu Leu Asp Leu Thr Lys Ser Ala Leu Arg Glu Leu Lys
50 55 60

Pro Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Val Ala Ile Ala Lys Thr Ile Arg Leu
100 105 110

Glu Ser Glu Val Thr Ala Ile Lys Asn Ala Leu Lys Lys Thr Asn Glu
115 120 125

Ala Val Ser Thr Leu Gly Asn Gly Val Arg Val Leu Ala Phe Ala Val
130 135 140

Arg Glu Leu Lys Asp Phe Val Ser Lys Asn Leu Thr Arg Ala Leu Asn
145 150 155 160

Lys Asn Lys Cys Asp Ile Asp Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Asn Met Pro Thr Ala Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Val Lys Ala Ala Pro
260 265 270

Ser Cys Ser Glu Lys Lys Gly Asn Tyr Ala Cys Leu Leu Arg Glu Asp
275 280 285

Gln Gly Trp Tyr Cys Gln Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Lys Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Arg Val Gly Ile Ile Lys Gln
370 375 380

Leu Asn Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Val Lys
420 425 430

Phe Pro Glu Asp Gln Phe Asn Val Ala Leu Asp Gln Val Phe Glu Asn
435 440 445

Ile Glu Asn Ser Gln Ala Leu Val Asp Gln Ser Asn Arg Ile Leu Ser
450 455 460

Ser Ala Glu
465

<210> SEQ ID NO 182
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 182

Leu Lys Glu Ser Tyr Leu Glu Glu Ser Cys Ser Thr Ile Thr Glu Gly
1 5 10 15

Tyr Leu Ser Val Leu Arg Thr Gly Trp Tyr Thr Asn Val Phe Thr Leu
20 25 30

Glu Val Gly Asp Val Glu Asn Leu Thr Cys Thr Asp Gly Pro Ser Leu
35 40 45

Ile Lys Thr Glu Leu Asp Leu Thr Lys Ser Ala Leu Arg Glu Leu Lys
50 55 60

Thr Val Ser Ala Asp Gln Leu Ala Arg Glu Glu Gln Ile Glu Asn Pro
65 70 75 80

Arg Gln Ser Arg Phe Val Leu Gly Ala Ile Ala Leu Gly Val Cys Thr
85 90 95

Ala Ala Ala Val Thr Ala Gly Ile Ala Ile Ala Lys Thr Ile Arg Leu
100 105 110

Glu Ser Glu Val Asn Ala Ile Lys Gly Ala Leu Lys Gln Thr Asn Glu
115 120 125

Ala Val Ser Thr Leu Gly Asn Gly Val Arg Val Leu Ala Phe Ala Val
130 135 140

Arg Glu Leu Lys Glu Phe Val Ser Lys Asn Leu Thr Ser Ala Leu Asn
145 150 155 160

Arg Asn Lys Cys Asp Ile Ala Asp Leu Lys Met Ala Val Ser Phe Ser
165 170 175

Gln Phe Asn Arg Arg Phe Leu Asn Val Val Arg Gln Phe Ser Asp Asn
180 185 190

Ala Gly Ile Thr Pro Ala Ile Ser Leu Asp Leu Met Thr Asp Ala Glu
195 200 205

Leu Ala Arg Ala Val Ser Tyr Met Pro Thr Ser Ala Gly Gln Ile Lys
210 215 220

Leu Met Leu Glu Asn Arg Ala Met Val Arg Arg Lys Gly Phe Gly Ile
225 230 235 240

Leu Ile Gly Val Tyr Gly Ser Ser Val Ile Tyr Met Val Gln Leu Pro
245 250 255

Ile Phe Gly Val Ile Asp Thr Pro Cys Trp Ile Ile Lys Ala Ala Pro
260 265 270

Ser Cys Ser Glu Lys Asn Gly Asn Tyr Ala Cys Leu Leu Arg Glu Asp
275 280 285

Gln Gly Trp Tyr Cys Lys Asn Ala Gly Ser Thr Val Tyr Tyr Pro Asn
290 295 300

Glu Lys Asp Cys Glu Thr Arg Gly Asp His Val Phe Cys Asp Thr Ala
305 310 315 320

Cys Gly Ile Asn Val Ala Glu Gln Ser Arg Glu Cys Asn Ile Asn Ile
325 330 335

Ser Thr Thr Asn Tyr Pro Cys Lys Val Ser Thr Gly Arg His Pro Ile
340 345 350

Ser Met Val Ala Leu Ser Pro Leu Gly Ala Leu Val Ala Cys Tyr Lys
355 360 365

Gly Val Ser Cys Ser Ile Gly Ser Asn Trp Val Gly Ile Ile Lys Gln
370 375 380

Leu Pro Lys Gly Cys Ser Tyr Ile Thr Asn Gln Asp Ala Asp Thr Val
385 390 395 400

Thr Ile Asp Asn Thr Val Tyr Gln Leu Ser Lys Val Glu Gly Glu Gln
405 410 415

His Val Ile Lys Gly Arg Pro Val Ser Ser Ser Phe Asp Pro Ile Lys
420 425 430

Phe Pro Glu Asp Gln Phe Asn Val Ala Leu Asp Gln Val Phe Glu Ser
435 440 445

Ile Glu Asn Ser Gln Ala Leu Val Asp Gln Ser Asn Lys Ile Leu Asn
450 455 460

Ser Ala Glu
465

<210> SEQ ID NO 183
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 183

-continued

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Val Ala Ile Ala Lys Thr Ile Arg Leu
            100                 105                 110

Glu Ser Glu Val Thr Ala Ile Lys Asn Ala Leu Lys Lys Thr Asn Glu
        115                 120                 125

Ala Val Ser Thr Leu Gly Asn Gly Val Arg Val Leu Ala Phe Ala Val
    130                 135                 140

Arg Glu Leu Lys Asp Phe Val Ser Lys Asn Leu Thr Arg Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Asn Met Pro Thr Ser Ala Gly Gln Ile Lys
    210                 215                 220

Leu Met Leu Glu Asn Arg Ala Met Val Arg Arg Lys Gly Phe Gly Phe
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Val Lys Ala Ala Pro
            260                 265                 270

Ser Cys Ser Gly Lys Lys Gly Asn Tyr Ala Cys Leu Leu Arg Glu Asp
        275                 280                 285

Gln Gly Trp Tyr Cys Gln Asn Ala Gly Ser Thr Val Tyr Tyr Pro Asn
    290                 295                 300

Glu Lys Asp Cys Glu Thr Arg Gly Asp His Val Phe Cys Asp Thr Ala
305                 310                 315                 320

Cys Gly Ile Asn Val Ala Glu Gln Ser Lys Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Asn Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415
```

```
His Val Ile Lys Gly Arg Pro Val Ser Ser Ser Phe Asp Pro Val Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Arg Ile Leu Ser
    450                 455                 460

Ser Ala Glu
465


<210> SEQ ID NO 184
<211> LENGTH: 467
<212> TYPE: PRT
<213> ORGANISM: Artificial Sequence
<220> FEATURE:
<223> OTHER INFORMATION: recombinant Metapneumovirus F protein

<400> SEQUENCE: 184

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300
```

```
Lys Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu
465


<210> SEQ ID NO 185
<211> LENGTH: 446
<212> TYPE: PRT
<213> ORGANISM: Artificial Sequence
<220> FEATURE:
<223> OTHER INFORMATION: recombinant Metapneumovirus F protein

<400> SEQUENCE: 185

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Ile Ala Lys Thr Ile Arg Leu Glu Ser Glu Val Thr
                85                  90                  95

Ala Ile Lys Asn Ala Leu Lys Lys Thr Asn Glu Ala Val Ser Thr Leu
            100                 105                 110

Gly Asn Gly Val Arg Val Leu Ala Phe Ala Val Arg Glu Leu Lys Asp
        115                 120                 125

Phe Val Ser Lys Asn Leu Thr Arg Ala Leu Asn Lys Asn Lys Cys Asp
    130                 135                 140

Ile Ala Asp Leu Lys Met Ala Val Ser Phe Ser Gln Phe Asn Arg Arg
145                 150                 155                 160

Phe Leu Asn Val Val Arg Gln Phe Ser Asp Asn Ala Gly Ile Thr Pro
                165                 170                 175

Ala Ile Ser Leu Asp Leu Met Thr Asp Ala Glu Leu Ala Arg Ala Val
            180                 185                 190
```

```
Ser Asn Met Pro Thr Ser Ala Gly Gln Ile Lys Leu Met Leu Glu Asn
        195                 200                 205

Arg Ala Met Val Arg Arg Lys Gly Phe Gly Phe Leu Ile Gly Val Tyr
    210                 215                 220

Gly Ser Ser Val Ile Tyr Met Val Gln Leu Pro Ile Phe Gly Val Ile
225                 230                 235                 240

Asp Thr Pro Cys Trp Ile Val Lys Ala Ala Pro Ser Cys Ser Gly Lys
                245                 250                 255

Lys Gly Asn Tyr Ala Cys Leu Leu Arg Glu Asp Gln Gly Trp Tyr Cys
            260                 265                 270

Gln Asn Ala Gly Ser Thr Val Tyr Tyr Pro Asn Glu Lys Asp Cys Glu
        275                 280                 285

Thr Arg Gly Asp His Val Phe Cys Asp Thr Ala Ala Gly Ile Asn Val
    290                 295                 300

Ala Glu Gln Ser Lys Glu Cys Asn Ile Asn Ile Ser Thr Thr Asn Tyr
305                 310                 315                 320

Pro Cys Lys Val Ser Thr Gly Arg His Pro Ile Ser Met Val Ala Leu
                325                 330                 335

Ser Pro Leu Gly Ala Leu Val Ala Cys Tyr Lys Gly Val Ser Cys Ser
            340                 345                 350

Ile Gly Ser Asn Arg Val Gly Ile Ile Lys Gln Leu Asn Lys Gly Cys
        355                 360                 365

Ser Tyr Ile Thr Asn Gln Asp Ala Asp Thr Val Thr Ile Asp Asn Thr
    370                 375                 380

Val Tyr Gln Leu Ser Lys Val Glu Gly Glu Gln His Val Ile Lys Gly
385                 390                 395                 400

Arg Pro Val Ser Ser Ser Phe Asp Pro Val Lys Phe Pro Glu Asp Gln
                405                 410                 415

Phe Asn Val Ala Leu Asp Gln Val Phe Glu Ser Ile Glu Asn Ser Gln
            420                 425                 430

Ala Leu Val Asp Gln Ser Asn Arg Ile Leu Ser Ser Ala Glu
        435                 440                 445


<210> SEQ ID NO 186
<211> LENGTH: 446
<212> TYPE: PRT
<213> ORGANISM: Artificial Sequence
<220> FEATURE:
<223> OTHER INFORMATION: recombinant Metapneumovirus F protein

<400> SEQUENCE: 186

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Ile Ala Lys Thr Ile Arg Leu Glu Ser Glu Val Thr
                85                  90                  95

Ala Ile Lys Asn Ala Leu Lys Thr Thr Asn Glu Ala Val Ser Thr Leu
            100                 105                 110
```

```
Gly Asn Gly Val Arg Val Leu Ala Phe Ala Val Arg Glu Leu Lys Asp
        115                 120                 125

Phe Val Ser Lys Asn Leu Thr Arg Ala Leu Asn Lys Asn Lys Cys Asp
    130                 135                 140

Ile Asp Asp Leu Lys Met Ala Val Ser Phe Ser Gln Phe Asn Arg Arg
145                 150                 155                 160

Phe Leu Asn Val Val Arg Gln Phe Ser Asp Asn Ala Gly Ile Thr Pro
                165                 170                 175

Ala Ile Ser Leu Asp Leu Met Thr Asp Ala Glu Leu Ala Arg Ala Val
            180                 185                 190

Ser Asn Met Pro Thr Ser Ala Gly Gln Ile Lys Leu Met Leu Glu Asn
        195                 200                 205

Arg Ala Met Val Arg Arg Lys Gly Phe Gly Ile Leu Ile Gly Val Tyr
    210                 215                 220

Gly Ser Ser Val Ile Tyr Met Val Gln Leu Pro Ile Phe Gly Val Ile
225                 230                 235                 240

Asp Thr Pro Cys Trp Ile Val Lys Ala Ala Pro Ser Cys Ser Gly Lys
                245                 250                 255

Lys Gly Asn Tyr Ala Cys Leu Leu Arg Glu Asp Gln Gly Trp Tyr Cys
            260                 265                 270

Gln Asn Ala Gly Ser Thr Val Tyr Tyr Pro Asn Glu Lys Asp Cys Glu
        275                 280                 285

Thr Arg Gly Asp His Val Phe Cys Asp Thr Ala Ala Gly Ile Asn Val
    290                 295                 300

Ala Glu Gln Ser Lys Glu Cys Asn Ile Asn Ile Ser Thr Thr Asn Tyr
305                 310                 315                 320

Pro Cys Lys Val Ser Thr Gly Arg His Pro Ile Ser Met Val Ala Leu
                325                 330                 335

Ser Pro Leu Gly Ala Leu Val Ala Cys Tyr Lys Gly Val Ser Cys Ser
            340                 345                 350

Ile Gly Ser Asn Arg Val Gly Ile Ile Lys Gln Leu Asn Lys Gly Cys
        355                 360                 365

Ser Tyr Ile Thr Asn Gln Asp Ala Asp Thr Val Thr Ile Asp Asn Thr
    370                 375                 380

Val Tyr Gln Leu Ser Lys Val Glu Gly Glu Gln His Val Ile Lys Gly
385                 390                 395                 400

Arg Pro Val Ser Ser Ser Phe Asp Pro Ile Lys Phe Pro Glu Asp Gln
                405                 410                 415

Phe Asn Val Ala Leu Asp Gln Val Phe Glu Asn Ile Glu Asn Ser Gln
            420                 425                 430

Ala Leu Val Asp Gln Ser Asn Arg Ile Leu Ser Ser Ala Glu
        435                 440                 445


<210> SEQ ID NO 187
<211> LENGTH: 446
<212> TYPE: PRT
<213> ORGANISM: Artificial Sequence
<220> FEATURE:
<223> OTHER INFORMATION: recombinant Metapneumovirus F protein

<400> SEQUENCE: 187

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30
```

```
Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Ile Ala Lys Thr Ile Arg Leu Glu Ser Glu Val Thr
                85                  90                  95

Ala Ile Lys Asn Ala Leu Lys Thr Thr Asn Glu Ala Val Ser Thr Leu
            100                 105                 110

Gly Asn Gly Val Arg Val Leu Ala Phe Ala Val Arg Glu Leu Lys Asp
        115                 120                 125

Phe Val Ser Lys Asn Leu Thr Arg Ala Leu Asn Lys Asn Lys Cys Asp
    130                 135                 140

Ile Asp Asp Leu Lys Met Ala Val Ser Phe Ser Gln Phe Asn Arg Arg
145                 150                 155                 160

Phe Leu Asn Val Val Arg Gln Phe Ser Asp Asn Ala Gly Ile Thr Pro
                165                 170                 175

Ala Ile Ser Leu Asp Leu Met Thr Asp Ala Glu Leu Ala Arg Ala Val
            180                 185                 190

Ser Asn Met Pro Thr Ser Ala Gly Gln Ile Lys Leu Met Leu Glu Asn
        195                 200                 205

Arg Ala Met Val Arg Arg Lys Gly Phe Gly Ile Leu Ile Gly Val Tyr
    210                 215                 220

Gly Ser Ser Val Ile Tyr Thr Val Gln Leu Pro Ile Phe Gly Val Ile
225                 230                 235                 240

Asp Thr Pro Cys Trp Ile Val Lys Ala Ala Pro Ser Cys Ser Glu Lys
                245                 250                 255

Lys Gly Asn Tyr Ala Cys Leu Leu Arg Glu Asp Gln Gly Trp Tyr Cys
            260                 265                 270

Gln Asn Ala Gly Ser Thr Val Tyr Tyr Pro Asn Glu Lys Asp Cys Glu
        275                 280                 285

Thr Arg Gly Asp His Val Phe Cys Asp Thr Ala Ala Gly Ile Asn Val
    290                 295                 300

Ala Glu Gln Ser Lys Glu Cys Asn Ile Asn Ile Ser Thr Thr Asn Tyr
305                 310                 315                 320

Pro Cys Lys Val Ser Thr Gly Arg His Pro Ile Ser Met Val Ala Leu
                325                 330                 335

Ser Pro Leu Gly Ala Leu Val Ala Cys Tyr Lys Gly Val Ser Cys Ser
            340                 345                 350

Ile Gly Ser Asn Arg Val Gly Ile Ile Lys Gln Leu Asn Lys Gly Cys
        355                 360                 365

Ser Tyr Ile Thr Asn Gln Asp Ala Asp Thr Val Thr Ile Asp Asn Thr
    370                 375                 380

Val Tyr Gln Leu Ser Lys Val Glu Gly Glu Gln His Val Ile Lys Gly
385                 390                 395                 400

Arg Pro Val Ser Ser Ser Phe Asp Pro Ile Lys Phe Pro Glu Asp Gln
                405                 410                 415

Phe Asn Val Ala Leu Asp Gln Val Phe Glu Asn Ile Glu Asn Ser Gln
            420                 425                 430

Ala Leu Val Asp Gln Ser Asn Arg Ile Leu Ser Ser Ala Glu
        435                 440                 445
```

<210> SEQ ID NO 188
<211> LENGTH: 446
<212> TYPE: PRT
<213> ORGANISM: Artificial Sequence
<220> FEATURE:
<223> OTHER INFORMATION: recombinant Metapneumovirus F protein

<400> SEQUENCE: 188

```
Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Lys
    50                  55                  60

Pro Val Ser Ala Asp Gln Leu Ala Arg Glu Glu Gln Ile Glu Asn Pro
65                  70                  75                  80

Arg Gln Ser Arg Ile Ala Lys Thr Ile Arg Leu Glu Ser Glu Val Thr
                85                  90                  95

Ala Ile Lys Asn Ala Leu Lys Lys Thr Asn Glu Ala Val Ser Thr Leu
            100                 105                 110

Gly Asn Gly Val Arg Val Leu Ala Phe Ala Val Arg Glu Leu Lys Asp
        115                 120                 125

Phe Val Ser Lys Asn Leu Thr Arg Ala Leu Asn Lys Asn Lys Cys Asp
    130                 135                 140

Ile Asp Asp Leu Lys Met Ala Val Ser Phe Ser Gln Phe Asn Arg Arg
145                 150                 155                 160

Phe Leu Asn Val Val Arg Gln Phe Ser Asp Asn Ala Gly Ile Thr Pro
                165                 170                 175

Ala Ile Ser Leu Asp Leu Met Thr Asp Ala Glu Leu Ala Arg Ala Val
            180                 185                 190

Ser Asn Met Pro Thr Ala Ala Gly Gln Ile Lys Leu Met Leu Glu Asn
        195                 200                 205

Arg Ala Met Val Arg Arg Lys Gly Phe Gly Ile Leu Ile Gly Val Tyr
    210                 215                 220

Gly Ser Ser Val Ile Tyr Met Val Gln Leu Pro Ile Phe Gly Val Ile
225                 230                 235                 240

Asp Thr Pro Cys Trp Ile Val Lys Ala Ala Pro Ser Cys Ser Glu Lys
                245                 250                 255

Lys Gly Asn Tyr Ala Cys Leu Leu Arg Glu Asp Gln Gly Trp Tyr Cys
            260                 265                 270

Gln Asn Ala Gly Ser Thr Val Tyr Tyr Pro Asn Glu Lys Asp Cys Glu
        275                 280                 285

Thr Arg Gly Asp His Val Phe Cys Asp Thr Ala Ala Gly Ile Asn Val
    290                 295                 300

Ala Glu Gln Ser Lys Glu Cys Asn Ile Asn Ile Ser Thr Thr Asn Tyr
305                 310                 315                 320

Pro Cys Lys Val Ser Thr Gly Arg His Pro Ile Ser Met Val Ala Leu
                325                 330                 335

Ser Pro Leu Gly Ala Leu Val Ala Cys Tyr Lys Gly Val Ser Cys Ser
            340                 345                 350

Ile Gly Ser Asn Arg Val Gly Ile Ile Lys Gln Leu Asn Lys Gly Cys
        355                 360                 365

Ser Tyr Ile Thr Asn Gln Asp Ala Asp Thr Val Thr Ile Asp Asn Thr
```

```
    370                 375                 380

Val Tyr Gln Leu Ser Lys Val Glu Gly Glu Gln His Val Ile Lys Gly
385                 390                 395                 400

Arg Pro Val Ser Ser Ser Phe Asp Pro Val Lys Phe Pro Glu Asp Gln
                405                 410                 415

Phe Asn Val Ala Leu Asp Gln Val Phe Glu Asn Ile Glu Asn Ser Gln
            420                 425                 430

Ala Leu Val Asp Gln Ser Asn Arg Ile Leu Ser Ser Ala Glu
        435                 440                 445


<210> SEQ ID NO 189
<211> LENGTH: 446
<212> TYPE: PRT
<213> ORGANISM: Artificial Sequence
<220> FEATURE:
<223> OTHER INFORMATION: recombinant Metapneumovirus F protein

<400> SEQUENCE: 189

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Ile Ala Lys Thr Ile Arg Leu Glu Ser Glu Val Asn
                85                  90                  95

Ala Ile Lys Gly Ala Leu Lys Gln Thr Asn Glu Ala Val Ser Thr Leu
            100                 105                 110

Gly Asn Gly Val Arg Val Leu Ala Phe Ala Val Arg Glu Leu Lys Glu
        115                 120                 125

Phe Val Ser Lys Asn Leu Thr Ser Ala Leu Asn Arg Asn Lys Cys Asp
    130                 135                 140

Ile Ala Asp Leu Lys Met Ala Val Ser Phe Ser Gln Phe Asn Arg Arg
145                 150                 155                 160

Phe Leu Asn Val Val Arg Gln Phe Ser Asp Asn Ala Gly Ile Thr Pro
                165                 170                 175

Ala Ile Ser Leu Asp Leu Met Thr Asp Ala Glu Leu Ala Arg Ala Val
            180                 185                 190

Ser Tyr Met Pro Thr Ser Ala Gly Gln Ile Lys Leu Met Leu Glu Asn
        195                 200                 205

Arg Ala Met Val Arg Arg Lys Gly Phe Gly Ile Leu Ile Gly Val Tyr
    210                 215                 220

Gly Ser Ser Val Ile Tyr Met Val Gln Leu Pro Ile Phe Gly Val Ile
225                 230                 235                 240

Asp Thr Pro Cys Trp Ile Ile Lys Ala Ala Pro Ser Cys Ser Glu Lys
                245                 250                 255

Asn Gly Asn Tyr Ala Cys Leu Leu Arg Glu Asp Gln Gly Trp Tyr Cys
            260                 265                 270

Lys Asn Ala Gly Ser Thr Val Tyr Tyr Pro Asn Glu Lys Asp Cys Glu
        275                 280                 285

Thr Arg Gly Asp His Val Phe Cys Asp Thr Ala Ala Gly Ile Asn Val
```

```
    290                 295                 300

Ala Glu Gln Ser Arg Glu Cys Asn Ile Asn Ile Ser Thr Thr Asn Tyr
305                 310                 315                 320

Pro Cys Lys Val Ser Thr Gly Arg His Pro Ile Ser Met Val Ala Leu
                325                 330                 335

Ser Pro Leu Gly Ala Leu Val Ala Cys Tyr Lys Gly Val Ser Cys Ser
            340                 345                 350

Ile Gly Ser Asn Trp Val Gly Ile Ile Lys Gln Leu Pro Lys Gly Cys
        355                 360                 365

Ser Tyr Ile Thr Asn Gln Asp Ala Asp Thr Val Thr Ile Asp Asn Thr
    370                 375                 380

Val Tyr Gln Leu Ser Lys Val Glu Gly Glu Gln His Val Ile Lys Gly
385                 390                 395                 400

Arg Pro Val Ser Ser Ser Phe Asp Pro Ile Lys Phe Pro Glu Asp Gln
                405                 410                 415

Phe Asn Val Ala Leu Asp Gln Val Phe Glu Ser Ile Glu Asn Ser Gln
            420                 425                 430

Ala Leu Val Asp Gln Ser Asn Lys Ile Leu Asn Ser Ala Glu
        435                 440                 445


<210> SEQ ID NO 190
<211> LENGTH: 446
<212> TYPE: PRT
<213> ORGANISM: Artificial Sequence
<220> FEATURE:
<223> OTHER INFORMATION: recombinant Metapneumovirus F protein

<400> SEQUENCE: 190

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg Ile Ala Lys Thr Ile Arg Leu Glu Ser Glu Val Thr
                85                  90                  95

Ala Ile Lys Asn Ala Leu Lys Lys Thr Asn Glu Ala Val Ser Thr Leu
            100                 105                 110

Gly Asn Gly Val Arg Val Leu Ala Phe Ala Val Arg Glu Leu Lys Asp
        115                 120                 125

Phe Val Ser Lys Asn Leu Thr Arg Ala Leu Asn Lys Asn Lys Cys Asp
    130                 135                 140

Ile Ala Asp Leu Lys Met Ala Val Ser Phe Ser Gln Phe Asn Arg Arg
145                 150                 155                 160

Phe Leu Asn Val Val Arg Gln Phe Ser Asp Asn Ala Gly Ile Thr Pro
                165                 170                 175

Ala Ile Ser Leu Asp Leu Met Thr Asp Ala Glu Leu Ala Arg Ala Val
            180                 185                 190

Ser Asn Met Pro Thr Ser Ala Gly Gln Ile Lys Leu Met Leu Glu Asn
        195                 200                 205

Arg Ala Met Val Arg Arg Lys Gly Phe Gly Phe Leu Ile Gly Val Tyr
```

```
    210                 215                 220

Gly Ser Ser Val Ile Tyr Met Val Gln Leu Pro Ile Phe Gly Val Ile
225                 230                 235                 240

Asp Thr Pro Cys Trp Ile Val Lys Ala Ala Pro Ser Cys Ser Gly Lys
                245                 250                 255

Lys Gly Asn Tyr Ala Cys Leu Leu Arg Glu Asp Gln Gly Trp Tyr Cys
            260                 265                 270

Gln Asn Ala Gly Ser Thr Val Tyr Tyr Pro Asn Glu Lys Asp Cys Glu
        275                 280                 285

Thr Arg Gly Asp His Val Phe Cys Asp Thr Ala Ala Gly Ile Asn Val
    290                 295                 300

Ala Glu Gln Ser Lys Glu Cys Asn Ile Asn Ile Ser Thr Thr Asn Tyr
305                 310                 315                 320

Pro Cys Lys Val Ser Thr Gly Arg His Pro Ile Ser Met Val Ala Leu
                325                 330                 335

Ser Pro Leu Gly Ala Leu Val Ala Cys Tyr Lys Gly Val Ser Cys Ser
            340                 345                 350

Ile Gly Ser Asn Arg Val Gly Ile Ile Lys Gln Leu Asn Lys Gly Cys
        355                 360                 365

Ser Tyr Ile Thr Asn Gln Asp Ala Asp Thr Val Thr Ile Asp Asn Thr
    370                 375                 380

Val Tyr Gln Leu Ser Lys Val Glu Gly Glu Gln His Val Ile Lys Gly
385                 390                 395                 400

Arg Pro Val Ser Ser Ser Phe Asp Pro Val Lys Phe Pro Glu Asp Gln
                405                 410                 415

Phe Asn Val Ala Leu Asp Gln Val Phe Glu Ser Ile Glu Asn Ser Gln
            420                 425                 430

Ala Leu Val Asp Gln Ser Asn Arg Ile Leu Ser Ser Ala Glu
        435                 440                 445


<210> SEQ ID NO 191
<211> LENGTH: 446
<212> TYPE: PRT
<213> ORGANISM: Artificial Sequence
<220> FEATURE:
<223> OTHER INFORMATION: recombinant Metapneumovirus F protein

<400> SEQUENCE: 191

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Ile Ala Lys Thr Ile Arg Leu Glu Ser Glu Val Asn
                85                  90                  95

Ala Ile Lys Gly Ala Leu Lys Thr Thr Asn Glu Ala Val Ser Thr Leu
            100                 105                 110

Gly Asn Gly Val Arg Val Leu Ala Phe Ala Val Arg Glu Leu Lys Glu
        115                 120                 125

Phe Val Ser Lys Asn Leu Thr Ser Ala Leu Asn Lys Asn Lys Cys Asp
```

```
    130                 135                 140

Ile Ala Asp Leu Lys Met Ala Val Ser Phe Ser Gln Phe Asn Arg Arg
145                 150                 155                 160

Phe Leu Asn Val Val Arg Gln Phe Ser Asp Asn Ala Gly Ile Thr Pro
                165                 170                 175

Ala Ile Ser Leu Asp Leu Met Thr Asp Ala Glu Leu Ala Arg Ala Val
            180                 185                 190

Ser Tyr Met Pro Thr Ser Ala Gly Gln Ile Lys Leu Met Leu Glu Asn
        195                 200                 205

Arg Ala Met Val Arg Arg Lys Gly Phe Gly Ile Leu Ile Gly Val Tyr
    210                 215                 220

Gly Ser Ser Val Ile Tyr Met Val Gln Leu Pro Ile Phe Gly Val Ile
225                 230                 235                 240

Asp Thr Pro Cys Trp Ile Ile Lys Ala Ala Pro Ser Cys Ser Glu Lys
                245                 250                 255

Asp Gly Asn Tyr Ala Cys Leu Leu Arg Glu Asp Gln Gly Trp Tyr Cys
            260                 265                 270

Lys Asn Ala Gly Ser Thr Val Tyr Tyr Pro Asn Lys Lys Asp Cys Glu
        275                 280                 285

Thr Arg Gly Asp His Val Phe Cys Asp Thr Ala Ala Gly Ile Asn Val
    290                 295                 300

Ala Glu Gln Ser Arg Glu Cys Asn Ile Asn Ile Ser Thr Thr Asn Tyr
305                 310                 315                 320

Pro Cys Lys Val Ser Thr Gly Arg His Pro Ile Ser Met Val Ala Leu
                325                 330                 335

Ser Pro Leu Gly Ala Leu Val Ala Cys Tyr Lys Gly Val Ser Cys Ser
            340                 345                 350

Ile Gly Ser Asn Arg Val Gly Ile Ile Lys Gln Leu Pro Lys Gly Cys
        355                 360                 365

Ser Tyr Ile Thr Asn Gln Asp Ala Asp Thr Val Thr Ile Asp Asn Thr
    370                 375                 380

Val Tyr Gln Leu Ser Lys Val Glu Gly Glu Gln His Val Ile Lys Gly
385                 390                 395                 400

Arg Pro Val Ser Ser Ser Phe Asp Pro Ile Lys Phe Pro Glu Asp Gln
                405                 410                 415

Phe Asn Val Ala Leu Asp Gln Val Phe Glu Ser Ile Glu Asn Ser Gln
            420                 425                 430

Ala Leu Val Asp Gln Ser Asn Lys Ile Leu Asn Ser Ala Glu
        435                 440                 445


<210> SEQ ID NO 192
<211> LENGTH: 504
<212> TYPE: PRT
<213> ORGANISM: Artificial Sequence
<220> FEATURE:
<223> OTHER INFORMATION: recombinant MPV F protein

<400> SEQUENCE: 192

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Thr Asp Gly Pro Ser Leu
        35                  40                  45

Ile Lys Thr Glu Leu Asp Leu Thr Lys Ser Ala Leu Arg Glu Leu Lys
```

```
    50                  55                  60

Thr Val Ser Ala Asp Gln Leu Ala Arg Glu Glu Gln Ile Glu Asn Pro
65                  70                  75                  80

Arg Lys Ala Arg Phe Val Leu Gly Ala Ile Ala Leu Gly Val Cys Thr
                85                  90                  95

Ala Ala Ala Val Thr Ala Gly Ile Ala Ile Ala Lys Thr Ile Arg Leu
            100                 105                 110

Glu Ser Glu Val Asn Ala Ile Lys Gly Ala Leu Lys Thr Thr Asn Glu
        115                 120                 125

Ala Val Ser Thr Leu Gly Asn Gly Val Arg Val Leu Ala Phe Ala Val
    130                 135                 140

Arg Glu Leu Lys Glu Phe Val Ser Lys Asn Leu Thr Ser Ala Leu Asn
145                 150                 155                 160

Lys Asn Lys Cys Asp Ile Ala Asp Leu Lys Met Ala Val Ser Phe Ser
                165                 170                 175

Gln Phe Asn Arg Arg Phe Leu Asn Val Val Arg Gln Phe Ser Asp Asn
            180                 185                 190

Ala Gly Ile Thr Pro Ala Ile Ser Leu Asp Leu Met Thr Asp Ala Glu
        195                 200                 205

Leu Ala Arg Ala Val Ser Tyr Met Pro Thr Ser Ala Gly Gln Ile Lys
    210                 215                 220

Leu Met Leu Glu Asn Arg Ala Met Val Arg Arg Lys Gly Phe Gly Ile
225                 230                 235                 240

Leu Ile Gly Val Tyr Gly Ser Ser Val Ile Tyr Met Val Gln Leu Pro
                245                 250                 255

Ile Phe Gly Val Ile Asp Thr Pro Cys Trp Ile Ile Lys Ala Ala Pro
            260                 265                 270

Ser Cys Ser Glu Lys Asp Gly Asn Tyr Ala Cys Leu Leu Arg Glu Asp
        275                 280                 285

Gln Gly Trp Tyr Cys Lys Asn Ala Gly Ser Thr Val Tyr Tyr Pro Asn
    290                 295                 300

Asp Lys Asp Cys Glu Thr Arg Gly Asp His Val Phe Cys Asp Thr Ala
305                 310                 315                 320

Cys Gly Ile Asn Val Ala Glu Gln Ser Arg Glu Cys Asn Ile Asn Ile
                325                 330                 335

Ser Thr Thr Asn Tyr Pro Cys Lys Val Ser Thr Gly Arg His Pro Ile
            340                 345                 350

Ser Met Val Ala Leu Ser Pro Leu Gly Ala Leu Val Ala Cys Tyr Lys
        355                 360                 365

Gly Val Ser Cys Ser Ile Gly Ser Asn Arg Val Gly Ile Ile Lys Gln
    370                 375                 380

Leu Pro Lys Gly Cys Ser Tyr Ile Thr Asn Gln Asp Ala Asp Thr Val
385                 390                 395                 400

Thr Ile Asp Asn Thr Val Tyr Gln Leu Ser Lys Val Glu Gly Glu Gln
                405                 410                 415

His Val Ile Lys Gly Arg Pro Val Ser Ser Ser Phe Asp Pro Ile Lys
            420                 425                 430

Phe Pro Glu Asp Gln Phe Asn Val Ala Leu Asp Gln Val Phe Glu Ser
        435                 440                 445

Ile Glu Asn Ser Gln Ala Leu Val Asp Gln Ser Asn Lys Ile Leu Asn
    450                 455                 460

Ser Ala Glu Ser Ala Ile Gly Gly Tyr Ile Pro Glu Ala Pro Arg Asp
465                 470                 475                 480
```

```
Gly Gln Ala Tyr Val Arg Lys Asp Gly Glu Trp Val Leu Leu Ser Thr
                485                 490                 495

Phe Leu Gly Gly Leu Val Pro Arg
            500


<210> SEQ ID NO 193
<211> LENGTH: 452
<212> TYPE: PRT
<213> ORGANISM: Artificial Sequence
<220> FEATURE:
<223> OTHER INFORMATION: recombinant MPV F protein

<400> SEQUENCE: 193

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ser Asp Gly Pro Ser Leu
        35                  40                  45

Ile Lys Thr Glu Leu Asp Leu Thr Lys Ser Ala Leu Arg Glu Leu Lys
    50                  55                  60

Thr Val Ser Ala Asp Gln Leu Ala Arg Glu Glu Gln Ile Glu Asn Pro
65                  70                  75                  80

Arg Gln Ser Arg Ile Ala Lys Thr Ile Arg Leu Glu Ser Glu Val Thr
                85                  90                  95

Ala Ile Lys Asn Ala Leu Lys Thr Thr Asn Glu Ala Val Ser Thr Leu
            100                 105                 110

Gly Asn Gly Val Arg Val Leu Ala Thr Ala Val Arg Glu Leu Lys Asp
        115                 120                 125

Phe Val Ser Lys Asn Leu Thr Arg Ala Ile Asn Lys Asn Lys Cys Asp
    130                 135                 140

Ile Asp Asp Leu Lys Met Ala Val Ser Phe Ser Gln Phe Asn Arg Arg
145                 150                 155                 160

Phe Leu Asn Val Val Arg Gln Phe Ser Asp Asn Ala Gly Ile Thr Pro
                165                 170                 175

Ala Ile Ser Leu Asp Leu Met Thr Asp Ala Glu Leu Ala Arg Ala Val
            180                 185                 190

Ser Asn Met Pro Thr Ser Ala Gly Gln Ile Lys Leu Met Leu Glu Asn
        195                 200                 205

Arg Ala Met Val Arg Arg Lys Gly Phe Gly Ile Leu Ile Gly Val Tyr
    210                 215                 220

Gly Ser Ser Val Ile Tyr Met Val Gln Leu Pro Ile Phe Gly Val Ile
225                 230                 235                 240

Asp Thr Pro Cys Trp Ile Val Lys Ala Ala Pro Ser Cys Ser Gly Lys
                245                 250                 255

Lys Gly Asn Tyr Ala Cys Leu Leu Arg Glu Asp Gln Gly Trp Tyr Cys
            260                 265                 270

Gln Asn Ala Gly Ser Thr Val Tyr Tyr Pro Asn Glu Lys Asp Cys Glu
        275                 280                 285

Thr Arg Gly Asp His Val Phe Cys Asp Thr Ala Ala Gly Ile Asn Val
    290                 295                 300

Ala Glu Gln Ser Lys Glu Cys Asn Ile Asn Ile Ser Thr Thr Asn Tyr
305                 310                 315                 320

Pro Cys Lys Val Ser Thr Gly Arg His Pro Ile Ser Met Val Ala Leu
                325                 330                 335
```

-continued

```
Ser Pro Leu Gly Ala Leu Val Ala Cys Tyr Lys Gly Val Ser Cys Ser
            340                 345                 350

Ile Gly Ser Asn Arg Val Gly Ile Ile Lys Gln Leu Asn Lys Gly Cys
        355                 360                 365

Ser Tyr Ile Thr Asn Gln Asp Ala Asp Thr Val Thr Ile Asp Asn Thr
    370                 375                 380

Val Tyr Gln Leu Ser Lys Val Glu Gly Glu Gln His Val Ile Lys Gly
385                 390                 395                 400

Arg Pro Val Ser Ser Ser Phe Asp Pro Ile Lys Phe Pro Glu Asp Gln
                405                 410                 415

Phe Asn Val Ala Leu Asp Gln Val Phe Glu Asn Ile Glu Asn Ser Gln
            420                 425                 430

Ala Leu Val Asp Gln Ser Asn Arg Ile Leu Ser Ser Ala Glu Gly Gly
        435                 440                 445

Leu Val Pro Arg
    450
```